United States Patent
Choi et al.

(10) Patent No.: US 11,542,269 B2
(45) Date of Patent: Jan. 3, 2023

(54) PRINS REACTION AND COMPOUNDS USEFUL IN THE SYNTHESIS OF HALICHONDRIN MACROLIDES AND ANALOGS THEREOF

(71) Applicant: EISAI R&D MANAGEMENT CO., LTD., Tokyo (JP)

(72) Inventors: Hyeong-Wook Choi, Andover, MA (US); Francis G. Fang, Andover, MA (US)

(73) Assignee: EISAI R&D MANAGEMENT CO., LTD., Tokyo (JP)

( * ) Notice: Subject to any disclaimer, the term of this patent is extended or adjusted under 35 U.S.C. 154(b) by 0 days.

(21) Appl. No.: 16/959,882

(22) PCT Filed: Jan. 3, 2019

(86) PCT No.: PCT/US2019/012178
§ 371 (c)(1),
(2) Date: Jul. 2, 2020

(87) PCT Pub. No.: WO2019/136145
PCT Pub. Date: Jul. 11, 2019

(65) Prior Publication Data
US 2020/0331928 A1 Oct. 22, 2020

Related U.S. Application Data

(60) Provisional application No. 62/613,307, filed on Jan. 3, 2018.

(51) Int. Cl.
| | | |
|---|---|---|
| *C07D 493/22* | (2006.01) | |
| *C07D 307/28* | (2006.01) | |
| *C07D 493/04* | (2006.01) | |
| *C07D 407/06* | (2006.01) | |
| *C07D 407/14* | (2006.01) | |
| *A61P 35/00* | (2006.01) | |

(52) U.S. Cl.
CPC ......... *C07D 493/22* (2013.01); *C07D 307/28* (2013.01); *C07D 407/06* (2013.01); *C07D 407/14* (2013.01); *C07D 493/04* (2013.01)

(58) Field of Classification Search
CPC .. C07D 307/28; C07D 493/22; C07D 407/06; C07D 407/14; C07D 493/04
See application file for complete search history.

(56) References Cited

U.S. PATENT DOCUMENTS

| | | |
|---|---|---|
| 4,107,206 A | 8/1978 | Hewett et al. |
| 5,338,865 A | 8/1994 | Kishi et al. |
| 5,436,238 A | 7/1995 | Kishi et al. |
| 5,451,573 A | 9/1995 | Hemmerle et al. |
| 6,194,586 B1 | 2/2001 | Martinelli et al. |
| 6,214,865 B1 | 4/2001 | Littlefield et al. |
| 6,365,759 B1 | 4/2002 | Littlefield et al. |
| 6,469,182 B1 | 10/2002 | Littlefield et al. |
| 6,653,341 B1 | 11/2003 | Littlefield et al. |
| 6,870,058 B2 | 3/2005 | Smith, III et al. |
| 7,470,720 B2 | 12/2008 | Littlefield et al. |
| 7,982,060 B2 | 7/2011 | Austad et al. |
| 8,093,410 B2 | 1/2012 | Chase et al. |
| 8,097,648 B2 | 1/2012 | Littlefield et al. |
| 8,119,839 B2 | 2/2012 | Yoshimura et al. |
| 8,148,554 B2 | 4/2012 | Seletsky et al. |
| 8,203,010 B2 | 6/2012 | Endo et al. |
| 8,350,067 B2 | 1/2013 | Endo et al. |
| 8,445,701 B2 | 5/2013 | Austad et al. |
| 8,598,373 B2 | 12/2013 | Hu |
| 8,618,313 B2 | 12/2013 | Benayoud et al. |
| 8,884,031 B2 | 11/2014 | Chase et al. |
| RE45,324 E | 1/2015 | Austad et al. |
| 8,927,597 B2 | 1/2015 | Endo et al. |
| 8,975,422 B2 | 3/2015 | Fang et al. |
| 8,987,479 B2 | 3/2015 | Chase et al. |
| 9,206,194 B2 | 12/2015 | Hu |
| 9,278,979 B2 | 3/2016 | Souza et al. |
| 9,303,039 B2 | 4/2016 | Zhang et al. |
| 9,303,050 B2 | 4/2016 | Benayoud et al. |
| 9,382,262 B2 | 7/2016 | Endo et al. |
| 9,469,651 B2 | 10/2016 | Hu |
| 9,604,993 B2 | 3/2017 | Chase et al. |
| 9,695,187 B2 | 7/2017 | Souza et al. |
| 9,695,188 B2 | 7/2017 | Hu et al. |
| 9,783,549 B2 | 10/2017 | Fang et al. |
| 9,802,953 B2 | 10/2017 | Chase et al. |
| 9,856,276 B2 | 1/2018 | Endo et al. |

(Continued)

FOREIGN PATENT DOCUMENTS

| | | |
|---|---|---|
| EP | 0572109 A1 | 12/1993 |
| EP | 0642345 B1 | 9/2000 |

(Continued)

OTHER PUBLICATIONS

Isagulyants et al., "Condensation of unsaturated compounds with formaldehyde (Prince reaction)." Advances in Chemistry. 37(1): 61-77 (1968).
Search Report issued in Russian Patent Application No. 2019102375, date of completion Jul. 1, 2021 (4 pages).
U.S. Appl. No. 16/684,332, Benayoud et al.
Aicher et al., "Synthetic studies towards halichondrins: synthesis of the C.27-C.38 segment," Tetrahedron Lett. 33(12):1549-52 (1992).
Aicher et al., "Total synthesis of halichondrin B and norhalichondrin B," J Am Chem Soc. 114(8):3162-4(1992).

(Continued)

*Primary Examiner* — Susanna Moore
(74) *Attorney, Agent, or Firm* — Clark & Elbing LLP

(57) ABSTRACT

The invention provides methods utilizing Prins reaction in the preparation of compounds that may be useful as intermediates in the synthesis of halichondrin macrolides and analogs thereof. The invention also provides compounds that may be useful as intermediates in the synthesis of a halichondrin macrolides and methods for preparing the same.

7 Claims, No Drawings

(56) References Cited

U.S. PATENT DOCUMENTS

| | | | |
|---|---|---|---|
| RE46,965 E | 7/2018 | Austad et al. |
| 10,030,032 B2 | 7/2018 | Hu et al. |
| 10,214,539 B2 | 2/2019 | Chase et al. |
| 10,221,189 B2 | 3/2019 | Fang et al. |
| 10,308,661 B2 | 6/2019 | Fang et al. |
| 10,344,038 B2 | 7/2019 | Kishi et al. |
| 10,450,324 B2 | 10/2019 | Hu et al. |
| 10,494,388 B2 | 12/2019 | Endo et al. |
| RE47,797 E | 1/2020 | Benayoud et al. |
| 10,611,773 B2 | 4/2020 | Fang et al. |
| 10,633,392 B2 | 4/2020 | Kishi et al. |
| 10,676,481 B2 | 6/2020 | Baran et al. |
| 10,717,743 B2 | 7/2020 | Chase et al. |
| 10,934,307 B2 | 3/2021 | Fang et al. |
| 2004/0092581 A1 | 5/2004 | Burzlaff et al. |
| 2006/0045846 A1 | 3/2006 | Horstmann et al. |
| 2009/0093649 A1 | 4/2009 | Nobis |
| 2009/0104285 A1 | 4/2009 | Littlefield et al. |
| 2009/0203771 A1 | 8/2009 | Inanaga et al. |
| 2018/0009825 A1 | 1/2018 | Kovi et al. |
| 2018/0230164 A1 | 8/2018 | Kishi et al. |
| 2019/0161495 A1 | 5/2019 | Chase et al. |
| 2019/0308992 A1 | 10/2019 | Fang et al. |

FOREIGN PATENT DOCUMENTS

| | | |
|---|---|---|
| JP | H06-211737 A | 8/1994 |
| JP | 2010-168320 A | 8/2010 |
| RU | 2112773 C1 | 6/1998 |
| RU | 2517167 C2 | 5/2014 |
| SU | 652180 A1 | 3/1979 |
| WO | WO-93/17690 A1 | 9/1993 |
| WO | WO-98/09942 A1 | 3/1998 |
| WO | WO-99/65894 A1 | 12/1999 |
| WO | WO-2005/118565 A1 | 12/2005 |
| WO | WO-2006/076100 A2 | 7/2006 |
| WO | WO-2008/010776 A1 | 1/2008 |
| WO | WO-2009/014105 A1 | 1/2009 |
| WO | WO-2009/046308 A1 | 4/2009 |
| WO | WO-2009/064029 A1 | 5/2009 |
| WO | WO-2009/124237 A1 | 10/2009 |
| WO | WO-2011/094339 A1 | 8/2011 |
| WO | WO-2012/147900 A1 | 11/2012 |
| WO | WO-2013/078559 A1 | 6/2013 |
| WO | WO-2013/142999 A1 | 10/2013 |
| WO | WO-2015/000070 A1 | 1/2015 |
| WO | WO-2015/066729 A1 | 5/2015 |
| WO | WO-2016/038624 A1 | 3/2016 |
| WO | WO-2016/179607 A1 | 11/2016 |
| WO | WO-2017/139664 A1 | 8/2017 |
| WO | WO-2018/006031 A1 | 1/2018 |
| WO | WO-2018/217894 A1 | 11/2018 |
| WO | WO-2019/136145 A1 | 7/2019 |

OTHER PUBLICATIONS

Aicher, Thesis, Chapter 4, "Synthetic studies towards halichondrin B," Doctor of Philosophy in Chemistry, Harvard University, 35-54, 1989 (26 pages).

AkzoNobel Polymer Chemicals, "Diisobutylaluminum hydride (DIBAL-H) and other isobutyl aluminum Alkyls (DIBAL-BOT, TIBAL) as specialty organic synthesis reagents," The AkzoNobel Technical Bulletin, 1-14 (2006).

Alley et al. "Comparison of the relative efficacies and toxicities of Halichondrin B analogues," Proceedings of the AACR-NCI-EORTC Conference on Molecular Targets and Cancer Therapeutics. C230:257 (2005).

Anderson, "Developing processes for crystallization-induced asymmetric transformation," Org Process Res Dev. 9:800-13 (2005).

Ando et al., "Z-selective intramolecular Horner-Wadsworth-Emmons reaction for the synthesis of macrocyclic lactones," Org Lett. 12(7):1460-3 (2010).

Austad et al. (2005): STN International HCAPLUS database, Columbus (OH), accession No. 2005: 1313925.

Austad et al., "Commercial manufacture of Halaven®: chemoselective transformations en route to structurally complex macrocyclic ketones," Synlett. 24 (2013). Supporting Information, (13 pages.).

Austad et al., "Commercial manufacture of Halaven®: chemoselective transformations en route to structurally complex macrocyclic ketones," Synlett. 24(3):333-7 (2013).

Austad et al., "Process development of Halaven®: synthesis of the C14—C35 fragment via iterative Nozaki-Hiyama-Kishi reaction—Williamson ether cyclization," Synlett. 24(3):327-32 (2013).

Bai et al., "Halichondrin B and Homohalichondrin B, marine natural products binding in the vinca domain of tubulin. Discovery of tubulin-based mechanism of action by analysis of differential cytotoxicity data," J Biol Chem. 266(24):15882-9 (1991).

Bernet et al., "Carbocyclische verbindungen aus monosacchariden. Umsetzungen in der glucosereihe," Helv Chim Acta. 62(6):1990-2016 (1979).

Blanchette et al., "Horner-Wadsworth-Emmons reaction: use of lithium chloride and an amine for base-sensitive compounds," Tetrahedron Lett. 25(21):2183-6 (1984).

Burke et al., "Enantioselective synthesis of a Halichondrin B C(20) → C(36) precursor," Tetrahedron Lett. 36(39):7023-6 (1995).

Burke et al., "Synthesis of a C(22)—C(34) Halichondrin B precursor via ring opening—double ring closing metathesis," J Org Chem. 63:8626-7 (1998).

Burke et al., "Synthesis of a C(22) → C(34) Halichondrin precursor via a double dioxanone-to-dihydropyran rearrangement," Tetrahedron Lett. 32(32):3961-4 (1991).

Burke et al., "Synthetic studies toward complex polyether macrolides of marine origin," Spec Publ R Soc Chem. 198:(Anti-Infectives) 73-85 (1997).

Carruthers et al., Main-group chemistry. *Modern Methods of Organic Synthesis, Fourth Edition.* Cambridge University Press, 65 (2004).

Chase et al., "Process development of Halaven®: Synthesis of the C1—C13 fragment from D-(-)-Gulono-1, 4-lactone," Synlett. 24(3):323-6 (2013).

Chen et al., "Ni(II)/Cr(II)-mediated coupling reaction: An asymmetric process," J Org Chem. 60(17):5386-7(1995).

Choi et al., "Asymmetric Ni(II)/Cr(II)-mediated coupling reaction: catalytic process," Org Lett. 4(25):4435-8 (2002).

Choi et al., "Prins reaction of homoallenyl alcohols: Access to substituted pyrans in the halichondrin series," Org Lett. 19(22): 6092-5 (2017).

Choi et al., "Supporting information for asymmetric Ni(II)/Cr(II)-mediated coupling reaction: catalytic process," Org Lett. 4(25) (2002) (8 pages).

Choi et al., "Synthetic studies on the marine natural product Halichondrins," Pure Appl Chem. 75(1):1-17 (2003).

Cooper et al., "Total Synthesis of Halichondrin B from common sugars: an F-ring intermediate from D-glucose and efficient construction of the C1 to C21 segment," Tetrahedron Lett. 34(51):8193-6 (1993).

Cunningham et al., "The influence of pH on the kinetic constants of alpha-chymotrypsin-catalyzed esterolysis," J Biol Chem. 221(1):287-99 (1956).

Dabydeen et al., "Comparison of the activities of the truncated Halichondrin B analog NSC 707389 (E7389) with those of the parent compound and a proposed binding site on tubulin," Mol Pharmacol. 70(6):1866-75 (2006).

Del Valle et al., "Total synthesis of (+)-trienomycins A and F via C—C bond-forming hydrogenation and transfer hydrogenation," J Am Chem Soc. 135(30):10986-89 (2013).

Dong et al., "New syntheses of E7389 C14—C35 and halichondrin C14—C38 building blocks: reductive cyclization and oxy-michael cyclization approaches," J Am Chem Soc. 131(43):15642-6 (2009).

Duan et al., "Synthetic studies on halichondrins: a new practical synthesis of the C.1-C.12 segment," Tetrahedron Lett. 34(47):7541-4 (1993).

Favretto et al., "Highly regioselective microwave-assisted synthesis of enantiopure C3-symmetric trialkanolamines," Tetrahedron Letters. 43(14): 2581-2584 (2002).

(56) References Cited

OTHER PUBLICATIONS

Fleming et al., "Nitrile anion cyclizations," Tetrahedron. 58(1):1-23 (2002).
Gesinski et al., "Symmetric macrocycles by a Prins dimerization and macrocyclization strategy," available in PMC Nov. 1, 2010, published in final edited form as: Org Lett. 11(22):5342-5 (2009) (13 pages).
Gradillas et al., "Macrocyclization by ring-closing metathesis in the total synthesis of natural products: reaction conditions and limitations," Angew Chem Int Ed Engl. 45(37): 6086-6101 (2006).
Guo et al., "Toolbox approach to the search for effective ligands for catalytic asymmetric Cr-mediated coupling reactions," J Am Chem Soc. 131(42):15387-93 (2009).
Hirata et al., "Halichondrins—antitumor polyether macrolides from a marine sponge," Pure Appl Chem. 58(5):701-10 (1986).
Hori et al., "Efficient synthesis of 2,3-trans-tetrahydropyrans and oxepanes: rearrangement-ring expansion of cyclic ethers having a chloromethanesulfonate," Tetrahedron Lett. 40(11):2145-8 (1999).
Horita et al., "Research on anti-tumor active site of marine source natural product, Halichondrin B," International Congress Series, 1157 (Towards Natural Medicine Research in the 21st Century), 327-336 (1998).
Horita et al., "Synthetic studies of halichondrin B, an antitumor polyether macrolide isolated from a marine sponge. 2. Efficient synthesis of C16—C26 fragments via construction of the D ring by a highly stereocontrolled iodoetherification," Synlett. 40-43 (1994).
Horita et al., "Synthetic studies of Halichondrin B, an antitumor polyether macrolide isolated from a marine sponge. 3. Synthesis of C27—C36 subunit via completely stereoselective C-glycosylation to the F ring," Synlett. 43-45 (1994).
Horita et al., "Synthetic studies of Halichondrin B, an antitumor polyether macrolide isolated from a marine sponge. 7. Synthesis of two C27—C36 units via construction of the F ring and completely stereoselective C-glycosylation using mixed Lewis acids," Chem Pharm Bull. 45(10):1558-72 (1997).
Horita et al., "Synthetic studies of Halichondrin B, an antitumor polyether macrolide isolated from a marine sponge. 8. Synthesis of the lactone part (C1—C36) via Horner-Emmons coupling between C1—C15 and C16—C36 fragments and yamaguchi lactonization," Tetrahedron Lett. 38(52):8965-8 (1997).
Horita et al., "Synthetic studies on Halichondrin B, an antitumor polyether macrolide isolated from a marine sponge. 9. Synthesis of the C16—C36 unit via stereoselective construction of the D and E rings," Chem Pharm Bull. 46(8):1199-216 (1998).
Horita et al., Synthetic study of a highly antitumorigenic marine phytochemical, Halichondrin B. *Phytochemicals and Phytopharmaceuticals*. Fereidoon Shahidi and Chi-Tang Ho, 386-397 (2000).
International Search Report and Written Opinion for International Application No. PCT/US2019/012178, dated Apr. 15, 2019 (19 pages).
Jackson et al., "A total synthesis of norhalichondrin B," Angew Chem Int Ed. 48(13):2346-50 (2009).
Jackson et al., "The halichondrins and E7389," Chem Rev. 109(7):3044-79 (2009).
Jiang et al., "A novel route to the F-ring of Halichondrin B. Diastereoselection in Pd(0)-mediated meso and C2 diol desymmetrization," Org Lett. 4(20):3411-4 (2002).
Jiang et al., "A practical synthesis of the F-ring of halichondrin B via ozonolytic desymmetrization of a C(2)-symmetric dihydroxycyclohexene," J Org Chem. 68(3):1150-3 (2003).
Kawaguchi et al., "Drug and crystal polymorphism," Journal of Human Environmental Engineering. 4(2):310-7 (2002) (10 pages).
Kim et al., "New syntheses of E7389 C14—C35 and Halichondrin C14—C38 building blocks: double-inversion approach," J Am Chem Soc. 131(43):15636-41 (2009).
Ko, "Prins reactions and applications," http://gbdong.cm.utexas.edu/seminar/old/Prins%20reactions%20and%20Applications_Haye%20Min%20Ko.pdf, retrieved Jan. 21, 2020, dated Nov. 28, 2012 (30 pages).
Kong et al., "Total synthesis of the spirocyclic imine marine toxin (−)-gymnodimine and an unnatural C4-epimer," J Am Chem Soc. 133(49): 19844-56 (2011).
Kurosu et al., "Fe/Cr- and Co/Cr-mediated catalytic asymmetric 2-Haloallylations of aldehydes," J Am Chem Soc. 126(39):12248-9 (2004).
Kurosu et al., "Supporting information for Fe/Cr- and Co/Cr-mediated catalytic asymmetric 2-haloallylations of aldehydes," J Am Chem Soc. 126(39) (2004) (31 pages).
Lee et al., "Extension of Pd-Mediated One-Pot Ketone Synthesis to Macrocyclization: Application to a New Convergent Synthesis of Eribulin," J Am Chem Soc. 138(50):16248-51 (2016).
Li et al., "Unified Synthesis of C1—C19 Building Blocks of Halichondrins via Selective Activation/Coupling of Polyhalogenated Nucleophiles in (Ni)/Cr-Mediated Reactions," J Am Chem Soc. 137(19):6226-31 (2015).
Mattocks, "371. Novel reactions of some alpha-acyloxy acid chlorides," J Chem Soc. Resumed. 1918-30 (1964).
Mattocks, "932. Novel reactions of some alpha-acyloxy-acid halides," J Chem Soc. 4840-5 (1964).
Mitsunobu, "The use of diethyl azodicarboxylate and triphenylphosphine in synthesis and transformation of natural products," Synthesis. 1-28 (1981).
Namba et al., "A simple but remarkably effective device for forming the C8—C14 polycyclic ring system of halichondrin B," J Am Chem Soc. 126(25): 7770-1 (2004) (10 pages).
Namba et al., "New catalytic cycle for couplings of aldehydes with organochromium reagents," Org Lett. 6(26):5031-3 (2004).
Narayan et al., "Novel second generation analogs of eribulin. Part II: Orally available and active against resistant tumors in vivo," Bioorg Med Chem Lett. 21(6):1634-8 (2011).
Newman, "Drug evaluation: eribulin, a simplified ketone analog of the tubulin inhibitor Halichondrin B, for the potential treatment of cancer," Curr Opin Invest Drugs. 8(12):1057-66 (2007).
Nicolaou et al., "Total synthesis of brevetoxin A: Part 3: construction of GHIJ and BCDE ring systems," Chem Eur J. 5(2):628-45 (1999).
Nicolaou et al., "Total synthesis of the CP molecules CP-263, 114 and CP-225,917—Part 1: synthesis of key intermediates and intelligence gathering," Angew Chem Int Ed. 38(11):1669-75 (1999).
PubChem Compound Summary for CID 10501910, <https://pubchem.ncbi.nlm.nih.gov/compound/10501910>, created Oct. 25, 2006, retrieved Aug. 30, 2017 (8 pages).
PubChem Compound Summary for Methyl 2-[(1S,3R,4S,5R,7R,8S,9S,11R)-4,8-diacetyloxy-5-(2-oxoethyl)-2,6,10-trioxatricyclo[7.4.0.03,7]tridecan-11-yl]acetate, <https://pubchem.ncbi.nlm.nih.gov/compound/10501910>, retrieved Jul. 1, 2020 (6 pages).
Ritter, "Synthetic transformations of vinyl and aryl triflates," Synthesis: Reviews. 8:735-62 (1993).
RN 185411-09-0, CN L-arabino-D-allo-Dodeconic acid, 3,7:6,10-dianhydro-8,9-O-cyclohexylidene-2,4,5-trideoxy-, methyl ester. Entry Date: Entered STN: Jan. 28, 1997 (1 page).
RN 546141-26-8, CN 1,2-Propanediol, 3-[(2R,3R,4R,5S)-tetrahydro-3-hydroxy-4-[(phenylsulfonyl)methyl]-5-(2-propen-1-yl)-2-furanyl]-, 1,2-dibenzoate, (2S)-. Entry Date: Entered STN: Jul. 11, 2003 (1 page).
RN 546141-39-3, CN 1,2-Propanediol, 3-[(2R,3R,4S,5S)-tetrahydro-3-methoxy-4-[(phenylsulfonyl)methyl]-5-(2-propen-1-yl)-2-furanyl]-, 1,2-dibenzoate, (2S)-. Entry Date: Entered STN: Jul. 11, 2003 (1 page).
RN 546141-40-6, CN 1,2-Propanediol, 3-[(2R,3R,4S,5S)-tetrahydro-3-methoxy-4-[(phenylsulfonyl)methyl]-5-(2-propen-1-yl)-2-furanyl]-, (2S)-. Entry Date: Entered STN: Jul. 11, 2003 (1 page).
Sakamoto et al., "Stereoselective ring expansion via bicyclooxonium ion. A novel approach to oxocanes," Org Lett. 4(5):675-8 (2002).
Schreiber, "Hydrogen transfer from tertiary amines to trifluoroacetic anhydride," Tetrahedron Lett. 21(11):1027-30 (1980).
Seletsky et al., "Structurally simplified macrolactone analogues of halichondrin B," Bioorg Med Chem Lett. 14(22):5547-50 (2004).
Stamos et al., "A mild preparation of vinyliodides from vinylsilanes," Tetrahedron Lett. 37(48): 8647-50(1996).

(56) References Cited

OTHER PUBLICATIONS

Stamos et al., "New synthetic route to the C.14-C.38 segment of Halichondrins," J Org Chem. 62(22):7552-3 (1997).
Stamos et al., "Ni(II)/Cr(II)-mediated coupling reaction: beneficial effects of 4-tert-butylpyridine as an additive and development of new and improved workup procedures," Tetrahedron Lett. 38(36):6355-8 (1997).
Stamos et al., "Synthetic studies on Halichondrins: a practical synthesis of the C.1-C.13 segment," Tetrahedron Lett. 37(48):8643-6 (1996).
Sutherland et al., "The synthesis of 6alpha- and 6beta-fluoroshikimic acids," J Chem Soc Chem Commun. 18:1386-7 (1989).
Takai et al., "Reactions of alkenylchromium reagents prepared from alkenyl trifluoromethanesulfonates (triflates) with chromium(II) chloride under nickel catalysis" J Am Chem Soc. 108(19):6048-50 (1986).
Tokunaga et al., "Asymmetric catalysis with water: efficient kinetic resolution of terminal epoxides by means of catalytic hydrolysis," Science. 277(5328):936-8 (1997).
Towle et al., "Halichondrin B macrocyclic ketone analog E7389: medicinal chemistry repair of lactone ester instability generated during structural simplification to clinical Candidate," Annual Meeting of the American Association for Cancer Research, Apr. 6-10, 2002, 5721 (3 pages).
Towle et al., "In vitro and in vivo anticancer activities of synthetic macrocyclic ketone analogues of Halichondrin B," Cancer Res. 61(3):1013-21 (2001).
Ueda et al., "Total synthesis of halichondrin A, the missing member in the halichondrin class of natural products," J Am Chem Soc. 136(13):5171-6 (2014).
Uemura et al., "Norhalichondrin A: an antitumor polyether macrolide from a marine sponge," J Am Chem Soc. 107(16):4796-8 (1985).
Vahdat et al., "Phase II study of eribulin mesylate, a Halichondrin B analog, in patients with metastatic breast cancer previously treated with an anthracycline and a taxane," J Clin Oncol. 27(18):2954-61 (2009).
Varseev et al., "Enantioselective total synthesis of (+)- neosymbioimine," Org Lett. 9(8):1461-4 (2007).
Wan et al., "Asymmetric Ni(II)/Cr(II)-mediated coupling reaction: Stoichiometric process," Org Lett. 4(25):4431-4 (2002) (includes supporting information) (12 pages).
Wan et al., "Asymmetric Ni(II)/Cr(II)-mediated coupling reaction: Stoichiometric process," Org Lett. 4(25):4431-4 (2002).
Wang et al., "Facile preparation of peracetates and per-3-bromobenzoates of alpha-mono- and disaccharides," Molecules. 10(10):1325-34 (2005).
Wang et al., "Structure-activity relationships of halichondrin B analogues: modifications at C.30-C.38" Bioorg Med Chem Lett. 10(10):1029-32 (2000).
Wang et al., "The syntheses of pharmaceutical intermediates in supercritical fluids," Ind Eng Chem Res. 39(12):4487-90 (2000).
Ward et al., "Catalytic enantioselective diels-alder reaction by self-assembly of the components on a Lewis acid template," Org Lett. 7(16):3533-6 (2005) (Abstract only) (2 pages).
Xie et al., "Synthesis of the C20—C26 building block of Halichondrins via a regiospecific and stereoselective SN2' reaction," Org Lett. 4(25): 4427-9 (2002).
Yahata et al., "Unified Synthesis of Right Halves of Halichondrins A-C," J Org Chem. 82(17):8792-8807 (2017).
Yamamoto et al., "Total synthesis of halichondrin C," J Am Chem Soc. 134(2):893-6 (2012).
Yan et al., "Selective activation/coupling of polyhalogenated nucleophiles in ni/cr-mediated reactions: synthesis of c1—c19 building block of halichondrin bs," J Am Chem Soc. 137(19):6219-25 (2015).
Yang et al., "Second generation synthesis of C27—C35 building block of E7389, a synthetic Halichondrin analogue," Org Lett. 11(20): 4516-9 (2009).
Youssefyeh, "Acylations of ketals and enol ethers," J Am Chem Soc. 85(23):3901-2 (1963).
Yu et al., "Atom-based enumeration: new eribulin analogues with low susceptibility to P-glycoprotein-mediated drug efflux," Bioorg Med Chem Lett. 22(24):7363-6 (2012).
Yu et al., "From micrograms to grams: scale-up synthesis of eribulin mesylate," Nat Prod Rep. 30(9):1158-64 (2013).
Yu et al., "Macrocyclic drugs and synthetic methodologies toward macrocycles," Molecules 18(6):6230-68 (2013).
Yu et al., "New synthetic route to the C.14-C.21 fragment of Halichondrin B," Book of Abstracts. 219th ACS National Meeting, San Francisco, CA, Mar. 26-30, 2000 (1 page).
Yu et al., Discovery of E7389 a fully synthetic macrocyclic ketone analog of Halichondrin B. *Anticancer Agents from Natural Products*. CRC Press, 241-265 (2005) (27 pages).
Zheng et al., "Macrocyclic ketone analogues of halichondrin B," Bioorg Med Chem Lett. 14(22):5551-4 (2004).
Zheng et al., "Synthetic macrocyclic ketone analogs of halichondrin B: structure-activity relationships" Proceedings of the American Association for Cancer Research, 41:301, Abstract #1915 (2000).
Hatakeyama et al., "Preparation of racemic and chiral alkyl(1,3-butadien-2-yl)methanol derivatives utilizing 1-trimethylsilyl-2,3-butadiene as a diene source," Tetrahedron Letters. 32(35):4509-12 (1991).

PRINS REACTION AND COMPOUNDS USEFUL IN THE SYNTHESIS OF HALICHONDRIN MACROLIDES AND ANALOGS THEREOF

BACKGROUND

The invention relates to intermediates useful in the synthesis of pharmaceutically active macrolide compounds and methods of synthesizing macrolide compounds. Halichondrin B is a potent anticancer agent originally isolated from the marine sponge *Halichondria okadai*, and subsequently found in *Axinella* sp., *Phakellia carteri*, and *Lissodendoryx* sp. A total synthesis of halichondrin B was published in 1992 (Aicher, T. D. et al., J. Am. Chem. Soc. 114:3162-3164). Further synthetic and structure-activity relationship studies have been disclosed in U.S. Pat. Nos. 5,338,865 and 5,436,238 and in Towle et al., *Annual Meeting of the American Association for Cancer Research*, Apr. 6-10, 2002, 5721 and Wang et al., *Bioorg. Med. Chem. Lett.*, 10:1029-1032, 2000. Eribulin mesylate (also called Halaven®, E7389, and the mesylate salt of B1939), a nontaxane microtubule dynamics inhibitor, is a structurally simplified, synthetic analog of halichondrin B. Methods and intermediates for the synthesis of certain halichondrin B analogs and intermediates are described in International Publication Nos. WO 2005/118565, WO 2009/046308, WO 2009/064029, and WO 2009/124237, WO 2015/066729, and WO 2016/179607; U.S. Pat. No. 6,214,865; Austad et al., Synlett 24(3):333-337, 2013; Austad et al., Synlett. 24(3):327-332, 2013; and Chase et al., Synlett 24(3):323-326, 2013. New methods for the synthesis of halichondrin and its analogs (e.g., macrolide analogs) are desirable.

SUMMARY OF THE INVENTION

In general, the present invention provides methods and compounds useful for the preparation of macrocyclic intermediates in the synthesis of a halichondrin macrolide or analog thereof. In particular, the methods disclosed herein may be useful in the preparation of a halichondrin macrolide or analog thereof through a synthesis including a C.23-C.24 bond-forming Prins reaction. Prins reaction precursors may be prepared using a Sakurai reaction, as described herein.

In one aspect, the invention provides a method of preparing a compound of formula (A):

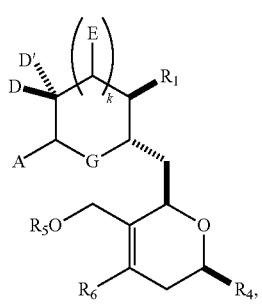

where
each of D and D' is independently H, optionally substituted alkyl, or OP$_1$, provided that only one of D and D' is OP$_1$, where P$_1$ is H, alkyl, a hydroxyl protecting group, and A is a C$_{1-6}$ saturated or C$_{2-6}$ unsaturated hydrocarbon skeleton, the skeleton being unsubstituted or having from 1 to 10 substituents independently selected from the group consisting of cyano, halo, azido, oxo, and Q$_1$, or A is a group of formula (1):

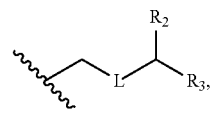

where
L is —(CH(OP$_2$))—, —(C(OH)(OP$_2$))—, or —C(O)—;
R$_2$ is H and P$_1$ is absent, H, alkyl, or a hydroxyl protecting group, or R$_2$ and P$_1$ combine to form a bond;
(i) R$_3$ is H, and P$_2$ is absent, H, optionally substituted alkyl, or a hydroxyl protecting group;
(ii) R$_3$ is —(CH$_2$)$_n$NP$_3$P$_4$, where P$_3$ is H or an N-protecting group, and (a) P$_2$ is absent, H, optionally substituted alkyl, or a hydroxyl protecting group, and P$_4$ is H or an N-protecting group, (b) P$_2$ and P$_4$ combine to form an alkylidene, or (c) each of P$_2$ and P$_4$ is H;
(iii) R$_3$ is —(CH$_2$)$_n$OP$_5$, where P$_2$ is absent, H, optionally substituted alkyl, or a hydroxyl protecting group, and P$_5$ is H, optionally substituted alkyl, or a hydroxyl protecting group; or P$_2$ and P$_5$, together with the atoms to which each is attached, combine to form a ketal, a cyclic carbonate, a dicarbonyl-dioxo, or silylene-dioxo; or
(iv) R$_3$ and P$_2$ combine to form an optionally substituted ethylene or a structure selected from the group consisting of:

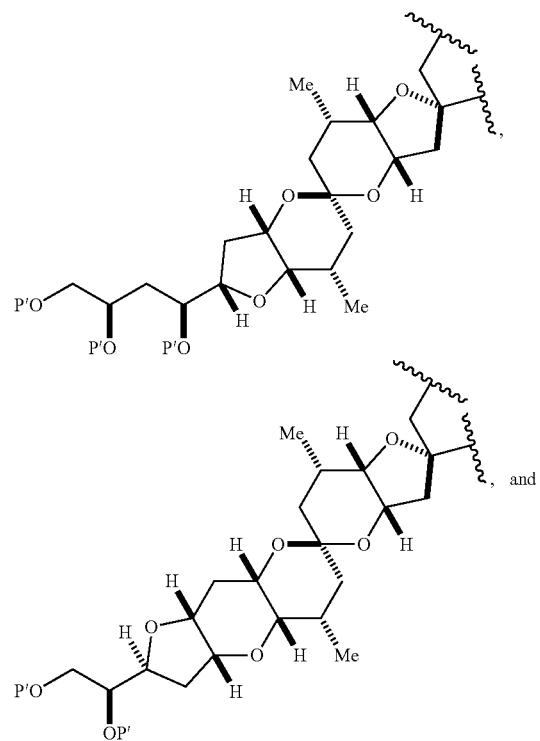

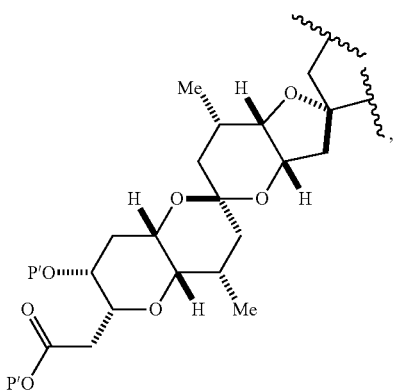

where each P' is independently H or a hydroxyl protecting group;

E is H, optionally substituted alkyl, or optionally substituted alkoxy;

G is O, S, CH$_2$, or NR$_N$, where R$_N$ is H, an N-protecting group, or optionally substituted alkyl;

each Q$_1$ is independently OR$_A$, SR$_A$, SO$_2$R$_A$, OSO$_2$R$_A$, NR$_B$R$_A$, NR$_B$(CO)R$_A$, NR$_B$(CO)(CO)R$_A$, NR$_B$(CO)NR$_B$R$_A$, NR$_B$(CO)OR$_A$, (CO)OR$_A$, O(CO)R$_A$, (CO)NR$_B$R$_A$, or O(CO)NR$_B$R$_A$, where each of R$_A$ and R$_B$ is independently H, alkyl, haloalkyl, hydroxyalkyl, aminoalkyl, aryl, haloaryl, hydroxyaryl, alkoxyaryl, arylalkyl, alkylaryl, haloarylalkyl, alkylhaloaryl, (alkoxyaryl)alkyl, heterocyclic radical, or heterocyclic radical-alkyl;

n, when present, is 0, 1, or 2;

k is 0 or 1;

R$_1$ is —OP$_6$, —CH(Y)$_2$, or —CH$_2$(Y), where P$_6$ is H or a hydroxyl protecting group;

R$_4$ is optionally substituted alkyl, optionally substituted alkenyl, optionally substituted alkynyl,

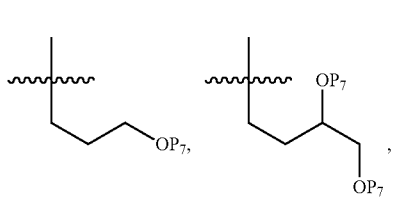

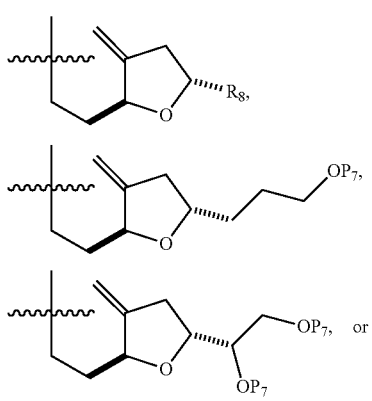

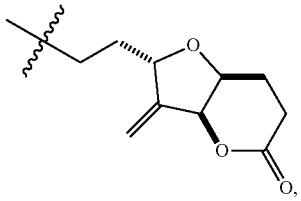

where
each P$_7$ is independently H or a hydroxyl protecting group; and
R$_8$ is —CH$_2$CH$_2$—COOR$_C$, —CH=CH—COOR$_C$, —CH$_2$CH$_2$—SO$_2$R$_D$, or —CH=CH—SO$_2$R$_D$;
R$_6$ is H, optionally substituted alkyl, or optionally substituted arylalkyl;
each Y is independently —COOR$_C$ or —SO$_2$R$_D$;
each R$_C$, when present, is independently optionally substituted alkyl, optionally substituted aryl, or optionally substituted arylalkyl; and
each R$_D$, when present, is independently optionally substituted aryl or optionally substituted non-enolizable alkyl.

The method includes producing the compound of formula (A) from a compound of formula (B), a compound of formula (C), and R$_5$OH, where R$_5$ is optionally substituted acyl. The compound of formula (B) is:

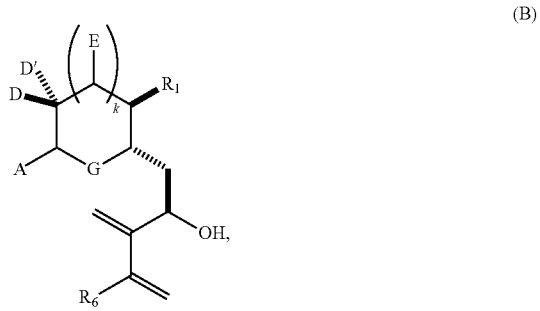

(B)

where all variables are as described for the compound of formula (A).

The compound of formula (C) is:

R$_4$-R$_7$,     (C)

where R$_7$ is —CHO or

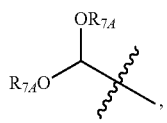

and each R$_{7A}$ is independently an optionally substituted alkyl.

In some embodiments, the producing the compound of formula (A) includes reacting the compound of formula (B), the compound of formula (C), R$_5$OH, and a Lewis acid (e.g., an oxophilic Lewis acid (e.g., boron trifluoride or a solvate thereof)).

In certain embodiments, the method further includes producing the compound of formula (B) including reacting a compound of formula (D), a compound of formula (E), and a second Lewis acid.

The compound of formula (D) is:

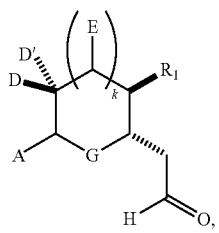

(D)

where all variables are as described for the compound of formula (B).

The compound of formula (E) is:

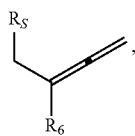

(E)

where $R_S$ is silyl, and $R_6$ is as described for the compound of formula (B).

In some embodiments, the second Lewis acid is an oxophilic second Lewis acid (e.g., boron trifluoride or a solvate thereof). In particular embodiments, the Lewis acid and the second Lewis acid are same. In further embodiments, the Lewis acid and the second Lewis acid are different.

In certain embodiments, the preparing the compound of formula (B) and the preparing the compound of formula (A) are performed as a single-pot transformation. In other embodiments, the method further includes epimerizing the product of reacting the compound of formula (D), the compound of formula (E), and the second Lewis acid.

In another aspect, the invention provides a method of preparing a compound of formula (B). The compound of formula (B) can be used as a reactant in the Prins reaction described herein. The method includes producing the compound of formula (B) from a compound of formula (D) and a compound of formula (E).

The compound of formula (B) is:

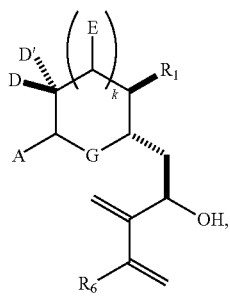

(B)

where
each of D and D' is independently H, optionally substituted alkyl, or $OP_1$, provided that only one of D and D' is $OP_1$, where $P_1$ is H, alkyl, a hydroxyl protecting group, and A is a $C_{1-6}$ saturated or $C_{2-6}$ unsaturated hydrocarbon skeleton, the skeleton being unsubstituted or having from 1 to 10 substituents independently selected from the group consisting of cyano, halo, azido, oxo, and $Q_1$, or A is a group of formula (1):

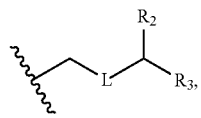

(1)

where
L is —(CH(OP$_2$))—, —(C(OH)(OP$_2$))—, or —C(O)—;
$R_2$ is H and $P_1$ is absent, H, alkyl, or a hydroxyl protecting group, or $R_2$ and $P_1$ combine to form a bond;
(i) $R_3$ is H, and $P_2$ is absent, H, optionally substituted alkyl, or a hydroxyl protecting group;
(ii) $R_3$ is —(CH$_2$)$_n$NP$_3$P$_4$, where $P_3$ is H or an N-protecting group, and (a) $P_2$ is absent, H, optionally substituted alkyl, or a hydroxyl protecting group, and $P_4$ is H or an N-protecting group, (b) $P_2$ and $P_4$ combine to form an alkylidene, or (c) each of $P_2$ and $P_4$ is H;
(iii) $R_3$ is —(CH$_2$)$_n$OP$_5$, where $P_2$ is absent, H, optionally substituted alkyl, or a hydroxyl protecting group, and $P_5$ is H, optionally substituted alkyl, or a hydroxyl protecting group; or $P_2$ and $P_5$, together with the atoms to which each is attached, combine to form a ketal, a cyclic carbonate, a dicarbonyl-dioxo, or silylene-dioxo; or
(iv) $R_3$ and $P_2$ combine to form an optionally substituted ethylene or a structure selected from the group consisting of:

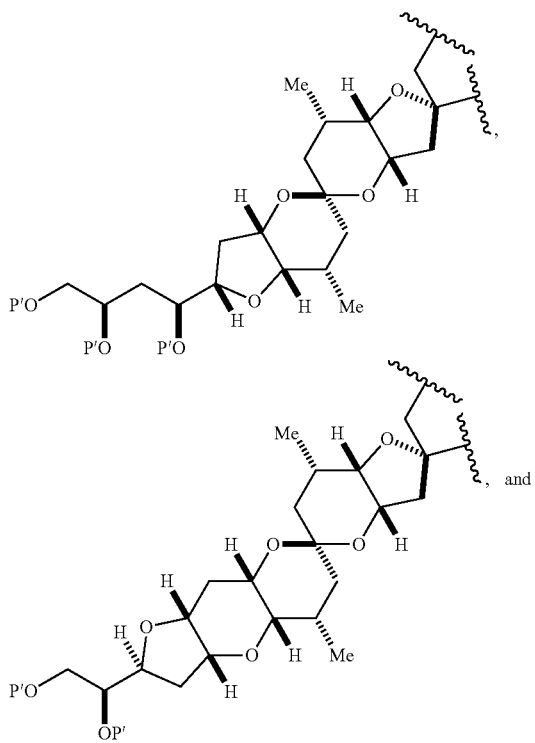

-continued

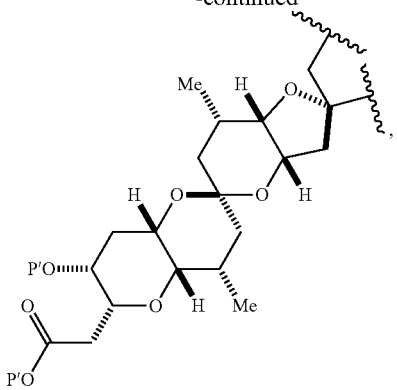

where each P' is independently H or a hydroxyl protecting group;

E is H, optionally substituted alkyl, or optionally substituted alkoxy;

G is O, S, CH$_2$, or NR$_N$, where R$_N$ is H, an N-protecting group, or optionally substituted alkyl;

each Q$_1$ is independently OR$_A$, SR$_A$, SO$_2$, OSO$_2$R$_A$, NR$_B$R$_A$, NR$_B$(CO)R$_A$, NR$_B$(CO)(CO)R$_A$, NR$_B$(CO)NR$_B$R$_A$, NR$_B$(CO)OR$_A$, (CO)OR$_A$, O(CO)R$_A$, (CO)NR$_B$R$_A$, or O(CO)NR$_B$R$_A$, where each of R$_A$ and R$_B$ is independently H, alkyl, haloalkyl, hydroxyalkyl, aminoalkyl, aryl, haloaryl, hydroxyaryl, alkoxyaryl, arylalkyl, alkylaryl, haloarylalkyl, alkylhaloaryl, (alkoxyaryl)alkyl, heterocyclic radical, or heterocyclic radical-alkyl;

n, when present, is 0, 1, or 2;

k is 0 or 1;

R$_1$ is —OP$_6$, —CH(Y)$_2$, or —CH$_2$(Y), where P$_6$ is H or a hydroxyl protecting group;

R$_6$ is H, optionally substituted alkyl, or optionally substituted aryl; and

Y is independently —COOR$_C$ or —SO$_2$R$_D$;

R$_C$, when present, is optionally substituted alkyl, optionally substituted aryl, or optionally substituted arylalkyl; and R$_D$, when present, is optionally substituted aryl or optionally substituted non-enolizable alkyl.

The compound of formula (D) is:

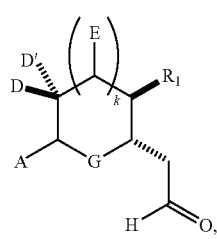

where all variables are as described for the compound of formula (B).

The compound of formula (E) is:

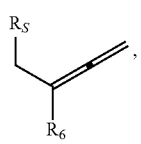

where R$_S$ is silyl, and R$_6$ is as described for the compound of formula (D).

In some embodiments, the producing the compound of formula (B) includes reacting the compound of formula (D), the compound of formula (E), and a Lewis acid (e.g., an oxophilic Lewis acid (e.g., boron trifluoride or a solvate thereof)).

In certain embodiments, the method further includes epimerizing the product of reacting the compound of formula (D), the compound of formula (E), and the Lewis acid.

In yet another aspect, the invention provides methods of preparing a halichondrin macrolide or analog thereof.

In particular embodiments, the halichondrin macrolide or an analogue thereof is:

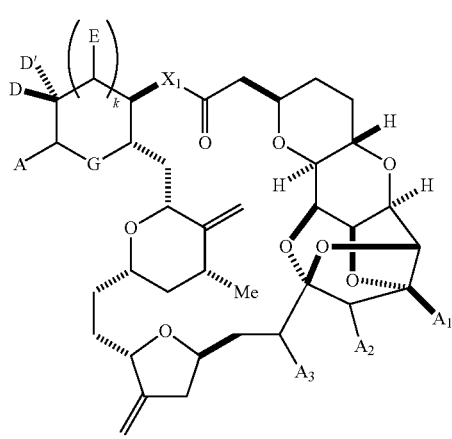

a halichondrin macrolide or analog thereof,
where
each of D and D' is independently H, optionally substituted alkyl, or OP$_1$, provided that only one of D and D' is OP$_1$, where P$_1$ is H, alkyl, a hydroxyl protecting group, and A is a C$_{1-6}$ saturated or C$_{2-6}$ unsaturated hydrocarbon skeleton, the skeleton being unsubstituted or having from 1 to 10 substituents independently selected from the group consisting of cyano, halo, azido, oxo, and Q$_1$, or A is a group of formula (1):

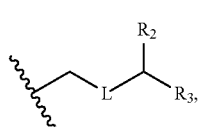

where
L is —(CH(OP$_2$))—, —(C(OH)(OP$_2$))—, or —C(O)—;
R$_2$ is H and P$_1$ is absent, H, alkyl, or a hydroxyl protecting group, or R$_2$ and P$_1$ combine to form a bond;

(i) $R_3$ is H, and $P_2$ is absent, H, optionally substituted alkyl, or a hydroxyl protecting group;

(ii) $R_3$ is —$(CH_2)_nNP_3P_4$, where $P_3$ is H or an N-protecting group, and (a) $P_2$ is absent, H, optionally substituted alkyl, or a hydroxyl protecting group, and $P_4$ is H or an N-protecting group, (b) $P_2$ and $P_4$ combine to form an alkylidene, or (c) each of $P_2$ and $P_4$ is H;

(iii) $R_3$ is —$(CH_2)_nOP_5$, where $P_2$ is absent, H, optionally substituted alkyl, or a hydroxyl protecting group, and $P_5$ is H, optionally substituted alkyl, or a hydroxyl protecting group; or $P_2$ and $P_5$, together with the atoms to which each is attached, combine to form a ketal, a cyclic carbonate, a dicarbonyl-dioxo, or silylene-dioxo; or (iv) $R_3$ and $P_2$ combine to form an optionally substituted ethylene or a structure selected from the group consisting of:

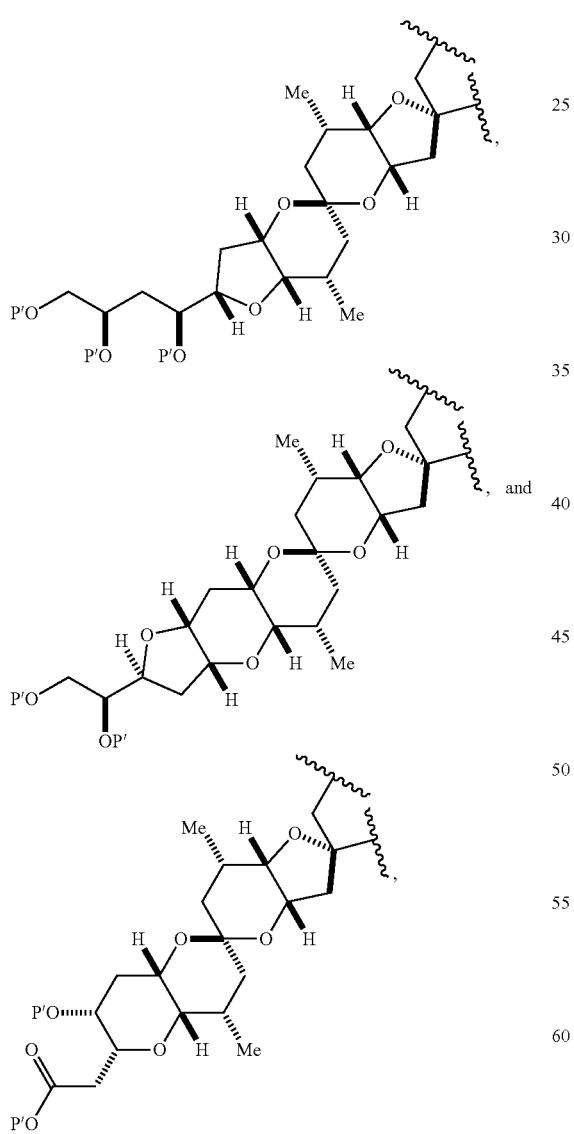

where each P' is independently H or a hydroxyl protecting group;

each of $A_1$, $A_2$, and $A_3$ is independently H or OP''', where each P''' is independently H or a hydroxyl protecting group;

E is H, optionally substituted alkyl, or optionally substituted alkoxy;

G is O, S, $CH_2$, or $NR_N$, where $R_N$ is H, an N-protecting group, or optionally substituted alkyl;

each $Q_1$ is independently $OR_A$, $SR_A$, $SO_2R_A$, $OSO_2R_A$, $NR_BR_A$, $NR_B(CO)R_A$, $NR_B(CO)(CO)R_A$, $NR_B(CO)NR_BR_A$, $NR_B(CO)OR_A$, $(CO)OR_A$, $O(CO)R_A$, $(CO)NR_BR_A$, or $O(CO)NR_BR_A$, where each of $R_A$ and $R_B$ is independently H, alkyl, haloalkyl, hydroxyalkyl, aminoalkyl, aryl, haloaryl, hydroxyaryl, alkoxyaryl, arylalkyl, alkylaryl, haloarylalkyl, alkylhaloaryl, (alkoxyaryl)alkyl, heterocyclic radical, or heterocyclic radical-alkyl;

n, when present, is 0, 1, or 2;

k is 0 or 1; and $X_1$ is —$CH_2$— or —O—.

In certain embodiments, the method includes (A) producing a compound of formula (IA) from a compound of formula (IIC), a compound of formula (III), and $R_5OH$, where $R_5$ is optionally substituted acyl;

and (B) producing the halichondrin macrolide or analog thereof from the compound of formula (IA).

The compound of formula (IA) is:

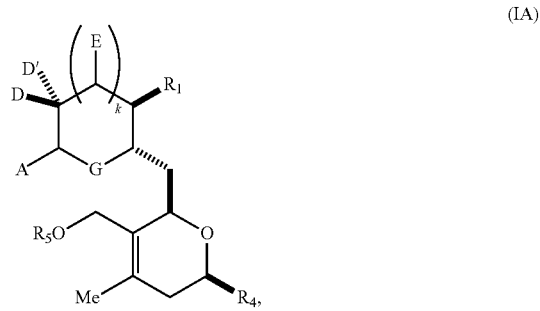

(IA)

where $R_1$ is —$OP_6$, —$CH(Y)_2$, or —$CH_2(Y)$, where $P_6$ is H or a hydroxyl protecting group, and each Y is independently —$COOR_C$ or —$SO_2R_D$;

$R_4$ is

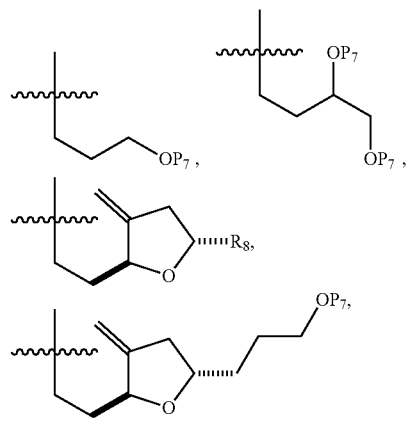

-continued

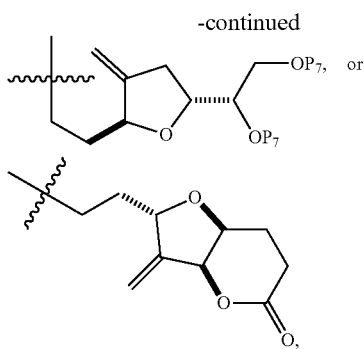

where
each $P_7$ is independently H or a hydroxyl protecting group;
$R_8$ is —$CH_2CH_2$—$COOR_C$, —CH=CH—$COOR_C$, —$CH_2CH_2$—$SO_2R_D$, or —CH=CH—$SO_2R_D$;
each $R_C$, when present, is independently optionally substituted alkyl, optionally substituted aryl, or optionally substituted arylalkyl; and
each $R_D$, when present, is independently optionally substituted aryl or optionally substituted non-enolizable alkyl;
$R_5$ is optionally substituted acyl; and
the remaining variables are as described for the halichondrin macrolide or analog thereof.
The compound of formula (IIC) is:

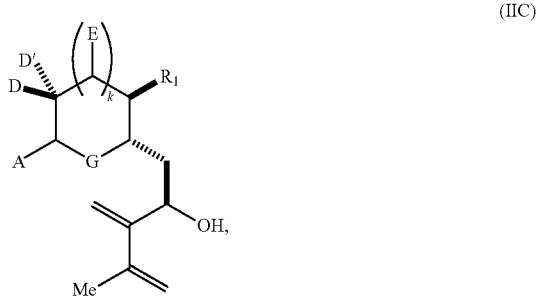

(IIC)

where all variables are as described for the compound of formula (IA).
The compound of formula (III) is:

$R_4$-$R_7$,  (III)

where $R_7$ is —CHO or

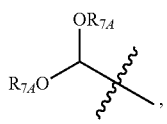

where each $R_{7A}$ is independently an optionally substituted alkyl; and $R_4$ is as described for the compound of formula (IA).
In particular embodiments, the method includes:
(A) producing a compound of formula (IVB) from a compound of formula (IIA), a compound of formula (IIB), a compound of formula (IIIA), a compound of formula (IVA), and $R_5OH$, where $R_5$ is optionally substituted acyl;

(B) producing a compound of formula (IVC) from the compound of formula (IVB);
(C) producing a compound of formula (IVD) from the compound of formula (IVC);
and
(D) producing the halichondrin macrolide or analog thereof from the compound of formula (IVD).
The compound of formula (IIA) is:

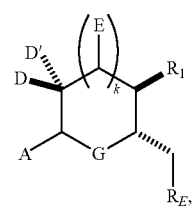

(IIA)

where
$R_1$ is —$OP_6$, —CH(Y)$_2$, or —$CH_2$(Y), where $P_6$ is H or a hydroxyl protecting group, and each Y is independently-$COOR_C$ or —$SO_2R_D$;
each $R_C$, when present, is independently optionally substituted alkyl, optionally substituted aryl, or optionally substituted arylalkyl;
each $R_D$, when present, is independently optionally substituted aryl or optionally substituted non-enolizable alkyl;
$R_E$ is —CHO or —$CH_{(1+m)}(OR_F)_{(2-m)}$,
where
m is 1, and $R^F$ is a hydroxyl protecting group, or
m is 0, and
(i) each $R^F$ is independently an alkyl or hydroxyl protecting group, or
(ii) both $R^F$ combine to form an alkylene;
and the remaining variables are as described for the halichondrin macrolide or analog thereof.
The compound of formula (IIB) is:

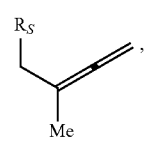

(IIB)

where $R_S$ is silyl.
The compound of formula (IIIA) is:

$R_{4A}$-$R_7$,  (IIIA)

where
$R_{4A}$ is

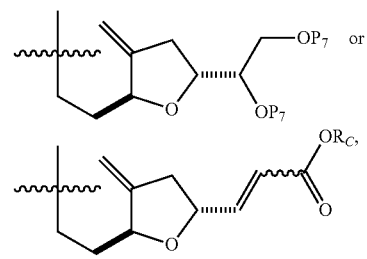

where $R_C$ is optionally substituted alkyl, optionally substituted aryl, or optionally substituted arylalkyl, and each $P_7$ is independently H or a hydroxyl protecting group;

$R_7$ is —CHO or

[structure with $OR_{7A}$ and $R_{7A}O$]

where each $R_{7A}$ is independently an optionally substituted alkyl.

The compound of formula (IVA) is:

(IVA)

[structure showing pyran ring with H, H, $OP_9$, $R_{15}$, $R_{11}$, $R_{12}$, $R_9$, $R_{10}$, $OP_9$, $R_{13}$, $R_{14}$, $A_1$, $R_{16}$, $OP_8$]

where
each $P_9$ is independently a hydroxyl protecting group;
$R_9$ is —CHO or —COOH;
(a1) $R_{10}$ is H or a hydroxyl protecting group, $R_{11}$ is alkyl ether, and $R_{12}$ is H;
(a2) $R_{10}$ is H or a hydroxyl protecting group, and $R_{11}$ and $R_{12}$ combine to form a double bond;
or
(a3) $R_{10}$ and $R_{11}$ combine to form a bond, and $R_{12}$ is H;
(b1) $A_1$ and $R_{14}$ combine to form oxo, $R_{13}$ is H or a hydroxyl protecting group, and $R_{15}$ is H;
or
(b2) $A_1$ is H or —OP''', and:
  (i) $R_{13}$ is H or a hydroxyl protecting group, and $R_{14}$ and $R_{15}$ combine to form a double bond;
  or
  (ii) $R_{13}$ and $R_{14}$ combine to form a bond, and $R_{15}$ is H or —OP'''; and
(c1) $R_{16}$ is H, and $P_8$ is H or a hydroxyl protecting group;
or
(c2) $R_{16}$ and $P_8$ combine to form a double bond;
and
each P''', when present, is independently H or a hydroxyl protecting group.

The compound of formula (IVB) is:

(IVB)

[structure showing pyran ring with H, H, $OP_9$, $R_{15}$, $R_{11}$, $R_{12}$, $R_{10}$, $OP_9$, $R_{13}$, $R_{14}$, $A_1$, $R_{16}$, $OP_8$, $X_4$, $X_1$, and cyclic structure with E, D', D, A, G, $R_G$, k]

where
$X_1$ is —O—, —C(Y)$_2$—, —CH(Y)—, or —CH$_2$—;
$X_4$ is oxo, or $X_4$, together with the atom to which it is attached, is —(CH(OP$_{12}$))—, where $P_{12}$ is H or a hydroxyl protecting group; and
$R_G$ is

[structure with $X_2$, O, O, $OR_5$, Me]

or

[structure with $X_2$, O, O, Me]

where
$R_5$ is an optionally substituted acyl; and
$X_2$ is H or —CH$_2$—X$_{2A}$—CH$_2$—CH=CH$_2$, where $X_{2A}$ is —O—, —C(R$_H$)$_2$—, or —NR$_I$—, where each $R_H$ is independently H or —COOR$_J$, R$_I$ is an N-protecting group, and R$_J$ is C$_{1-6}$ alkyl; and
the remaining variables are as described for the compound of formula (IIA) and the compound of formula (IVA).

The compound of formula (IVC) is:

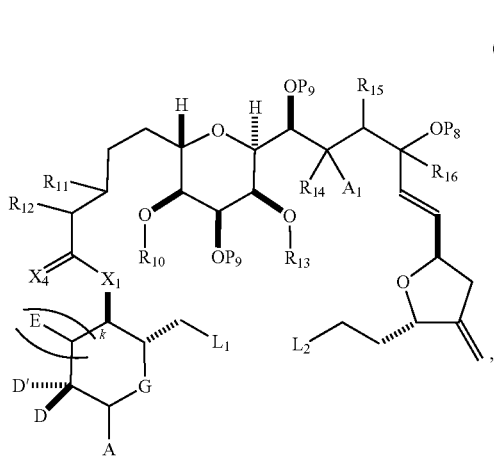

(IVC)

where
L₁ is

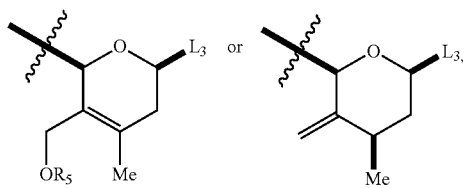

where L₂ and L₃ combine to form a bond;
and the remaining variables are as described for the compound of formula (IVB).

The compound of formula (IVD) is:

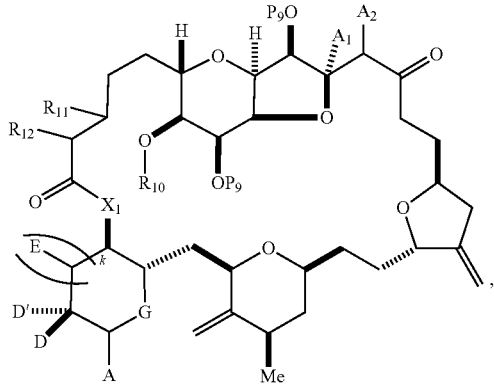

(IVD)

where each of $A_1$ and $A_2$ is independently H or —OP''', and the remaining variables are as described for the compound of formula (IVC).

In further embodiments, step (A) includes:
(E) producing a compound of formula (IA) from the compound of formula (IIA), the compound of formula (IIIA), and R₅OH, where the compound of formula (IA) is:

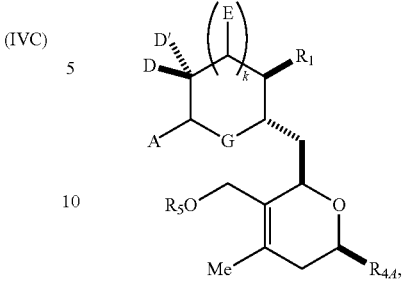

(IA)

where $R_{4A}$ is as described for the compound of formula (IIIA), and the remaining variables are as described for the compound of formula (IA) above;
and
(F) producing the compound of formula (IVB) from the compound of formula (IF) and the compound of formula (IVA).

In yet further embodiments, step (E) includes reacting the compound of formula (IIA), the compound of formula (IIIA), R₅OH, and a Lewis acid (e.g., an oxophilic Lewis acid (e.g., boron trifluoride or a solvate thereof)).

In still further embodiments, step (F) includes reacting $R_{4A}$ that is

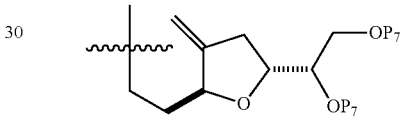

with a glycol cleaving agent, and a Horner-Wadsworth-Emmons reaction with $(R_CO)_2P(O)$—$CH_2$—$COOR_C$ to produce $R_{4A}$ that is

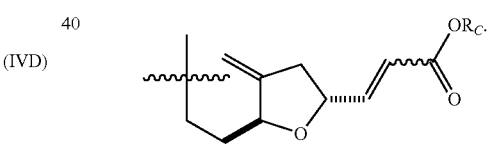

In other embodiments, step (F) includes reacting $R_{4A}$ that is

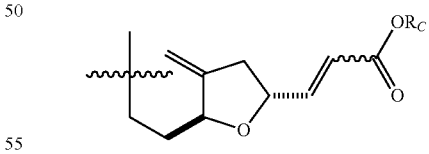

with a 1,2-reducing agent and further reacting with an allyl halide or allyl pseudohalide.

In yet other embodiments, $R_9$ is —CHO, $X_1$ is —C(Y)₂—, —CH(Y)—, or —CH₂—, and step (A) includes reacting $R_9$ with $R_1$ that is —CH(Y)₂ or —CH₂(Y) treated with a Brønsted base. In still other embodiments, $X_1$ is —O—, and step (A) includes esterifying $R_1$ that is —OP₆, where P₆ is H, with $R_9$ that is —COOH.

In some embodiments, step (B) includes reacting the compound of formula (IVB) with an olefin metathesis catalyst.

In particular embodiments, $P_9$ is H, $R_{16}$ is H, and step (C) includes:

oxidizing the compound of formula (IVC) to produce a compound of formula (IVCa):

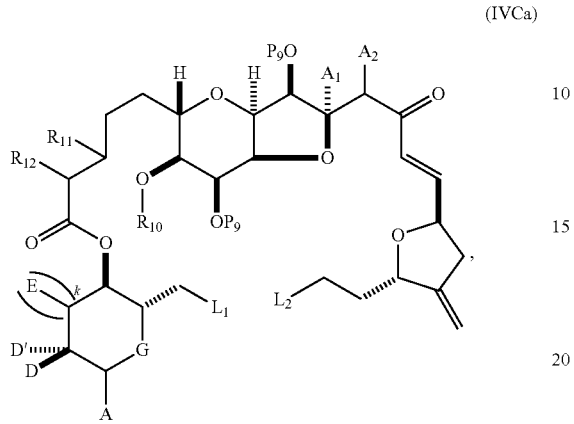

(IVCa)

where all variables are as described for the compound of formula (IVC);

and reacting the compound of formula (IVCa) with a 1,4-reducing agent to produce the compound of formula (IVD).

In certain embodiments, the compound of formula (IVB) is, or is converted to, a compound of formula (IVBa) prior to producing the compound of formula (IVC), where the compound of formula (IVBa) is:

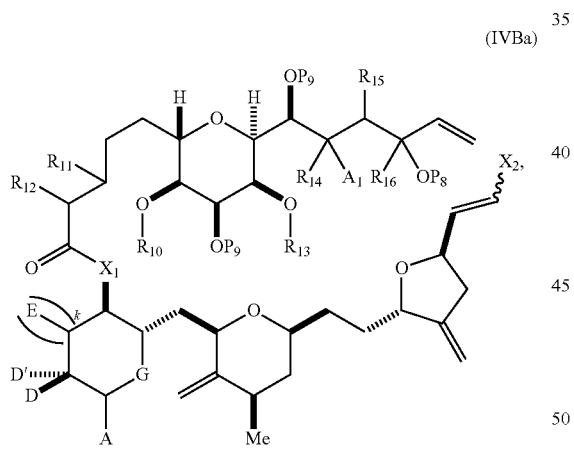

(IVBa)

where all variables are as described for the compound of formula (IVB).

In further embodiments, the producing the halichondrin macrolide or analog thereof includes reacting the compound of formula (IVD) with a hydroxyl protecting group removing agent.

In yet further embodiments, the method includes:
(A) producing a compound of formula (VB) from a compound of formula (IIA), a compound of formula (IIB), a compound of formula (IIIB), a compound of formula (VA), and $R_5OH$,
where $R_5$ is optionally substituted acyl;
(B) producing a compound of formula (VC) from the compound of formula (VB), and
(C) producing the halichondrin macrolide or analog thereof from the compound of formula (VC).

The compound of formula (IIA) is:

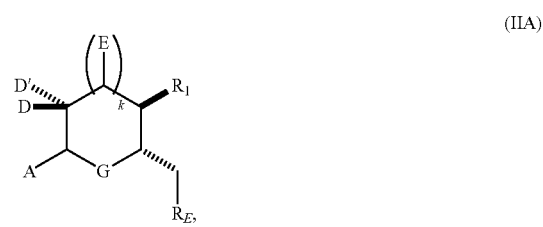

(IIA)

where
$R_1$ is $-OP_6$, $-CH(Y)_2$, or $-CH_2(Y)$, where $P_6$ is H or a hydroxyl protecting group, and each Y is independently $-COOR_C$ or $-SO_2R_D$;

each $R_C$, when present, is independently optionally substituted alkyl, optionally substituted aryl, or optionally substituted arylalkyl;

$R_D$, when present, is optionally substituted aryl or optionally substituted non-enolizable alkyl;

$R_E$ is $-CHO$ or $-CH_{(1+m)}(OR_F)_{(2-m)}$,
where
m is 1, and $R^F$ is a hydroxyl protecting group,
or
m is 0, and
(i) each $R^F$ is independently an alkyl or hydroxyl protecting group, or
(ii) both $R^F$ combine to form an alkylene;

and the remaining variables are as described for the halichondrin macrolide or analog thereof.

The compound of formula (IIB) is:

(IIB)

where $R_S$ is silyl.

The compound of formula (IIIB) is:

$R_{4B}-R_7$, (IIIB)

where
$R_{4B}$ is but-3-en-1-yl,

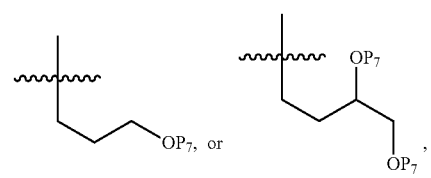

where each $P_7$ is independently H or a hydroxyl protecting group;

and $R_7$ is —CHO or

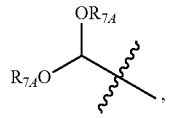

where each $R_{7A}$ is independently an optionally substituted alkyl.

The compound of formula (VA) is:

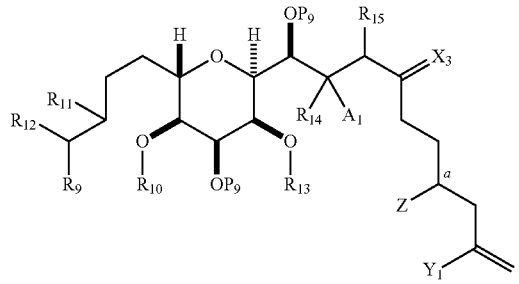

(VA)

where a designates (R)-stereogenic center, and Z is a sulfonate, chloride, bromide, or iodide; or a designates (S)-stereogenic center, and Z is $OR_{16}$, where $R_{16}$ is a hydroxyl protecting group;

(a1) $R_{10}$ is a hydroxyl protecting group, $R_{11}$ is alkyl ether, and $R_{12}$ is H;

(a2) $R_{10}$ is a hydroxyl protecting group, and $R_{11}$ and $R_{12}$ combine to form a double bond;

or (a3) $R_{10}$ and $R_{11}$ combine to form a bond, and $R_{12}$ is H;

(b1) $A_1$ and $R_{14}$ combine to form oxo, $R_{13}$ is a hydroxyl protecting group, and $R_{15}$ is H;

or (b2) $A_1$ is H or —OP'', and:

(i) $R_{13}$ is a hydroxyl protecting group, and $R_{14}$ and $R_{15}$ combine to form a double bond;

or (ii) $R_{13}$ and $R_{14}$ combine to form a bond, and $R_{15}$ is H or —OP'';

$Y_1$ is iodide, bromide, or trifluoromethanesulfonate;

$R_9$ is —CHO or —COOH;

each $P_9$ is independently a hydroxyl protecting group, and $X_3$ is oxo; or both $P_9$ groups and $X_3$, together with the atoms to which each is attached, combine to form a ketal; and each P'' is independently a hydroxyl protecting group.

The compound of formula (VB) is:

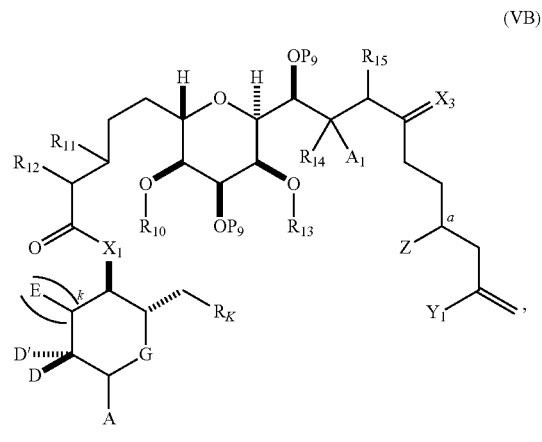

(VB)

where $X_1$ is —$CH_2$—, —CH(Y)—, —$C(Y)_2$—, or —O—, where each Y is independently —$COOR_C$ or —$SO_2R_D$;

each $R_C$, when present, is independently optionally substituted alkyl, optionally substituted aryl, or optionally substituted arylalkyl;

each $R_D$, when present, is independently optionally substituted aryl or optionally substituted non-enolizable alkyl; and $R_K$ is

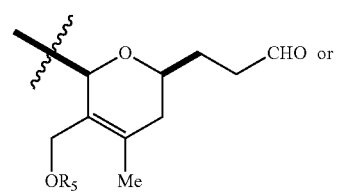

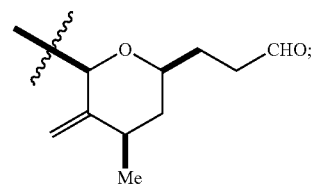

$R_5$ is optionally substituted acyl; and the remaining variables are as described for the compound of formula (VA) and the compound of formula (IIA).

The compound of formula (VC) is:

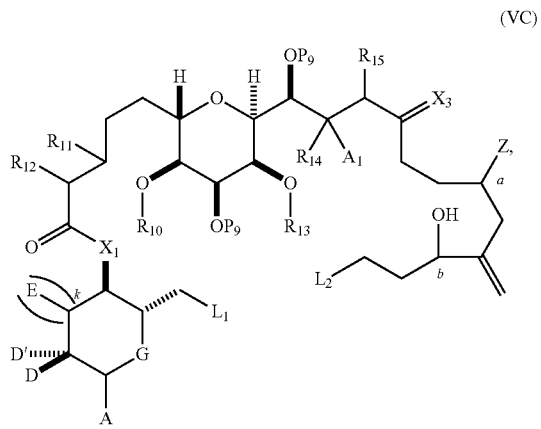

(VC)

where $L_1$ is

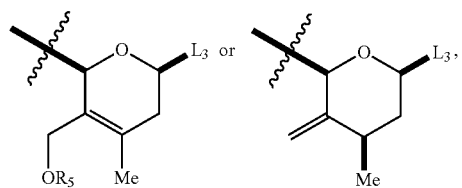

where $L_2$ and $L_3$ combine to form a bond;

b designates (S)-stereogenic center, if a designates (R)-stereogenic center; and b designates (R)-stereogenic center, if a designates (S)-stereogenic center; and the remaining variables are as described for the compound of formula (VB).

In certain embodiments, step (A) includes:

(D) producing a compound of formula (ID) from the compound of formula (IIA), the compound of formula (IIB), the compound of formula (IIIB), and $R_5OH$, where $R_5$ is optionally substituted acyl, and where the compound of formula (ID) is:

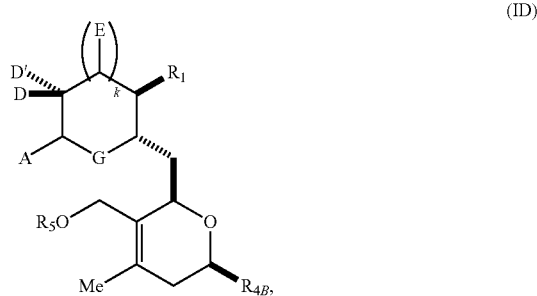

(ID)

where all variables are as described for the compound of formula (IIA) the compound of formula (IIB), the compound of formula (IIIB), and $R_5OH$;

and (E) producing the compound of formula (VB) from the compound of formula (ID) and the compound of formula (VA).

In some embodiments, the producing the compound of formula (ID) includes reacting the compound of formula (IIC), the compound of formula (IIIB), $R_5OH$, and a Lewis acid (e.g., an oxophilic Lewis acid (e.g., boron trifluoride or a solvate thereof)).

In certain embodiments, step (D) includes a Sakurai reaction between the compound of formula (IIA) and the compound of formula (IIB) to produce a compound of formula (IIC), and a Prins reaction between the compound of formula (IIC), the compound of formula (IIIB), and $R_5OH$.

In further embodiments, the compound of formula (IIC) is:

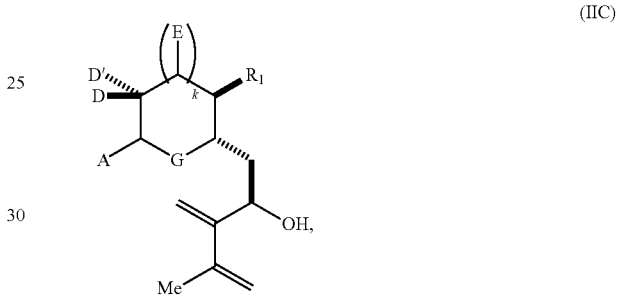

(IIC)

where all variables are as described for the compound of formula (IIA).

In yet further embodiments, $X_1$ is $—CH_2—$, $—CH(Y)—$, or $—C(Y)_2—$, and step (A) includes reacting $R_9$, where $R_9$ is $—CHO$, with $R_1$ that is $—CH(Y)_2$ or $—CH_2(Y)$ treated with a Brønsted base, to produce $—CO—X_1—$. In still further embodiments, $X_1$ is $—O—$, and step (A) includes esterifying $R_9$ that is $—COOH$ with $R_1$ that is $—OP_6$, where $P_6$ is H, to produce $—CO—X_1—$.

In other embodiments, step (B) includes reacting the compound of formula (VB) with a Cr(II) salt and a Ni(II) salt. In yet other embodiments, step (C) includes a step of nucleophilic ring-closing of the compound of formula (VC). In still other embodiments, both $P_9$ groups and $X_3$, together with the atoms to which each is attached, combine to form a ketal. In some embodiments, $R_{10}$ and $R_{11}$ combine to form a bond, and $R_{12}$ is H. In certain embodiments, $R_{4B}$ is but-3-en-1-yl, and step (A) includes reacting the but-3-en-1-yl group with a dihydroxylating agent to produce $R_{4B}$ that is

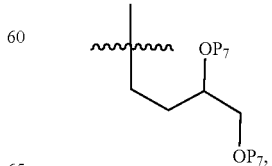

and cleaving the

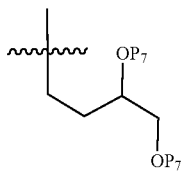

through a reaction with a glycol cleaving agent.

In particular embodiments, $R_{4B}$ is

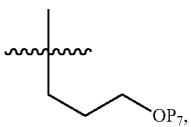

and step (A) includes reacting the

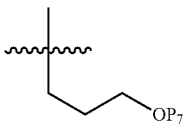

with an oxidizing agent capable of converting an alcohol into a carbonyl group.

In further embodiments, $R_{4B}$ is

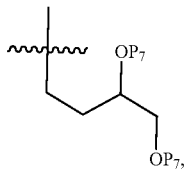

and step (A) includes cleaving the

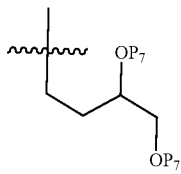

through a reaction with a glycol cleaving agent.

In yet further embodiments, the method includes:
(A) producing a compound of formula (IF) from a compound of formula (IIA), a compound of formula (IIB), a compound of formula (IIIC), and $R_5OH$, where $R_5$ is optionally substituted acyl;
(B) producing a compound of formula (IG) from the compound of formula (IF), and
(C) producing the halichondrin macrolide or analog thereof from the compound of formula (IG) and one or more intermediates.

The compound of formula (IF) is:

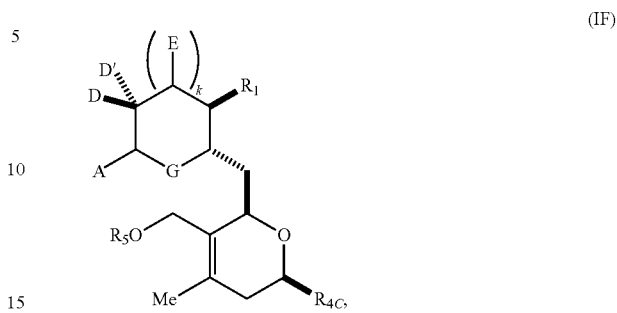

where $R_1$ is $-OP_6$, $-CH(Y)_2$, or $-CH_2(Y)$, where $P_6$ is H or a hydroxyl protecting group, and each Y is independently $-COOR_C$ or $-SO_2R_D$;

each $R_C$, when present, is independently optionally substituted alkyl, optionally substituted aryl, or optionally substituted arylalkyl;

each $R_D$, when present, is independently optionally substituted aryl or optionally substituted non-enolizable alkyl;

$R_{4C}$ is

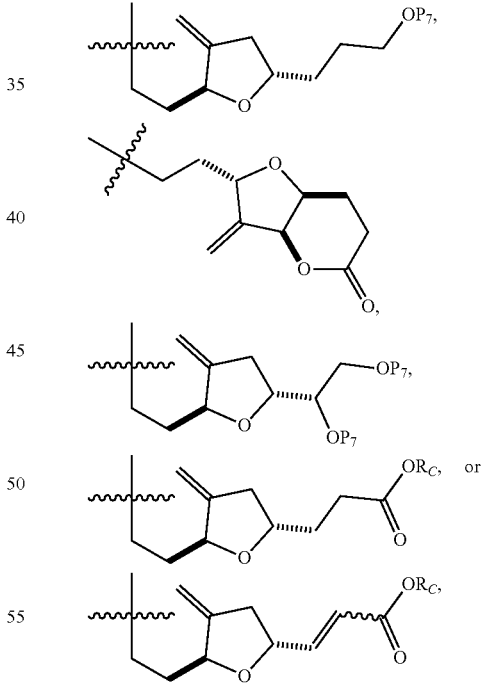

where $R_C$ is optionally substituted alkyl, optionally substituted aryl, or optionally substituted arylalkyl, and each $P_7$ is independently H or a hydroxyl protecting group;

$R_5$ is optionally substituted acyl; and the remaining variables are as described for the halichondrin macrolide or analog thereof.

The compound of formula (IIA) is:

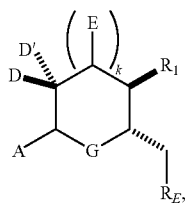
(IIA)

where
R₁ is —OP₆, —CH(Y)₂, or —CH₂(Y), where P₆ is H or a hydroxyl protecting group, and each Y is independently —COOR$_C$ or —SO₂R$_D$;

each R$_C$, when present, is independently optionally substituted alkyl, optionally substituted aryl, or optionally substituted arylalkyl;

R$_D$, when present, is optionally substituted aryl or optionally substituted non-enolizable alkyl;

R$_E$ is —CHO or —CH$_{(1+M)}$(OR$_F$)$_{(2-m)}$, where
m is 1, and R$_F$ is a hydroxyl protecting group,
or
m is 0, and
 (i) each R$_F$ is independently an alkyl or hydroxyl protecting group, or
 (ii) both R$_F$ combine to form an alkylene; and
the remaining variables are as described for the compound of formula (IF).

The compound of formula (IIB) is:

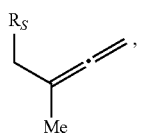
(IIB)

where R$_S$ is silyl.

The compound of formula (IIIC) is:

R$_{4C}$-R$_7$,   (IIIC)

where R$_7$ is —CHO or

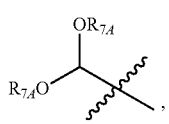

where each R$_{7A}$ is independently an optionally substituted alkyl, and R$_{4C}$ is as described for the compound of formula (IF).

The compound of formula (IG) is:

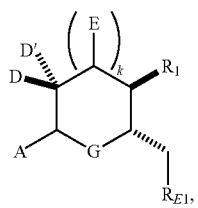
(IG)

where
R$_{E1}$ is

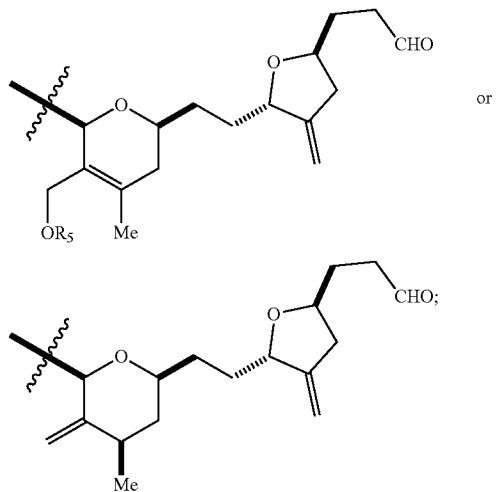
or and
the remaining variables are as described for the compound of formula (IF).

In some embodiments, step (B) includes reacting R$_{4C}$ that is

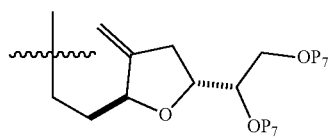

with a glycol cleaving agent to produce an aldehyde, reacting the aldehyde with (R$_C$O)₂P(O)—CH₂—COOR$_C$ to produce R$_{4C}$ that is

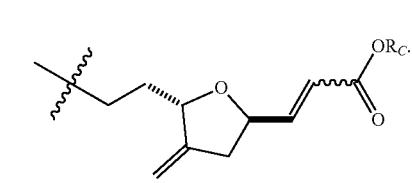

In certain embodiments, step (B) includes reducing $R_{4C}$ that is

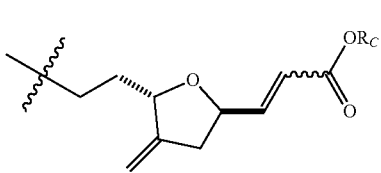

with a 1,4-reducing agent to produce $R_{4C}$ that is

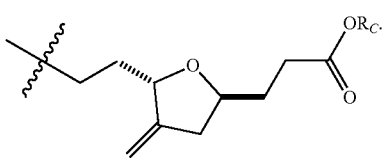

In further embodiments, step (B) includes reducing $R_{4C}$ that is

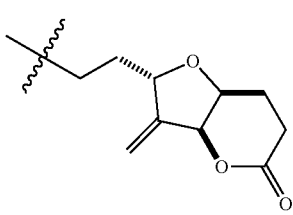

with an allylic reducing agent to produce $R_{4C}$ that is

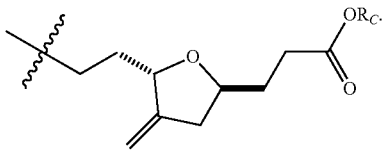

In-yet-further embodiments, step (B) includes reducing $R_{4C}$ that is

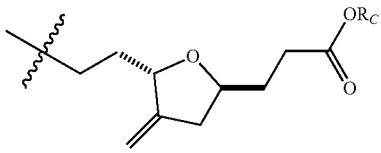

with a 1,2-reducing agent to produce a carbonyl group in $R_{E1}$.

In still further embodiments, the step reducing $R_{4C}$ that is

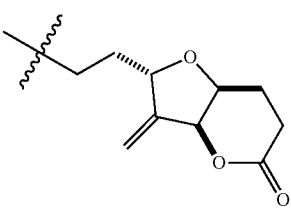

includes an esterification reaction producing $R_{4C}$ that is

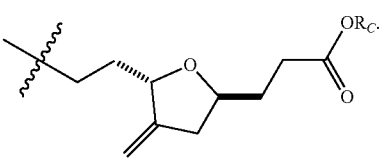

In particular embodiments, step (B) includes reacting $R_{4C}$ that is

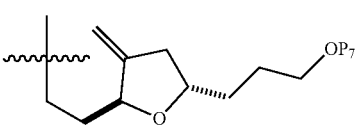

with an oxidizing agent capable of converting an alcohol to a carbonyl group in $R_{E1}$.

In certain embodiments, the one or more intermediates is a compound of formula (VIA):

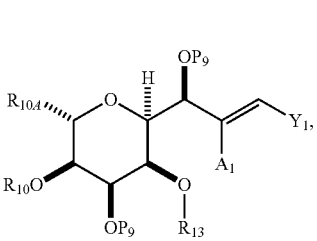

(VIA)

where
$R_{10A}$ is $-CH_2-CH=CH_2$, $-(CH_2)_2-CH=CH_2$, or $-(CH_2)_3-OP_{10}$;

each $R_{10}$, $R_{13}$, $P_9$ and $P_{10}$ is independently a hydroxyl protecting group;

$A_1$ is H or $-OP''$; and $Y_1$ is chloro, bromo, iodo, trifluoromethanesulfonate, or trialkylsilane;

and step (C) includes:

(D) producing a compound of formula (VIB) from the compound of formula (IG) and the compound of formula (VIA).

The compound of formula (VIB) is:

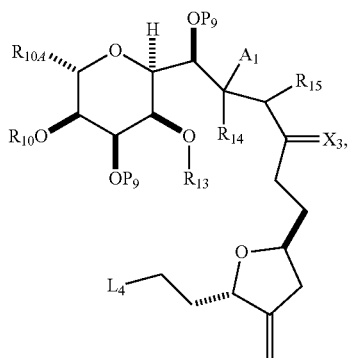

(VIB)

where
$L_4$ is

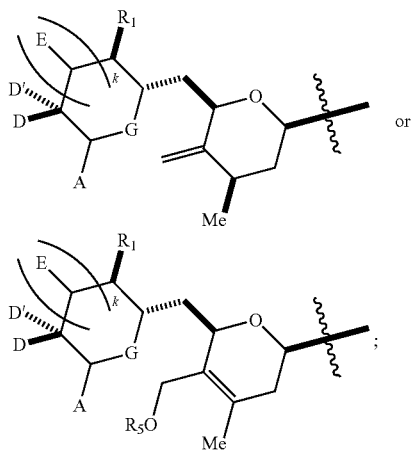

or ;

$R_1$ is —$OP_6$ or —CH(Y), where $P_6$ is H or a hydroxyl protecting group, and Y is —$COOR_C$ or —CHO;

$A_1$ and $R_{14}$ combine to form oxo, $R_{13}$ is H or a hydroxyl protecting group, and $R_{15}$ is H;

or $A_1$ is H or —OP''', and:

(i) $R_{13}$ is H or a hydroxyl protecting group, and $R_{14}$ and $R_{15}$ combine to form a double bond;

or (ii) $R_{13}$ and $R_{14}$ combine to form a bond, and $R_{15}$ is H or —OP''';

each $P_9$ is independently a hydroxyl protecting group, and $X_3$ is oxo or $X_3$, together with the carbon atom to which it is attached, is —(CH($OP_{11}$))—, where $P_{11}$ is H or a hydroxyl protecting group; or both $P_9$ groups and $X_3$, together with the atoms to which each is attached, combine to form a ketal; and the remaining variables are as described for the compound of formula (VIA) and the compound of formula (IG).

In yet further embodiments, step (D) includes reacting the compound of formula (VIA) and the compound of formula (IG) with a Cr(II) salt and a Ni(II) salt.

In still further embodiments, $R_{10A}$ is —$CH_2$—CH=$CH_2$, and step (C) includes:

(E) producing a compound of formula (VIC) from the compound of formula (VIB) and $R_{17}$—$CH_2CH$=$CH_2$, where $R_{17}$ is —COOH or a metallic or metalloid moiety;

(F) producing a compound of formula (VID) from the compound of formula (VIC); and (G) producing the halichondrin macrolide or analog thereof from the compound of formula (VID).

The compound of formula (VIC) is:

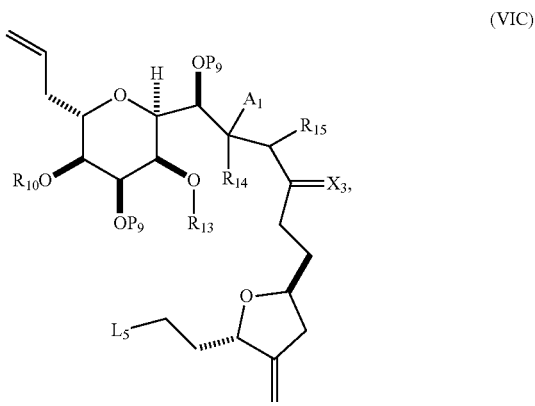

(VIC)

where
$L_5$ is

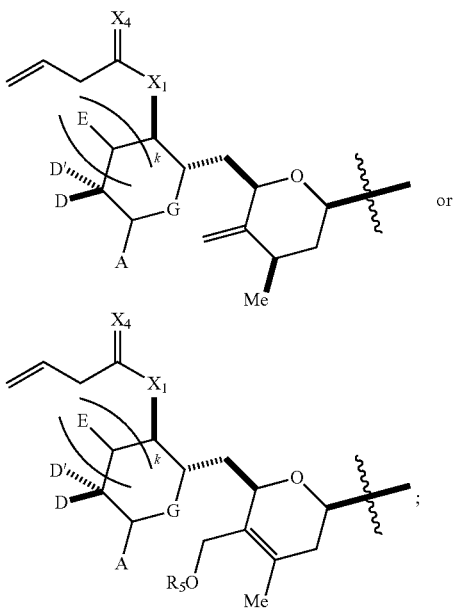

or ;

$X_1$ is —$CH_2$— or —O—;

$X_4$ is oxo, or $X_4$, together with the atom to which it is attached, is —(CH($OP_{12}$))—, where $P_{12}$ is H or a hydroxyl protecting group; and the remaining variables are as described for the compound of formula (VIB).

The compound of formula (VID) is:

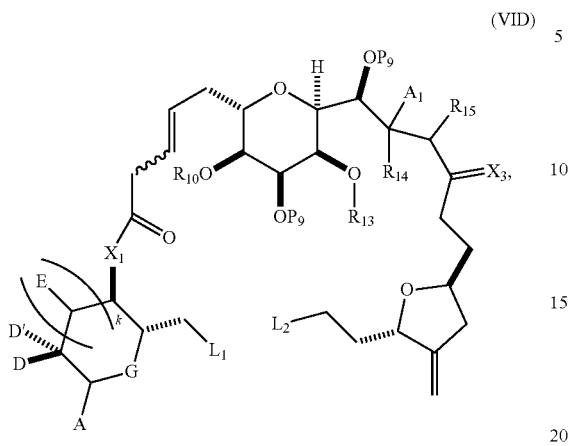

(VID)

where
L₁ is

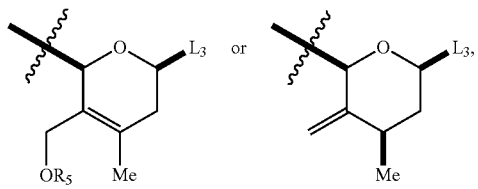

where L₂ and L₃ combine to form a bond; and
the remaining variables are as described for the compound of formula (VIC).

In some embodiments, $R_1$ is —CH₂(Y), $X_1$ is —CH₂—, $X_4$ is oxo or —(CH(OP₁₂))—, and step (E) includes reacting the compound of formula (VIB) with $R_{17}$—CH₂CH=CH₂, where $R_{17}$ is a metallic or metalloid moiety. In other embodiments, $R_1$ is —OP₆, $P_6$ is H, $X_1$ is —O—, $X_4$ is oxo, and step (E) includes esterifying the compound of formula (VIB) with $R_{17}$—CH₂CH=CH₂, where $R_{17}$ is —COOH. In yet other embodiments, the producing step (F) includes reacting the compound of formula (VIC) with an olefin metathesis catalyst. In still other embodiments, step (G) includes reacting the compound of formula (VID) with a hydroxyl protecting group removing agent.

In certain embodiments, $R_{10A}$ is —CH₂—CH₂—CH=CH₂, $R_1$ is —OP₆ or —CH₂(Y), where $P_6$ is H or a hydroxyl protecting group, and Y is —COOR_C, and step (C) includes:

(H) producing a compound of formula (VIE) from the compound of formula (VIB) and $R_{17}$—CH=CH₂, where $R_{17}$ is —COOH or a metallic or metalloid moiety;

(I) producing a compound of formula (VIF) from the compound of formula (VIE);

and (J) producing the halichondrin macrolide or analog thereof from the compound of formula (VIF).

The compound of formula (VIE) is:

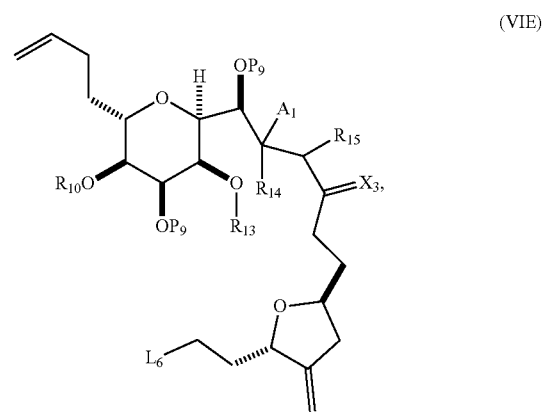

(VIE)

where
L₆ is

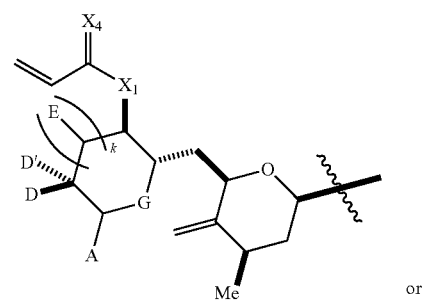

or

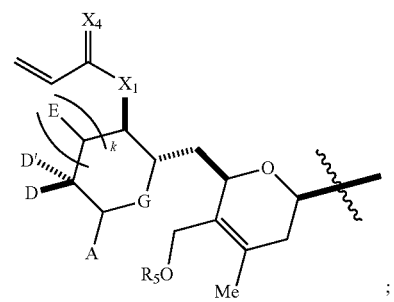

;

$X_1$ is —CH₂— or —O—; and $X_4$ is oxo, or $X_4$, together with the atom to which it is attached, is —(CH(OP₁₂))—, where $P_{12}$ is H or a hydroxyl protecting group; and the remaining variables are as described for the compound of formula (VIB).

The compound of formula (VIF) is:

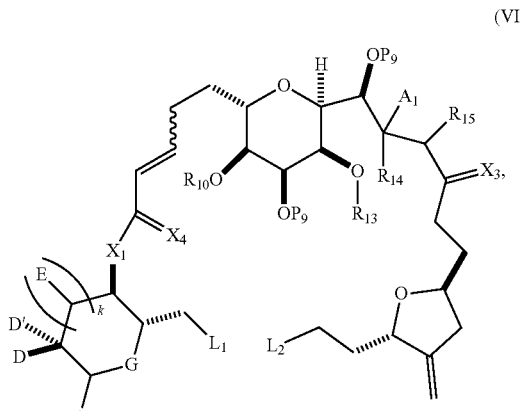
(VIF)

where
L₁ is

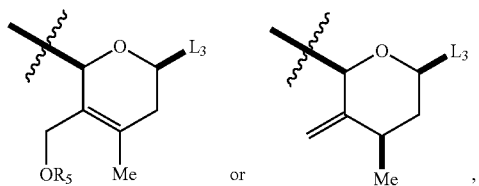

where L₂ and L₃ combine to form a bond; and
the remaining variables are as described for the compound of formula (VIE).

In some embodiments, step (1) includes reacting the compound of formula (VIE) with an olefin metathesis catalyst. In particular embodiments, step (J) includes reacting the compound of formula (VIF) with a hydroxyl protecting group removing agent.

In certain embodiments, $R_{10A}$ is —(CH₂)₃—OP₁₀, and step (C) includes:

(K) producing a compound of formula (VIG) from the compound of formula (VIB) and $(R_CO)_2P(O)$—CH₂—$R_P$, where each $R_C$ is independently optionally substituted alkyl, optionally substituted aryl, or optionally substituted arylalkyl, and $R_P$ is H or —COOH;

(L) producing a compound of formula (VIF) from the compound of formula (VIG); and (M) producing the halichondrin macrolide or analog thereof from the compound of formula (VIF).

The compound of formula (VIG) is:

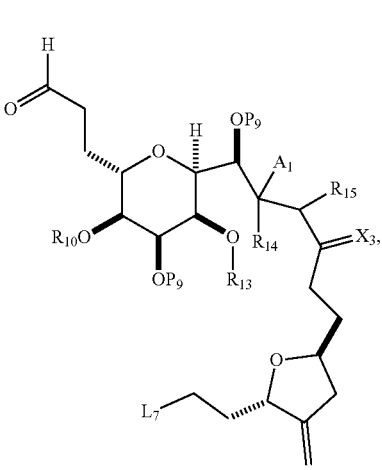
(VIG)

where
L₇ is

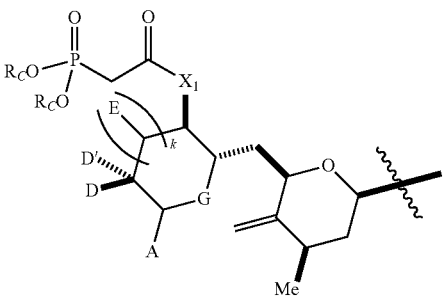

or

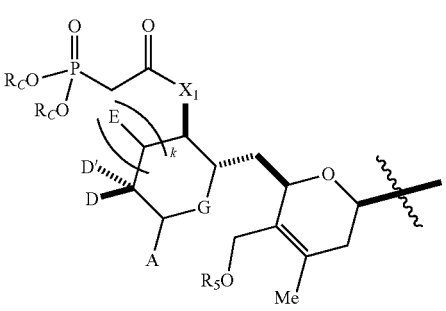

X₁ is —CH₂— or —O—; and
the remaining variables are as described for the compound of formula (VIB) and for $(R_CO)_2P(O)$—CH₂—$R_P$.

The compound of formula (VIF) is:

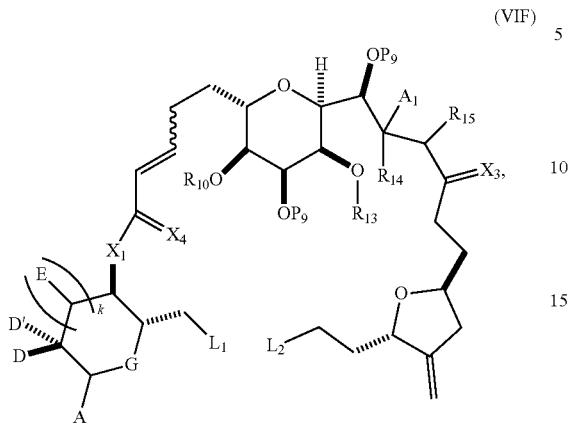

(VIF)

where
L₁ is

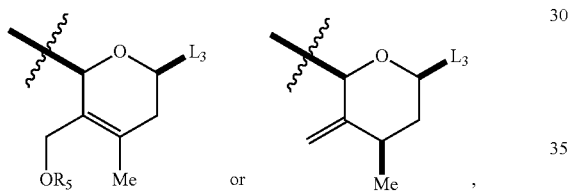

where L₂ and L₃ combine to form a bond; and
X₄ is oxo; and
the remaining variables are as described for the compound of formula (VIG).

In further embodiments, the producing step (K) includes reacting the compound of formula (VIB) with $(R_CO)_2P(O)$—$CH_2$—$R_P$ under Claisen reaction conditions, where $R_P$ is H and $R_1$ is —$CH_2(Y)$. In yet further embodiments, the producing step (K) includes esterifying the compound of formula (VIB) with $(R_CO)_2P(O)$—$CH_2$—R, where $R_P$ is —COOH and $R_1$ is —$OP_6$, where $P_6$ is H. In still further embodiments, step (M) includes reacting the compound of formula (VIF) with a hydroxyl protecting group removing agent.

In some embodiments, step (C) includes:
(N) producing a compound of formula (VIIB) from the compound of formula (IG) and a compound of formula (VIIA);
(O) producing a compound of formula (VIIC) from the compound of formula (VIIB); and
(P) producing the halichondrin macrolide or analog thereof from the compound of formula (VIIC).

The compound of formula (VIIA) is:

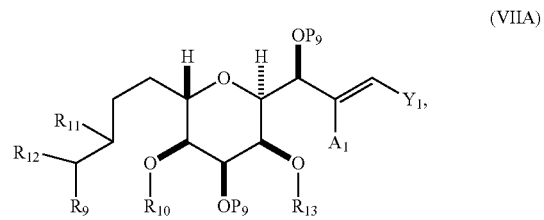

(VIIA)

where
(i) $R_{10}$ is a hydroxyl protecting group, $R_{11}$ is alkyl ether, and $R_{12}$ is H;
(ii) $R_{10}$ is a hydroxyl protecting group, and $R_{11}$ and $R_{12}$ combine to form a double bond;
or
(iii) $R_{10}$ and $R_{11}$ combine to form a bond, and $R_{12}$ is H;
$R_9$ is —$CH_2$—OP" or —COOP";
$R_{13}$ and each $P_9$ is independently a hydroxyl protecting group;
$A_1$ is H or —OP";
each P" is independently H or a hydroxyl protecting group; and
$Y_1$ is chloro, bromo, iodo, trifluoromethanesulfonate, or trialkylsilane.

The compound of formula (VIIB) is:

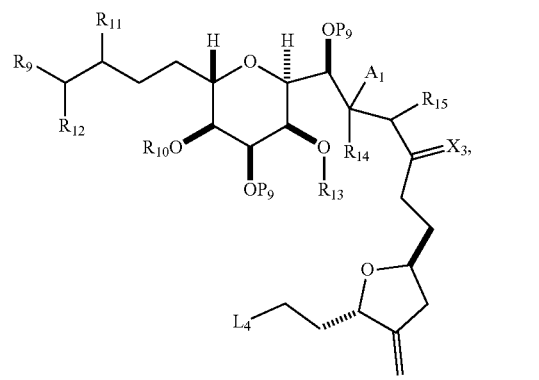

(VIIB)

where
L₄ is

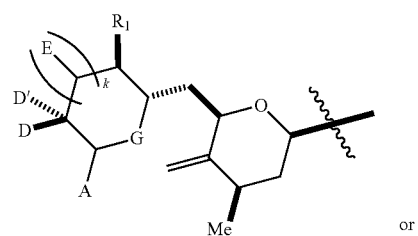

or

-continued

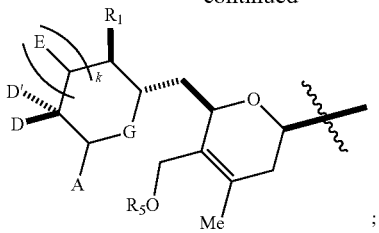

R₁ is —OP₆, —CH₂(Y), or —CH(Y)₂, where P₆ is H or a hydroxyl protecting group, and Y is —COOR_C or —CHO;

A₁ and R₁₄ combine to form oxo, R₁₃ is H or a hydroxyl protecting group, and R₁₅ is H;
or
A₁ is H or —OP''', and:
(i) R₁₃ is H or a hydroxyl protecting group, and R₁₄ and R₁₅ combine to form a double bond;
or
(ii) R₁₃ and R₁₄ combine to form a bond, and R₁₅ is H or —OP''';

R₉ is —CHO or —COOP''';

each P₉ is independently a hydroxyl protecting group, and X₃ is oxo or X₃, together with the carbon atom to which it is attached, is —(CH(OP₁₁))—, where P₁₁ is H or a hydroxyl protecting group; or both P₉ groups and X₃, together with the atoms to which each is attached, combine to form a ketal; and the remaining variables are as described for the compound of formula (IG) and the compound of formula (VIIA).

The compound of formula (VIIC) is:

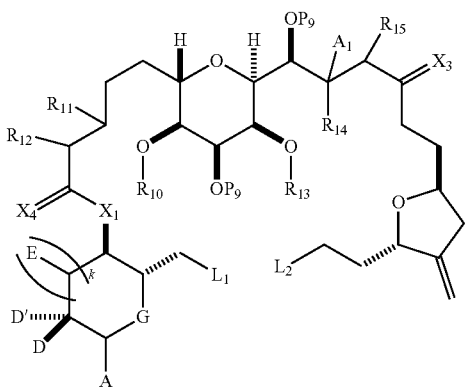

(VIIC)

where
L₁ is

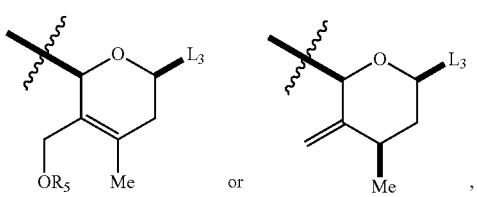

where L₂ and L₃ combine to form a bond;
X₁ is —CH₂—, —CH(Y)—, —C(Y)₂—, or —O—, where each Y is independently —COOR_C or —SO₂R_D;

each R_C, when present, is independently optionally substituted alkyl, optionally substituted aryl, or optionally substituted arylalkyl; and each R_D, when present, is independently optionally substituted aryl or optionally substituted non-enolizable alkyl;

X₄ is oxo, or X₄, together with the atom to which it is attached, is —(CH(OP₁₂))—, where P₁₂ is H or a hydroxyl protecting group; and the remaining variables are as described for the compound of formula (VIIB).

In certain embodiments, step (N) includes reacting the compound of formula (VIIA) and the compound of formula (IH) with a Cr(II) salt and a Ni(II) salt. In particular embodiments, step (O) includes an esterification reaction between R₁ that is —OP₆, where P₆ is H, and R₉ that is —COOH. In further embodiments, step (O) includes a reaction between R₁ that is —CH(Y)₂ or —CH₂(Y), and R₉ that is —CHO. In yet further embodiments, step (P) includes reacting the compound of formula (VIIC) with a hydroxyl protecting group removing agent.

In still further embodiments, the method includes:
(A) producing a compound of formula (VIID) from a compound of formula (IIA), a compound of formula (IIB), a compound of formula (IIIC), a compound of formula (VIIA), and R₅OH, where R₅ is optionally substituted acyl;
(B) producing a compound of formula (VIIE) from the compound of formula (VIID);
and
(C) producing the halichondrin macrolide or analog thereof from the compound of formula (VIIC).

The compound of formula (IIA) is:

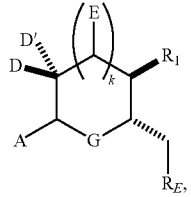

(IIA)

where
R₁ is —OP₆, —CH(Y)₂, or —CH₂(Y), where P₆ is H or a hydroxyl protecting group, and each Y is independently -COOR_C or —SO₂R_D;

each R_C, when present, is independently optionally substituted alkyl, optionally substituted aryl, or optionally substituted arylalkyl;

each R_D, when present, is independently optionally substituted aryl or optionally substituted non-enolizable alkyl;

R_E is —CHO or —CH_{(1+m)}(OR_F)_{(2-m)},
where
m is 1, and R_F is a hydroxyl protecting group,
or
m is 0, and
(i) each R_F is independently an alkyl or hydroxyl protecting group, or
(ii) both R_F combine to form an alkylene; and the remaining variables are as described for the halichondrin macrolide or analog thereof.

The compound of formula (IIB) is:

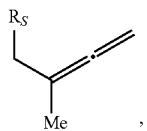
(IIB)

where $R_S$ is silyl.

The compound of formula (IIIC) is:

$R_{4C}$-$R_7$,  (IIIC)

where $R_7$ is —CHO or

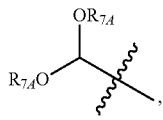

where each $R_{7A}$ is independently an optionally substituted alkyl;

$R_{4C}$ is

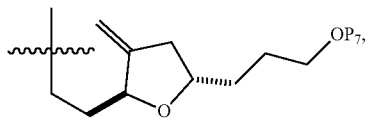

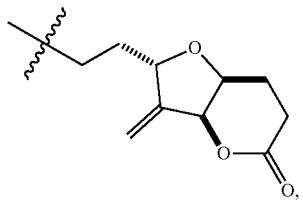

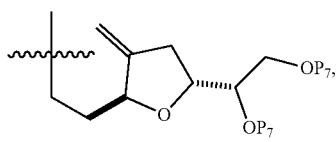

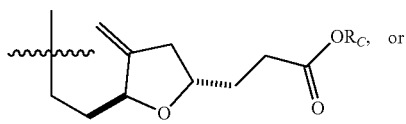

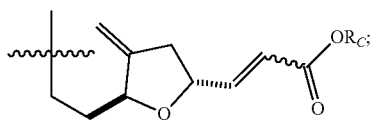

where each $P_7$, when present, is independently H or a hydroxyl protecting group.

The compound of formula (VIIA) is:

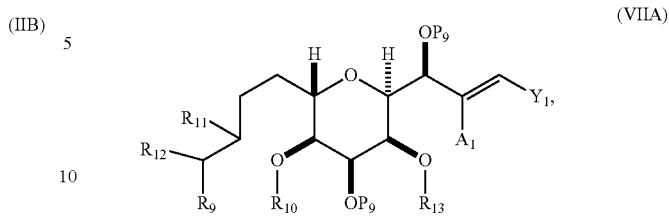
(VIIA)

where
(i) $R_{10}$ is a hydroxyl protecting group, $R_{11}$ is alkyl ether, and $R_{12}$ is H;
(ii) $R_{10}$ is a hydroxyl protecting group, and $R_{11}$ and $R_{12}$ combine to form a double bond;
or
(iii) $R_{10}$ and $R_{11}$ combine to form a bond, and $R_{12}$ is H;
$R_9$ is —CHO or —COOH;
$R_{13}$ and each $P_9$ is independently a hydroxyl protecting group;
$A_1$ is H or —OP'', where P'' is H or a hydroxyl protecting group; and
$Y_1$ is chloro, bromo, iodo, trifluoromethanesulfonate, or trialkylsilane.

The compound of formula (VIID) is:

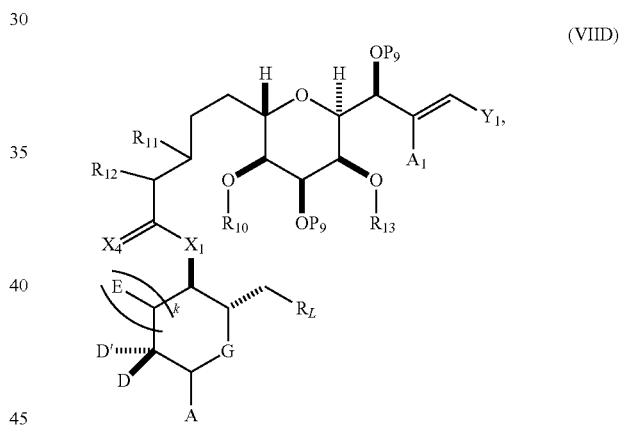
(VIID)

where
$X_1$ is —$CH_2$—, —CH(Y)—, —C(Y)$_2$—, or —O—, where each Y is independently —COOR$_C$ or —SO$_2$R$_D$;
$X_4$ is oxo, or $X_4$, together with the atom to which it is attached, is —(CH(OP$_{12}$))—, where $P_{12}$ is H or a hydroxyl protecting group;
$R_L$ is

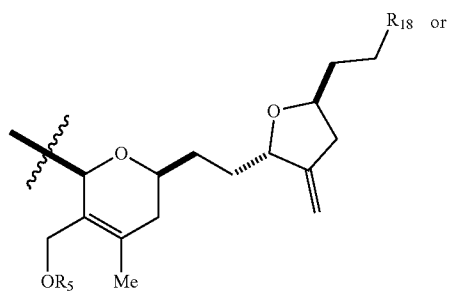

-continued

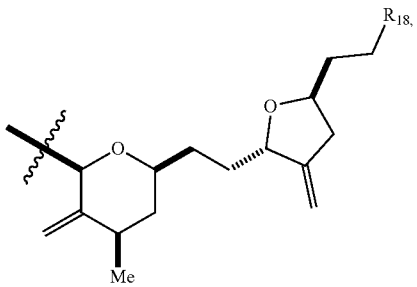

where
R$_{18}$ is —CHO or —CH$_2$OP$_7$;
R$_5$ is optionally substituted acyl; and
the remaining variables are as described for the compound of formula (IIA).
The compound of formula (VIIE) is:

(VIIE)

[structure]

where
L$_1$ is

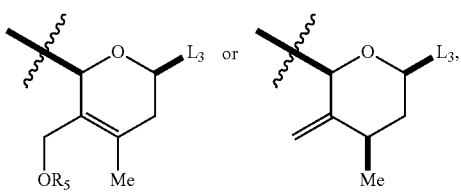

where L$_2$ and L$_3$ combine to form a bond;
each P$_9$ is independently a hydroxyl protecting group, and X$_3$ is oxo or X$_3$, together with the carbon atom to which it is attached, is —(CH(OP$_{11}$))—, where P$_{11}$ is H or a hydroxyl protecting group; and
the remaining variables are as described for the compound of formula (VIID).

In some embodiments, step (A) includes:
(D) producing a compound of formula (IIC) from the compound of formula (IIA) and the compound of formula (IIB);
(E) producing a compound of formula (IF) from the compound of formula (IIC), the compound of formula (IIIC), and R$_5$OH;
and
(F) producing the compound of formula (VIIB) from the compound of formula (VIIA) and the compound of formula (IF).
The compound of formula (IIC) is:

(IIC)

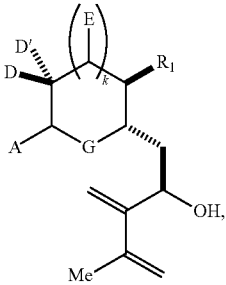

where the variables are as described for the compound of formula (IIA).
The compound of formula (IF) is:

(IF)

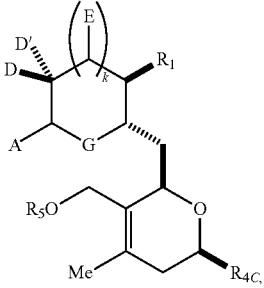

where the variables are as described for the compound of formula (IIC), the compound of formula (IIIC), and R$_5$OH.

In certain embodiments, the producing the compound of formula (IF) includes reacting the compound of formula (IIC), the compound of formula (IIIC), R$_5$OH, and a Lewis acid (e.g., an oxophilic Lewis acid (e.g., boron trifluoride or a solvate thereof)).

In particular embodiments, step (F) includes:
(G) producing a compound of formula (IH) from the compound of formula (IF); and
(H) producing the compound of formula (VIID) from the compound of formula (IH) and the compound of formula (VIIA).

The compound of formula (IH) is:

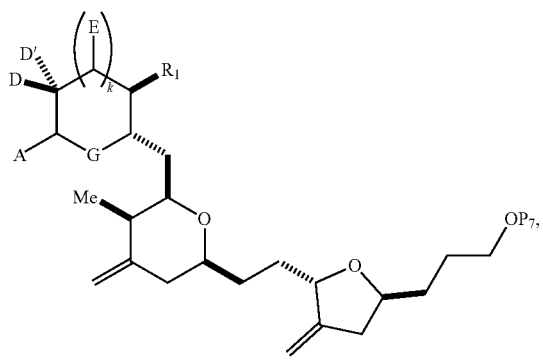

(IH)

where the variables are as described for the compound of formula (IF).

In some embodiments, the producing step (G) includes reacting the compound of formula (IF) with an allylic reducing agent.

In certain embodiments, step (A) includes reducing $R_{4C}$ that is

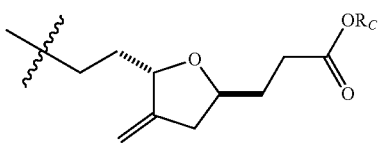

with a 1,2-reducing agent.

In particular embodiments, step (A) includes reducing $R_{4C}$ that is

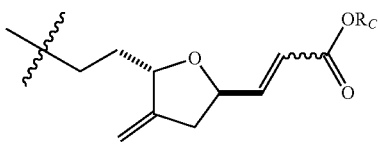

with a 1,4-reducing agent to produce a reduction product, and reducing the reduction product with a 1,2-reducing agent.

In further embodiments, step (A) includes reducing $R_{4C}$ that is

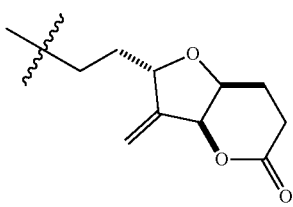

with an allylic reducing agent to produce an acid product, and reducing the acid product with a 1,2-reducing agent capable of converting the carboxylic acid to an aldehyde.

In yet further embodiments, step (A) includes cleaving $R_{4C}$ that is

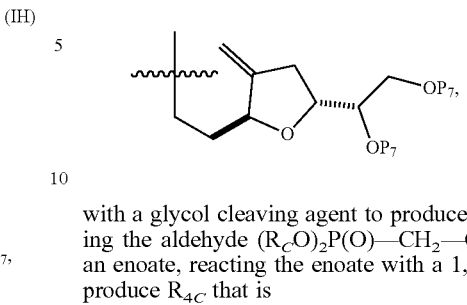

with a glycol cleaving agent to produce an aldehyde, reacting the aldehyde $(R_CO)_2P(O)$—$CH_2$—$COOR_C$ to produce an enoate, reacting the enoate with a 1,4-reducing agent to produce $R_{4C}$ that is

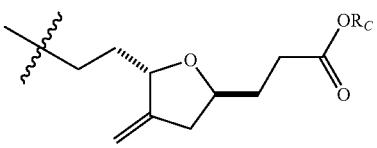

and reacting $R_{4C}$ that is

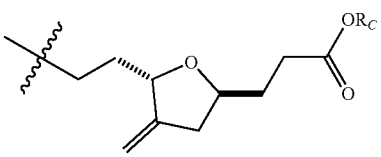

with a 1,2-reducing agent capable of converting the carboxylic acid to an aldehyde.

In still further embodiments, step (A) includes an esterification reaction between $R_1$ that is —$OP_6$, where $P_6$ is H, and Re that is —COOH. In other embodiments, step (A) includes a reaction between $R_1$ that is —$CH(Y)_2$ or —$CH_2$(Y), and $R_9$ that is —CHO. In yet other embodiments, step (B) includes reacting the compound of formulas (VIID) with a Cr(II) salt and a Ni(II) salt. In still other embodiments, step (C) includes reacting the compound of formula (VIIE) with a hydroxyl protecting group removing agent.

In some embodiments, the method includes:
(A) producing a compound of formula (VIIIB) from a compound of formula (VIIIA), a compound of formula (IIA), a compound of formula (IIB), and a compound of formula (IIIC), and $R_5OH$, where $R_5$ is optionally substituted acyl;
(B) producing a compound of formula (VIIIC) from the compound of formula (VIIIB); and
(C) producing the halichondrin macrolide or analog thereof from the compound of formula (VIIIC).

The compound of formula (IIA) is:

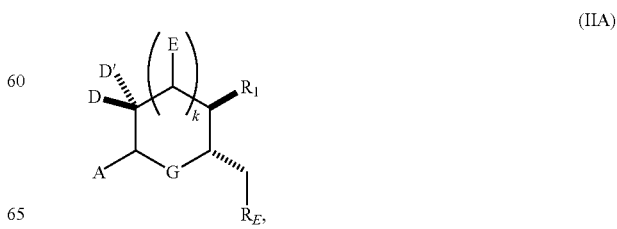

(IIA)

where
- $R_1$ is —$OP_6$, —CH(Y)$_2$, or —CH$_2$(Y), where $P_6$ is H or a hydroxyl protecting group, and each Y is independently —COOR$_C$ or —SO$_2$R$_D$;
- each $R_C$, when present, is independently optionally substituted alkyl, optionally substituted aryl, or optionally substituted arylalkyl;
- each $R_D$, when present, is independently optionally substituted aryl or optionally substituted non-enolizable alkyl;
- $R_E$ is —CHO or —CH$_{(1+m)}$(OR$_F$)$_{(2-m)}$,
  where
    m is 1, and $R_F$ is a hydroxyl protecting group, or
    m is 0
    (i) each $R_F$ is independently an alkyl or hydroxyl protecting group, or
    (ii) both $R_F$ combine to form an alkylene; and
the remaining variables are as described for the halichondrin macrolide or analog thereof.

The compound of formula (IIB) is:

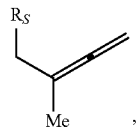
(IIB)

where $R_S$ is silyl.

The compound of formula (IIIC) is:

$R_{4C}$-$R_7$,   (IIIC)

where
$R_{4C}$ is

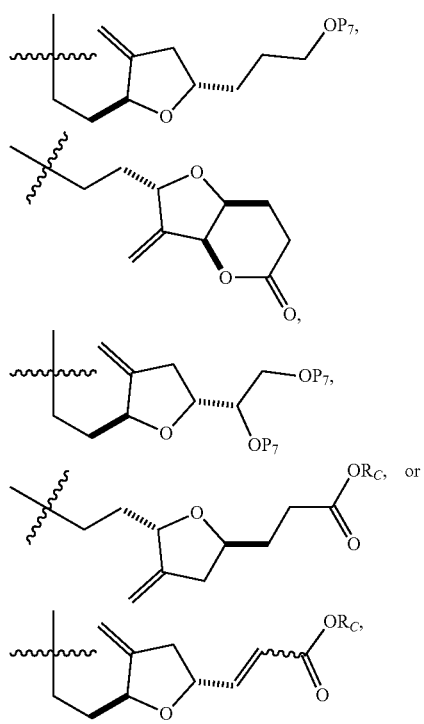

where
- each $R_C$, when present, is independently optionally substituted alkyl, optionally substituted aryl, or optionally substituted arylalkyl;
- each $P_7$, when present, is independently H or a hydroxyl protecting group;
- $R_7$ is —CHO or

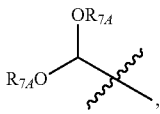

where each $R_A$ is independently an optionally substituted alkyl.

The compound of formula (VIIIA) is:

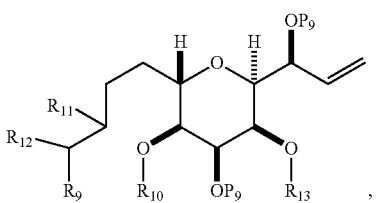
(VIIIA)

where
(i) $R_{10}$ is a hydroxyl protecting group, $R_{11}$ is alkyl ether, and $R_{12}$ is H;
(ii) $R_{10}$ is a hydroxyl protecting group, and $R_4$ and $R_5$ combine to form a double bond; or
(iii) $R_{10}$ and $R_{11}$ combine to form a bond, and $R_{12}$ is H;
$R_9$ is —CHO or —COOH;
and
each $P_9$ and $R_{13}$ is independently a hydroxyl protecting group.

The compound of formula (VIIIB) is:

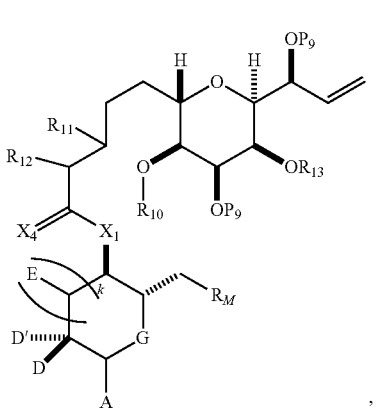
(VIIIB)

where
$X_1$ is —CH$_2$—, —CH(Y)—, —C(Y)$_2$—, or —O—, where each Y is independently —COOR$_C$ or —SO$_2$R$_D$;

$R_M$ is

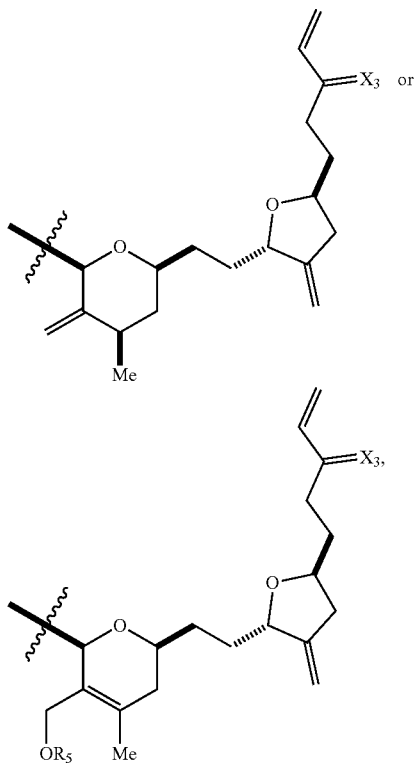

where $R_5$ is optionally substituted acyl; and $X_3$ is oxo or $X_3$, together with the carbon atom to which it is attached, is $-(CH(OP_{11}))-$, where $P_{11}$ is H or a hydroxyl protecting group;

$X_4$ is oxo, or $X_4$, together with the atom to which it is attached, is $-(CH(OP_{12}))-$, where $P_{12}$ is H or a hydroxyl protecting group; and the remaining groups are as described for the compound of formula (IIA) and the compound of formula (VIIIA).

The compound of formula (VIIIC) is:

(VIIIC)

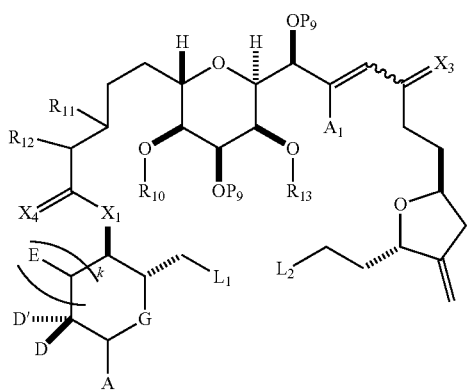

where $L_1$ is

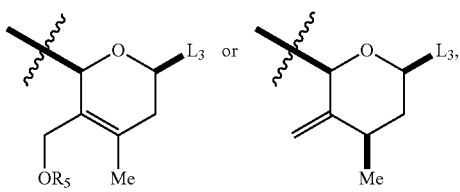

where $L_2$ and $L_3$ combine to form a bond;

$A_1$ is H or $-OP'''$, where $P'''$ is H or a hydroxyl protecting group; and the remaining variables are as described for the compound of formula (VIIIB).

In certain embodiments, step (A) includes:

(D) producing a compound of formula (IIC) from the compound of formula (IIA) and the compound of formula (IIB);

(E) producing a compound of formula (IF) from the compound of formula (IIC), the compound of formula (IIIC), and $R_5OH$;

(F) producing a compound of formula (IJ) from the compound of formula (IF);

and (G) producing the compound of formula (VIIIB) from the compound of formula (VIIIA) and the compound of formula (IJ).

The compound of formula (IIC) is:

(IIC)

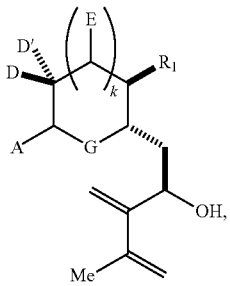

where the variables are as described for the compound of formula (IIA).

The compound of formula (IF) is:

(IF)

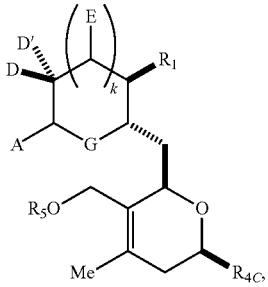

where the variables are as described for the compound of formula (IIA), the compound of formula (IIIC), and $R_5OH$.

The compound of formula (IJ) is:

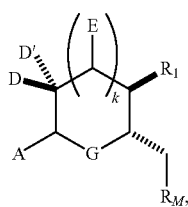

where the variables are as described for the compound of formula (VIIIB).

In particular embodiments, step (D) includes reacting the compound of formula (IIB), the compound of formula (IIA), and a Lewis acid (e.g., the Lewis acid is an oxophilic Lewis acid (e.g., boron trifluoride or a solvate thereof)). In further embodiments, step (E) includes reacting the compound of formula (IIC), the compound of formula (IIIC), $R_5OH$ and a Lewis acid (e.g., the Lewis acid is an oxophilic Lewis acid (e.g., boron trifluoride or a solvate thereof)). In yet further embodiments, the Lewis acid in step (D) and the Lewis acid in step (E) are different. In still further embodiments, the Lewis acid in step (D) and the Lewis acid in step (E) are same.

In some embodiments, step (F) includes converting

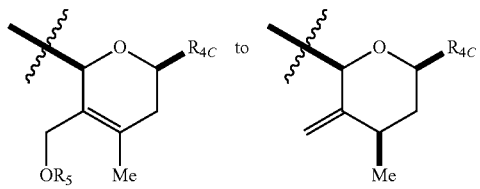

using an allylic reducing agent.

In particular embodiments, step (A) includes reacting $R_{4C}$ that is

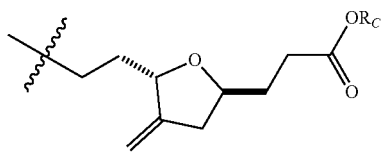

with a 1,2-reducing agent to produce a product, and reacting the product with a vinyl nucleophile.

In certain embodiments, step (A) includes reacting $R_{4C}$ that is

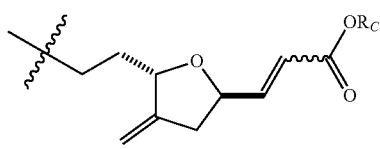

with a 1,4-reducing agent to produce a product, reducing the product with a 1,2-reducing agent to produce a reduced product, and reacting the reduced product with a vinyl nucleophile.

In further embodiments, step (A) includes reacting $R_{4C}$ that is

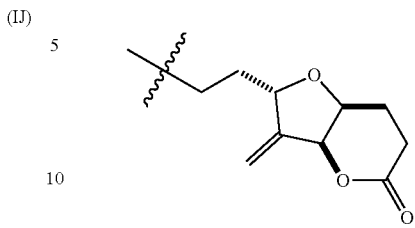

with an allylic reducing agent to produce an acid, reducing the acid with a 1,2-reducing agent to produce a reduced product, and reacting the reduced product with a vinyl nucleophile.

In yet further embodiments, step (A) includes cleaving $R_{4C}$ that is

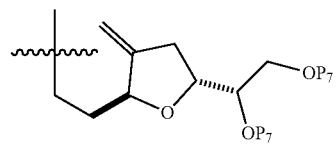

with a glycol cleaving agent to produce an aldehyde, reacting the aldehyde with $(R_CO)_2P(O)—CH_2—COOR_C$ to produce an enoate, reacting the enoate with a 1,4-reducing agent to produce a product, reducing the product with a 1,2-reducing agent to product a reduced product, and reacting the reduced product with a vinyl nucleophile.

In still further embodiments, step (A) includes an esterification reaction between $R_1$ that is $—OP_6$, where $P_6$ is H, and $R_9$ that is —COOH.

In other embodiments, step (A) includes a reaction between $R_1$ that is $—CH(Y)_2$ or $—CH_2(Y)$, and $R_9$, where $R_9$ is —CHO. In yet other embodiments, step (B) includes reacting the compound of formula (VIIIB) with an olefin metathesis catalyst. In still other embodiments, step (C) includes reacting the compound of formula (VIIIC) with a hydroxyl protecting group removing agent.

In some embodiments, the method includes:
(A) producing a compound of formula (IXB) from a compound of formula (IXA), a compound of formula (IIB), a compound of formula (IIA), a compound of formula (IIIE), and $R_5OH$, where $R_5$ is optionally substituted acyl; and
(B) producing the halichondrin macrolide or analog thereof from the compound of formula (IXB).

The compound of formula (IXA) is:

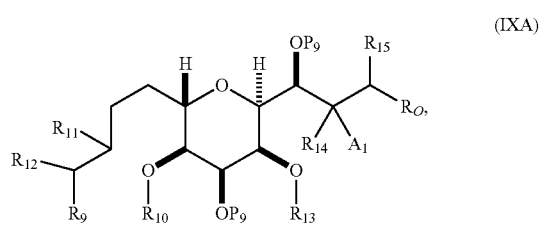

where
R$_9$ is —CHO or —COOP";
(a1) R$_{10}$ is a hydroxyl protecting group, R$_{11}$ is alkyl ether, and R$_{12}$ is H;
(a2) R$_{10}$ is a hydroxyl protecting group, and R$_{11}$ and R$_{12}$ combine to form a double bond;
or
(a3) R$_{10}$ and R$_{11}$ combine to form a bond, and R$_{12}$ is H;
A$_1$ and R$_{14}$ combine to form oxo, R$_{13}$ is H or a hydroxyl protecting group, and R$_{15}$ is H;
or
A$_1$ is H or —OP''', and:
(i) R$_{13}$ is H or a hydroxyl protecting group, and R$_{14}$ and R$_{15}$ combine to form a double bond;
or
(ii) R$_{13}$ and R$_{14}$ combine to form a bond, and R$_{15}$ is H or —OP;
R$_O$ is —CHO, —CH$_2$OP''', —CH=CH$_2$, —CH(OP''')CH$_2$OP''', —C(O)—CH$_2$P(O)(OR$_C$)$_2$, or halogen;
each R$_C$, when present, is independently optionally substituted alkyl, optionally substituted aryl, or optionally substituted arylalkyl; and
each P''' is independently H or a hydroxyl protecting group; and
each P$_9$ is independently a hydroxyl protecting group.
The compound of formula (IIA) is:

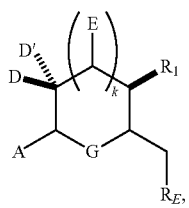

(IIA)

where
R$_1$ is —OP$_6$, —CH(Y)$_2$, or —CH$_2$(Y), where P$_6$ is H or a hydroxyl protecting group, and each Y is independently-COOR$_C$ or —SO$_2$R$_D$;
each R$_D$, when present, is independently optionally substituted aryl or optionally substituted non-enolizable alkyl;
R$_E$ is —CHO or —CH$_{(1+m)}$(OR$_F$)$_{(2-m)}$,
where
m is 1, and R$_F$ is a hydroxyl protecting group,
or
m is 0, and
(i) each R$_F$ is independently an alkyl or hydroxyl protecting group, or
(ii) both R$_F$ combine to form an alkylene; and
the remaining variables are as described for the halichondrin macrolide or analog thereof.
The compound of formula (IIIE) is:

R$_{4E}$-R$_7$,  (IIIE)

where
R$_{4E}$ is

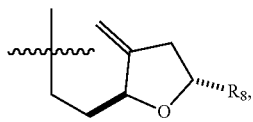

-continued

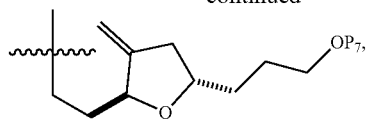

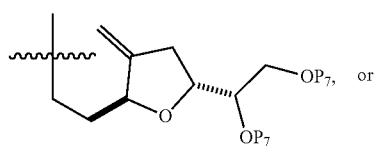

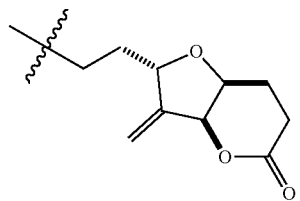

where
each P$_7$ is independently H or a hydroxyl protecting group; and
R$_8$ is —CH$_2$CH$_2$—COOR$_C$, —CH=CH—COOR$_C$, —CH$_2$CH$_2$—SO$_2$R$_D$, or —CH=CH—SO$_2$R$_D$;
and
R$_7$ is —CHO or

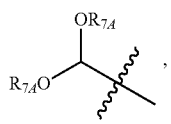

where each R$_{7A}$ is independently an optionally substituted alkyl.

The compound of formula (IIB) is:

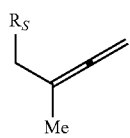

(IIB)

where R$_S$ is silyl.

The compound of formula (IXB) is:

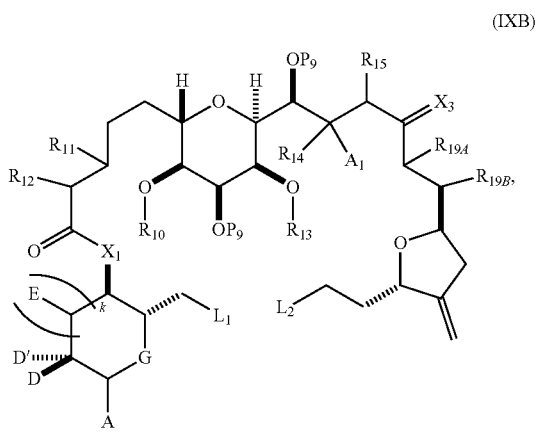

(IXB)

where $X_1$ is —$CH_2$—, —CH(Y)—, —$C(Y)_2$—, or —O—;

$L_1$ is

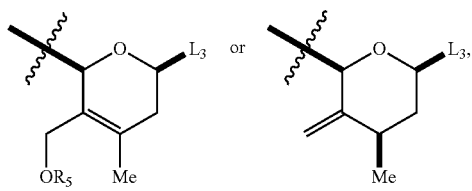

where $L_2$ and $L_3$ combine to form a bond;

$R_5$ is optionally substituted acyl;

$A_1$ and $R_{14}$ combine to form oxo, $R_{13}$ is H or a hydroxyl protecting group, and $R_{15}$ is H;

or $A_1$ is H or —OP'", and:

(i) $R_{13}$ is H or a hydroxyl protecting group, and $R_{14}$ and $R_{15}$, together with the atoms to which each is attached, combine to form a double bond;

or (ii) $R_{13}$ and $R_{14}$ combine to form a bond, and $R_{15}$ is H or —OP'";

each $P_9$ is independently H or a hydroxyl protecting group, and $X_3$ is oxo, or $X_3$, together with the atom to which it is attached, combines to form —(CH(OP$_{11}$))—, where $P_{11}$ is H or a hydroxyl protecting group;

or both $P_9$ and $X_3$, together with the atoms to which each is attached, combine to form a ketal;

$R_{19A}$ is H, —OP'", or Y, and $R_{19B}$ is H; or $R_{19A}$ and $R_{19B}$, together with the atoms to which each is attached, combine to form a double bond; and the remaining variables are as described for the compound of formula (IXA) and the compound of formula (IIA).

In some embodiments, step (A) includes reacting $R_E$ that is —CHO with the compound of formula (IIB) and a first Lewis acid to produce a group of the structure

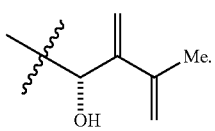 [SMILES: *[C@@H](O)C(=C)C(=C)C]

In certain embodiments, step (A) includes reacting the group of the structure

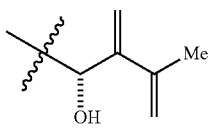 [SMILES: *[C@@H](O)C(=C)C(=C)C]

with $R_7$, $R_5$OH, and a second Lewis acid to produce a group of the structure

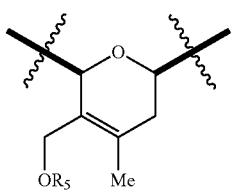

In particular embodiments, the first Lewis acid and/or second Lewis acid is an oxophilic Lewis acid (e.g., boron trifluoride or a solvate thereof). In further embodiments, the first Lewis acid is same as the second Lewis acid. In still further embodiments, the first Lewis acid is same as the second Lewis acid.

In other embodiments, step (A) includes converting $R_{4E}$ that is

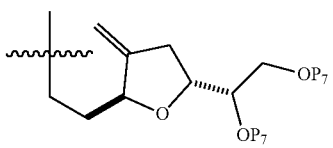

to a group of the structure

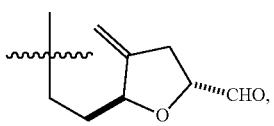

and reacting this group with $R_O$ that is —C(O)—$CH_2$P(O)(OR$_C$)$_2$ under Horner-Wadsworth-Emmons reaction conditions.

In yet other embodiments, step (A) includes reacting $R_{4E}$ that is

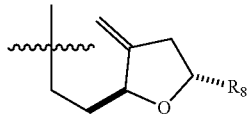

with $R_O$ that is —CHO under Claisen reaction conditions, where $R_8$ is —$CH_2CH_2$—$COOR_C$ or —$CH_2CH_2$—$SO_2R_D$.

In still other embodiments, step (A) includes converting $R_{4E}$ that is

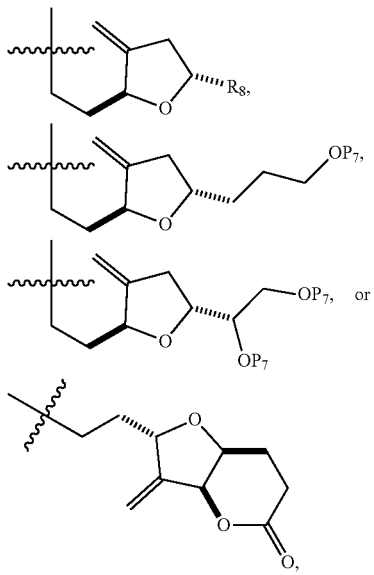

to a group of the structure

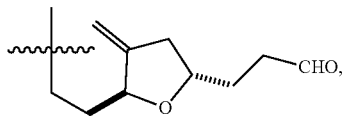 [SMILES: *CC[C@@H]1O[C@@H](CCC=O)CC1=C]

and reacting this group with $R_O$ that is a halogen under Nozaki-Hiyama-Kishi reaction conditions, where $R_8$, when present, is —$CH_2CH_2$—$COOR_C$ or —CH=CH—$COOR_C$, and $R_{14}$ and $R_{15}$ combine to form a double bond.

In some embodiments, step (A) includes reacting $R_1$ that is —$OP_6$ and $R_9$ under esterification reaction conditions to produce a group of the structure —$X_1$—C(O)—, where $P_6$ is H, $R_9$ is —COOH, and $X_1$ is —O—. In certain embodiments, step (A) includes reacting $R_1$ that is —$CH(Y)_2$ or —$CH_2(Y)$ with $R_9$ under Claisen reaction conditions to produce a group of the structure —$X_1$—C(O)—, where Re is —CHO, and $X_1$ is —$C(Y)_2$— or —CH(Y)—, respectively. In particular embodiments, step (B) includes reacting the compound of formula (IXB) with a hydroxyl protecting group removing agent. In further embodiments, D' is $OP_1$, where $P_1$ is alkyl. In yet further embodiments, D is H. In still further embodiments, A is of the following structure:

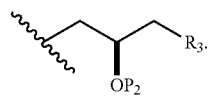

In other embodiments, k is 0. In yet other embodiments, $R_3$ is —$(CH_2)_nNP_3P_4$ or —$(CH_2)_nOP_5$, where n is 0. In still other embodiments, D' is H. In some embodiments, A and D combine to form the following structure:

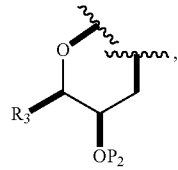

where, the bond to oxygen atom originates at the carbon atom, to which D is attached in formula (IA), and where $R_3$ is —$(CH_2)_nNP_3P_4$ or —$(CH_2)_nOP_5$, where n is 2.

In certain embodiments, k is 1, and E is optionally substituted alkyl. In particular embodiments, G is O.

In still another aspect, the invention provides a method of preparing an intermediate in the synthesis of a halichondrin macrolide or analog thereof.

In some embodiments, the intermediate is:

(Z)

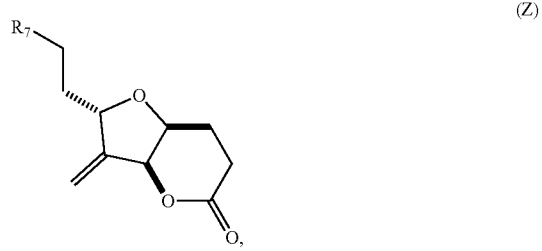

where $R_7$ is —CHO or

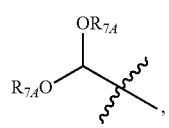

and
each $R_{7A}$ is independently alkyl or a hydroxyl protecting group; or
both $R_{7A}$ combine to form an optionally substituted alkylene.

In certain embodiments, the method includes:
(A) producing a compound of formula (Z2) from a compound of formula (Z1) and

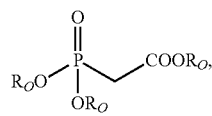

where each $R_O$ is independently optionally substituted alkyl, where the compound of formula (Z1) is:

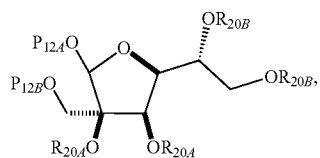
(Z1)

where each $R_{20A}$ is independently a hydroxyl protecting group, or both $R_{20A}$, together with the atoms to which each is attached, combine to form an acetal, cyclic carbonate, dicarbonyl-dioxo, or silylene-dioxo;

each $R_{20B}$ is independently a hydroxyl protecting group, or both $R_{20B}$, together with the atoms to which each is attached, combine to form an acetal, ketal, cyclic carbonate, dicarbonyl-dioxo, or silylene-dioxo;

$P_{12A}$ is H;

$P_{12B}$ is H or a hydroxyl protecting group;

and the compound of formula (Z2) is:

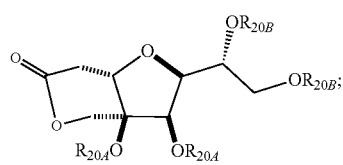
(Z2)

(B) producing a compound of formula (Z3) from the compound of formula (Z2) and

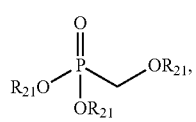

where each $R_{21}$ is independently optionally substituted alkyl, where the compound of formula (Z3) is:

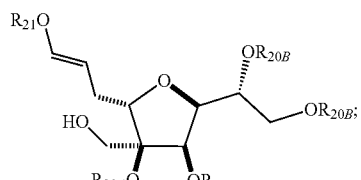
(Z3)

(C) producing a compound of formula (Z4) from the compound of formula (Z3), where the compound of formula (Z4) is:

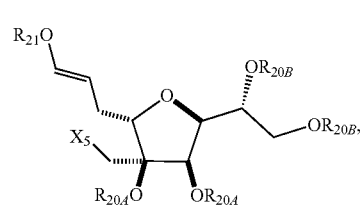
(Z4)

where $X_5$ is a halogen;

(D) producing a compound of formula (Z5) from the compound of formula (Z4), where the compound of formula (Z5) is:

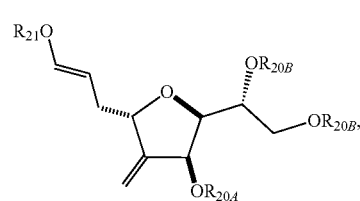
(Z5)

where $R_{20A}$ is H or a hydroxyl protecting group; and each $R_{20B}$ is independently H or a hydroxyl protecting group, or both $R_{20B}$, together with the atoms to which each is attached, combine to form an acetal, ketal, cyclic carbonate, dicarbonyl-dioxo, or silylene-dioxo;

(E) producing a compound of formula (Z6) from the compound of formula (Z5) and $R_{7A}OH$

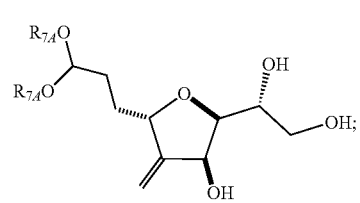
(Z6)

(F) producing a compound of formula (Z7) from the compound of formula (Z6) and

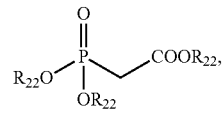

where each $R_{22}$ is independently optionally substituted alkyl, and the compound of formula (Z7) is:

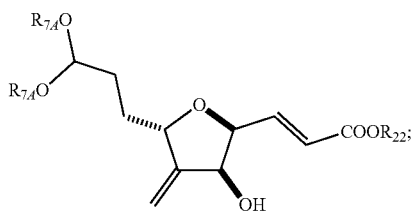
(Z7)

and (G) producing the compound of formula (Z) from the compound of formula (Z7).

In particular embodiments, step (E) includes reacting the compound of formula (Z5) with $R_{7A}OH$ and a Brønsted acid. In further embodiments, step (F) includes reacting the compound of formula (Z6) with a glycol cleaving agent to produce an aldehyde product, and reacting the aldehyde product with

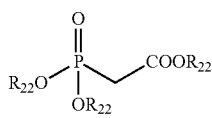

under Horner-Wadsworth-Emmons reaction conditions. In yet further embodiments, step (G) includes reacting the compound of formula (Z6) with a 1,4-reducing agent.

In still further embodiments, the intermediate is:

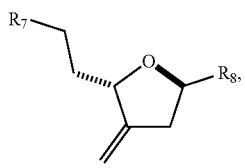
(Z8)

where
$R_7$ is —CHO or

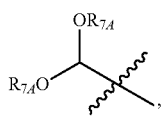

and
each $R_{7A}$ is independently alkyl or a hydroxyl protecting group; or
both $R_{7A}$ combine to form an optionally substituted alkylene;
$R_8$ is —$CH_2CH_2$—$COOR_C$, —CH=CH—$COOR_C$, —$CH_2CH_2$—$SO_2R_D$, or —CH=CH—$SO_2R_D$;
$R_C$, when present, is independently optionally substituted alkyl, optionally substituted aryl, or optionally substituted arylalkyl; and $R_D$, when present, is independently optionally substituted aryl or optionally substituted non-enolizable alkyl.

In other embodiments, the method includes:
(A) producing a compound of formula (Z2) from a compound of formula (Z1) and

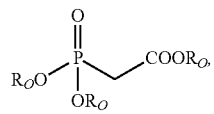

where each $R_O$ is independently optionally substituted alkyl, where the compound of formula (Z1) is:

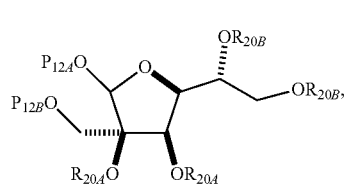
(Z1)

where
each $R_{20A}$ is independently a hydroxyl protecting group, or both $R_{20A}$, together with the atoms to which each is attached, combine to form an acetal, ketal, cyclic carbonate, dicarbonyl-dioxo, or silylene-dioxo;
each $R_{20B}$ is independently a hydroxyl protecting group, or both $R_{20B}$, together with the atoms to which each is attached, combine to form an acetal, ketal, cyclic carbonate, dicarbonyl-dioxo, or silylene-dioxo;
$P_{12A}$ is H;
$P_{12}B$ is H or a hydroxyl protecting group;
and the compound of formula (Z2) is:

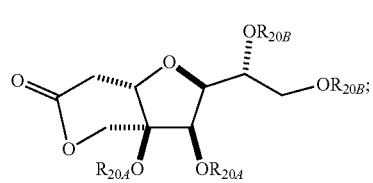
(Z2)

(B) producing a compound of formula (Z3) from the compound of formula (Z2) and

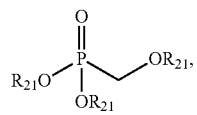

where each $R_{21}$ is independently optionally substituted alkyl, where the compound of formula (Z3) is:

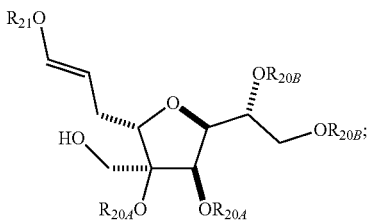

(Z3)

(C) producing a compound of formula (Z4) from the compound of formula (Z3), where the compound of formula (Z4) is:

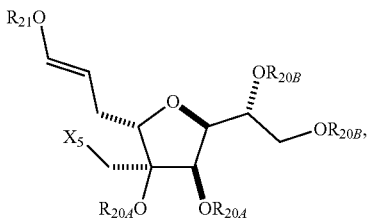

(Z4)

where $X_5$ is a halogen;

(D) producing a compound of formula (Z5) from the compound of formula (Z4), where the compound of formula (Z5) is:

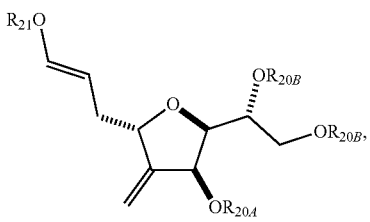

(Z5)

where $R_{20A}$ is H or a hydroxyl protecting group; and each $R_{20B}$ is independently H or a hydroxyl protecting group, or both $R_{20B}$, together with the atoms to which each is attached, combine to form an acetal, ketal, cyclic carbonate, dicarbonyl-dioxo, or silylene-dioxo;

(E) producing a compound of formula (Z5A) from the compound of formula (Z5) and $R_{7A}$OH, where the compound of formula (Z5A) is:

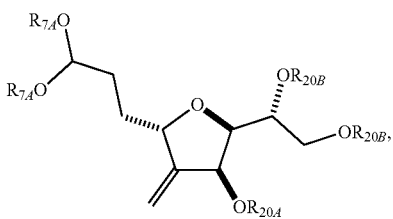

(Z5A)

where $R_{20A}$ is H or a hydroxyl protecting group; and each $R_{20B}$ is independently H or a hydroxyl protecting group, or both $R_{20B}$, together with the atoms to which each is attached, combine to form an acetal, ketal, cyclic carbonate, dicarbonyl-dioxo, or silylene-dioxo;

(F) producing a compound of formula (Z5B) from the compound of formula (Z5A), where the compound of formula (Z5B) is:

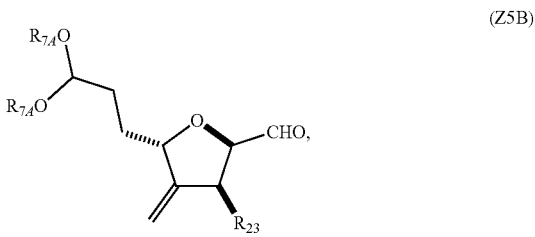

(Z5B)

where $R_{23}$ is H or —$OR_{20A}$;

and (G) producing the compound of formula (Z8) from the compound of formula (Z5B) and

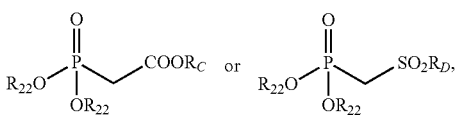

in which each $R_{22}$ is independently optionally substituted alkyl.

In further embodiments, step (E) includes reacting the compound of formula (Z5) with $R_{7A}$OH and a Brønsted acid. In yet further embodiments, step (F) includes reacting the compound of formula (Z5A), in which both $R_{20B}$ are H, with a glycol cleaving agent. In still further embodiments, step (E) or step (F) further includes reacting —$OR_{20A}$, where $R_{20A}$ is optionally substituted acyl with an allylic reducing agent. In other embodiments, step (G) includes reacting the compound of formula (Z5B) with

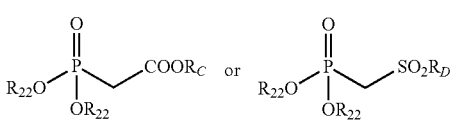

under Horner-Wadsworth-Emmons reaction conditions to produce the compound of formula (Z8), in which $R_8$ is —CH=CH—COOR$_C$ or —CH=CH—SO$_2$R$_D$, respectively. In yet other embodiments, step (G) further includes reacting the compound of formula (Z8), in which $R_8$ is —CH=CH—COOR$_C$ or —CH=CH—SO$_2$R$_D$, with a 1,4-reducing agent to produce the compound of formula (Z8), in which $R_8$ is —CH$_2$CH$_2$—COOR$_C$ or —CH$_2$CH$_2$—SO$_2$R$_D$, respectively. In still other embodiments, the producing the compound of formula (Z2) includes reacting the compound of formula (Z1) with

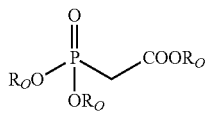

under Horner-Wadsworth-Emmons reaction conditions. In some embodiments, step (B) includes reacting the compound of formula (Z2) with a 1,2-reducing agent to produce a reduction product, and reacting the reduction product with

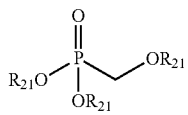

under Horner-Wadsworth-Emmons reaction conditions. In certain embodiments, step (C) includes substituting free hydroxyl group in the compound of formula (Z3) with a halogen. In particular embodiments, step (D) includes subjecting the compound of formula (Z4) to reductive metal conditions.

In a further aspect, the invention provides the compounds of formula (II), (IID), (IIE), (IIF), (IIG), (IIH), (IIi), (IVAb), (VAb), (VIIAa), (VIAa), (VIIID), (IXD), (IXF), (IXG), (Z), (Z1), (Z2), (Z3), (Z4), (Z5), (Z5A), (Z5B), or (Z6).

The compound of formula (II) is:

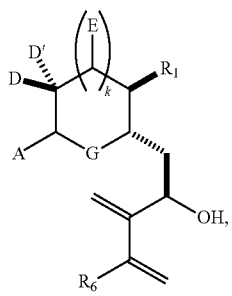

(II)

where
each of D and D' is independently H, optionally substituted alkyl, or $OP_1$, provided that only one of D and D' is $OP_1$, where $P_1$ is H, alkyl, a hydroxyl protecting group, and A is a $C_{1-6}$ saturated or $C_{2-6}$ unsaturated hydrocarbon skeleton, the skeleton being unsubstituted or having from 1 to 10 substituents independently selected from the group consisting of cyano, halo, azido, oxo, and $Q_1$, or A is a group of formula (1):

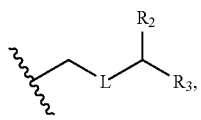

(1)

where
L is —(CH($OP_2$))—, —(C(OH)($OP_2$))—, or —C(O)—;
$R_2$ is H and $P_1$ is absent, H, alkyl, or a hydroxyl protecting group, or $R_2$ and $P_1$ combine to form a bond;

(i) $R_3$ is H, and $P_2$ is absent, H, optionally substituted alkyl, or a hydroxyl protecting group;
(ii) $R_3$ is —$(CH_2)_n NP_3 P_4$, where $P_3$ is H or an N-protecting group, and (a) $P_2$ is absent, H, optionally substituted alkyl, or a hydroxyl protecting group, and $P_4$ is H or an N-protecting group, (b) $P_2$ and $P_4$ combine to form an alkylidene, or (c) each of $P_2$ and $P_4$ is H;
(iii) $R_3$ is —$(CH_2)_n OP_5$, where $P_2$ is absent, H, optionally substituted alkyl, or a hydroxyl protecting group, and $P_5$ is H, optionally substituted alkyl, or a hydroxyl protecting group; or $P_2$ and $P_5$, together with the atoms to which each is attached, combine to form a ketal, a cyclic carbonate, a dicarbonyl-dioxo, or silylene-dioxo; or
(iv) $R_3$ and $P_2$ combine to form an optionally substituted ethylene or a structure selected from the group consisting of:

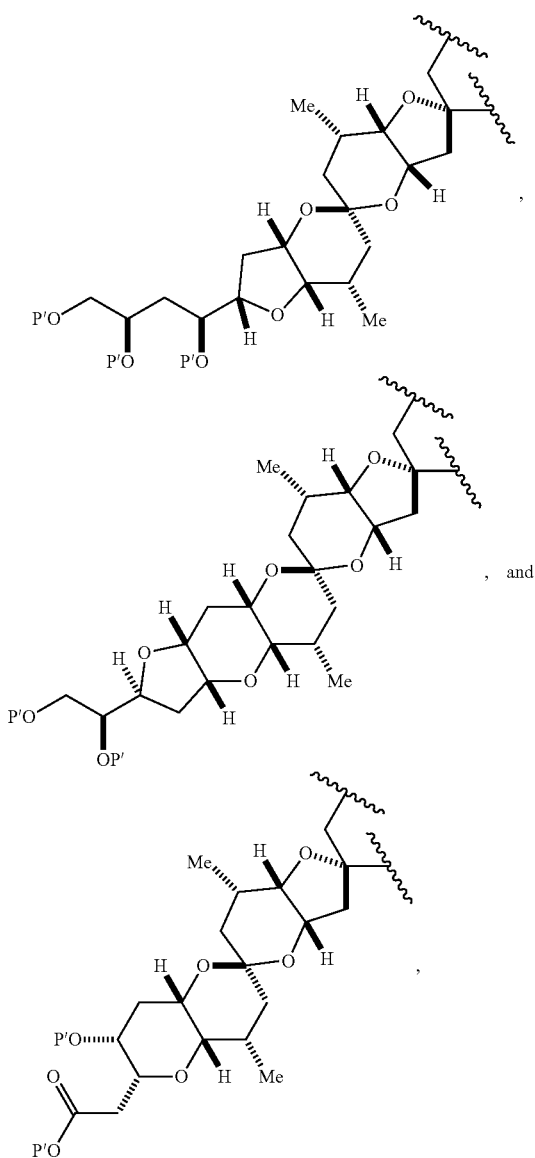

where each P' is independently H or a hydroxyl protecting group;

E is H, optionally substituted alkyl, or optionally substituted alkoxy;

G is O, S, CH$_2$, or NR$_N$, where R$_N$ is H, an N-protecting group, or optionally substituted alkyl;

each Q$_1$ is independently OR$_A$, SR$_A$, SO$_2$R$_A$, OS$_2$R$_A$, NR$_B$R$_A$, NR$_B$(CO)R$_A$, NR$_B$(CO)(CO)R$_A$, NR$_B$(CO)NR$_B$R$_A$, NR$_B$(CO)OR$_A$, (CO)OR$_A$, O(CO)R$_A$, (CO)NR$_B$R$_A$, or O(CO)NR$_B$R$_A$, where each of R$_A$ and R$_B$ is independently H, alkyl, haloalkyl, hydroxyalkyl, aminoalkyl, aryl, haloaryl, hydroxyaryl, alkoxyaryl, arylalkyl, alkylaryl, haloarylalkyl, alkylhaloaryl, (alkoxyaryl)alkyl, heterocyclic radical, or heterocyclic radical-alkyl;

n, when present, is 0, 1, or 2;

k is 0 or 1;

R$_1$ is —OP$_6$, —CH(Y)$_2$, or —CH$_2$(Y), where P$_6$ is H or a hydroxyl protecting group;

R$_6$ is H, optionally substituted alkyl, or optionally substituted aryl; and

Y is independently —COOR$_C$ or —SO$_2$R$_D$;

R$_C$, when present, is optionally substituted alkyl, optionally substituted aryl, or optionally substituted arylalkyl; and R$_D$, when present, is optionally substituted aryl or optionally substituted non-enolizable alkyl.

The compound of formula (VIIAa) is:

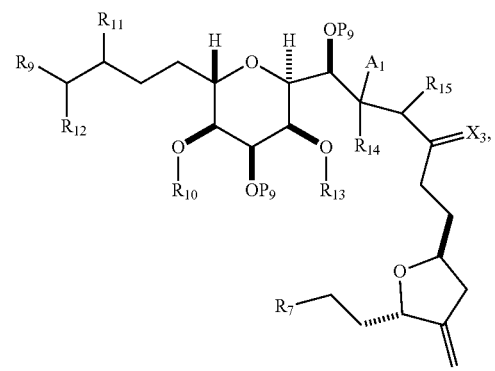

(VIIAa)

where

R$_7$ is —CH$_2$OP$_A$, —CHO, or

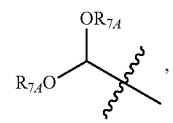

where each R$_{7A}$ is independently an optionally substituted alkyl;

R$_9$ is —CH$_2$—OP'", —CHO, or —COOP'";

(i) R$_{10}$ is a hydroxyl protecting group, R$_{11}$ is alkyl ether, and R$_{12}$ is H;

(ii) R$_{10}$ is a hydroxyl protecting group, and R$_{11}$ and R$_{12}$ combine to form a double bond;

or (iii) R$_{10}$ and R$_{11}$ combine to form a bond, and R$_{12}$ is H;

A$_1$ and R$_{14}$ combine to form oxo, R$_{13}$ is H or a hydroxyl protecting group, and R$_{15}$ is H;

or

A$_1$ is H or —OP'", and:

(i) R$_{13}$ is H or a hydroxyl protecting group, and R$_{14}$ and R$_{15}$ combine to form a double bond;

or (ii) R$_{13}$ and R$_{14}$ combine to form a bond, and R$_{15}$ is H or —OP'";

each P'" is independently H or a hydroxyl protecting group; and each P$_9$ is independently a hydroxyl protecting group, and X$_3$ is oxo or X$_3$, together with the carbon atom to which it is attached, is —(CH(OP$_{11}$))—, where P$_1$ is H or a hydroxyl protecting group; or both P groups and X$_3$, together with the atoms to which each is attached, combine to form a ketal.

The compound of formula (VIAa) is:

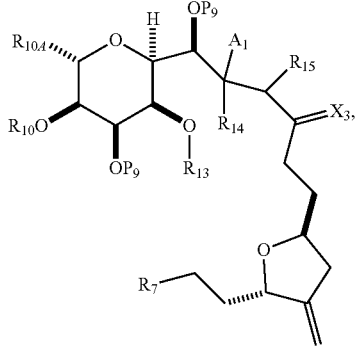

(VIAa)

where

R$_7$ is —CHO or

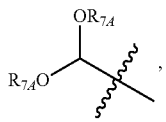

where each R$_{7A}$ is independently an optionally substituted alkyl;

R$_{10A}$ is —CH$_2$—CH=CH$_2$, —(CH$_2$)$_2$—CH=CH$_2$, or —(CH$_2$)$_3$—OP$_{10}$;

each of R$_{10}$ and P$_{10}$ is independently a hydroxyl protecting group;

A$_1$ and R$_{14}$ combine to form oxo, R$_{13}$ is H or a hydroxyl protecting group, and R$_{15}$ is H;

or

A$_1$ is H or —OP'", and:

(i) R$_{13}$ is H or a hydroxyl protecting group, and R$_{14}$ and R$_{15}$ combine to form a double bond;

or (ii) R$_{13}$ and R$_{14}$ combine to form a bond, and R$_{15}$ is H or —OP'";

and each P$_9$ is independently a hydroxyl protecting group, and X$_3$ is oxo or X$_3$, together with the carbon atom to which it is attached, is —(CH(OP$_{11}$))—, where P$_1$ is H or a hydroxyl protecting group; or both P$_9$ groups and X$_3$, together with the atoms to which each is attached, combine to form ketal.

The A compound of formula (IID) or (IIF) is:

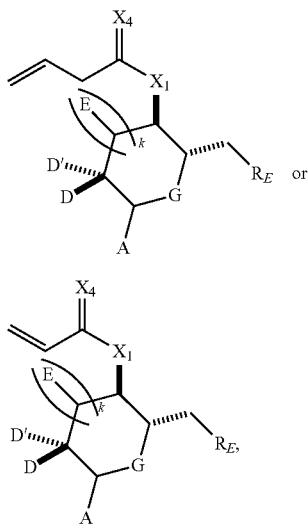

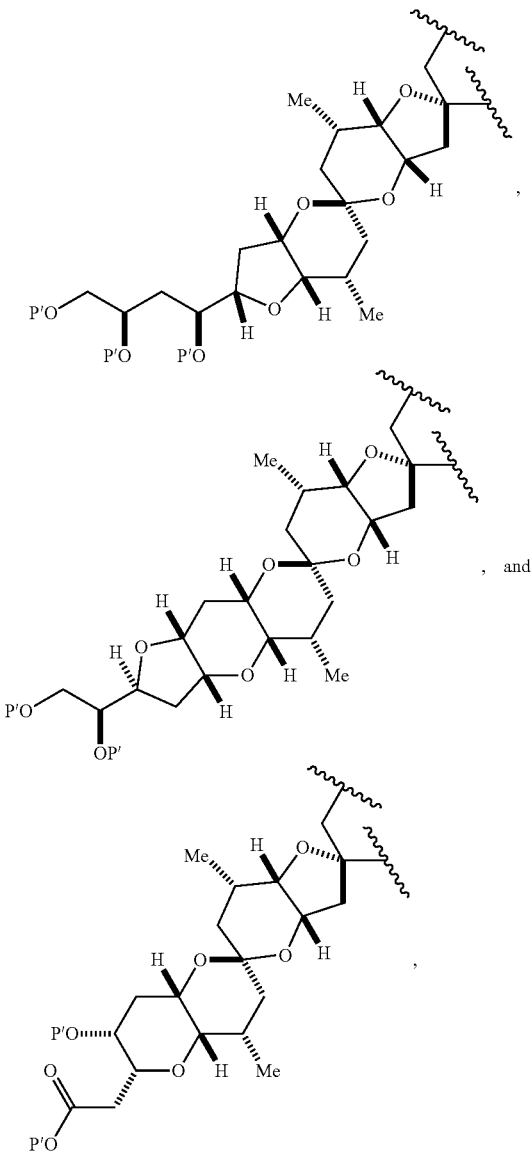

where
each of D and D' is independently H, optionally substituted alkyl, or $OP_1$, provided that only one of D and D' is $OP_1$, where $P_1$ is H, alkyl, a hydroxyl protecting group, and A is a $C_{1-6}$ saturated or $C_{2-6}$ unsaturated hydrocarbon skeleton, the skeleton being unsubstituted or having from 1 to 10 substituents independently selected from the group consisting of cyano, halo, azido, oxo, and $Q_1$, or A is a group of formula (1):

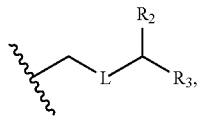

where
L is —(CH(OP$_2$))—, —(C(OH)(OP$_2$))—, or —C(O)—;
$R_2$ is H and $P_1$ is absent, H, alkyl, or a hydroxyl protecting group, or $R_2$ and $P_1$ combine to form a bond;
  (i) $R_3$ is H, and $P_2$ is absent, H, optionally substituted alkyl, or a hydroxyl protecting group;
  (ii) $R_3$ is —(CH$_2$)$_n$NP$_3$P$_4$, where $P_3$ is H or an N-protecting group, and (a) $P_2$ is absent, H, optionally substituted alkyl, or a hydroxyl protecting group, and $P_4$ is H or an N-protecting group, (b) $P_2$ and $P_4$ combine to form an alkylidene, or (c) each of $P_2$ and $P_4$ is H;
  (iii) $R_3$ is —(CH$_2$)$_n$OP$_5$, where $P_2$ is absent, H, optionally substituted alkyl, or a hydroxyl protecting group, and $P_5$ is H, optionally substituted alkyl, or a hydroxyl protecting group; or $P_2$ and $P_5$, together with the atoms to which each is attached, combine to form a ketal, a cyclic carbonate, a dicarbonyl-dioxo, or silylene-dioxo; or
  (iv) $R_3$ and $P_2$ combine to form an optionally substituted ethylene or a structure selected from the group consisting of:

where each P' is independently H or a hydroxyl protecting group;
E is H, optionally substituted alkyl, or optionally substituted alkoxy;
G is O, S, CH$_2$, or NR$_N$, where R$_N$ is H, an N-protecting group, or optionally substituted alkyl;
each $Q_1$ is independently OR$_A$, SR$_A$, SO$_2$R$_A$, OSO$_2$R$_A$, NR$_B$R$_A$, NR$_B$(CO)R$_A$, NR$_B$(CO)(CO)R$_A$, NR$_B$(CO)NR$_B$R$_A$, NR$_B$(CO)OR$_A$, (CO)OR$_A$, O(CO)R$_A$, (CO)NR$_B$R$_A$, or O(CO)NR$_B$R$_A$, where each of R$_A$ and R$_B$ is independently H, alkyl, haloalkyl, hydroxyalkyl, aminoalkyl, aryl, haloaryl, hydroxyaryl, alkoxyaryl, arylalkyl, alkylaryl, haloarylalkyl, alkylhaloaryl, (alkoxyaryl)alkyl, heterocyclic radical, or heterocyclic radical-alkyl;
n, when present, is 0, 1, or 2;
k is 0 or 1;
$X_1$ is —CH$_2$— or —O—;
$X_4$ is oxo, or $X_4$, together with the atom to which it is attached, is —(CH(OP$_{12}$))—, where Pa is H or a hydroxyl protecting group; and $R_E$ is —CHO or —CH$_{(1+m)}$(OR$_F$)$_{(2-m)}$, where
  m is 1, and R$_F$ is a hydroxyl protecting group,
  or
  m is 0, and
    (i) each R$_F$ is independently an alkyl or hydroxyl protecting group, or
    (ii) both R$_F$ combine to form an alkylene.
The compound of formula (IIE) or (IIG):

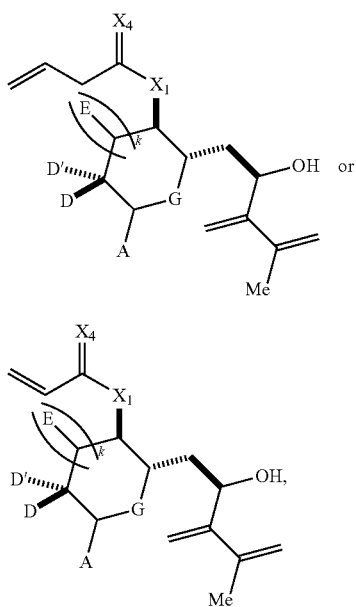

(IIE)

(IIG)

where
each of D and D' is independently H, optionally substituted alkyl, or OP$_1$, provided that only one of D and D' is OP$_1$, where P$_1$ is H, alkyl, a hydroxyl protecting group, and A is a C$_{1-6}$ saturated or C$_{2-6}$ unsaturated hydrocarbon skeleton, the skeleton being unsubstituted or having from 1 to 10 substituents independently selected from the group consisting of cyano, halo, azido, oxo, and Q$_1$, or A is a group of formula (1):

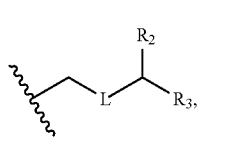

(1)

where
  L is —(CH(OP$_2$))—, —(C(OH)(OP$_2$))—, or —C(O)—;
  R$_2$ is H and P$_1$ is absent, H, alkyl, or a hydroxyl protecting group, or R$_2$ and P$_1$ combine to form a bond;
    (i) R$_3$ is H, and P$_2$ is absent, H, optionally substituted alkyl, or a hydroxyl protecting group;
    (ii) R$_3$ is —(CH$_2$)$_n$NP$_3$P$_4$, where P$_3$ is H or an N-protecting group, and (a) P$_2$ is absent, H, optionally substituted alkyl, or a hydroxyl protecting group, and P$_4$ is H or an N-protecting group, (b) P$_2$ and P$_4$ combine to form an alkylidene, or (c) each of P$_2$ and P$_4$ is H;
    (iii) R$_3$ is —(CH$_2$)$_n$OP$_5$, where P$_2$ is absent, H, optionally substituted alkyl, or a hydroxyl protecting group, and P$_6$ is H, optionally substituted alkyl, or a hydroxyl protecting group; or P$_2$ and P$_5$, together with the atoms to which each is attached, combine to form a ketal, a cyclic carbonate, a dicarbonyl-dioxo, or silylene-dioxo; or
    (iv) R$_3$ and P$_2$ combine to form an optionally substituted ethylene or a structure selected from the group consisting of:

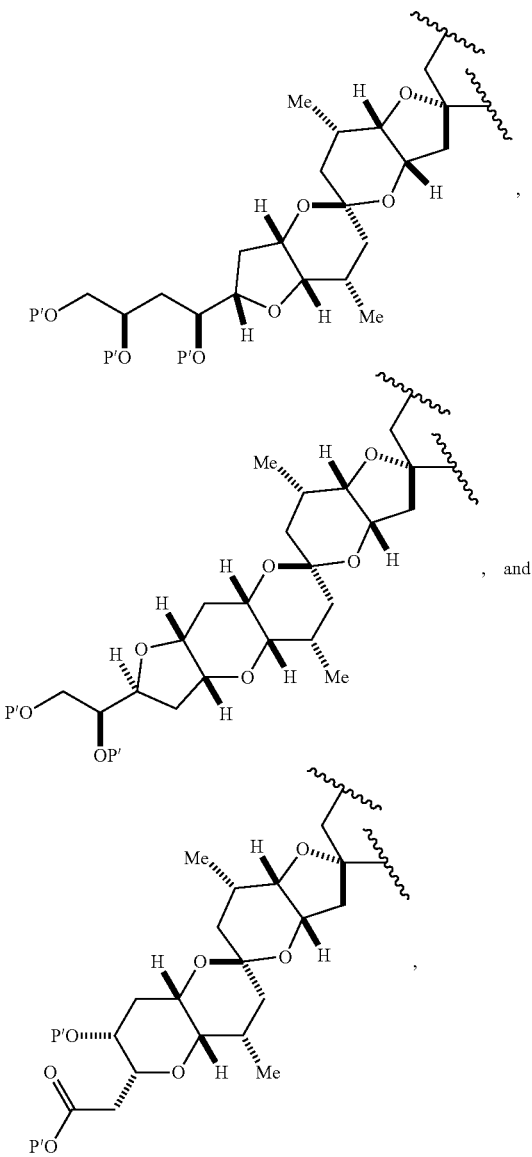

, and where each P' is independently H or a hydroxyl protecting group;
E is H, optionally substituted alkyl, or optionally substituted alkoxy;
G is O, S, CH$_2$, or NR$_N$, where R$_N$ is H, an N-protecting group, or optionally substituted alkyl;
each Q$_1$ is independently OR$_A$, SR$_A$, SO$_2$R$_A$, OSO$_2$R$_A$, NR$_B$R$_A$, NR$_B$(CO)R$_A$, NR$_B$(CO)(CO)R$_A$, NR$_B$(CO)NR$_B$R$_A$, NR$_B$(CO)OR$_A$, (CO)OR$_A$, O(CO)R$_A$, (CO)NR$_B$R$_A$, or O(CO)NR$_B$R$_A$, where each of R$_A$ and R$_B$ is independently H, alkyl, haloalkyl, hydroxyalkyl, aminoalkyl, aryl, haloaryl, hydroxyaryl, alkoxyaryl, arylalkyl, alkylaryl, haloarylalkyl, alkylhaloaryl, (alkoxyaryl)alkyl, heterocyclic radical, or heterocyclic radical-alkyl;

n, when present, is 0, 1, or 2;

k is 0 or 1;

$X_1$ is —$CH_2$— or —O—; and $X_4$ is oxo, or $X_4$, together with the atom to which it is attached, is —(CH(O$P_{12}$))—, where $P_{12}$ is H or a hydroxyl protecting group.

The compound of formula (IIH) is:

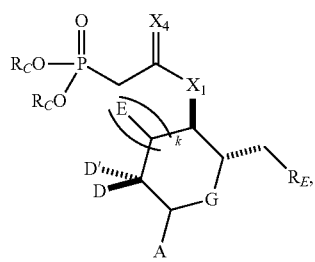

(IIH)

where each of D and D' is independently H, optionally substituted alkyl, or O$P_1$, provided that only one of D and D' is O$P_1$, where $P_1$ is H, alkyl, a hydroxyl protecting group, and A is a $C_{1-6}$ saturated or $C_{2-6}$ unsaturated hydrocarbon skeleton, the skeleton being unsubstituted or having from 1 to 10 substituents independently selected from the group consisting of cyano, halo, azido, oxo, and $Q_1$, or A is a group of formula (1):

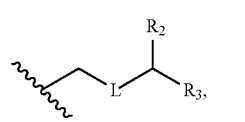

(1)

where

L is —(CH(O$P_2$))—, —(C(OH)(O$P_2$))—, or —C(O)—;

$R_2$ is H and $P_1$ is absent, H, alkyl, or a hydroxyl protecting group, or $R_2$ and $P_1$ combine to form a bond;

(i) $R_3$ is H, and $P_2$ is absent, H, optionally substituted alkyl, or a hydroxyl protecting group;

(ii) $R_3$ is —$(CH_2)_n$N$P_3P_4$, where $P_3$ is H or an N-protecting group, and (a) $P_2$ is absent, H, optionally substituted alkyl, or a hydroxyl protecting group, and $P_4$ is H or an N-protecting group, (b) $P_2$ and $P_4$ combine to form an alkylidene, or (c) each of $P_2$ and $P_4$ is H;

(iii) $R_3$ is —$(CH_2)_n$O$P_5$, where $P_2$ is absent, H, optionally substituted alkyl, or a hydroxyl protecting group, and $P_5$ is H, optionally substituted alkyl, or a hydroxyl protecting group; or $P_2$ and $P_5$, together with the atoms to which each is attached, combine to form a ketal, a cyclic carbonate, a dicarbonyl-dioxo, or silylene-dioxo; or (iv) $R_3$ and $P_2$ combine to form an optionally substituted ethylene or a structure selected from the group consisting of:

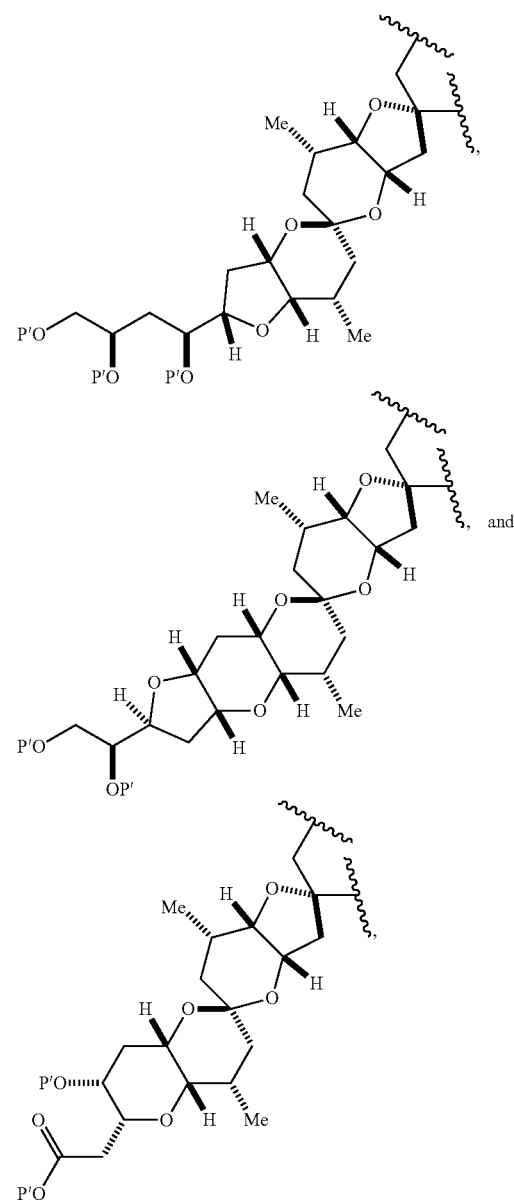

where each P' is independently H or a hydroxyl protecting group;

E is H, optionally substituted alkyl, or optionally substituted alkoxy;

G is O, S, $CH_2$, or N$R_N$, where $R_N$ is H, an N-protecting group, or optionally substituted alkyl;

each $Q_1$ is independently O$R_A$, S$R_A$, $SO_2R_A$, $OSO_2R_A$, $NR_BR_A$, $NR_B$(CO)$R_A$, $NR_B$(CO)(CO)$R_A$, $NR_B$(CO)$NR_BR_A$, $NR_B$(CO)O$R_A$, (CO)O$R_A$, O(CO)$R_A$, (CO)$NR_BR_A$, or O(CO)$NR_BR_A$, where each of $R_A$ and $R_B$ is independently H, alkyl, haloalkyl, hydroxyalkyl, aminoalkyl, aryl, haloaryl, hydroxyaryl, alkoxyaryl, arylalkyl, alkylaryl, haloarylalkyl, alkylhaloaryl, (alkoxyaryl)alkyl, heterocyclic radical, or heterocyclic radical-alkyl;

n, when present, is 0, 1, or 2;

k is 0 or 1;

each $R_C$ is independently optionally substituted alkyl, optionally substituted aryl, or optionally substituted arylalkyl;

$X_1$ is —$CH_2$— or —O—;

$X_4$ is oxo, or $X_4$, together with the atom to which it is attached, is —(CH(O$P_{12}$))—, where $P_{12}$ is H or a hydroxyl protecting group; and $R_E$ is —CHO or —$CH_{(1+m)}(OR_F)_{(2-m)}$, where
m is 1, and $R_F$ is a hydroxyl protecting group,
or
m is 0, and
(i) each $R_F$ is independently an alkyl or hydroxyl protecting group, or
(ii) both $R_F$ combine to form an alkylene.

The compound of formula (IIi) is:

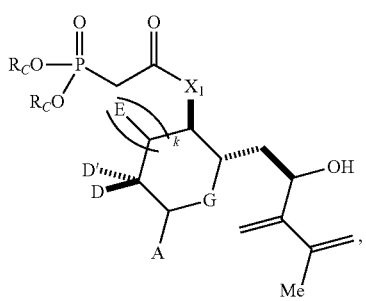

(IIi)

where
each of D and D' is independently H, optionally substituted alkyl, or O$P_1$, provided that only one of D and D' is O$P_1$, where $P_1$ is H, alkyl, a hydroxyl protecting group, and A is a $C_{1-6}$ saturated or $C_{2-6}$ unsaturated hydrocarbon skeleton, the skeleton being unsubstituted or having from 1 to 10 substituents independently selected from the group consisting of cyano, halo, azido, oxo, and $Q_1$, or A is a group of formula (1):

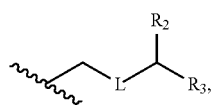

(1)

where
L is —(CH(O$P_2$))—, —(C(OH)(O$P_2$))—, or —C(O)—;
$R_2$ is H and $P_1$ is absent, H, alkyl, or a hydroxyl protecting group, or $R_2$ and $P_1$ combine to form a bond;
(i) $R_3$ is H, and $P_2$ is absent, H, optionally substituted alkyl, or a hydroxyl protecting group;
(ii) $R_3$ is —$(CH_2)_n NP_3P_4$, where $P_3$ is H or an N-protecting group, and (a) $P_2$ is absent, H, optionally substituted alkyl, or a hydroxyl protecting group, and $P_4$ is H or an N-protecting group, (b) $P_2$ and $P_4$ combine to form an alkylidene, or (c) each of $P_2$ and $P_4$ is H;
(iii) $R_3$ is —$(CH_2)_n OP_5$, where $P_2$ is absent, H, optionally substituted alkyl, or a hydroxyl protecting group, and $P_5$ is H, optionally substituted alkyl, or a hydroxyl protecting group; or $P_2$ and $P_5$, together with the atoms to which each is attached, combine to form a ketal, a cyclic carbonate, a dicarbonyl-dioxo, or silylene-dioxo; or (iv) $R_3$ and $P_2$ combine to form an optionally substituted ethylene or a structure selected from the group consisting of:

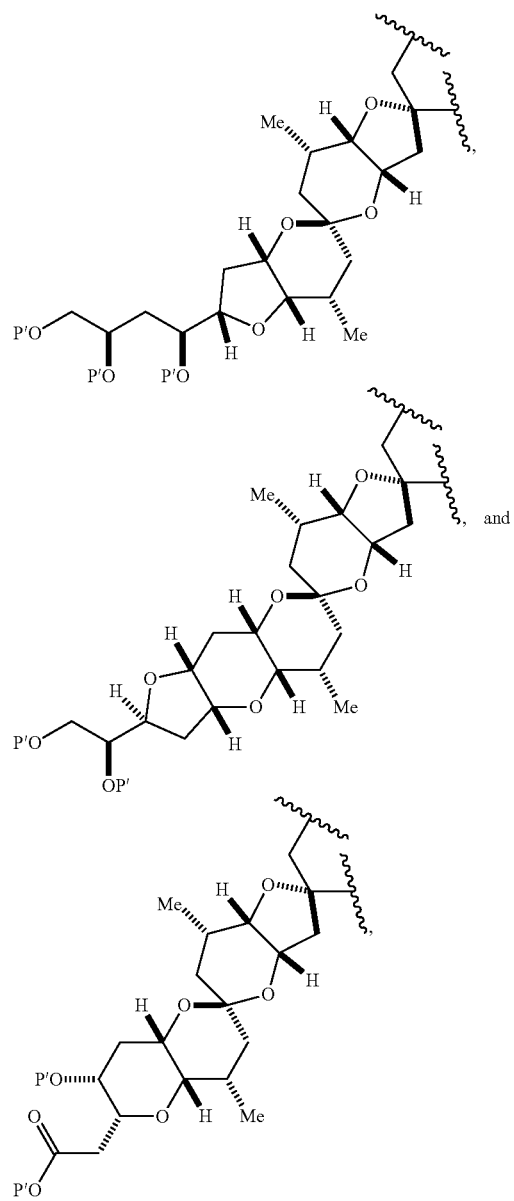

where each P' is independently H or a hydroxyl protecting group;
E is H, optionally substituted alkyl, or optionally substituted alkoxy;
G is O, S, $CH_2$, or $NR_N$, where $R_N$ is H, an N-protecting group, or optionally substituted alkyl;
each $Q_1$ is independently $OR_A$, $SR_A$, $SO_2R_A$, $OSO_2R_A$, $NR_BR_A$, $NR_B(CO)R_A$, $NR_B(CO)(CO)R_A$, $NR_B(CO)NR_BR_A$, $NR_B(CO)OR_A$, $(CO)OR_A$, $O(CO)R_A$, $(CO)NR_BR_A$, or $O(CO)NR_BR_A$, where each of $R_A$ and $R_B$ is independently H, alkyl, haloalkyl, hydroxyalkyl, aminoalkyl, aryl, haloaryl, hydroxyaryl, alkoxyaryl, arylalkyl, alkylaryl, haloarylalkyl, alkylhaloaryl, (alkoxyaryl)alkyl, heterocyclic radical, or heterocyclic radical-alkyl;

n, when present, is 0, 1, or 2;
k is 0 or 1;
each $R_C$ is independently optionally substituted alkyl, optionally substituted aryl, or optionally substituted arylalkyl; and
$X_1$ is —CH— or —O—.

The compound of formula (VIIID) is:

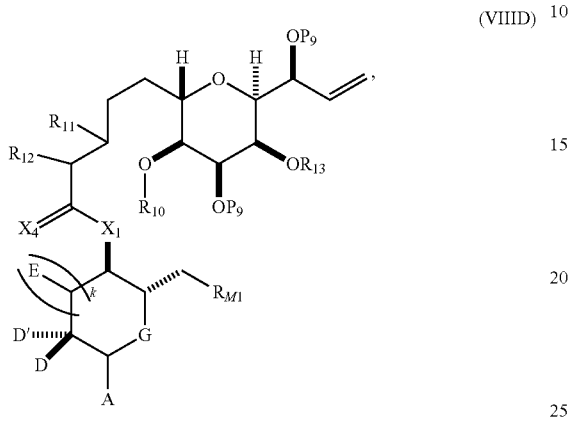

(VIIID)

where
each of D and D' is independently H, optionally substituted alkyl, or $OP_1$, provided that only one of D and D' is $OP_1$, where $P_1$ is H, alkyl, a hydroxyl protecting group, and A is a $C_{1-6}$ saturated or $C_{2-6}$ unsaturated hydrocarbon skeleton, the skeleton being unsubstituted or having from 1 to 10 substituents independently selected from the group consisting of cyano, halo, azido, oxo, and Q or A is a group of formula (1):

(1)

where
L is —(CH($OP_2$))—, —(C(OH)($OP_2$))—, or —C(O)—;
$R_2$ is H and $P_1$ is absent, H, alkyl, or a hydroxyl protecting group, or $R_2$ and $P_1$ combine to form a bond;
 (i) $R_3$ is H, and $P_2$ is absent, H, optionally substituted alkyl, or a hydroxyl protecting group;
 (ii) $R_3$ is —$(CH_2)_n NP_3 P_4$, where $P_3$ is H or an N-protecting group, and (a) $P_2$ is absent, H, optionally substituted alkyl, or a hydroxyl protecting group, and $P_4$ is H or an N-protecting group, (b) $P_2$ and $P_4$ combine to form an alkylidene, or (c) each of $P_2$ and $P_4$ is H;
 (iii) $R_3$ is —$(CH_2)_n OP_5$, where $P_2$ is absent, H, optionally substituted alkyl, or a hydroxyl protecting group, and $P_6$ is H, optionally substituted alkyl, or a hydroxyl protecting group; or $P_2$ and $P_5$, together with the atoms to which each is attached, combine to form a ketal, a cyclic carbonate, a dicarbonyl-dioxo, or silylene-dioxo; or
 (iv) $R_3$ and $P_2$ combine to form an optionally substituted ethylene or a structure selected from the group consisting of:

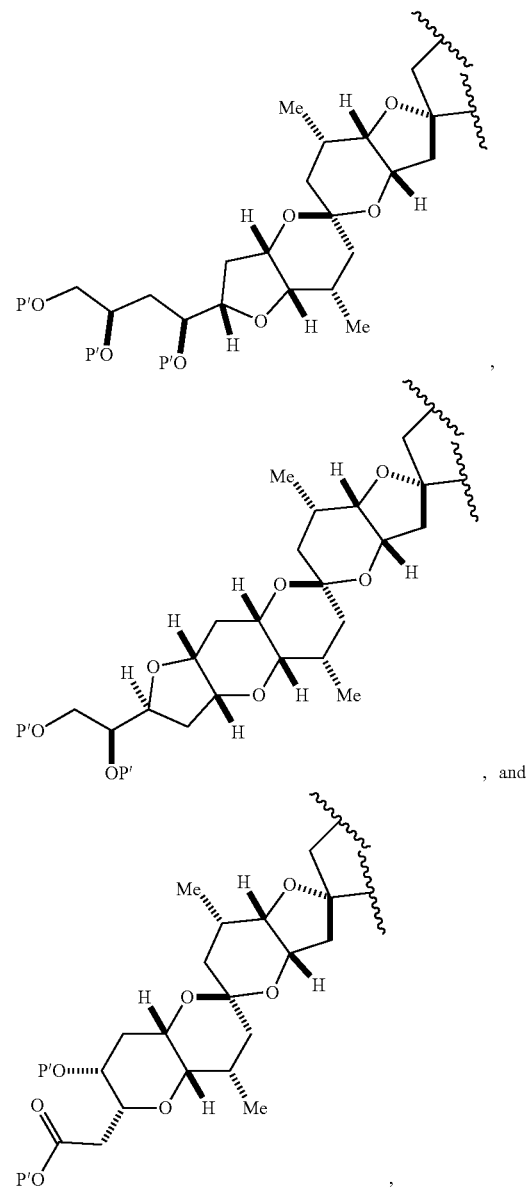

, and where each P' is independently H or a hydroxyl protecting group;
E is H, optionally substituted alkyl, or optionally substituted alkoxy;
G is O, S, $CH_2$, or $NR_N$, where $R_N$ is H, an N-protecting group, or optionally substituted alkyl;
each $Q_1$ is independently $OR_A$, $SR_A$, $SO_2R_A$, $OS_2R_A$, $NR_BR_A$, $NR_B(CO)R_A$, $NR_B(CO)(CO)R_A$, $NR_B(CO)NR_BR_A$, $NR_B(CO)OR_A$, $(CO)OR_A$, $O(CO)R_A$, $(CO)NR_BR_A$, or $O(CO)NR_BR_A$, where each of $R_A$ and $R_B$ is independently H, alkyl, haloalkyl, hydroxyalkyl, aminoalkyl, aryl, haloaryl, hydroxyaryl, alkoxyaryl, arylalkyl, alkylaryl, haloarylalkyl, alkylhaloaryl, (alkoxyaryl)alkyl, heterocyclic radical, or heterocyclic radical-alkyl;
n, when present, is 0, 1, or 2;
k is 0 or 1;
$X_1$ is —$CH_2$—, —CH(Y)—, —C(Y)$_2$—, or —O—, where each Y is independently —$COOR_C$ or —$SO_2R_D$;

X₄ is oxo, or X₄, together with the atom to which it is attached, is —(CH(OP₁₂))—, where P₁₂ is H or a hydroxyl protecting group;

each P₉ and R₁₃ is independently a hydroxyl protecting group;

(i) R₁₀ is a hydroxyl protecting group, R₁₁ is alkyl ether, and R₁₂ is H;

(ii) R₁₀ is a hydroxyl protecting group, and R₄ and R₅ combine to form a double bond; or (iii) R₁₀ and R₁₁ combine to form a bond, and R₁₂ is H;

R_{M1} is

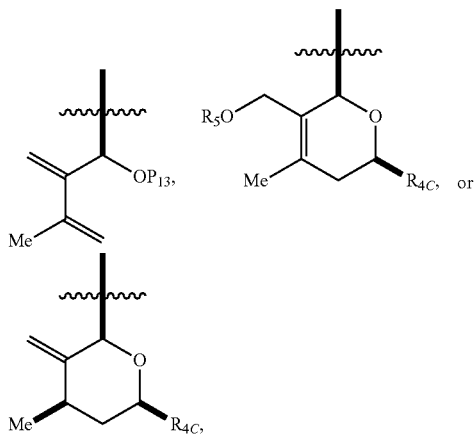

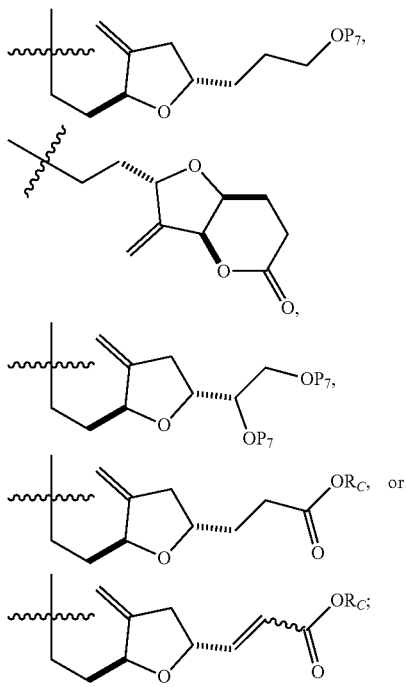

where
R₅ is optionally substituted acyl;
P₁₃ is H or a hydroxyl protecting group; and
R_{4C} is

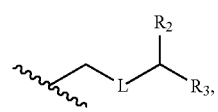

where R_C is optionally substituted alkyl, optionally substituted aryl, or optionally substituted arylalkyl; and P₇, when present, is independently H or a hydroxyl protecting group.

The compound of formula (IVAb) is:

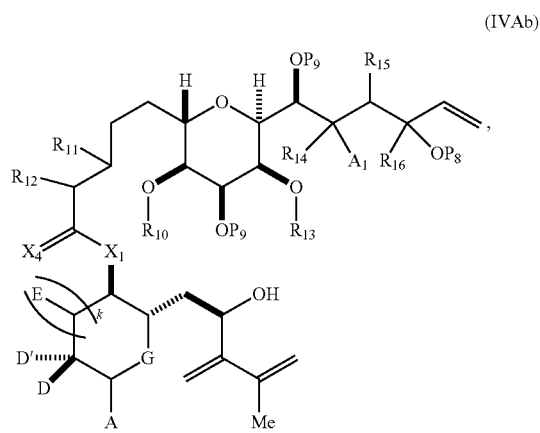

(IVAb)

where
each of D and D' is independently H, optionally substituted alkyl, or OP₁, provided that only one of D and D' is OP₁, where P₁ is H, alkyl, a hydroxyl protecting group, and A is a C₁₋₆ saturated or C₂₋₆ unsaturated hydrocarbon skeleton, the skeleton being unsubstituted or having from 1 to 10 substituents independently selected from the group consisting of cyano, halo, azido, oxo, and Q₁, or A is a group of formula (1):

(1)

where
L is —(CH(OP₂))—, —(C(OH)(OP₂))—, or —C(O)—;

R₂ is H and P₁ is absent, H, alkyl, or a hydroxyl protecting group, or R₂ and P₁ combine to form a bond;

(i) R₃ is H, and P₂ is absent, H, optionally substituted alkyl, or a hydroxyl protecting group;

(ii) R₃ is —(CH₂)ₙNP₃P₄, where P₃ is H or an N-protecting group, and (a) P₂ is absent, H, optionally substituted alkyl, or a hydroxyl protecting group, and P₄ is H or an N-protecting group, (b) P₂ and P₄ combine to form an alkylidene, or (c) each of P₂ and P₄ is H;

(iii) R₃ is —(CH₂)ₙOP₅, where P₂ is absent, H, optionally substituted alkyl, or a hydroxyl protecting group, and P₆ is H, optionally substituted alkyl, or a hydroxyl protecting group; or P₂ and P₅, together with the atoms to which each is attached, combine to form a ketal, a cyclic carbonate, a dicarbonyl-dioxo, or silylene-dioxo; or (iv) R₃ and P₂ combine to form an optionally substituted ethylene or a structure selected from the group consisting of:

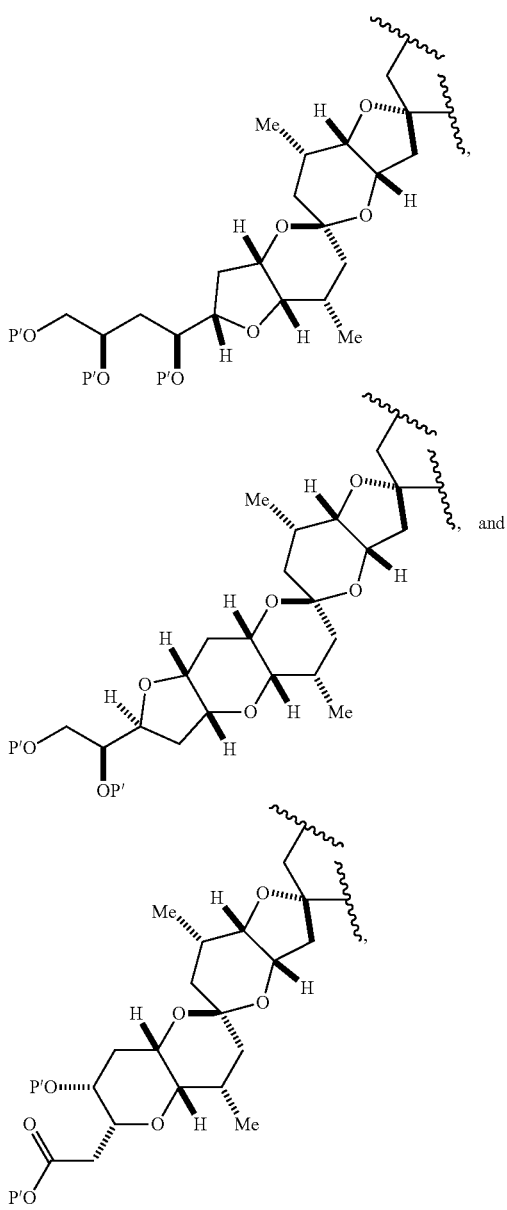

where each P' is independently H or a hydroxyl protecting group;

E is H, optionally substituted alkyl, or optionally substituted alkoxy;

G is O, S, CH$_2$, or NR$_N$, where R$_N$ is H, an N-protecting group, or optionally substituted alkyl;

each Q$_1$ is independently OR$_A$, SR$_A$, SO$_2$R$_A$, OSO$_2$R$_A$, NR$_B$R$_A$, NR$_B$(CO)R$_A$, NR$_B$(CO)(CO)R$_A$, NR$_B$(CO)NR$_B$R$_A$, NR$_B$(CO)OR$_A$, (CO)OR$_A$, O(CO)R$_A$, (CO)NR$_B$R$_A$, or O(CO)NR$_B$R$_A$, where each of R$_A$ and R$_B$ is independently H, alkyl, haloalkyl, hydroxyalkyl, aminoalkyl, aryl, haloaryl, hydroxyaryl, alkoxyaryl, arylalkyl, alkylaryl, haloarylalkyl, alkylhaloaryl, (alkoxyaryl)alkyl, heterocyclic radical, or heterocyclic radical-alkyl;

n, when present, is 0, 1, or 2;

k is 0 or 1;

X$_1$ is —CH$_2$—, —CH(Y)—, —C(Y)$_2$—, or —O—, where each Y is independently —COOR$_C$ or —SO$_2$R$_D$;

each R$_C$, when present, is independently optionally substituted alkyl, optionally substituted aryl, or optionally substituted arylalkyl;

each R$_D$, when present, is independently optionally substituted aryl or optionally substituted non-enolizable alkyl;

X$_4$ is oxo, or X$_4$, together with the atom to which it is attached, is —(CH(OP$_{12}$))—, where P$_{12}$ is H or a hydroxyl protecting group;

each P$_6$ is independently a hydroxyl protecting group;

(a1) R$_{10}$ is H or a hydroxyl protecting group, R$_{11}$ is alkyl ether, and R$_{12}$ is H;

(a2) R$_{10}$ is H or a hydroxyl protecting group, and R$_{11}$ and R$_{12}$ combine to form a double bond;
or (a3) R$_{10}$ and R$_{11}$ combine to form a bond, and R$_{12}$ is H;

(b1) A$_1$ and R$_{14}$ combine to form oxo, R$_{13}$ is H or a hydroxyl protecting group, and R$_{15}$ is H;
or (b2) A$_1$ is H or —OP''', and:
  (i) R$_{13}$ is H or a hydroxyl protecting group, and R$_{14}$ and R$_{15}$ combine to form a double bond;
  or
  (ii) R$_{13}$ and R$_{14}$ combine to form a bond, and R$_{15}$ is H or —OP'''; and (c1) R$_{16}$ is H, and P$_6$ is H or a hydroxyl protecting group;
or (c2) R$_{16}$ and P$_3$ combine to form a double bond;
and each P''', when present, is independently H or a hydroxyl protecting group.

The compound of formula (VAb) is:

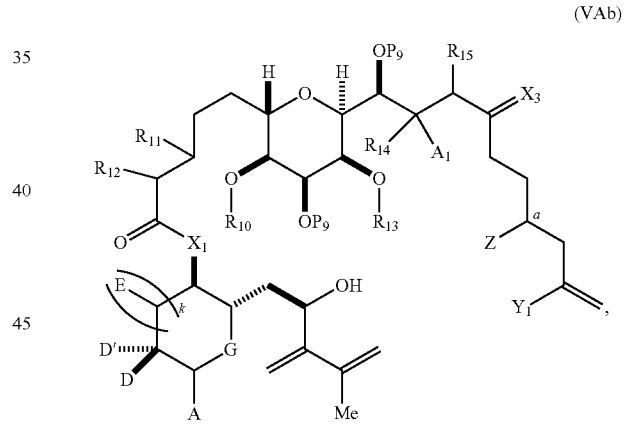

(VAb)

where each of D and D' is independently H, optionally substituted alkyl, or OP$_1$, provided that only one of D and D' is OP$_1$, where P$_1$ is H, alkyl, a hydroxyl protecting group, and A is a C$_{1-6}$ saturated or C$_{2-6}$ unsaturated hydrocarbon skeleton, the skeleton being unsubstituted or having from 1 to 10 substituents independently selected from the group consisting of cyano, halo, azido, oxo, and Q$_1$, or A is a group of formula (1):

(1)

where

L is —(CH(OP$_2$))—, —(C(OH)(OP$_2$))—, or —C(O)—;

R$_2$ is H and P$_1$ is absent, H, alkyl, or a hydroxyl protecting group, or R$_2$ and P$_1$ combine to form a bond;

(i) R$_3$ is H, and P$_2$ is absent, H, optionally substituted alkyl, or a hydroxyl protecting group;

(ii) R$_3$ is —(CH$_2$)$_n$NP$_3$P$_4$, where P$_3$ is H or an N-protecting group, and (a) P$_2$ is absent, H, optionally substituted alkyl, or a hydroxyl protecting group, and P$_4$ is H or an N-protecting group, (b) P$_2$ and P$_4$ combine to form an alkylidene, or (c) each of P$_2$ and P$_4$ is H;

(iii) R$_3$ is —(CH$_2$)$_n$OP$_5$, where P$_2$ is absent, H, optionally substituted alkyl, or a hydroxyl protecting group, and P$_5$ is H, optionally substituted alkyl, or a hydroxyl protecting group; or P$_2$ and P$_5$, together with the atoms to which each is attached, combine to form a ketal, a cyclic carbonate, a dicarbonyl-dioxo, or silylene-dioxo; or (iv) R$_3$ and P$_2$ combine to form an optionally substituted ethylene or a structure selected from the group consisting of:

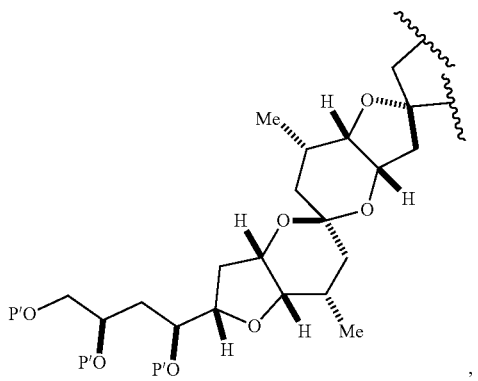

,

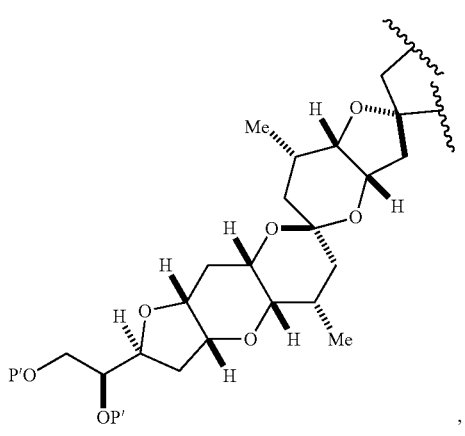

, and

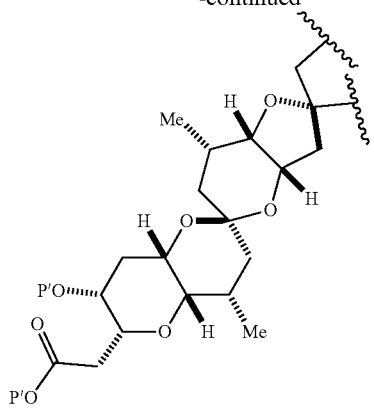

, where each P'' is independently H or a hydroxyl protecting group;

E is H, optionally substituted alkyl, or optionally substituted alkoxy;

G is O, S, CH$_2$, or NR$_N$, where R$_N$ is H, an N-protecting group, or optionally substituted alkyl;

each Q$_1$ is independently OR$_A$, SR$_A$, SO$_2$R$_A$, OSO$_2$R$_A$, NR$_B$R$_A$, NR$_B$(CO)R$_A$, NR$_B$(CO)(CO)R$_A$, NR$_B$(CO)NR$_B$R$_A$, NR$_B$(CO)OR$_A$, (CO)OR$_A$, O(CO)R$_A$, (CO)NR$_B$R$_A$, or O(CO)NR$_B$R$_A$, where each of R$_A$ and R$_B$ is independently H, alkyl, haloalkyl, hydroxyalkyl, aminoalkyl, aryl, haloaryl, hydroxyaryl, alkoxyaryl, arylalkyl, alkylaryl, haloarylalkyl, alkylhaloaryl, (alkoxyaryl)alkyl, heterocyclic radical, or heterocyclic radical-alkyl;

n, when present, is 0, 1, or 2;

k is 0 or 1;

a designates (R)-stereogenic center, and Z is a sulfonate, chloride, bromide, or iodide; or a designates (S)-stereogenic center, and Z is OR$_{16}$, where R$_{16}$ is a hydroxyl protecting group;

X$_1$ is —CH—, —CH(Y)—, —C(Y)$_2$—, or —O—, where each Y is independently —COOR$_C$ or —SO$_2$R$_D$;

each P$_9$ is independently a hydroxyl protecting group, and X$_3$ is oxo; or both P$_9$ groups and X$_3$, together with the atoms to which each is attached, combine to form ketal;

Y$_1$ is iodide, bromide, or trifluoromethanesulfonate;

each R$_C$, when present, is independently optionally substituted alkyl, optionally substituted aryl, or optionally substituted arylalkyl; and each R$_D$, when present, is independently optionally substituted aryl or optionally substituted non-enolizable alkyl;

(a1) R$_{10}$ is a hydroxyl protecting group, R$_{11}$ is alkyl ether, and R$_{12}$ is H;

(a2) R$_{10}$ is a hydroxyl protecting group, and R$_{11}$ and R$_{12}$ combine to form a double bond;
or
(a3) R$_{10}$ and R$_{11}$ combine to form a bond, and R$_{12}$ is H;

(b1) A$_1$ and R$_{14}$ combine to form oxo, R$_{13}$ is a hydroxyl protecting group, and R$_{15}$ is H;
or
(b2) A$_1$ is H or —OP''', and:
  (i) R$_{13}$ is a hydroxyl protecting group, and R$_{14}$ and R$_{15}$ combine to form a double bond;
  or
  (ii) R$_{13}$ and R$_{14}$ combine to form a bond, and R$_{15}$ is H or —OP''';

and
each P''' is independently a hydroxyl protecting group.
The compound of formula (IXD) is:

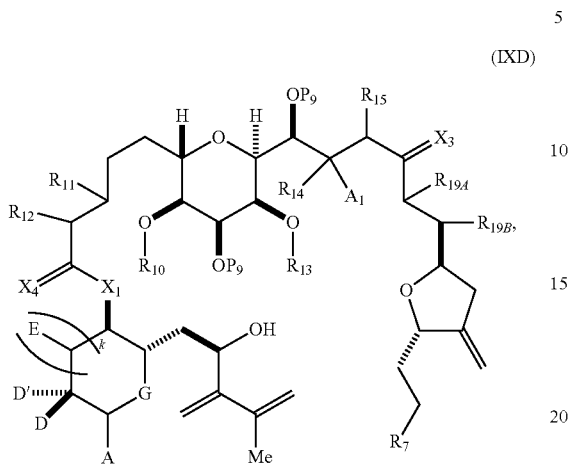
(IXD)

where
each of D and D' is independently H, optionally substituted alkyl, or $OP_1$, provided that only one of D and D' is $OP_1$, where $P_1$ is H, alkyl, a hydroxyl protecting group, and A is a $C_{1-6}$ saturated or $C_{2-6}$ unsaturated hydrocarbon skeleton, the skeleton being unsubstituted or having from 1 to 10 substituents independently selected from the group consisting of cyano, halo, azido, oxo, and $Q_1$, or A is a group of formula (1):

(1)

where
L is —(CH($OP_2$))—, —(C(OH)($OP_2$))—, or —C(O)—;
$R_2$ is H and $P_1$ is absent, H, alkyl, or a hydroxyl protecting group, or $R_2$ and $P_1$ combine to form a bond;
  (i) $R_3$ is H, and $P_2$ is absent, H, optionally substituted alkyl, or a hydroxyl protecting group;
  (ii) $R_3$ is —$(CH_2)_n NP_3 P_4$, where $P_3$ is H or an N-protecting group, and (a) $P_2$ is absent, H, optionally substituted alkyl, or a hydroxyl protecting group, and $P_4$ is H or an N-protecting group, (b) $P_2$ and $P_4$ combine to form an alkylidene, or (c) each of $P_2$ and $P_4$ is H;
  (iii) $R_3$ is —$(CH_2)_n OP_5$, where $P_2$ is absent, H, optionally substituted alkyl, or a hydroxyl protecting group, and $P_5$ is H, optionally substituted alkyl, or a hydroxyl protecting group; or $P_2$ and $P_5$, together with the atoms to which each is attached, combine to form a ketal, a cyclic carbonate, a dicarbonyl-dioxo, or silylene-dioxo; or
  (iv) $R_3$ and $P_2$ combine to form an optionally substituted ethylene or a structure selected from the group consisting of:

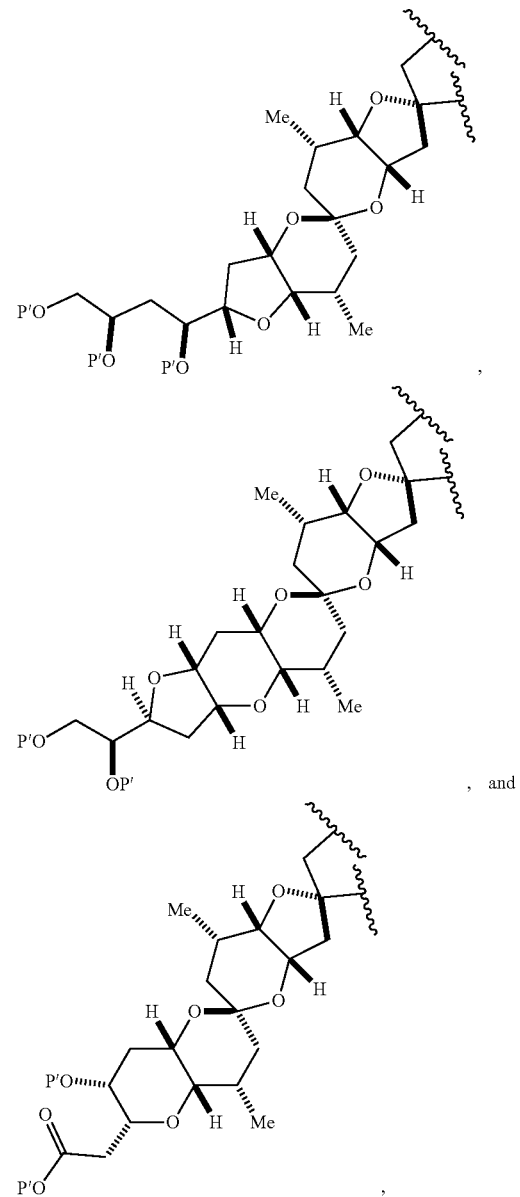
, and where each P' is independently H or a hydroxyl protecting group;
E is H, optionally substituted alkyl, or optionally substituted alkoxy;
G is O, S, $CH_2$, or $NR_N$, where $R_N$ is H, an N-protecting group, or optionally substituted alkyl;
each $Q_1$ is independently $OR_A$, $SR_A$, $SO_2R_A$, $OSO_2R_A$, $NR_B R_A$, $NR_B(CO)R_A$, $NR_B(CO)(CO)R_A$, $NR_B(CO)NR_B R_A$, $NR_B(CO)OR_A$, $(CO)OR_A$, $O(CO)R_A$, $(CO)NR_B R_A$, or $O(CO)NR_B R_A$, where each of $R_A$ and $R_B$ is independently H, alkyl, haloalkyl, hydroxyalkyl, aminoalkyl, aryl, haloaryl, hydroxyaryl, alkoxyaryl, arylalkyl, alkylaryl, haloarylalkyl, alkylhaloaryl, (alkoxyaryl)alkyl, heterocyclic radical, or heterocyclic radical-alkyl;
n, when present, is 0, 1, or 2;
k is 0 or 1;
$X_1$ is —$CH_2$—, —CH(Y)—, —$C(Y)_2$—, or —O—, each Y is independently —$COOR_C$ or —$SO_2R_D$;

each $R_C$, when present, is independently optionally substituted alkyl, optionally substituted aryl, or optionally substituted arylalkyl;

each $R_D$, when present, is independently optionally substituted aryl or optionally substituted non-enolizable alkyl;

$X_4$ is oxo, or $X_4$, together with the atom to which it is attached, is —(CH(OP$_{12}$))—, where $P_{12}$ is H or a hydroxyl protecting group;

$R_7$ is —CHO, —CH$_2$OP$_A$ or

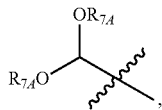

, where each $R_{7A}$ is independently an optionally substituted alkyl;

(i) $R_{10}$ is a hydroxyl protecting group, $R_{11}$ is alkyl ether, and $R_{12}$ is H;

(ii) $R_{10}$ is a hydroxyl protecting group, and $R_{11}$ and $R_{12}$ combine to form a double bond; or (iii) $R_{10}$ and $R_{11}$ combine to form a bond, and $R_{12}$ is H;

$A_1$ and $R_{14}$ combine to form oxo, $R_{13}$ is H or a hydroxyl protecting group, and $R_{15}$ is H;

or $A_1$ is H or —OP''', and (i) $R_{13}$ is H or a hydroxyl protecting group, and $R_{14}$ and $R_{15}$, together with the atoms to which each is attached, combine to form a double bond;

or (ii) $R_{13}$ and $R_{14}$ combine to form a bond, and $R_{15}$ is H or —OP'''; each $P_9$ is independently H or a hydroxyl protecting group, each $P_9$ is independently a hydroxyl protecting group, and $X_3$ is oxo, or $X_3$, together with the atom to which it is attached, combines to form —(CH(OP$_{11}$))—, where $P_{11}$ is H or a hydroxyl protecting group; or both $P_9$ and $X_3$, together with the atoms to which each is attached, combine to form a ketal; and $R_{19A}$ is H, —OP''', or Y, and $R_{19B}$ is H; or $R_{19A}$ and $R_{19B}$, together with the atoms to which each is attached, combine to form a double bond.

The compound of formula (IXF) is:

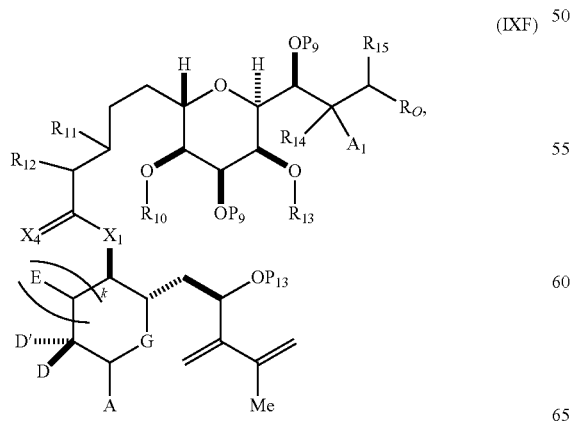

(IXF)

where each of D and D' is independently H, optionally substituted alkyl, or OP$_1$, provided that only one of D and D' is OP$_1$, where $P_1$ is H, alkyl, a hydroxyl protecting group, and A is a $C_{1-6}$ saturated or $C_{2-6}$ unsaturated hydrocarbon skeleton, the skeleton being unsubstituted or having from 1 to 10 substituents independently selected from the group consisting of cyano, halo, azido, oxo, and $Q_1$, or A is a group of formula (1):

(1)

where

L is —(CH(OP$_2$))—, —(C(OH)(OP$_2$))—, or —C(O)—;

$R_2$ is H and $P_1$ is absent, H, alkyl, or a hydroxyl protecting group, or $R_2$ and $P_1$ combine to form a bond;

(i) $R_3$ is H, and $P_2$ is absent, H, optionally substituted alkyl, or a hydroxyl protecting group;

(ii) $R_3$ is —(CH$_2$)$_n$NP$_3$P$_4$, where $P_3$ is H or an N-protecting group, and (a) $P_2$ is absent, H, optionally substituted alkyl, or a hydroxyl protecting group, and $P_4$ is H or an N-protecting group, (b) $P_2$ and $P_4$ combine to form an alkylidene, or (c) each of $P_2$ and $P_4$ is H;

(iii) $R_3$ is —(CH$_2$)$_n$OP$_5$, where $P_2$ is absent, H, optionally substituted alkyl, or a hydroxyl protecting group, and $P_6$ is H, optionally substituted alkyl, or a hydroxyl protecting group; or $P_2$ and $P_5$, together with the atoms to which each is attached, combine to form a ketal, a cyclic carbonate, a dicarbonyl-dioxo, or silylene-dioxo; or (iv) $R_3$ and $P_2$ combine to form an optionally substituted ethylene or a structure selected from the group consisting of:

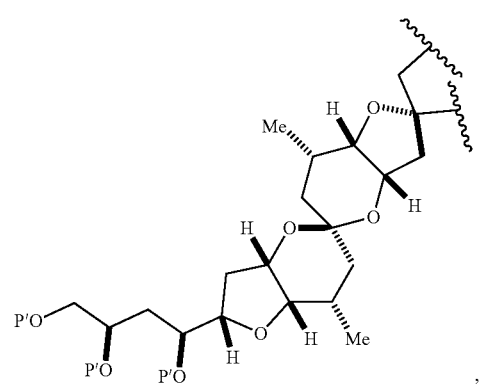

,

-continued

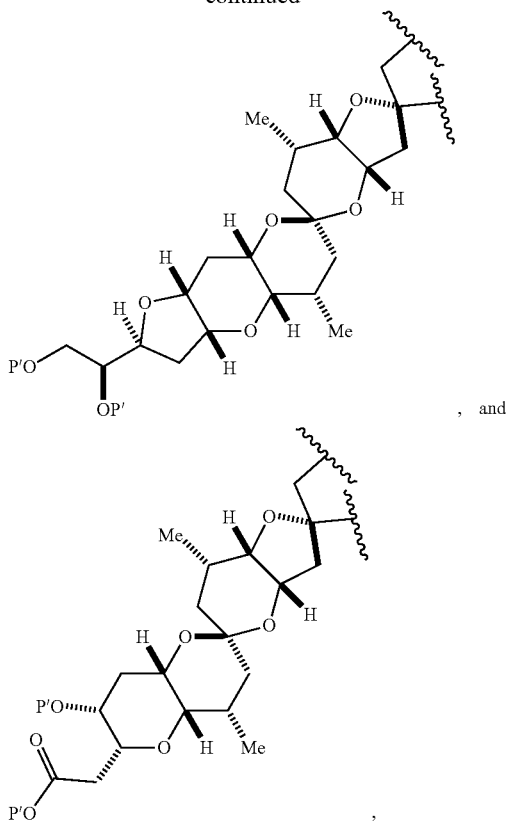, and where each P' is independently H or a hydroxyl protecting group;
E is H, optionally substituted alkyl, or optionally substituted alkoxy;
G is O, S, $CH_2$, or $NR_N$, where $R_N$ is H, an N-protecting group, or optionally substituted alkyl;
each $Q_1$ is independently $OR_A$, $SR_A$, $SO_2R_A$, $OSO_2R_A$, $NR_BR_A$, $NR_B(CO)R_A$, $NR_B(CO)(CO)R_A$, $NR_B(CO)NR_BR_A$, $NR_B(CO)OR_A$, $(CO)OR_A$, $O(CO)R_A$, $(CO)NR_BR_A$, or $O(CO)NR_BR_A$, where each of $R_A$ and $R_B$ is independently H, alkyl, haloalkyl, hydroxyalkyl, aminoalkyl, aryl, haloaryl, hydroxyaryl, alkoxyaryl, arylalkyl, alkylaryl, haloarylalkyl, alkylhaloaryl, (alkoxyaryl)alkyl, heterocyclic radical, or heterocyclic radical-alkyl;
n, when present, is 0, 1, or 2;
k is 0 or 1;
$X_1$ is $-CH_2-$, $-CH(Y)-$, $-C(Y)_2-$, or $-O-$, where each Y is independently $-COOR_C$ or $-SO_2R_D$;
$X_4$ is oxo, or $X_4$, together with the atom to which it is attached, is $-(CH(OP_{12}))-$, where $P_{12}$ is H or a hydroxyl protecting group;
each $R_C$, when present, is independently optionally substituted alkyl, optionally substituted aryl, or optionally substituted arylalkyl;
each $R_D$, when present, is independently optionally substituted aryl or optionally substituted non-enolizable alkyl;
$R_O$ is $-CHO$, $-CH_2OP''$, $-CH=CH_2$, $-CH(OP'')CH_2OP''$, $-C(O)-CH_2P(O)(OR_C)_2$, or halogen;
(i) $R_{10}$ is a hydroxyl protecting group, $R_{11}$ is alkyl ether, and $R_{12}$ is H;

(ii) $R_{10}$ is a hydroxyl protecting group, and $R_{11}$ and $R_{12}$ combine to form a double bond; or
(iii) $R_{10}$ and $R_{11}$ combine to form a bond, and $R_{12}$ is H;
$A_1$ and $R_{14}$ combine to form oxo, $R_{13}$ is H or a hydroxyl protecting group, and $R_{15}$ is H;
or
$A_1$ is H or $-OP''$, and
(i) $R_{13}$ is H or a hydroxyl protecting group, and $R_{14}$ and $R_{15}$, together with the atoms to which each is attached, combine to form a double bond;
or
(ii) $R_{13}$ and $R_{14}$ combine to form a bond, and $R_{15}$ is H or $-OP''$; each $P_9$ is independently H or a hydroxyl protecting group;
and
each of P'', $P_9$, and $P_{13}$ is independently H or a hydroxyl protecting group.
The compound of formula (IXG) is:

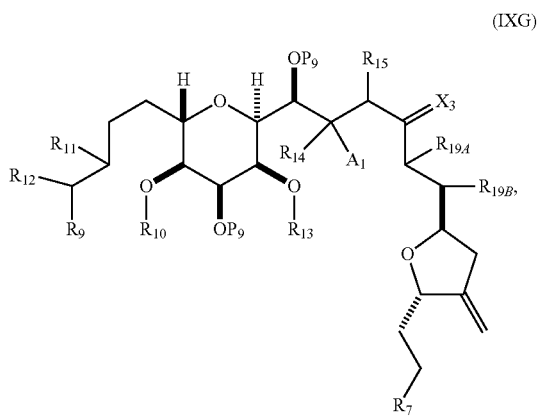

(IXG)

where
$R_7$ is $-CHO$, $-CH_2OP_A$, or

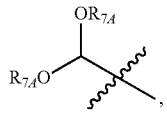, where each $R_{7A}$ is independently an optionally substituted alkyl;
(i) $R_{10}$ is a hydroxyl protecting group, $R_{11}$ is alkyl ether, and $R_{12}$ is H;
(ii) $R_{10}$ is a hydroxyl protecting group, and $R_{11}$ and $R_{12}$ combine to form a double bond; or
(iii) $R_{10}$ and $R_{11}$ combine to form a bond, and $R_{12}$ is H;
$A_1$ and $R_{14}$ combine to form oxo, $R_{13}$ is H or a hydroxyl protecting group, and $R_{15}$ is H;
or
$A_1$ is H or $-OP''$, and
(i) $R_{13}$ is H or a hydroxyl protecting group, and $R_{14}$ and $R_{15}$, together with the atoms to which each is attached, combine to form a double bond;
or
(ii) $R_{13}$ and $R_{14}$ combine to form a bond, and $R_{15}$ is H or $-OP''$; each $P_9$ is independently H or a hydroxyl protecting group,
each $P_9$ is independently a hydroxyl protecting group, and $X_3$ is oxo, or $X_3$, together with the atom to which it is attached, combines to form —(CH(OP$_{11}$))—, where P$_{11}$ is H or a hydroxyl protecting group; or both P$_9$ and X$_3$, together with the atoms to which each is attached, combine to form a ketal; and R$_{19A}$ is H, —OP''', or Y, and R$_{19B}$ is H; or R$_{19A}$ and R$_{19B}$, together with the atoms to which each is attached, combine to form a double bond.

In a yet further aspect, the invention provides a compound of formula (Z), (Z1), (Z2), (Z3), (Z4), (Z5), (Z5A), (Z5B), or (Z6), as described herein.

In the halichondrin macrolide and halichondrin macrolide analog structures herein, when P$_1$ is absent, each of D and D' is independently H or optionally substituted alkyl, and, when P$_2$ is absent, L is —C(O)—.

Definitions

Compounds useful in the invention may be isotopically labeled compounds. Useful isotopes include hydrogen, carbon, nitrogen, and oxygen (e.g., $^2$H, $^3$H, $^{13}$C, $^{14}$C, $^{15}$N, $^{18}$O, and $^{17}$O). Isotopically-labeled compounds can be prepared by synthesizing a compound using a readily available isotopically-labeled reagent in place of a non-isotopically-labeled reagent.

For any of the following chemical definitions, a number following an atomic symbol indicates that total number of atoms of that element that are present in a particular chemical moiety. As will be understood, other atoms, such as hydrogen atoms, or substituent groups, as described herein, may be present, as necessary, to satisfy the valences of the atoms. For example, an unsubstituted C$_2$ alkyl group has the formula —CH$_2$CH$_3$. When used with the groups defined herein, a reference to the number of carbon atoms includes the divalent carbon in acetal and ketal groups but does not include the carbonyl carbon in acyl, ester, carbonate, or carbamate groups. A reference to the number of oxygen, nitrogen, or sulfur atoms in a heteroaryl group only includes those atoms that form a part of a heterocyclic ring.

By "acetal" is meant —O—(CHR)—O—, where R is H, optionally substituted alkyl, optionally substituted alkenyl, optionally substituted aryl, or optionally substituted arylalkyl, or R group is a bond to an enumerated carbon atom, as shown in Chart 1, within the intermediate or within the halichondrin macrolide or analog thereof.

By "acetyl" is meant an acyl, in which R is —CX$_n$H$_{3-n}$, where n is 0, 1, 2, or 3, and each X is independently alkoxy or halogen, provided that, when n is 3, each X is independently halogen, and, when n is 2, either both of the X groups are independently halogen or both of the X groups are independently alkoxy. An acetyl group may be substituted (i.e., n is 1, 2, or 3) or unsubstituted (i.e., n is 0).

By "acyl" is meant —C(O)R, where R is H, alkyl, alkenyl, aryl, or arylalkyl. In exemplary acyl groups, R is H, C$_{1-12}$ alkyl (e.g., C$_{1-8}$, C$_{1-6}$, C$_{1-4}$, C$_{2-7}$, C$_{3-12}$, or C$_{3-6}$ alkyl), C$_{2-12}$ alkenyl (e.g., C$_{2-8}$, C$_{2-6}$, C$_{2-4}$, C$_{3-12}$, or C$_{3-6}$ alkenyl), C$_{6-20}$ aryl (e.g., C$_{6-14}$, C$_{6-10}$, C$_{8-20}$, or C$_{8-14}$ aryl), monocyclic C$_{1-6}$ heteroaryl (e.g., monocyclic C$_{1-4}$ or C$_{2-6}$ heteroaryl), C$_{4-19}$ heteroaryl (e.g., C$_{4-10}$ heteroaryl), (C$_{6-14}$)aryl(C$_{1-6}$)alkyl, (1-6)heteroaryl(C$_{1-6}$)alkyl, or (C$_{4-9}$)heteroaryl(C$_{1-6}$)alkyl. As defined herein, any heteroaryl group present in an acyl group has from 1 to 4 heteroatoms selected independently from O, N, and S. An acyl group can be unsubstituted or substituted (e.g., optionally substituted acyl). In the optionally substituted acyl group, the substituent R is H, optionally substituted alkyl, optionally substituted alkenyl, optionally substituted aryl, or optionally substituted arylalkyl. In some embodiments, acyl is C$_{2-10}$ acyl.

By "acylating agent" is meant a compound that reacts with an amine or a hydroxyl group to produce an amide or an ester, respectively. An acylating agent has a formula R-LG, where R is acyl, and LG is halogen, carbonate, or —OR', where R' is acyl.

By "alkoxide" is meant an anionic compound RO$^-$, where R is alkyl. A counterion for alkoxide can be an alkali metal cation, an alkali earth metal cation, or a tetraalkylammonium cation. Alkoxide can be optionally substituted in the same manner as alkyl.

By "alkoxy" is meant —OR, where R is alkyl. Alkoxy can be optionally substituted in the same manner as alkyl.

By "alkoxyalkyl" is meant —OR, where R is alkyl substituted by alkoxy. Each portion of the alkoxyalkyl can be optionally substituted in the same manner as alkyl.

By "alkoxyaryl" is meant —R'(R")$_n$, where n is 1 or 2, R' is arylene and R" is alkoxy, as defined herein. R' can be further optionally substituted in the same manner as aryl. R" can be optionally substituted in the same manner as alkyl.

By "alkoxyarylalkyl" is meant —R'(R"(R''')$_n$), where n is an integer from 1 to 3, R' is alkylene, R" is arylene, and R''' is alkoxy, as defined herein. R' can be optionally substituted in the same manner as alkyl. R" can be further optionally substituted in the same manner as aryl. R''' can be optionally substituted in the same manner as alkyl.

By "alkyl" is meant a straight or branched chain saturated cyclic (i.e., cycloalkyl) or acyclic hydrocarbon group of from 1 to 12 carbons, unless otherwise specified. In some embodiments, alkyl is C$_{1-6}$ alkyl. Exemplary alkyl groups include C$_{1-8}$, C$_{1-6}$, C$_{1-4}$, C$_{2-7}$, C$_{3-12}$, and C$_{3-6}$ alkyl. Specific examples include methyl, ethyl, 1-propyl, 2-propyl, 2-methyl-1-propyl, 1-butyl, 2-butyl, and the like. Alkyl group can be optionally substituted with 1, 2, 3, or 4 substituents selected from the group consisting of halogen, hydroxy, alkoxy, aryloxy, arylalkyloxy, amino, oxo, alkylthio, alkylenedithio, alkylamino, [alkenyl]alkylamino, [aryl] alkylamino, [arylalkyl]alkylamino, dialkylamino, silyl, sulfonyl, cyano, nitro, carboxyl, and azido.

By "alkylamino" is meant-NHR, where R is alkyl. By "[alkenyl]alkylamino" is meant-NRR', where R is alkyl, and R' is alkenyl. By "[aryl]alkylamino" is meant —NRR', where R is alkyl, and R' is aryl. By "[arylalkyl]alkylamino" is meant —NRR', where R is alkyl, and R' is arylalkyl. By "dialkylamino" is meant —NR$_2$, where each R is alkyl, selected independently.

By "alkylaryl" is meant —R'(R")$_n$, where n is an integer from 1 to 3, R' is arylene, and R" is alkyl. Alkylaryl can be optionally substituted in the same manner as defined for each R' and R" group.

By "alkylene" is meant a multivalent alkyl group. Alkylene groups can be optionally substituted in the same manner as alkyl groups. Alkylene may be a divalent alkylene. For example, a C$_1$ alkylene group is —CH$_2$—.

By "alkylenedithio" is meant —S-alkylene-S—. Alkylenedithio can be optionally substituted in the same manner as an alkylene group.

By "alkylhaloaryl" is meant —R'(R")$_n$—R''', where n is an integer from 1 to 5 and R' is arylene, R" is halogen, and R''' is alkylene, as defined herein. R' can be further optionally substituted in the same manner as aryl. R''' can be further optionally substituted in the same manner as alkyl.

By "alkylthio" is meant —SR, where R is alkyl. Alkylthio can be optionally substituted in the same manner as an alkyl group.

By "alkenyl" is meant a straight or branched chain cyclic or acyclic hydrocarbon group of, unless otherwise specified, from 2 to 12 carbons and containing one or more carbon-carbon double bonds. In some embodiments, alkenyl is $C_{2-6}$ alkenyl. Exemplary alkenyl groups include $C_{2-8}$, $C_{2-7}$, $C_{2-6}$, $C_{2-4}$, $C_{3-12}$, and $C_{3-6}$ alkenyl. Specific examples include ethenyl (i.e., vinyl), 1-propenyl, 2-propenyl (i.e., allyl), 2-methyl-1-propenyl, 1-butenyl, 2-butenyl (i.e., crotyl), and the like. Alkenyl group can be optionally substituted in the same manner as alkyl groups. Alkenyl groups, used in any context herein, may also be substituted with an aryl group.

By "amido" is meant —NHR, where R is acyl. Amido can be optionally substituted in the same manner as acyl.

By "aminal" is meant —O—CR$_2$—NR'—, where each R is independently H, optionally substituted alkyl, optionally substituted alkenyl, optionally substituted aryl, or optionally substituted arylalkyl, or both R groups are together optionally substituted alkylene, and R' is H or an N-protecting group. In particular, R' can be an N-protecting group (e.g., Boc).

By "amino" is meant —NR$_2$, where N and R$_2$ combine to form azido, or each R is independently H or an N-protecting group, or both R combine to form an N-protecting group. Amino can be unmasked, when each R is H, or masked, when at least one R is not H. Thus, optionally masked amino can be masked or unmasked amino.

By "aminoalkyl" is meant —R'(R'')$_n$, where n is 1 or 2, R' is alkylene, and R'' is amino, as defined herein. R' can be optionally substituted in the same manner as an alkyl group.

By "aryl" is meant a monocyclic or multicyclic ring system having one or more aromatic rings, where the ring system is carbocyclic. Exemplary aryl groups include $C_{6-20}$, $C_{6-15}$, $C_{6-10}$, $C_{8-20}$, and $C_{8-15}$ aryl. A preferred aryl group is a $C_{6-10}$ aryl group. Specific examples of carbocyclic aryl groups include phenyl, indanyl, indenyl, naphthyl, phenanthryl, anthracyl, and fluorenyl. Aryl group can be optionally substituted with 1, 2, 3, 4, or 5 substituents selected from the group consisting of alkyl, alkenyl, aryl, arylalkyl, halogen, alkoxy, aryloxy, arylalkyloxy, alkylthio, alkylenedithio, alkylamino, [alkenyl]alkylamino, [aryl]alkylamino, [arylalkyl]alkylamino, dialkylamino, silyl, sulfonyl, cyano, nitro, carboxyl, and azido.

By "arylalkyl" is meant —R'R'', where R' is alkylene, and R'' is aryl. Arylalkyl can be optionally substituted in the same manner as defined for each R' and R'' group.

By "arylalkyloxy" is meant —OR, where R is arylalkyl. Arylalkyloxy can be optionally substituted in the same manner as defined for arylalkyl.

By "arylene" is meant a multivalent aryl group. Arylene groups can be optionally substituted in the same manner as aryl groups. For example, a $C_6$ arylene group is phenylene.

By "aryloxy" is meant —OR, where R is aryl. Aryloxy can be optionally substituted in the same manner as aryl.

By "azido" is meant —N$_3$.

By "boronate" is meant —OB(R)O—, where R is alkyl, alkenyl, aryl, arylalkyl, alkoxy, or 2,6-diacetamidophenyl. Boronate can be substituted, when R is a substituted alkyl, substituted alkenyl, substituted aryl, substituted arylalkyl, or substituted alkoxy. Alternatively, boronate can be unsubstituted, when R is unsubstituted alkyl, unsubstituted alkenyl, aryl, unsubstituted arylalkyl, unsubstituted alkoxy, or 2,6-diacetamidophenyl.

By "carbamate" is meant a group, when a hydroxyl protecting group, having the formula —OC(O)NR$_2$, or, when an amine protecting group, having the formula —NR'—C(O)OR, where each R and R' is independently H, optionally substituted alkyl, optionally substituted alkenyl, optionally substituted aryl, or optionally substituted arylalkyl.

By "carbonate" is meant —OC(O)OR, where R is optionally substituted alkyl, optionally substituted alkenyl, optionally substituted aryl, or optionally substituted arylalkyl.

By "carbonyl" is meant —C(O)—.

By "carboxyl" is meant —C(O)OH, in free acid, ionized, or salt form.

By "carboxylic acid" is meant R—OH, where R is optionally substituted acyl.

By "carboxylic acid anhydride" is meant R—O—R, where each R is independently optionally substituted acyl.

By "cyclic carbonate" is meant —OC(O)O— that is part of a ring.

By "dicarbonyl" is meant —C(O)—C(O)—. Dicarbonyldioxo is —OC(O)—COO—.

By "ester" is meant —OC(O)R, where —C(O)R is an optionally substituted acyl group.

By "ether" is meant —OR, where R is alkyl, alkenyl, arylalkyl, silyl, or 2-tetrahydropyranyl. Ether can be optionally substituted as defined for each R group.

By "halichondrin macrolide" is meant a lactone including the structure of carbons 1-30 as shown in Chart 1, where carbons 29 and 30 form part of a five- or six-membered ring.

By "haloalkyl" is meant —R'(R'')$_n$, where n is an integer from 1 to 5 and R' is alkylene and R'' is halogen, as defined herein. R' can be further optionally substituted in the same manner as alkyl By "haloaryl" is meant —R'(R'')$_n$, where n is an integer from 1 to 5 and R' is arylene and R'' is halogen, as defined herein. R' can be further optionally substituted in the same manner as aryl.

By "haloarylalkyl" is meant —R'(R''(R''')$_n$), where n is an integer from 1 to 5 and R'' is alkylene, R'' is arylene, and R''' is halogen, as defined herein. R' can be further optionally substituted in the same manner as alkyl. R'' can be further optionally substituted in the same manner as aryl.

By "halogen" is meant fluoro, chloro, bromo, or iodo.

By "heterocyclic radical" is meant a 5-, 6- or 7-membered ring, unless otherwise specified, containing one, two, three, or four heteroatoms independently selected from the group containing nitrogen, oxygen, and sulfur. The 5-membered ring has zero to one double bonds, and the 6- and 7-membered rings have zero to two double bonds. Certain heterocyclyl groups include from 1 to 9 carbon atoms. Other such groups may include up to 12 carbon atoms. The term "heterocyclyl" also represents a heterocyclic compound having a bridged multicyclic structure in which one or more carbons and/or heteroatoms bridges two non-adjacent members of a monocyclic ring, e.g., a quinuclidinyl group. The term "heterocyclyl" includes bicyclic, tricyclic, and tetracyclic groups in which any of the above heterocyclic rings is fused to one, two, or three carbocyclic rings, e.g., an aryl ring, a cyclohexane ring, a cyclohexene ring, a cyclopentane ring, a cyclopentene ring, or another monocyclic heterocyclic ring, such as indolyl, quinolyl, isoquinolyl, tetrahydroquinolyl, benzofuryl, benzothienyl and the like. Examples of fused heterocyclyls include tropanes and 1,2,3,5,8,8a-hexahydroindolizine. Heterocyclics include pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, homopiperidinyl, pyrazinyl, piperazinyl, pyrimidinyl, pyridazinyl, oxazolyl, oxazolidinyl, isoxazolyl, isoxazolidiniyl, morpholinyl, thiomorpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl, thiazolidinyl, isothiazolyl, isoindazoyl, triazolyl, tetrazolyl, oxadiazolyl, purinyl, thiadiazolyl (e.g., 1,3, 4-thiadiazole), tetrahydrofuranyl, dihydrofuranyl, tetrahydrothienyl, dihydrothienyl, dihydroindolyl, tetrahydroquinolyl, tetrahydroisoquinolyl, pyranyl, dihydropyranyl, dithiazolyl, benzofuranyl, benzothienyl and the like. Still other exemplary heterocyclyls include: 2,3,4,5-tetrahydro-2-oxo-oxazolyl; 2,3-dihydro-2-oxo-1H-imidazolyl; 2,3,4,5-tetrahydro-5-oxo-1H-pyrazolyl (e.g., 2,3,4,5-tetrahydro-2-phenyl-5-oxo-1H-pyrazolyl); 2,3,4,5-tetrahydro-2,4-dioxo-1H-imidazolyl (e.g., 2,3,4,5-tetrahydro-2,4-dioxo-5-methyl-5-phenyl-1H-imidazolyl); 2,3-dihydro-2-thioxo-1,3,4-oxadiazolyl (e.g., 2,3-dihydro-2-thioxo-5-phenyl-1,3,4-oxadiazolyl); 4,5-dihydro-5-oxo-1H-triazolyl (e.g., 4,5-dihydro-3-methyl-4-amino 5-oxo-1H-triazolyl); 1,2,3,4-tetrahydro-2,4-dioxopyridinyl (e.g., 1,2,3,4-tetrahydro-2,4-dioxo-3,3-diethylpyridinyl); 2,6-dioxo-piperidinyl (e.g., 2,6-dioxo-3-ethyl-3-phenylpiperidinyl); 1,6-dihydro-6-oxopyridiminyl; 1,6-dihydro-4-oxopyrimidinyl (e.g., 2-(methylthio)-1,6-dihydro-4-oxo-5-methylpyrimidin-1-yl); 1,2,3,4-tetrahydro-2,4-dioxopyrimidinyl (e.g., 1,2,3,4-tetrahydro-2,4-dioxo-3-ethylpyrimidinyl); 1,6-dihydro-6-oxo-pyridazinyl (e.g., 1,6-dihydro-6-oxo-3-ethylpyridazinyl); 1,6-dihydro-6-oxo-1,2,4-triazinyl (e.g., 1,6-dihydro-5-isopropyl-6-oxo-1,2,4-triazinyl); 2,3-dihydro-2-oxo-1H-indolyl (e.g., 3,3-dimethyl-2,3-dihydro-2-oxo-1H-indolyl and 2,3-dihydro-2-oxo-3,3'-spiropropane-1H-indol-1-yl); 1,3-dihydro-1-oxo-2H-iso-indolyl; 1,3-dihydro-1,3-dioxo-2H-iso-indolyl; 1H-benzopyrazolyl (e.g., 1-(ethoxycarbonyl)-1H-benzopyrazolyl); 2,3-dihydro-2-oxo-1H-benzimidazolyl (e.g., 3-ethyl-2,3-dihydro-2-oxo-1H-benzimidazolyl); 2,3-dihydro-2-oxo-benzoxazolyl (e.g., 5-chloro-2,3-dihydro-2-oxo-benzoxazolyl); 2,3-dihydro-2-oxo-benzoxazolyl; 2-oxo-2H-benzopyranyl; 1,4-benzodioxanyl; 1,3-benzodioxanyl; 2,3-dihydro-3-oxo,4H-1,3-benzothiazinyl; 3,4-dihydro-4-oxo-3H-quinazolinyl (e.g., 2-methyl-3,4-dihydro-4-oxo-3H-quinazolinyl); 1,2,3,4-tetrahydro-2,4-dioxo-3H-quinazolyl (e.g., 1-ethyl-1,2,3,4-tetrahydro-2,4-dioxo-3H-quinazolyl); 1,2,3,6-tetrahydro-2,6-dioxo-7H-purinyl (e.g., 1,2,3,6-tetrahydro-1,3-dimethyl-2,6-dioxo-7H-purinyl); 1,2,3,6-tetrahydro-2,6-dioxo-1H-purinyl (e.g., 1,2,3,6-tetrahydro-3,7-dimethyl-2,6-dioxo-1H-purinyl); 2-oxobenz[c,d]indolyl; 1,1-dioxo-2H-naphth[1,8-c,d]isothiazolyl; and 1,8-naphthylenedicarboxamido. Heterocyclic groups also include groups of the formula

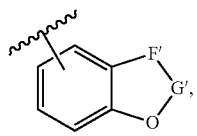

where

F' is selected from the group consisting of —CH$_2$—, —CH$_2$O— and —O—, and G' is selected from the group consisting of —C(O)— and —(C(R')(R"))$_v$—, where each of R' and R" is, independently, selected from the group consisting of hydrogen or alkyl of one to four carbon atoms, and v is one to three and includes groups, such as 1,3-benzodioxolyl, 1,4-benzodioxanyl, and the like. Any of the heterocyclyl groups mentioned herein may be optionally substituted with one, two, three, four or five substituents independently selected from the group consisting of: (1) alkanoyl (e.g., formyl, acetyl, and the like); (2) alkyl (e.g., alkoxyalkylene, alkylsulfinylalkylene, aminoalkylene, azidoalkylene, acylalkylene, haloalkylene (e.g., perfluoroalkyl), hydroxyalkylene, nitroalkylene, or thioalkoxyalkylene); (3) alkenyl; (4) alkynyl; (5) alkoxy (e.g., perfluoroalkoxy); (6) alkylsulfinyl; (7) aryl; (8) amino; (9) aryl-alkylene; (10) azido; (11) cycloalkyl; (12) cycloalkylalkylene; (13) cycloalkenyl; (14) cycloalkenyl-alkylene; (15) halo; (16) heterocyclyl (e.g., heteroaryl); (17) (heterocyclyl)oxy; (18) (heterocyclyl)aza; (19) hydroxy; (20) oxo; (21) nitro; (22) sulfide; (23) thioalkoxy; (24) —(CH$_2$)$_q$CO$_2$R$^A$, where q is an integer from zero to four, and R$^A$ is selected from the group consisting of (a) alkyl, (b) aryl, (c) hydrogen, and (d) aryl-alkylene; (25) —(CH$_2$)$_q$CONR$^B$R$^C$, where q is an integer from zero to four and where R$^B$ and R$^C$ are independently selected from the group consisting of (a) hydrogen, (b) alkyl, (c) aryl, and (d) aryl-alkylene; (26) —(CH$_2$)$_q$SO$_2$R$^D$, where q is an integer from zero to four and where R$^D$ is selected from the group consisting of (a) alkyl, (b) aryl, and (c) aryl-alkylene; (27) —(CH$_2$)$_q$SO$_2$NR$^E$R$^F$, where q is an integer from zero to four and where each of R$^E$ and R$^F$ is, independently, selected from the group consisting of (a) hydrogen, (b) alkyl, (c) aryl, and (d) aryl-alkylene; (28) thiol; (29) aryloxy; (30) cycloalkoxy; (31) arylalkoxy; (31) heterocyclyl-alkylene (e.g., heteroaryl-alkylene); (32) silyl; (33) cyano; and (34) —S(O)R$^H$ where R$^H$ is selected from the group consisting of (a) hydrogen, (b) alkyl, (c) aryl, and (d) aryl-alkylene. In some embodiments, each of these groups can be further substituted as described herein. For example, the alkylene group of an aryl-C$_1$-alkylene or a heterocyclyl-C$_1$-alkylene can be further substituted with an oxo group to afford the respective aryloyl and (heterocyclyl)oyl substituent group. In addition, when a heterocyclyl group is present in a bioreversible group of the invention it may be substituted with an ester, thioester, or disulfide group that is bound to a conjugating moiety, a hydrophilic functional group, or an auxiliary moiety as defined herein.

By "heterocyclic radical alkyl," as used herein, represents an alkyl group substituted with a heterocyclic radical. The heterocyclic radical and alkyl portions may be substituted as the individual groups as described herein.

By "hydroxyalkyl" is meant —R'(R")$_n$, where n 1 or 2, R' is alkylene and R" is hydroxyl, as defined herein. R' can be further optionally substituted in the same manner as alkyl.

By "hydroxyaryl" is meant —R'(R")$_n$, where n is 1 or 2, R' is arylene and R" is hydroxyl, as defined herein. R' can be further optionally substituted in the same manner as aryl.

By "hydroxyl" is meant —OH.

By "hydroxyl protecting group" is meant any group capable of protecting the oxygen atom to which it is attached from reacting or bonding. Hydroxyl protecting groups are known in the art, e.g., as described in Wuts, Greene's Protective Groups in Organic Synthesis, Wiley-Interscience, 4th Edition, 2006. Exemplary protecting groups (with the oxygen atom to which they are attached) are independently selected from the group consisting of esters, carbonates, carbamates, sulfonates, and ethers. In exemplary ester hydroxyl protecting groups, R of the acyl group is C$_{1-12}$ alkyl (e.g., C$_{1-8}$, C$_{1-6}$, C$_{1-4}$, C$_{2-7}$, C$_{3-12}$, and C$_{3-6}$ alkyl), C$_{2-12}$ alkenyl (e.g., C$_{2-8}$, C$_{2-6}$, C$_{2-4}$, C$_{3-12}$, and C$_{3-6}$ alkenyl), carbocyclic C$_{6-20}$ aryl (e.g., C$_{6-15}$, C$_{6-10}$, C$_{8-20}$, and C$_{8-15}$ aryl), monocyclic C$_{1-6}$ heteroaryl (e.g., C$_{1-4}$ and C$_{2-6}$ heteroaryl), C$_{4-19}$ heteroaryl (e.g., C$_{4-10}$ heteroaryl), (C$_{6-15}$)aryl (C$_{1-6}$)alkyl, (C$_{4-19}$)heteroaryl(C$_{1-6}$)alkyl, or (C$_{1-6}$)heteroaryl (C$_{1-6}$)alkyl. Specific examples of acyl groups for use in esters include formyl, benzoylformyl, acetyl (e.g., unsubstituted or chloroacetyl, trifluoroacetyl, methoxyacetyl, triphenylmethoxyacetyl, and p-chlorophenoxyacetyl), 3-phenylpropionyl, 4-oxopentanoyl, 4,4-(ethylenedithio)pentanoyl, pivaloyl (Piv), vinylpivaloyl, crotonoyl, 4-methoxy-crotonoyl, naphthoyl (e.g., 1- or 2-naphthoyl), and benzoyl (e.g., unsubstituted or substituted, e.g., p-methoxybenzoyl, phthaloyl (including salts, such a triethylamine and potassium), p-bromobenzoyl, and 2,4,6-trimethylbenzoyl). As defined herein, any heteroaryl group present in an ester group has from 1 to 4 heteroatoms selected independently from O, N, and S. In exemplary carbonate hydroxyl protecting groups, R is $C_{1-12}$ alkyl (e.g., $C_{1-8}$, $C_{1-6}$, $C_{1-4}$, $C_{2-7}$, $C_{3-12}$, and $C_{3-6}$ alkyl), $C_{2-12}$ alkenyl (e.g., $C_{2-8}$, $C_{2-6}$, $C_{2-4}$, $C_{3-12}$, and $C_{3-6}$ alkenyl), carbocyclic $C_{6-20}$ aryl (e.g., $C_{6-15}$, $C_{6-10}$, $C_{8-20}$, and $C_{8-15}$ aryl), monocyclic $C_{1-6}$ heteroaryl (e.g., $C_{1-4}$ and $C_{2-6}$ heteroaryl), $C_{4-19}$ heteroaryl (e.g., $C_{4-10}$ heteroaryl), ($C_{6-15}$)aryl($C_{1-6}$)alkyl, ($C_{4-19}$)heteroaryl($C_{1-6}$)alkyl, or ($C_{1-6}$)heteroaryl($C_{1-6}$)alkyl. Specific examples include methyl, 9-fluorenylmethyl, ethyl, 2,2,2-trichloroethyl, 2-(trimethylsilyl)ethyl, 2-(phenylsulfonyl)ethyl, vinyl, allyl, t-butyl, p-nitrobenzyl, and benzyl carbonates. As defined herein, any heteroaryl group present in a carbonate group has from 1 to 4 heteroatoms selected independently from O, N, and S. In exemplary carbamate hydroxyl protecting groups, each R is independently H, $C_{1-12}$ alkyl (e.g., $C_{1-8}$, $C_{1-6}$, $C_{1-4}$, $C_{2-7}$, $C_{3-12}$, and $C_{3-6}$ alkyl), $C_{2-12}$ alkenyl (e.g., $C_{2-8}$, $C_{2-6}$, $C_{2-4}$, $C_{3-12}$, and $C_{3-6}$ alkenyl), carbocyclic $C_{6-20}$ aryl (e.g., $C_{6-15}$, $C_{6-10}$, $C_{8-20}$, and $C_{8-15}$ aryl), monocyclic $C_{1-6}$ heteroaryl (e.g., $C_{1-4}$ and $C_{2-6}$ heteroaryl), $C_{4-19}$ heteroaryl (e.g., $C_{4-10}$ heteroaryl), ($C_{6-15}$)aryl($C_{1-6}$)alkyl, ($C_{4-19}$)heteroaryl($C_{1-6}$) alkyl, or ($C_{1-6}$)heteroaryl($C_{1-6}$)alkyl. Specific examples include N-phenyl and N-methyl-N-(o-nitrophenyl) carbamates. As defined herein, any heteroaryl group present in a carbamate group has from 1 to 4 heteroatoms selected independently from O, N, and S. Exemplary ether hydroxyl protecting groups include $C_{1-12}$ alkyl (e.g., $C_{1-8}$, $C_{1-6}$, $C_{1-4}$, $C_{2-7}$, $C_{3-12}$, and $C_{3-6}$ alkyl), $C_{2-12}$ alkenyl (e.g., $C_{2-8}$, $C_{2-6}$, $C_{2-4}$, $C_{3-12}$, and $C_{3-6}$ alkenyl), ($C_{6-15}$)aryl($C_{1-6}$)alkyl, ($C_{4-19}$)heteroaryl($C_{1-6}$)alkyl, ($C_{1-6}$)heteroaryl($C_{1-6}$)alkyl, ($C_{1-6}$)alkoxy($C_{1-6}$)alkyl, ($C_{1-6}$)alkylthio($C_{1-6}$)alkyl, ($C_{6-10}$)aryl($C_{1-6}$)alkoxy(16)alkyl, and silyl (e.g., tri($C_{1-6}$ alkyl)silyl, tri($C_{6-10}$ aryl or $C_{1-6}$ heteroaryl)silyl, di($C_{6-10}$ aryl or $C_{1-6}$ heteroaryl)($C_{1-6}$ alkyl)silyl, and ($C_{6-10}$ aryl or $C_{1-6}$ heteroaryl)di($C_{1-6}$ alkyl)silyl). Specific examples of alkylethers include methyl and t-butyl, and an example of an alkenyl ether is allyl. Ether hydroxyl protecting groups can be used to protect a carboxyl group (e.g., with a $C_{1-12}$ alkyl (e.g., $C_{1-8}$, $C_{1-6}$, $C_{1-4}$, $C_{2-7}$, $C_{3-12}$, and $C_{3-6}$ alkyl), ($C_{6-15}$)aryl ($C_{1-6}$)alkyl, ($C_{1-6}$)alkoxy($C_{1-6}$)alkyl, ($C_{1-6}$)alkylthio($C_{1-6}$) alkyl, or ($C_{6-10}$)aryl($C_{1-6}$)alkoxy($C_{1-6}$)alkyl). Examples of alkoxyalkyls and alkylthioalkyls that can be used as ether hydroxyl protecting groups include methoxymethyl, methylthiomethyl, (2-methoxyethoxy)methyl, and β-(trimethylsilyl)ethoxymethyl. Examples of arylalkyl groups that can be used as ether hydroxyl protecting groups include benzyl, p-methoxybenzyl (MPM), 3,4-dimethoxybenzyl, triphenylmethyl (trityl), o-nitrobenzyl, p-nitrobenzyl, p-halobenzyl, 2,6-dichlorobenzyl, p-cyanobenzyl, naphthylmethyl, and 2- and 4-picolyl ethers. Specific examples of silylethers include trimethylsilyl (TMS), triethylsilyl (TES), t-butyldimethylsilyl (TBS), t-butyldiphenylsilyl (TBDPS), triisopropylsilyl (TIPS), and triphenylsilyl (TPS) ethers. An example of an arylalkyloxyalkylether is benzyloxymethyl ether. As defined herein, any heteroaryl group present in an ether group has from 1 to 4 heteroatoms selected independently from O, N, and S. Vicinal or 1,3-diols may be protected with a diol protecting group (e.g., to produce a "cyclic protected diol"), such as acetal (e.g., containing $C_{1-6}$ alkylene), ketal (e.g., containing $C_{3-6}$ alkylene or $C_{3-6}$ cycloalkyl), cyclic silylene, cyclic carbonate, and cyclic boronate. Examples of acetal and ketal groups include methylene-dioxo, ethylidene-dioxo, benzylidene-dioxo, isopropylidene-dioxo, cyclohexylidene-dioxo, and cyclopentylidene-dioxo. An example of a cyclic silylene is di-t-butylsilylene. Another diol protecting group is 1,1,3,3-tetraisopropylsiloxanediyl. Examples of cyclic boronates include methyl, ethyl, phenyl, and 2,6-diacetamidophenyl boronates. Protecting groups may be substituted as is known in the art; for example, aryl and arylalkyl groups, such as phenyl, benzyl, naphthyl, or pyridinyl, can be substituted with $C_{1-6}$ alkyl, $C_{1-6}$ alkoxy, nitro, cyano, carboxyl, or halogen. Alkyl groups, such as methyl, ethyl, isopropyl, n-propyl, t-butyl, n-butyl, and sec-butyl, and alkenyl groups, such as vinyl and allyl, can also be substituted with oxo, arylsulfonyl, halogen, and trialkylsilyl groups. Preferred protecting groups are TBS and Piv. Protecting groups that are orthogonal are removed under different conditions, as is known in the art.

By "imido" is meant $—NR_2$, where each R is independently optionally substituted acyl.

By "ketal" is meant $—CR_2—O—$, where each R is independently optionally substituted alkyl, optionally substituted alkenyl, optionally substituted aryl, or optionally substituted arylalkyl, or both R groups are together optionally substituted alkylene, or each of the R groups is a bond to an enumerated carbon atom, as shown in Chart 1, within the intermediate or within the halichondrin macrolide or analog thereof.

By "macrocyclic" is meant a compound containing at least one n-membered ring, where n is equal to or greater than 10.

By "non-enolizable" is meant a group that, either alone or in combination with a group to which it is attached, cannot form an enol through a deprotonation/reprotonation sequence. For example, a "non-enolizable alkyl" can be bonded to a sulfone group or to a carbonyl group through a quaternary carbon atom (i.e., the carbon atom that is not bonded to a hydrogen atom).

By "N-protecting group" is meant a group protecting a nitrogen atom in a molecule from participating in one or more undesirable reactions during chemical synthesis (e.g., oxidation reactions, or certain nucleophilic and electrophilic substitutions). Commonly used N-protecting groups are disclosed in Wuts, Greene's Protective Groups in Organic Synthesis, Wiley-Interscience, 4th Edition, 2006. Exemplary N-protecting groups include acyl (e.g., formyl, acetyl, trifluoroacetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, and 4-bromobenzoyl); sulfonyl-containing groups (e.g., benzenesulfonyl, p-toluenesulfonyl, o-nitrobenzenesulfonyl, and p-nitrobenzenesulfonyl); carbamate forming groups (e.g., benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyl oxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxy carbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, and phenylthiocarbonyl), arylalkyl (e.g., triphenylmethyl); silyl groups (e.g., trimethylsilyl); and imine-forming groups (e.g., diphenylmethylene). Preferred N-protecting groups are acetyl, benzoyl, phenylsulfonyl, p-toluenesulfonyl, p-nitrobenzenesulfonyl, o-nitrobenzenesulfonyl, t-butyloxycarbonyl (Boc), and benzyloxycarbonyl (Cbz).

By "oxo" or (O) is meant =O.

By "pharmaceutically acceptable salt" is meant a salt within the scope of sound medical judgment, suitable for use in contact with the tissues of humans and animals without undue toxicity, irritation, allergic response and the like and commensurate with a reasonable benefit/risk ratio. Pharmaceutically acceptable salts are well known in the art. For example, pharmaceutically acceptable salts are described in: Berge et al., J. Pharmaceutical Sciences 66:1-19, 1977 and in Pharmaceutical Salts: Properties, Selection, and Use, (Eds. P. H. Stahl and C. G. Wermuth), Wiley-VCH, 2008. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts and the like. A preferred salt is the mesylate salt.

By "pseudohalogen" is meant —O—SO$_2$R, where R is optionally substituted alkyl, optionally substituted aryl, or optionally substituted arylalkyl. Non-limiting examples of pseudohalogens include trifluoromethanesulfonate and nonaflate.

By "silyl" is meant —SiR$_3$, where each R is independently alkyl, alkenyl, aryl, or arylalkyl. Examples of silyl groups include tri(C$_{1-6}$ alkyl)silyl, tri(C$_{6-10}$ aryl or C$_{1-6}$ heteroaryl)silyl, di(C$_{6-10}$ aryl or C$_{1-6}$ heteroaryl)(C$_{1-6}$ alkyl) silyl, and (C$_{6-10}$ aryl or C$_{1-6}$ heteroaryl)di(C$_{1-6}$ alkyl)silyl. It will be understood that, when a silyl group includes two or more alkyl, alkenyl, aryl, heteroaryl, or arylalkyl groups, these groups are independently selected. As defined herein, any heteroaryl group present in a silyl group has from 1 to 4 heteroatoms selected independently from 0, N, and S. Silyl can be optionally substituted in the same manner as defined for each R group.

By "silylene" is meant —SiR$_2$—, where each R is independently alkyl, alkenyl, aryl, arylalkyl, or alkoxy. By "dialkylsilylene" is meant a silylene, where each R is alkyl. Silylene can be optionally substituted in the same manner as defined for each R group. Silylene-dioxo is a group having the formula —O—SiR$_2$—O—.

By "strong base" is meant a Brønsted base, the conjugate acid of which has pKa that is greater than or equal to 13. Non-limiting examples of strong bases include alkyl alkali metals (e.g., butyl lithium or Schlosser's base), Grignard reagents (e.g., alkyl magnesium halide), alkali or alkali earth alkoxides, alkali or alkali earth amides (e.g., diisopropylamide, tetramethylpiperidide, or bis(trimethylsilyl)amide), and phosphazene bases (e.g., Schwesinger base). Non-limiting examples of the alkali amides are lithium diisopropylamide, lithium tetramethylpiperidide, lithium bis(trimethylsilyl)amide, sodium bis(trimethylsilyl)amide, and potassium bis(trimethylsilyl)amide.

By "sulfonamide" is meant —NR, where R is sulfonyl.

By "sulfonate" is meant —OS(O)$_2$R, where R is optionally substituted alkyl, optionally substituted alkenyl, optionally substituted aryl, or optionally substituted arylalkyl. In exemplary sulfonates, R is C$_{1-12}$ alkyl (e.g., C$_{1-8}$, C$_{1-6}$, C$_{1-4}$, C$_{2-7}$, C$_{3-12}$, or C$_{3-6}$ alkyl), C$_{2-12}$ alkenyl (e.g., C$_{2-8}$, C$_{2-6}$, C$_{2-4}$, C$_{3-12}$, or C$_{3-6}$ alkenyl), carbocyclic C$_{6-20}$ aryl (e.g., C$_{6-15}$, C$_{6-10}$, C$_{8-20}$, or C$_{8-15}$ aryl), monocyclic C$_{1-6}$ heteroaryl (e.g., C$_{1-4}$ and C$_{2-6}$ heteroaryl), C$_{4-19}$ heteroaryl (e.g., C$_{4-10}$ heteroaryl), (C$_{6-15}$)aryl(C$_{1-6}$)alkyl, (C$_{4-19}$)heteroaryl(C$_{1-6}$)alkyl, or (C$_{1-6}$)heteroaryl(C$_{1-6}$)alkyl. As defined herein, any heteroaryl group present in a sulfonate group has from 1 to 4 heteroatoms selected independently from O, N, and S.

By "sulfonyl" is meant —S(O)$_2$R, where R is optionally substituted alkyl, optionally substituted alkenyl, optionally substituted aryl, optionally substituted arylalkyl, or silyl. Preferred R groups for sulfonyl are the same as those described above for sulfonates.

By "thioacetal" is meant —S—(CHR)—S—, where R is H, optionally substituted alkyl, optionally substituted alkenyl, optionally substituted aryl, or optionally substituted arylalkyl.

By "thioketal" is meant —S—(CR$_2$)—S—, where each R is independently optionally substituted alkyl, optionally substituted alkenyl, optionally substituted aryl, or optionally substituted arylalkyl.

By "triflate" is meant trifluoromethanesulfonate.

The pKa values recited herein refer to the pKa values of a conjugate Brønsted acid in water at room temperature, unless stated otherwise.

References to compounds described herein encompass their salts, where applicable.

DETAILED DESCRIPTION

The present invention provides compounds and methods that may be useful in the synthesis of halichondrin macrolides and analogs thereof (see Chart 1). Preferably, the halichondrin macrolide analog is eribulin or a salt thereof (e.g., eribulin mesylate). Preferably, the halichondrin macrolide is a halichondrin B macrolide. The carbon-atom numbering schemes for a halichondrin macrolide and analog thereof are shown in Chart 1.

Chart 1

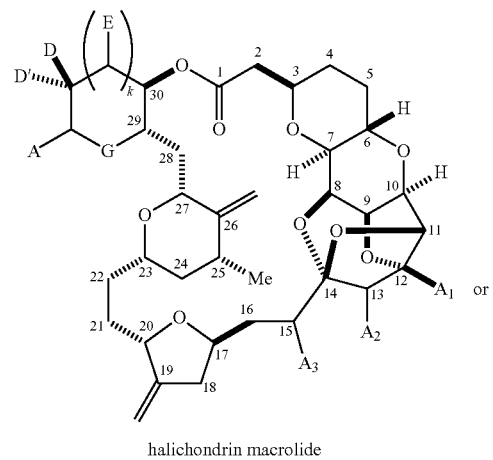

halichondrin macrolide

-continued

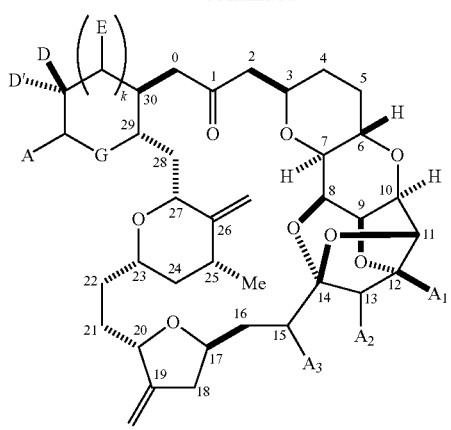

halichondrin macrolide analog

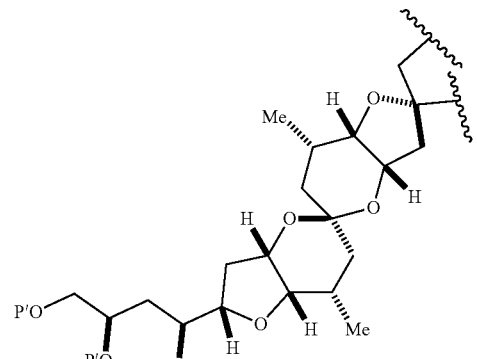

,

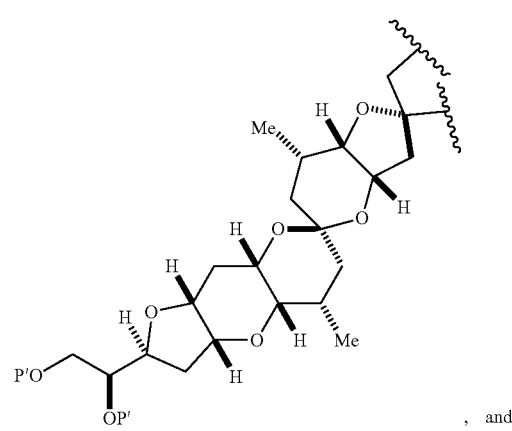

, and

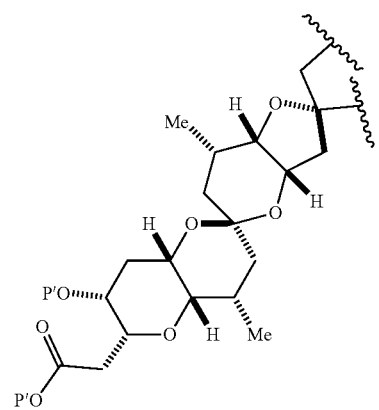

, in which each of D and D' is independently H, optionally substituted alkyl, or $OP_1$, provided that only one of D and D' is $OP_1$, where $P_1$ is H, alkyl, a hydroxyl protecting group, and A is a $C_{1-6}$ saturated or $C_{2-6}$ unsaturated hydrocarbon skeleton, the skeleton being unsubstituted or having from 1 to 10 substituents independently selected from the group consisting of cyano, halo, azido, oxo, and 1, or A is a group of formula (1):

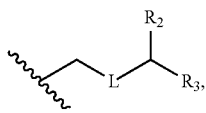
(1)

where
L is —(CH($OP_2$))—, —(C(OH)($OP_2$))—, or —C(O)—;
$R_2$ is H and $P_1$ is absent, H, alkyl, or a hydroxyl protecting group, or $R_2$ and $P_1$ combine to form a bond;
  (i) $R_3$ is H, and $P_2$ is absent, H, optionally substituted alkyl, or a hydroxyl protecting group;
  (ii) $R_3$ is —$(CH_2)_n NP_3 P_4$, where $P_3$ is H or an N-protecting group, and (a) $P_2$ is absent, H, optionally substituted alkyl, or a hydroxyl protecting group, and $P_4$ is H or an N-protecting group, (b) $P_2$ and $P_4$ combine to form an alkylidene, or (c) each of $P_2$ and $P_4$ is H;
  (iii) $R_3$ is —$(CH_2)_n OP'''$, where $P_2$ is absent, H, optionally substituted alkyl, or a hydroxyl protecting group, and $P_6$ is H, optionally substituted alkyl, or a hydroxyl protecting group; or $P_2$ and $P_5$, together with the atoms to which each is attached, combine to form a ketal, a cyclic carbonate, a dicarbonyl-dioxo, or silylene-dioxo; or
  (iv) $R_3$ and $P_2$ combine to form an optionally substituted ethylene or a structure selected from the group consisting of:

where each P' is independently H or a hydroxyl protecting group;
each of $A_1$, $A_2$, and $A_3$ is independently H or OP'', where each P'' is independently H or a hydroxyl protecting group;
E is H, optionally substituted alkyl, or optionally substituted alkoxy;
G is O, S, $CH_2$, or $NR_N$, where $R_N$ is H, an N-protecting group, or optionally substituted alkyl;
each $Q_1$ is independently $OR_A$, $SR_A$, $SO_2 R_A$, $OSO_2 R_A$, $NR_B R_A$, $NR_B(CO)R_A$, $NR_B(CO)(CO)R_A$, $NR_B(CO)NR_B R_A$, $NR_B(CO)OR_A$, $(CO)OR_A$, $O(CO)R_A$, (CO)

$NR_BR_A$, or $O(CO)NR_BR_A$, where each of $R_A$ and $R_B$ is independently H, alkyl, haloalkyl, hydroxyalkyl, aminoalkyl, aryl, haloaryl, hydroxyaryl, alkoxyaryl, arylalkyl, alkylaryl, haloarylalkyl, alkylhaloaryl, (alkoxyaryl)alkyl, heterocyclic radical, or heterocyclic radical-alkyl;

n, when present, is 0, 1, or 2; and k is 0 or 1.

In the halichondrin macrolide and halichondrin macrolide analog structures, when $P_1$ is absent, each of D and D' is independently H or optionally substituted alkyl, and, when $P_2$ is absent, L is —C(O)—.

Prins Reaction

In one aspect, the invention provides a compound of formula (A) and methods of its preparation. The compound of formula (A) may be prepared from a compound of formula (B), a compound of formula (C), and $R_5OH$, where $R_5$ is optionally substituted acyl. For example, a compound of formula (B), a compound of formula (C), and $R_5OH$ may be subjected to Prins reaction conditions, e.g., as known in the art. For example, the compound of formula (B), the compound of formula (C), and $R_5OH$ may be reacted with a Lewis acid (e.g., an oxophilic Lewis acid (e.g., boron trifluoride or solvate thereof)).

The compound of formula (A) is:

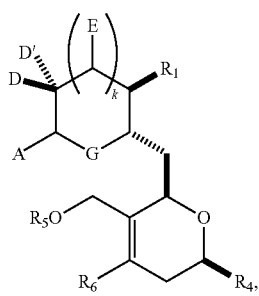

(A)

where each of D and D' is independently H, optionally substituted alkyl, or $OP_1$, provided that only one of D and D' is $OP_1$, where $P_1$ is H, alkyl, a hydroxyl protecting group, and A is a $C_{1-6}$ saturated or $C_{2-6}$ unsaturated hydrocarbon skeleton, the skeleton being unsubstituted or having from 1 to 10 substituents independently selected from the group consisting of cyano, halo, azido, oxo, and $Q_1$, or A is a group of formula (1):

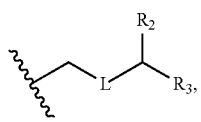

(1)

where

L is —(CH(OP$_2$))—, —(C(OH)(OP$_2$))—, or —C(O)—;

$R_2$ is H and $P_1$ is absent, H, alkyl, or a hydroxyl protecting group, or $R_2$ and $P_1$ combine to form a bond;

(i) $R_3$ is H, and $P_2$ is absent, H, optionally substituted alkyl, or a hydroxyl protecting group;

(ii) $R_3$ is —(CH$_2$)$_n$NP$_3$P$_4$, where $P_3$ is H or an N-protecting group, and (a) $P_2$ is absent, H, optionally substituted alkyl, or a hydroxyl protecting group, and $P_4$ is H or an N-protecting group, (b) $P_2$ and $P_4$ combine to form an alkylidene, or (c) each of $P_2$ and $P_4$ is H;

(iii) $R_3$ is —(CH$_2$)$_n$OP$_5$, where $P_2$ is absent, H, optionally substituted alkyl, or a hydroxyl protecting group, and $P_6$ is H, optionally substituted alkyl, or a hydroxyl protecting group; or $P_2$ and $P_5$, together with the atoms to which each is attached, combine to form a ketal, a cyclic carbonate, a dicarbonyl-dioxo, or silylene-dioxo; or (iv) $R_3$ and $P_2$ combine to form an optionally substituted ethylene or a structure selected from the group consisting of:

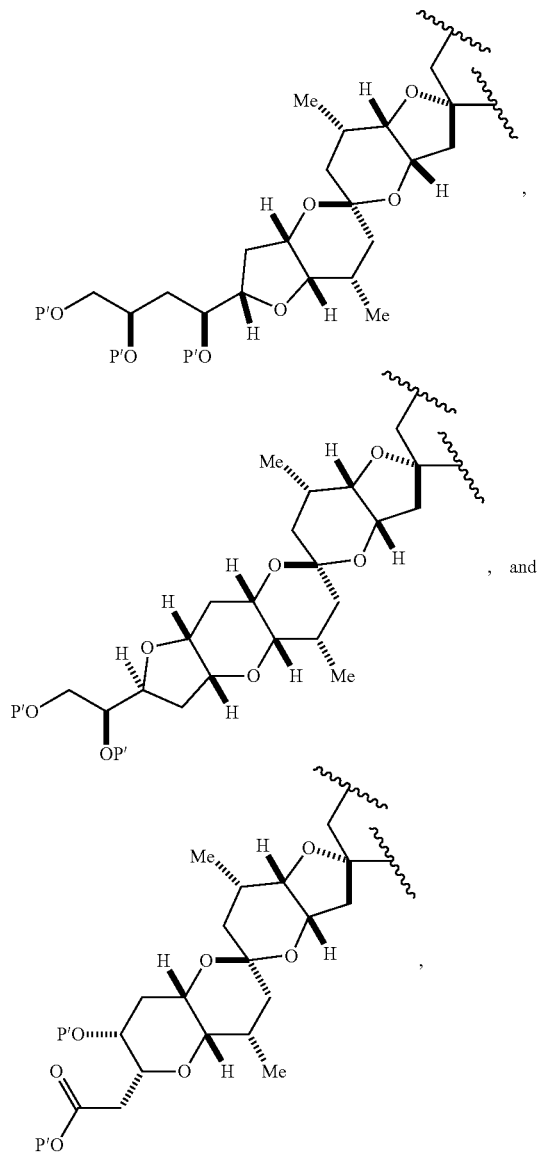

where each P'' is independently H or a hydroxyl protecting group;

E is H, optionally substituted alkyl, or optionally substituted alkoxy;

G is O, S, CH$_2$, or NR$_N$, where R$_N$ is H, an N-protecting group, or optionally substituted alkyl;

each Q$_1$ is independently OR$_A$, SR$_A$, SO$_2$R$_A$, OSO$_2$R$_A$, NR$_B$R$_A$, NR$_B$(CO)R$_A$, NR$_B$(CO)(CO)R$_A$, NR$_B$(CO)NR$_B$R$_A$, NR$_B$(CO)OR$_A$, (CO)OR$_A$, O(CO)R$_A$, (CO)NR$_B$R$_A$, or O(CO)NR$_B$R$_A$, where each of R$_A$ and R$_B$ is independently H, alkyl, haloalkyl, hydroxyalkyl, aminoalkyl, aryl, haloaryl, hydroxyaryl, alkoxyaryl, arylalkyl, alkylaryl, haloarylalkyl, alkylhaloaryl, (alkoxyaryl)alkyl, heterocyclic radical, or heterocyclic radical-alkyl;

n, when present, is 0, 1, or 2;

k is 0 or 1;

R$_1$ is —OP$_6$, —CH(Y)$_2$, or —CH$_2$(Y), where P$_6$ is H or a hydroxyl protecting group;

R$_4$ is optionally substituted alkyl, optionally substituted alkenyl, optionally substituted alkynyl,

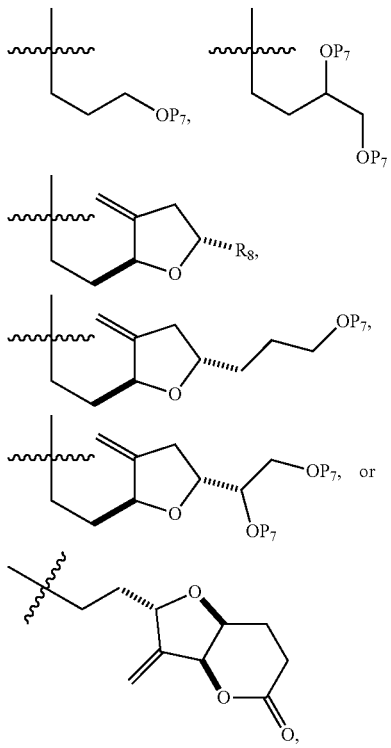

where
each P$_7$ is independently H or a hydroxyl protecting group; and
R$_8$ is —CH$_2$CH$_2$—COOR$_C$, —CH=CH—COOR$_C$, —CH$_2$CH$_2$—SO$_2$R$_D$, or —CH=CH—SO$_2$R$_D$;

R$_5$ is optionally substituted acyl;

R$_6$ is H, optionally substituted alkyl, or optionally substituted arylalkyl;

each Y is independently —COOR$_C$ or —SO$_2$R$_D$;

each R$_C$, when present, is independently optionally substituted alkyl, optionally substituted aryl, or optionally substituted arylalkyl; and each R$_D$, when present, is independently optionally substituted aryl or optionally substituted non-enolizable alkyl.

In the compound of formula (A), when P$_1$ is absent, each of D and D' is independently H or optionally substituted alkyl, and, when P$_2$ is absent, L is —C(O)—.

The compound of formula (B) is:

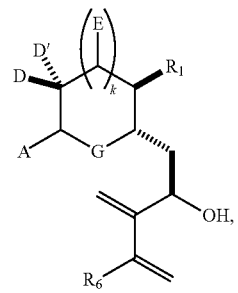

(B)

where all variables are as described for formula (A).

The compound of formula (C) is:

R$_4$-R$_7$, (C)

where
R$_7$ is —CHO or

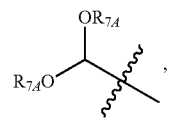

where each R$_{7A}$ is independently an optionally substituted alkyl, and
R$_4$ is as described for the compound of formula (A).

The compound of formula (B) may be prepared from a compound of formula (D) and a compound of formula (E). For example, the compound of formula (D) and the compound of formula (E) may be subjected to Sakurai reaction conditions, e.g., as known in the art. In certain embodiments, the compound of formula (D) may be reacted with the compound of formula (E) and a Lewis acid (e.g., an oxophilic Lewis acid (e.g., boron trifluoride or a solvate thereof)) to produce the compound of formula (B).

The compound of formula (D) is:

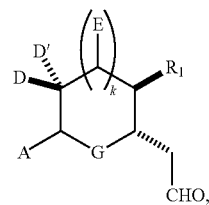

(D)

where
all variables are as described for the compound of formula (B).

The compound of formula (E) is:

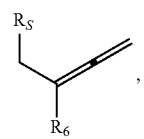

(E)

where $R_S$ is silyl (e.g., $Me_3Si$—); and $R_6$ is as described for the compound of formula (B).

The Sakurai reaction producing the compound of formula (B) introduces the secondary alcohol stereogenic center in the compound of formula (B). If the stereoselectivity of the Sakurai reaction is less than desirable, the Sakurai reaction product can be subjected to epimerization to enrich the product in the compound of formula (B) relative to its diastereomer. In a non-limiting example, the Sakurai reaction products (the compound of formula (B) and its C.27 diastereomer) can be reacted with an oxidizing agent capable of converting an alcohol to a carbonyl group (e.g., Dess-Martin periodinane) to give a compound of formula (F), and the compound (F) can then be subjected to enantioselective 1,2-reduction reaction conditions (e.g., Corey-Bakshi-Shibata reaction). Alternatively, if the diastereoselectivity of the Sakurai reaction favors the formation of the diastereomer of the compound of formula (B), the Mitsunobu reaction may be used to invert the secondary alcohol stereocenter in a diastereomeric Sakurai reaction product mixture.

The compound of formula (F) is:

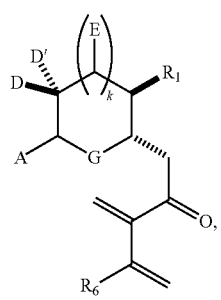

(F)

where all variables are as described for formula (B).

Enantioselective 1,2-reduction reaction conditions are known in the art. In a non-limiting example, the enantioselective 1,2-reduction reaction is Corey-Bakshi-Shibata reaction. Corey-Bakshi-Shibata reduction can include reacting a ketone with CBS catalyst and borane or a solvate thereof. In a non-limiting example, (S)-CBS-oxazaborolidine catalyst can be used with borane or a solvate thereof (e.g., $BH_3 \cdot THF$) to control the stereochemistry of the resulting secondary alcohol in the preparation of the compound of formula (II) from the compound of formula (F).

Mitsunobu reaction conditions are known in the art. In a non-limiting example, the diastereomeric Sakurai reaction product mixture may be reacted with an azadicarboxylate compound (e.g., DIAD), phosphine (e.g., $PPh_3$), and a carboxylic acid (e.g., 3,5-dinitrobenzoic acid) to produce a compound of formula (G):

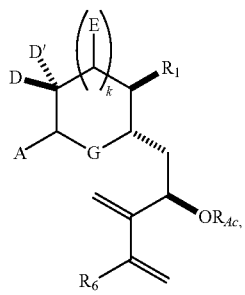

(G)

where $R_{Ac}$ is optionally substituted acyl; and the remaining variables are as described for formula (B).

The compound of formula (G) may be converted to the compound of formula (B). In a non-limiting example, the compound of formula (G) may be subjected to alcoholysis or hydrolysis reaction conditions (e.g., $Mg(OMe)_2$ in MeOH) to produce the compound of formula (B). Alternatively, the compound of formula (G) may be reacted with a 1,2-reducing agent to produce the compound of formula (B).

In the compounds described herein, $R_6$ may be optionally substituted alkyl (e.g., methyl).

In the compounds described herein, D may be H. In the compounds described herein, D' may be $OP_1$ (e.g., $P_1$ may be alkyl (e.g., methyl)). In the compounds described herein, G may be 0.

In the compounds described herein, k may be 0, and $R_1$ may be —$CH_2(Y)$, where Y may be —$SO_2R_D$ where, $R_D$ is optionally substituted aryl (e.g., phenyl) or optionally substituted non-enolizable alkyl.

In the compounds described herein, E may be optionally substituted alkyl (e.g., methyl).

In the compounds described herein, D may be H, and A may be:

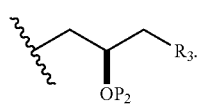

In the compounds described herein, k may be 0, and $R_1$ may be —$CH(Y)_2$, or —$CH_2(Y)$. In the compounds described herein, $R_3$ may be —$(CH_2)_nNP_3P_4$ or —$(CH_2)_nOP_5$, where n may be 0.

In the compounds described herein, A and D may combine to form the following structure:

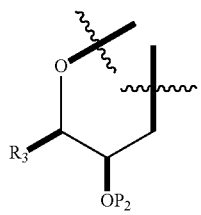

where the bond to the oxygen atom originates at the carbon atom to which D is attached in formula (A) or formula (B). In the compounds described herein, $R_3$ may be —$(CH_2)_nNP_3P_4$ or —$(CH_2)_nOP_5$, and n is 2.

In the compounds described herein, k may be 1, and E may be optionally substituted alkyl (e.g., methyl). In the compounds described herein, $R_1$ may be —$CH_2(Y)$, where Y may be —$COOR_D$, where $R_D$ may be optionally substituted alkyl (e.g., methyl).

Preparation of Halichondrin Macrolides and Analogs Thereof

A halichondrin macrolide or analog thereof may be prepared as described herein and using methods and reactions known in the art. Non-limiting examples of methods and reactions useful for the preparation of a halichondrin macrolide or analog thereof include U.S. patent application publication Nos. 2016/0264594, 2015/0158881, 2011/0184190, 2011/0054194, 2009/0203771, and 2009/0198074; International patent application publication No. WO 2016/179607; U.S. Pat. Nos. 5,338,865, 5,436,238, 6,214,865, and 8,445,701; and in Towle et al., *Annual Meeting of the American Association for Cancer Research*, Apr. 6-10, 2002, 5721; Wang et al., *Bioorg. Med. Chem. Lett.*, 10:1029-1032, 2000; Aicher et al., *J. Am. Chem. Soc.*, 114:3162-3164, 1992; Ueda et al., *J. Am. Chem. Soc.*, 136:5171-5176; and Yamamoto et al., *J. Am. Chem. Soc.*, 134:893-896, 2012.

As described herein, one of skill in the art can identify the sequence of reactions involving hydroxyl protecting group removing agents and Brønsted acids to convert the compounds described below into a halichondrin macrolide or analog thereof. One of skill in the art can recognize that certain functional groups require protecting groups known in the art to reduce or prevent undesired reactivity. One of skill in the art can select appropriate protecting groups to be used in the syntheses described herein.

Chart 2 illustrates the macrocycle disconnections that may be useful for the preparation of a halichondrin macrolide or analog thereof.

Chart 2

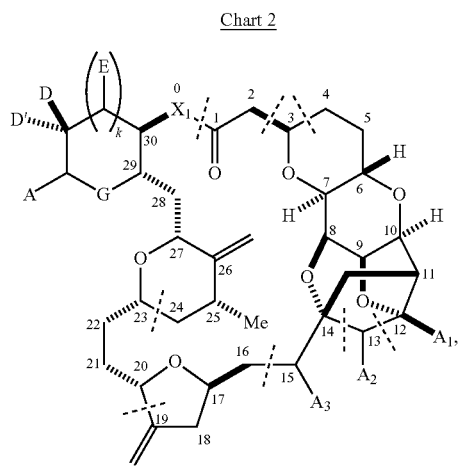

a halichondrin macrolide or analog thereof where $X_1$ is —O— or —$CH_2$—, and the remaining variables are as described in Chart 1.

Table 1 lists the macrocyclic retrosynthesis disconnections shown in Chart 2 and indicates corresponding exemplary bond-forming reactions as described herein. Any of these various reactions can be employed in the synthesis of halichondrin macrolide or analogs thereof. For example, these reactions may be employed to couple various fragments together or to form the macrocycle.

TABLE 1

| Disconnection | Exemplary Reaction | Reference(s) |
|---|---|---|
| C.1-$X_1$ | Esterification (e.g., of the compound of formula (VIIB)) Claisen reaction (e.g., of the compound of formula (VIIB)) | U.S. Pat. No. 5,338,865 U.S. Pat. No. 6,214,865 US 2016/0264594 |
| C.2-C.3 | Olefin Metathesis (e.g., of the compound of formula (VIE)) Horner-Wadsworth-Emmons (e.g., of the compound of formula (VIG)) | US 2016/0264594 WO 2016/179607 |
| C.3-C.4 | Olefin Metathesis (e.g., of the compound of formula (VIC)) | US 2016/0264594 WO 2016/179607 |
| C.12-C.13 | Olefin Metathesis (e.g., of the compound of formula (VIIIB)) | WO 2016/179607 |
| C.13-C.14 | Nozaki-Hiyama-Kishi (e.g., of the compound of formula (VIID)) | US 2009/0203771 |
| C.15-C.16 | Olefin metathesis (e.g., of the compound of formula (IVB)) | US 2016/0264594 WO 2016/179607 |
| C.19-C.20 | Nozaki-Hiyama-Kishi (e.g., of the compound of formula (VB)) | US 2016/0264594 WO 2016/179607 |
| C.23-C.24 | Prins reaction (e.g., producing the compound of formula (IXB)) | — |

The methods of preparing a halichondrin macrolide or analog thereof disclosed herein include a C.23-C.24 bond-forming Prins reaction either as a macrocyclization step or as a step in the synthesis of non-macrocyclic intermediates. In some approaches, a halichondrin macrolide or analog thereof (e.g., eribulin or a salt thereof (e.g., eribulin mesylate)) may be prepared from the compound of formula (IA) using methods and reaction conditions known in the art.

A compound of formula (IA) may be produced from a compound of formula (IIA), a compound of formula (IIB), a compound of formula (III), and $R_5OH$. The compound of formula (IA) is:

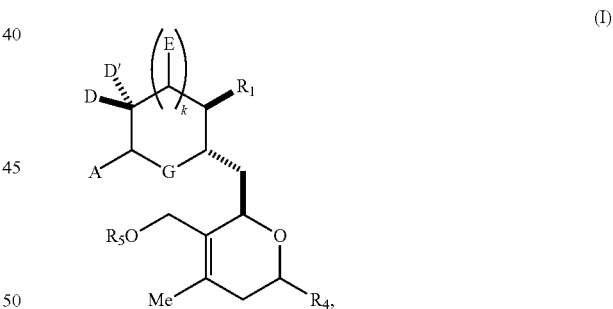

(I)

where $R_1$ is —$OP_6$, —$CH(Y)_2$, or —$CH_2(Y)$, where $P_6$ is H or a hydroxyl protecting group, and each Y is independently —$COOR_C$ or —$SO_2R_D$;

$R_4$ is

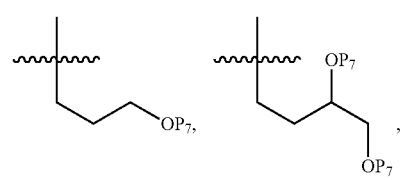

-continued

[Structure: furan ring with R8]

[Structure: furan ring with OP7 chain]

[Structure: furan ring with OP7, OP7 substituents]

[Structure: bicyclic lactone]

where
each $P_7$ is independently H or a hydroxyl protecting group;
$R_8$ is —$CH_2CH_2$—$COOR_C$, —CH=CH—$COOR_C$, —$CH_2CH_2$—$SO_2R_D$, or —CH=CH—$SO_2R_D$;
each $R_C$, when present, is independently optionally substituted alkyl, optionally substituted aryl, or optionally substituted arylalkyl; and
each $R_D$, when present, is independently optionally substituted aryl or optionally substituted non-enolizable alkyl; and
$R_5$ is optionally substituted acyl;
and the remaining variables are as described for the halichondrin macrolide or analog thereof (e.g., eribulin or a salt thereof (e.g., eribulin mesylate)).

In the compound of formula (IA), when $P_1$ is absent, each of D and D' is independently H or optionally substituted alkyl.

The compound of formula (IIA) is:

(IIA)

[Structure of formula IIA: cyclohexane ring with D', D, E, R1, A, G, R_E substituents]

where
$R_E$ is —CHO or —$CH_{(1+m)}(OR_F)_{(2-m)}$,
where
m is 1, and $R_F$ is a hydroxyl protecting group, or
m is 0, and
(i) each $R_F$ is independently an alkyl or hydroxyl protecting group, or
(ii) both $R_F$ combine to form an alkylene;
and
the remaining variables are as described for the compound of formula (IA).

The compound of formula (IIB) is:

(IIB)

[Structure: $R_S$—$CH_2$—C(Me)=$CH_2$]

where $R_S$ is silyl (e.g., $Me_3Si$—).
The compound of formula (III) is:

$R_4$-$R_7$,  (III)

where
$R_7$ is —CHO or

[Structure: $R_{7A}O$—CH(O$R_{7A}$)—]

where each $R_{7A}$ is independently an optionally substituted alkyl, and $R_4$ is as described for the compound of formula (IA).

Preparation of the compound of formula (IA) may include reacting the compound of formula (IIA) (in which $R_E$ is —CHO), the compound of formula (IIB), and a Lewis acid (e.g., an oxophilic Lewis acid (e.g., boron trifluoride or a solvate thereof)) to produce a compound of formula (IIC):

(IIC)

[Structure of formula IIC: cyclohexane ring with substituents, connected to CH(OH) and C(Me)=$CH_2$]

where the variables are as described for the compound of formula (IA).

The compound of formula (III) and the compound of formula (IIC) may be reacted under Prins reaction conditions to produce the compound of formula (IA). Prins reaction conditions are known in the art. In a non-limiting example, the compound of formula (III) and the compound of formula (IIC) may be reacted with a Lewis acid (e.g., an oxophilic Lewis acid (e.g., boron trifluoride or a solvate thereof)).

The following describes exemplary conditions for macrocyclization at the indicated positions. These reaction conditions may also be used to couple two or more fragments prior to macrocyclization.

C.1-$X_1$ Bond-Forming Macrocyclization

A halichondrin macrolide or analog thereof (e.g., eribulin or a salt thereof (e.g., eribulin mesylate)) may be prepared through a C.0-C.1 or a O-C.1 bond-forming macrocyclization according to the following synthesis strategy from a compound of formula (VIIB):

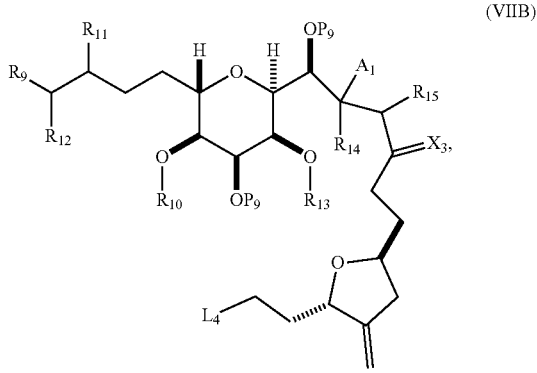

(VIIB)

where
(i) R$_{10}$ is a hydroxyl protecting group, R$_{11}$ is alkyl ether, and R$_{12}$ is H
(ii) R$_{10}$ is a hydroxyl protecting group, and R$_{11}$ and R$_{12}$ combine to form a double bond;
or
(iii) R$_{10}$ and R$_{11}$ combine to form a bond, and R$_{12}$ is H;
L$_4$ is

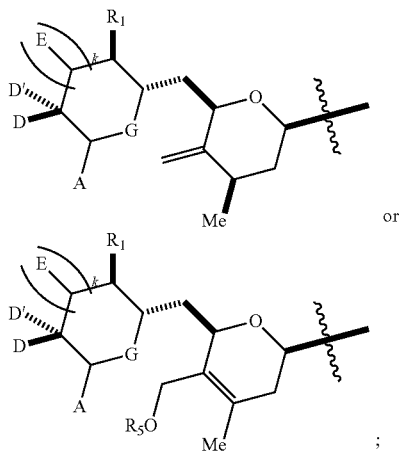

R$_1$ is —OP$_6$, —CH$_2$(Y), or —CH(Y)$_2$, where P$_6$ is H or a hydroxyl protecting group, and Y is —COOR$_C$ or —CHO;
each R$_C$, when present, is independently optionally substituted alkyl, optionally substituted aryl, or optionally substituted arylalkyl; and
A$_1$ and R$_{14}$ combine to form oxo, R$_{13}$ is H or a hydroxyl protecting group, and R$_{15}$ is H;
or
A$_1$ is H or —OP''', and:
(i) R$_{13}$ is H or a hydroxyl protecting group, and R$_{14}$ and R$_{15}$ combine to form a double bond;
or
(ii) R$_{13}$ and R$_{14}$ combine to form a bond, and R$_{15}$ is H or —OP''';
R$_5$ is optionally substituted acyl;
R$_9$ is —CHO or —COOP''';
each P''' is independently H or a hydroxyl protecting group;
each P$_9$ is independently a hydroxyl protecting group, and X$_3$ is oxo or X$_3$, together with the carbon atom to which it is attached, is —(CH(OP$_{11}$))—, where P$_{11}$ is H or a hydroxyl protecting group; or both P$_9$ groups and X$_3$, together with the atoms to which each is attached, combine to form a ketal;
and the remaining variables are as described for the halichondrin macrolide or analog thereof.

The compound of formula (VIIB) is converted to a compound of formula (VIIC):

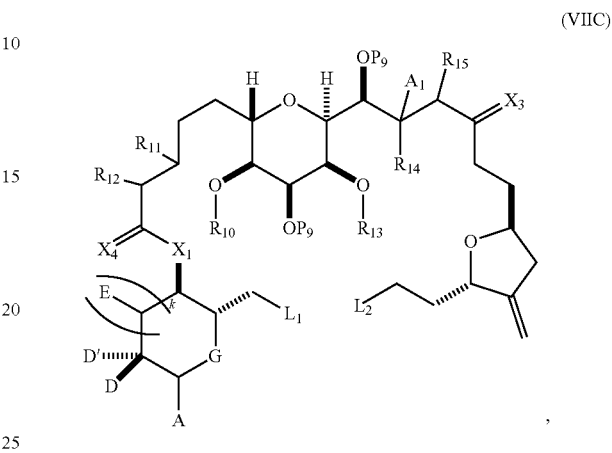

(VIIC)

where
L$_1$ is

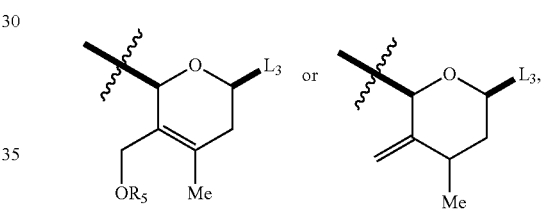

where L$_2$ and L$_3$ combine to form a bond;
X$_1$ is —CH$_2$—, —CH(Y)—, —C(Y)$_2$—, or —O—;
X$_4$ is oxo, or X$_4$, together with the atom to which it is attached, is —(CH(OP$_{12}$))—, where P$_{12}$ is H or a hydroxyl protecting group;
and the remaining variables are as described for the compound of formula (VIIB).

Preparation of the compound of formula (VIIC) may include an esterification reaction between R$_1$ that is —OP$_6$, where P$_6$ is H, and R$_9$ that is —COOH. Alternatively, preparation of the compound of formula (VIIC) may include a reaction between R$_1$ that is —CH(Y)$_2$ or —CH$_2$(Y), and R$_9$ that is —CHO (e.g., under Claisen reaction conditions). Oxidation of the Claisen product (X$_4$, together with the atom to which it is attached, is —(CH(OP$_{12}$))—, where P$_{12}$ is H) with an oxidizing agent capable of converting an alcohol to a carbonyl group may produce X$_4$ that is oxo. Further desulfonylation or decarboxylation of this compound of formula (VIIC) may produce the compound of formula (VIIC), in which X$_1$ is —CH$_2$—.

The compound of formula (VIIC) is then converted to the halichondrin macrolide or analog thereof using methods described herein and those known in the art, e.g., those described in U.S. Pat. No. 5,338,865, US 2016/0264594, US 2009/0203771, and WO 2016/179607. For example, preparation of the halichondrin macrolide or analog thereof may include reacting the compound of formula (VIIC) with a hydroxyl protecting group removing agent.

The compound of formula (VIIB) may be prepared from a compound of formula (VIIA), the compound of formula (IIA), the compound of formula (IIB), a compound of formula (IIIC), and R₅OH. The compound of formula (VIIA) is:

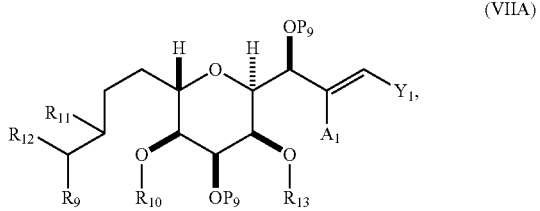

(VIIA)

where
(i) $R_{10}$ is a hydroxyl protecting group, $R_{11}$ is alkyl ether, and $R_{12}$ is H;
(ii) $R_{10}$ is a hydroxyl protecting group, and $R_{11}$ and $R_{12}$ combine to form a double bond;
or
(iii) $R_{10}$ and $R_{11}$ combine to form a bond, and $R_{12}$ is H;
$R_9$ is —CH₂—OP''', —CHO, or —COOP''';
$R_{13}$ and each $P_9$ is independently a hydroxyl protecting group;
$A_1$ is H or —OP''';
each P''' is independently H or a hydroxyl protecting group; and
$Y_1$ is chloro, bromo, iodo, trifluoromethanesulfonate, or trialkylsilane.

The compound of formula (IIIC) is:

$R_{4C}$-$R_7$,     (IIIC)

where
$R_7$ is —CHO, —CH₂OP$_A$, or

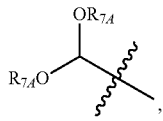

where each $R_{7A}$ is independently an optionally substituted alkyl; and $R_{4C}$ is

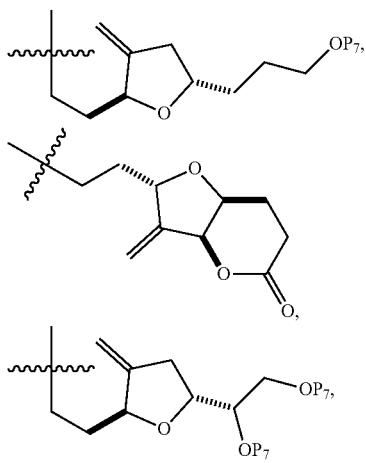

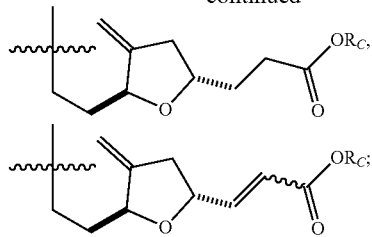

where
$R_C$ is optionally substituted alkyl, optionally substituted aryl, or optionally substituted arylalkyl;
$P_A$ is H or a hydroxyl protecting group; and
$P_7$, when present, is independently H or a hydroxyl protecting group.

Preparation of the compound of formula (VIIB) can be accomplished as follows. The compound of formula (IIIC), in which $R_7$ is —CH₂OP$_A$ or

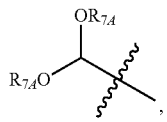

may be converted to a compound of formula (IIID):

$R_{4D}$-$R_7$,     (IIID)

where
$R_{4D}$ is

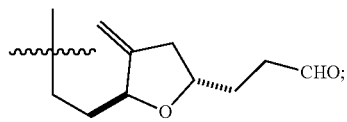

and
all remaining variables are as described for the compound of formula (C).

The compound of formula (IIID) may be reacted with the compound of formula (VIIA) under Nozaki-Hiyama-Kishi reaction conditions (e.g., with a Cr(II) salt and a Ni(II) salt as described herein) to form a compound of formula (VIIAa):

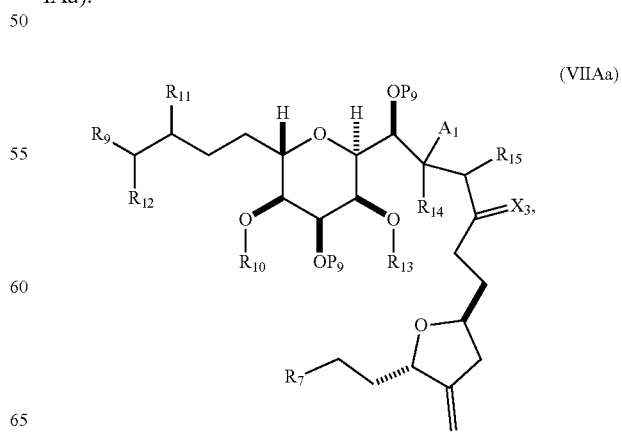

(VIIAa)

where

R$_7$ is —CH$_2$OP$_A$, —CHO, or

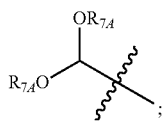

and all remaining variables are as described for the compound of formula (VIIB) and the compound of formula (IIID).

The compound of formula (VIIAa), in which R$_7$ is —CHO, may be reacted with a compound of formula (IIC) and R$_5$OH under Prins reaction conditions to form the compound of formula (VIIB).

Alternatively, preparation of the compound of formula (VIIB) can be accomplished by reacting the compound of formula (IG) and the compound of formula (VIIA) under Nozaki-Hiyama-Kishi reaction conditions (e.g., with a Cr(II) salt and a Ni(II) salt as described herein).

The compound of formula (IG) is:

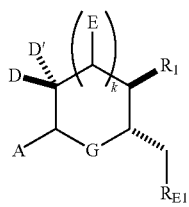

(IG)

where

R$_E$1 is

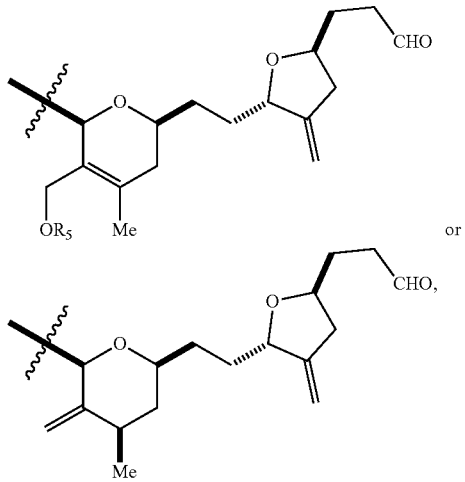

where R$_5$ is optionally substituted acyl;

and the remaining variables are as described for the compound of formula (VIIB).

The compound of formula (IG) may be formed from a compound of formula (IF):

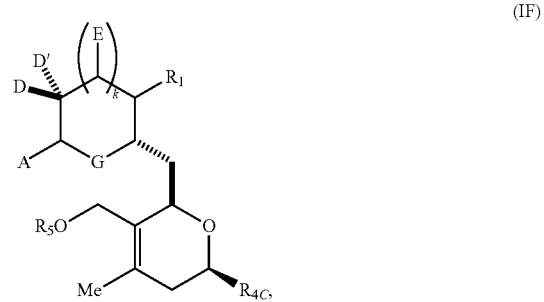

(IF)

where all variables are as described for the compound of formula (IG) and the compound of formula (C).

R$_{4C}$ that is

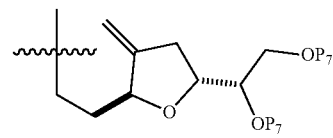

may be reacted with a glycol cleaving agent to produce an aldehyde, which may then be reacted with (R$_C$O)$_2$P(O)—CH$_2$—COOR$_C$ to produce R$_{4C}$ that is

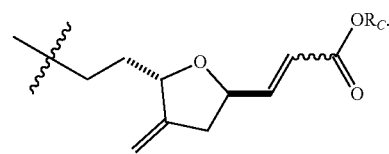

R$_{4C}$ that is

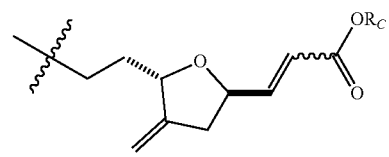

may be reacted with a 1,4-reducing agent to produce R$_{4C}$ that is

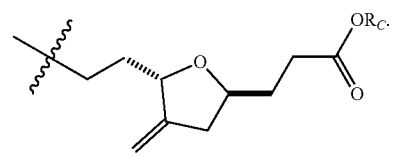

$R_{4C}$ that is

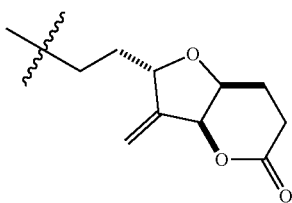

may be reacted with an allylic reducing agent to produce $R_{4C}$ that is

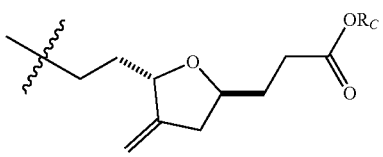

(e.g., producing this $R_{4C}$ may further include an esterification reaction after the reaction with an allylic reducing agent).

$R_{4C}$ that is

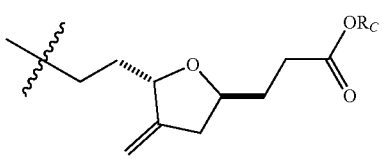

may be reacted with a 1,2-reducing agent to produce

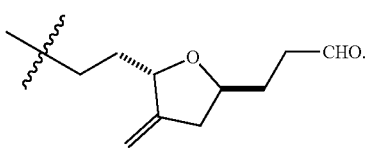

$R_{4C}$ that is

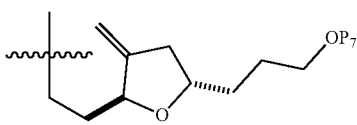

may be reacted with an oxidizing agent capable of converting an alcohol to a carbonyl group in

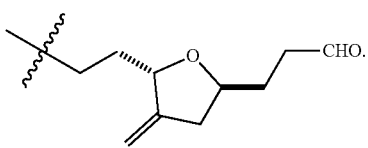

In general, the method described herein includes an allylic reduction at C.25. This reaction can be performed at any point prior to the formation of the halichondrin macrolide or analog thereof. For example,

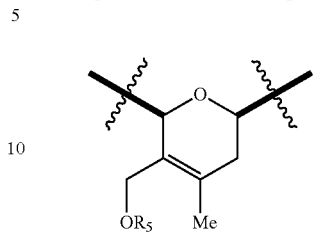

may be converted to

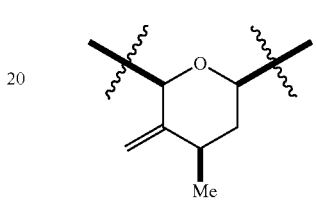

using an allylic reducing agent.

C.2-C.3 and C.3-C.4 Bond-Forming Macrocyclizations

In another approach, a halichondrin macrolide or analog thereof (e.g., eribulin or a salt thereof (e.g., eribulin mesylate)) may be prepared through a C.2-C.3 or a C.3-C.4 bond-forming macrocyclization according to the following strategy.

In some embodiments, a halichondrin macrolide or analog thereof is prepared from a compound of formula (VIB) is:

(VIB)

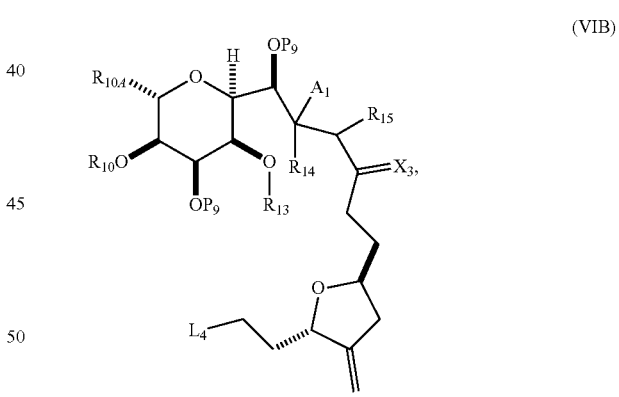

where $L_4$ is

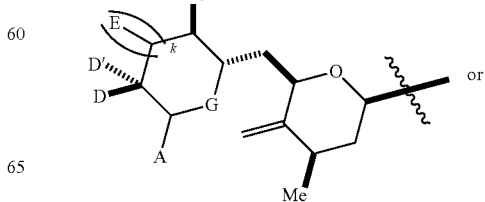 or

-continued

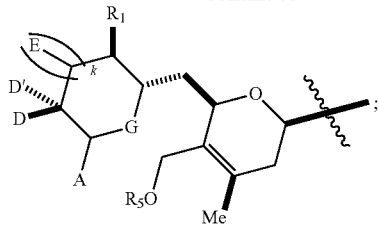

$R_1$ is —$OP_6$ or —CH(Y), where $P_6$ is H or a hydroxyl protecting group, and Y is —$COOR_C$ or —CHO;

$R_5$ is optionally substituted acyl;

$R_{10A}$ is —$CH_2$—CH=$CH_2$, —$(CH_2)_2$—CH=$CH_2$, or —$(CH_2)_3$—$OP_{10}$;

each of $R_{10}$ and $P_{10}$ is independently a hydroxyl protecting group;

$A_1$ and $R_{14}$ combine to form oxo, $R_{13}$ is H or a hydroxyl protecting group, and $R_{15}$ is H;

or $A_1$ is H or —OP''', and:

(i) $R_{13}$ is H or a hydroxyl protecting group, and $R_{14}$ and $R_{15}$ combine to form a double bond;

or (ii) $R_{13}$ and $R_{14}$ combine to form a bond, and $R_{15}$ is H or —OP''';

each $P_9$ is independently a hydroxyl protecting group, and $X_3$ is oxo or $X_3$, together with the carbon atom to which it is attached, is —(CH($OP_{11}$))—, where $P_{11}$ is H or a hydroxyl protecting group; or both $P_9$ groups and $X_3$, together with the atoms to which each is attached, combine to form a ketal; and the remaining variables are as described for the halichondrin macrolide or analog thereof.

The compound of formula (VIB) may be converted to the halichondrin macrolide or analog thereof (e.g., eribulin or a salt thereof (e.g., eribulin mesylate)) using reaction conditions known in the art, e.g., as described herein.

In particular embodiments, preparation of the halichondrin macrolide or analog thereof from the compound of formula (VIB) through C.3-C.4 bond-forming macrocyclization includes producing a compound of formula (VIC) from the compound of formula (VIB). The compound of formula (VIC) is (VIC)

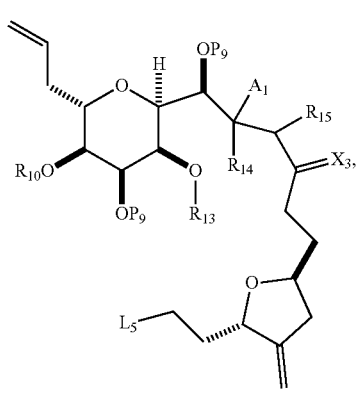

where $L_5$ is

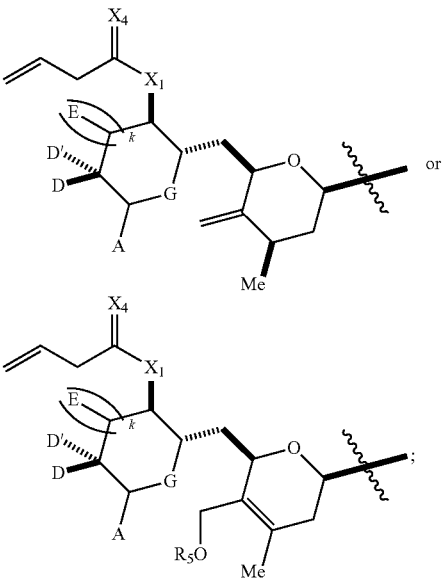

$X_1$ is —$CH_2$— or —O—;

$X_4$ is oxo, or $X_4$, together with the atom to which it is attached, is —(CH($OP_{12}$))—, where $P_{12}$ is H or a hydroxyl protecting group; and the remaining variables are as described for the compound of formula (VIB).

The compound of formula (VIC) may be prepared by reacting the compound of formula (VIB) with $R_{17}$—$CH_2CH$=$CH_2$, where $R_{17}$ is —COOH or a metallic or metalloid moiety. The compound of formula (VIB), in which $R_1$ is —$CH_2$(Y), may be reacted with $R_{17}$—$CH_2CH$=$CH_2$, in which $R_{17}$ is a metallic or metalloid moiety, to produce the compound of formula (VIC), in which $X_1$ is —$CH_2$—, and $X_4$ is oxo or —(CH($OP_{12}$))—. The compound of formula (VIB), in which $R_1$ is —$OP_6$, and $P_6$ is H, may be esterified with $R_{17}$—$CH_2CH$=$CH_2$, where $R_{17}$ is —COOH, to produce the compound of formula (VIC), in which $X_1$ is —O—, and $X_4$ is oxo.

The compound of formula (VIC) is then converted to a compound of formula (VI):

(VID)

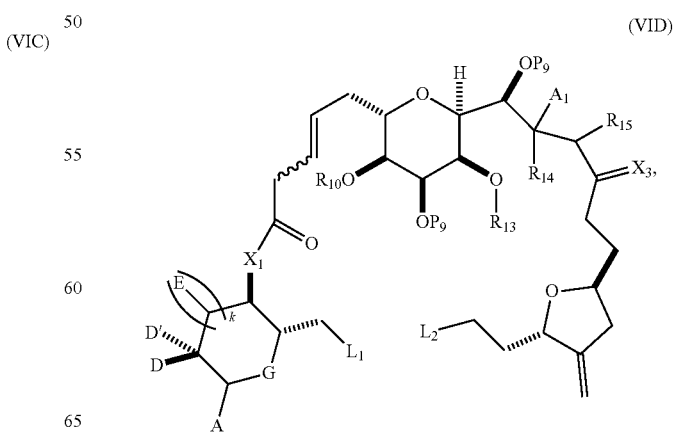

where
$L_1$ is

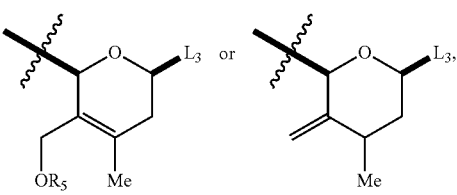

where $L_2$ and $L_3$ combine to form a bond;

and the remaining variables are as described for the compound of formula (VIC).

The compound of formula (VID) is produced through a reaction of the compound of formula (VIC) with an olefin metathesis catalyst.

The compound of formula (VID) may be converted to the halichondrin macrolide or analog thereof using methods described herein and those known in the art, e.g., those described in US 2016/0264594, US 2009/0203771, and WO 2016/179607.

Preparation of the halichondrin macrolide or analog thereof may include reacting the compound of formula (VID) with a hydroxyl protecting group removing agent. A reaction of the compound of formula (VID) with a hydroxyl protecting group removing agent may lead to the C.3-C.4 double bond isomerization to give an enoate/enone described herein upon exposure to basic (e.g., isomerization mediated by a hydroxyl protecting group removing agent, such as a fluoride source) or acidic (e.g., isomerization mediated by a Brønsted acid) conditions. The resulting enoate/enone may undergo a reaction with a hydroxyl of $-OR_{10}$.

In certain embodiments, preparation of the halichondrin macrolide or analog thereof from the compound of formula (VIB) through C.2-C.3 bond-forming macrocyclization includes producing a compound of formula (VIE) from the compound of formula (VIB). The compound of formula (VIE) is:

(VIE)

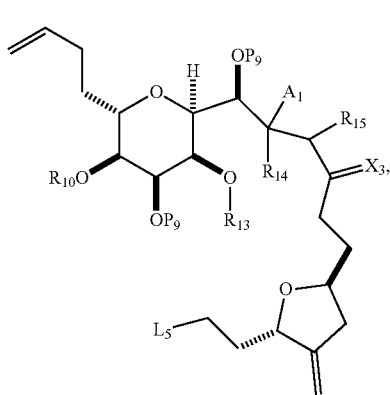

where
$L_6$ is

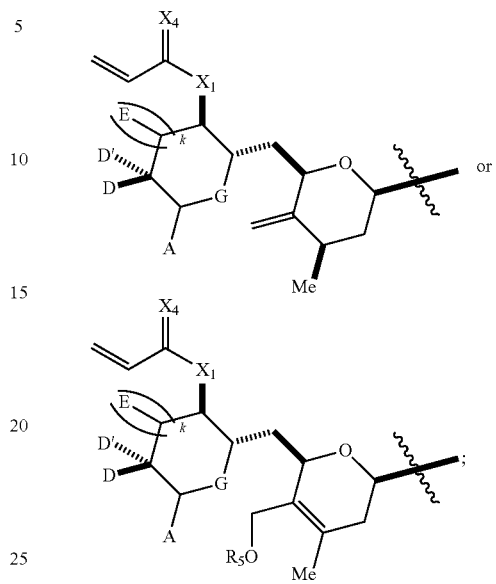

$X_1$ is $-CH_2-$ or $-O-$;

$X_4$ is oxo, or $X_4$, together with the atom to which it is attached, is $-(CH(OP_{12}))-$, where $P_{12}$ is H or a hydroxyl protecting group; and the remaining variables are as described for the compound of formula (VIB).

The compound of formula (VIB) may be converted to a compound of formula (VIE) through a reaction with $R_{17}-CH=CH_2$, where $R_{17}$ is $-COOH$ or a metallic or metalloid moiety. For example, the compound of formula (VIB), in which $R_1$ is $-CH_2(Y)$, can be reacted with $R_1-CH_2CH=CH_2$, where $R_{17}$ is a metallic or metalloid moiety, to give the compound of formula (VIE), in which $X_1$ is $-CH_2-$, and $X_4$ is oxo or $-(CH(OP_{12}))-$. Alternatively, the compound of formula (VIB), in which $R_1$ is $-OP_6$, and $P_6$ is H, can be esterified with $R_{17}-CH_2CH=CH_2$, where $R_{17}$ is $-COOH$, to give the compound of formula (VIE), in which $X_1$ is $-O-$, and $X_4$ is oxo.

The compound of formula (VIE) may be converted to a compound of formula (VIF):

(VIF)

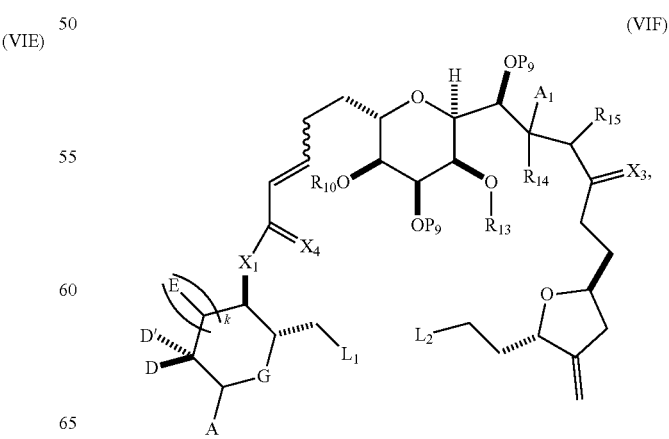

where $L_1$ is

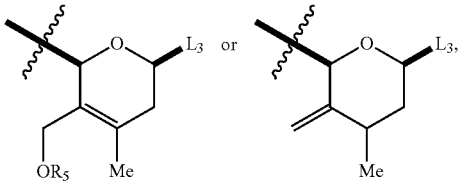

where $L_2$ and $L_3$ combine to form a bond;

and the remaining variables are as described for the formula (VIE).

The compound of formula (VIF) may be produced by a reaction of the compound of formula (VIE) with an olefin metathesis catalyst.

Alternatively, the compound of formula (VIF), in which $X_4$ is oxo, may be prepared from a compound of formula (VIG):

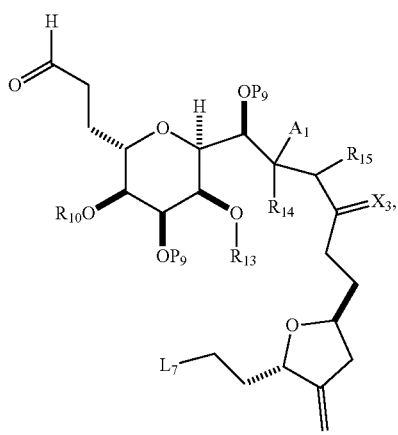

(VIG)

where $L_7$ is

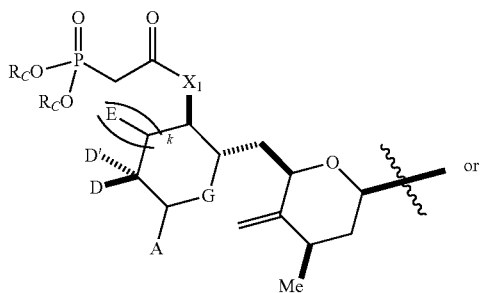

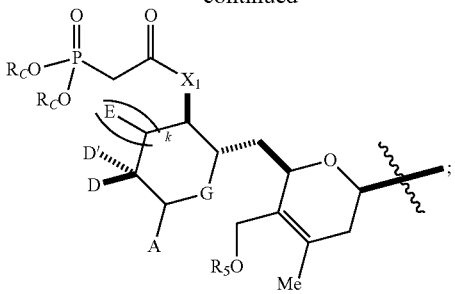

$X_1$ is —$CH_2$— or —O—;

each $R_C$ is independently optionally substituted alkyl, optionally substituted aryl, or optionally substituted arylalkyl;

and the remaining variables are as described for the compound of formula (VIF).

The compound of formula (VIG) may be prepared by reacting the compound of formula (VIB) with $(R_CO)_2P(O)$—$CH_2$—$R_P$, where each $R_C$ is independently optionally substituted alkyl, optionally substituted aryl, or optionally substituted arylalkyl, and $R_P$ is H or —COOH. For example, the compound of formula (VIB), in which $R_1$ is —$CH_2(Y)$, may be reacted with $(R_CO)_2P(O)$—$CH_2$—$R_P$, in which $R_P$ is H, under Claisen reaction conditions to produce the compound of formula (VIG). Alternatively, the compound of formula (VIB), in which $R_1$ is —$OP_6$, where $P_6$ is H, may be esterified with $(R_C)_2P(O)$—$CH_2$—$R_P$, in which $R_P$ is —COOH, to produce the compound of formula (VIG).

The compound of formula (VIG) is then converted to the compound of formula (VIF), e.g., through a Horner-Wadsworth-Emmons reaction, where all variables are as described for the compound of formula (VIG).

The compound of formula (VIF) is then converted to the halichondrin macrolide or analog thereof using methods described herein and those known in the art, e.g., those described in US 2016/0264594, US 2009/0203771, and WO 2016/179607.

The compound of formula (VIB) may be prepared from a compound of formula (VIA), a compound of formula (IIA), a compound of formula (IIB), a compound of formula (IIIC), and $R_5OH$.

The compound of formula (VIA) is:

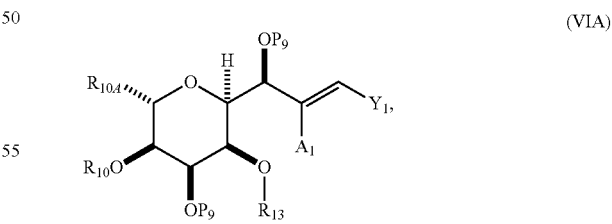

(VIA)

where each $R_{10}$, $R_{13}$, and $P_9$ is independently a hydroxyl protecting group;

$A_1$ is H or —OP'";

$Y_1$ is chloro, bromo, iodo, trifluoromethanesulfonate, or trialkylsilane; and $R_{10A}$ is as described for the compound of formula (VIB).

The compound of formula (IIA) is:

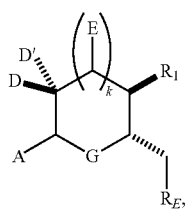
(IIA)

where
$R_E$ is —CHO or —CH$_{(1+m)}$(OR$_F$)$_{(2-m)}$,
where
m is 1, and $R_F$ is a hydroxyl protecting group,
or
m is 0, and
(i) each $R_F$ is independently an alkyl or hydroxyl protecting group, or
(ii) both $R_F$ combine to form an alkylene;
and the remaining variables are as described for the compound of formula (VIB).

The compound of formula (IIB) is:

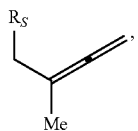
(IIB)

where $R_S$ is silyl;
The compound of formula (IIIC) is:

$R_{4C}$-$R_7$,     (IIIC)

where
$R_{4C}$ is

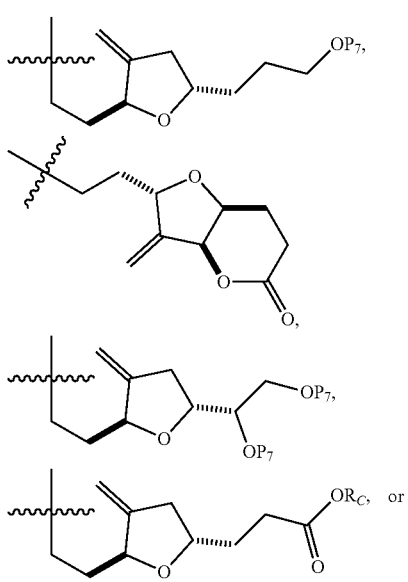

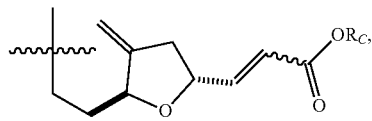

where $R_C$ is optionally substituted alkyl, optionally substituted aryl, or optionally substituted arylalkyl, and each $P_7$ is independently H or a hydroxyl protecting group; and $R_7$ is —CHO or

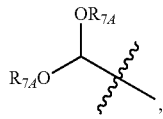

where each $R_{7A}$ is independently an optionally substituted alkyl;

Preparation of the compound of formula (VIB) includes a Sakurai reaction between $R_E$ that is —CHO and the compound of formula (IIB) producing a group of the structure:

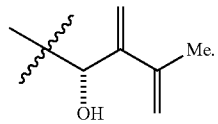 [SMILES: *[C@@H](O)C(=C)C(=C)C]

This product may then be reacted with the compound of formula (IIIC) under Prins reaction condition to produce a group of the structure:

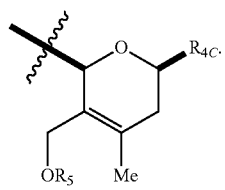

This group may be converted to

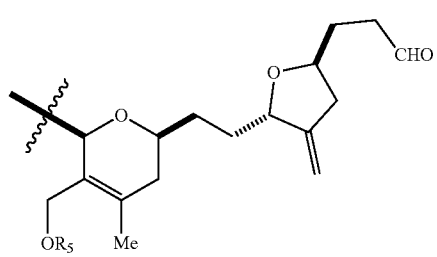

or

-continued

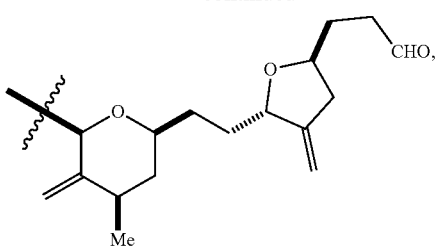

as described herein.

If the stereochemistry of the secondary alcohol in the Sakurai reaction product differs from the desired stereochemistry, this group may be subjected to epimerization reaction conditions described herein (e.g., oxidation followed by Corey-Bakshi-Shibata reduction; alternatively, Mitsunobu reaction may be used to invert the stereogenic center).

If $R_E$ is $-CH_{(1+m)}(OR_F)_{(2-m)}$, preparation of the compound of formula (IVB) may further include conversion of $R_E$ to $-CHO$ under acetal deprotecting conditions, e.g., through a reaction with an aqueous Brønsted acid (e.g., when m is 0), or through oxidation using an oxidizing agent capable of converting an alcohol to a carbonyl group (e.g., when m is 1).

$R_{4C}$ that is

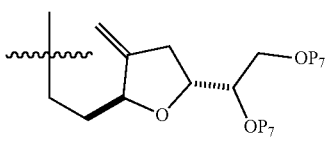

may be reacted with a glycol cleaving agent to produce an aldehyde, which may then be reacted with $(R_CO)_2P(O)-CH_2-COOR_C$ to produce $R_{4C}$ that is

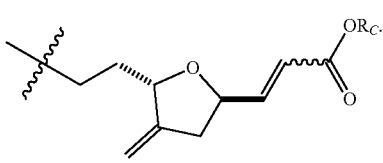

$R_{4C}$ that is

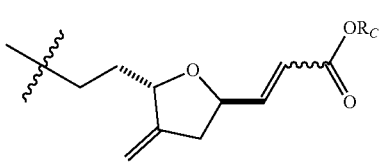

may be reacted with a 1,4-reducing agent to produce $R_{4C}$ that is

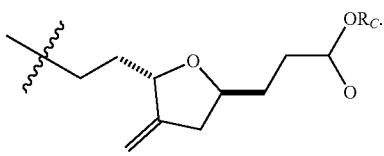

$R_{4C}$ that is

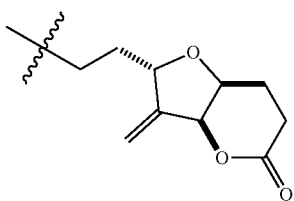

may be reacted with an allylic reducing agent to produce $R_{4C}$ that is

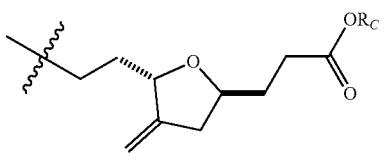

(e.g., producing this $R_{4C}$ may further include an esterification reaction after the reaction with an allylic reducing agent).

$R_{4C}$ that is

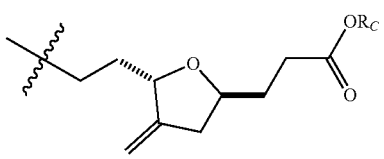

may be reacted with a 1,2-reducing agent to produce

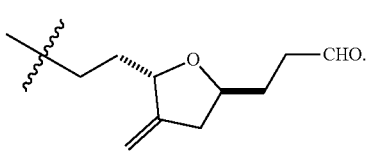

$R_{4C}$ that is

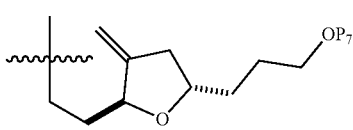

may be reacted with an oxidizing agent capable of converting an alcohol to a carbonyl group in

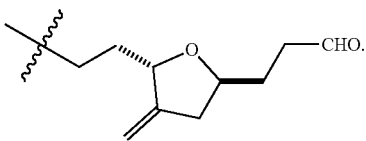

In some embodiments, the compound of formula (VIB) is produced from the compound of formula (VIA) and a compound of formula (IG):

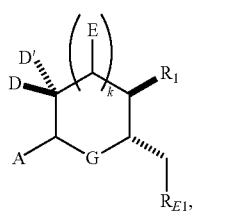

where
$R_{E1}$ is

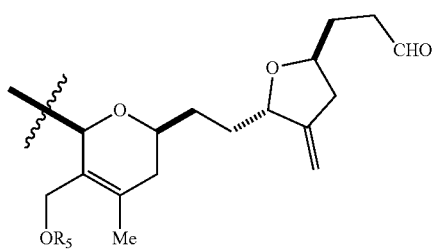 or 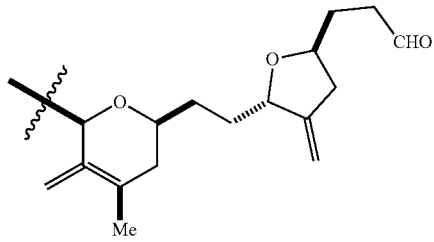

where $R_5$ is optionally substituted acyl;
and the remaining variables are as described for the compound of formula (VIB).

The compound of formula (VIA) is reacted with the compound of formula (IG) under Nozaki-Hiyama-Kishi reaction conditions to produce the compound of formula (VIB). For example, Nozaki-Hiyama-Kishi reaction on the compound of formula (VIA) and the compound of formula (IG) can include reacting the compound of formula (VIA) and the compound of formula (IG) with a Cr(II) salt and a Ni(II) salt.

The compound of formula (IG) may be prepared from the compound of formula (IIA), the compound of formula (IIB), the compound of formula (IIIC), and $R_5OH$, where $R_5$ is optionally substituted acyl.

In further embodiments, the compound of formula (VIB) may be prepared according to the following strategy. The compound of formula (IIIC) may be converted to the compound of formula (IIID) as described herein. Further, the compound of formula (IIID) may be reacted with the compound of formula (VIA) under Nozaki-Hiyama-Kishi reaction conditions to produce a compound of formula (VIAa):

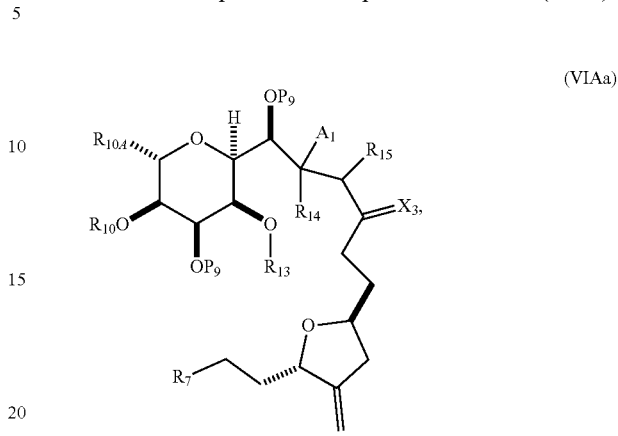

where all variables are as described for the compound of formula (VIB) and the compound of formula (IIIC).

The compound of formula (VIAa), in which $R_7$ is —CHO, may be reacted with a compound of formula (IIC) and $R_5OH$ under Prins reaction conditions to form the compound of formula (VIB).

In yet further embodiments, the compound of formula (VIC) may be prepared according to the following strategy. The compound of formula (IIA), in which $R_E$ is —$CH_{(1+m)}$ $(OR_F)_{(2-m)}$, may be reacted with $R_{17}$—$CH_2CH$=$CH_2$, where R is —COOH or a metalloid or metallic moiety, to produce a compound of formula (IID):

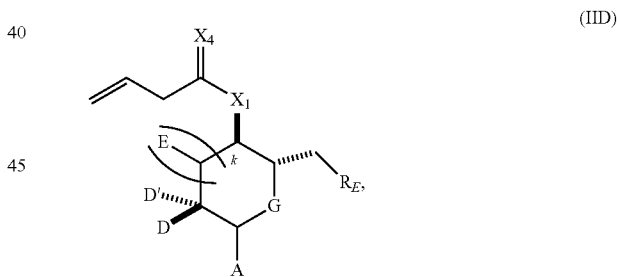

where all variables are as described for the compound of formula (VIC).

For example, the compound of formula (IIA), in which $R_1$ is —$CH_2(Y)$, may be reacted with $R_{17}$—$CH_2CH$=$CH_2$, in which $R_{17}$ is a metallic or metalloid moiety, to produce the compound of formula (VIC), in which $X_1$ is —$CH_2$—, and $X_4$ is oxo or —($CH(OP_{12})$)—. The compound of formula (IIA), in which $R_1$ is —$OP_6$, and $P_6$ is H, may be esterified with $R_{17}$—$CH_2CH$=$CH_2$, where $R_{17}$ is —COOH, to produce the compound of formula (ID), in which $X_1$ is —O—, and $X_4$ is oxo.

The compound of formula (IID), in which $R_E$ is —CHO, may be reacted with the compound of formula (IIB) under Sakurai reaction conditions to produce a compound of formula (IIE):

(IIE)

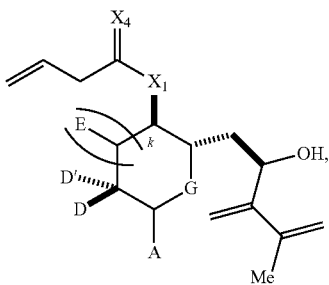

where all variables are as described for the compound of formula (VIC).

The compound of formula (IIE) may be reacted with the compound of formula (VIAa) and $R_5OH$ under Prins reaction conditions to produce the compound of formula (VIC), in which $L_5$ is:

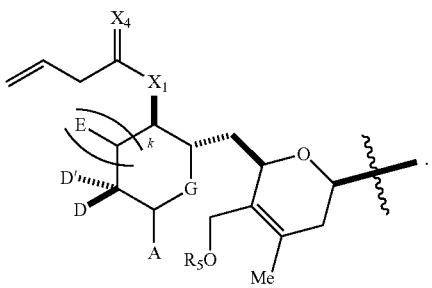

In still further embodiments, the compound of formula (VIE) may be prepared according to the following strategy. The compound of formula (IIA) may be converted to a compound of formula (IIF) through a reaction with $R_{17}$—CH=CH$_2$, where $R_{17}$ is —COOH or a metallic or metalloid moiety. The compound of formula (IIF) is:

(IIF)

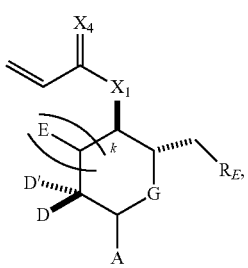

where all variables are as described for the compound of formula (VIE).

For example, the compound of formula (IIA), in which $R_1$ is —CH$_2$(Y), can be reacted with $R_{17}$—CH$_2$CH=CH$_2$, where $R_{17}$ is a metallic or metalloid moiety, to give the compound of formula (IIF), in which $X_1$ is —CH$_2$—, and $X_4$ is oxo or —(CH(OP$_{12}$))—. Alternatively, the compound of formula (IIA), in which $R_1$ is —OP$_6$, and $P_6$ is H, can be esterified with $R_{17}$—CH$_2$CH=CH$_2$, where $R_{17}$ is —COOH, to give the compound of formula (IIF), in which $X_1$ is —O—, and $X_4$ is oxo.

The compound of formula (IIF), in which $R_E$ is —CHO, may be reacted with the compound of formula (IIB) under Sakurai reaction conditions to produce a compound of formula (IIG):

(IIG)

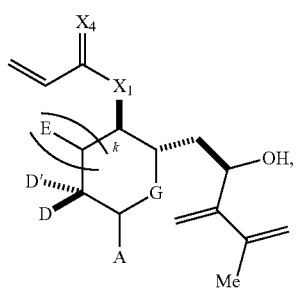

where all variables are as described for the compound of formula (VIE).

The compound of formula (IIF) may be reacted with the compound of formula (VIAa) and $R_5OH$ under Prins reaction conditions to produce the compound of formula (VIE), in which $L_6$ is:

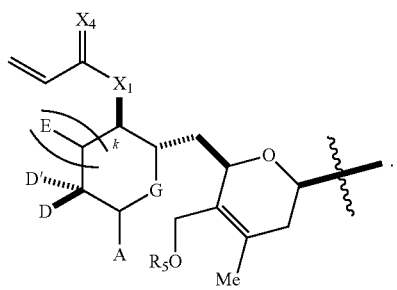

In some embodiments, the compound of formula (VIG) may be prepared according to the following strategy. The compound of formula (IIA) may be converted to a compound of formula (IIH) through a reaction with $(R_CO)_2P(O)$—CH$_2$—R$_P$, where each $R_C$ is independently optionally substituted alkyl, optionally substituted aryl, or optionally substituted arylalkyl, and $R_P$ is H or —COOH. The compound of formula (IIH) is:

(IIH)

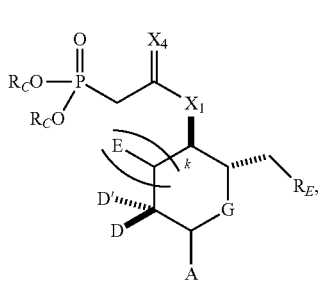

where
each $R_C$ is independently optionally substituted alkyl, optionally substituted aryl, or optionally substituted arylalkyl;
$X_4$ is oxo, or $X_4$, together with the atom to which it is attached, is —(CH(OP$_{12}$))—, where $P_{12}$ is H or a hydroxyl protecting group; and all remaining variables are as described for the compound of formula (VIG).

The compound of formula (IIH), in which $X_4$ is oxo, may be converted to a compound of formula (IIi) through a reaction with the compound of formula (IIB) under Sakurai reaction conditions. The compound of formula (IIi) is:

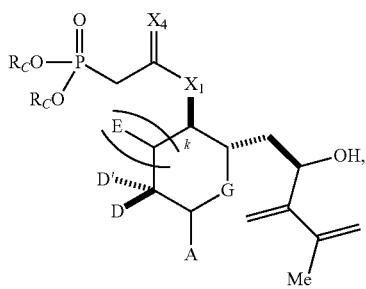
(IIi)

where all variables are as described for the compound of formula (IIH).

The compound of formula (IIi) may be reacted with the compound of formula (VIAa), in which $R_{10A}$ is —$CH_2$—$CH$=$CH_2$ or —$(CH_2)_3$—$OP_{10}$, to produce a compound of formula (VIGa):

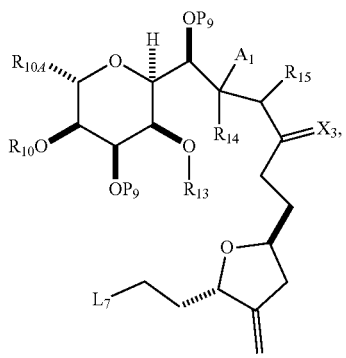
(VIGa)

where
$R_{10A}$ is —$CH_2$—$CH$=$CH_2$ or —$(CH_2)_3$—$OP_{10}$,
$L_7$ is

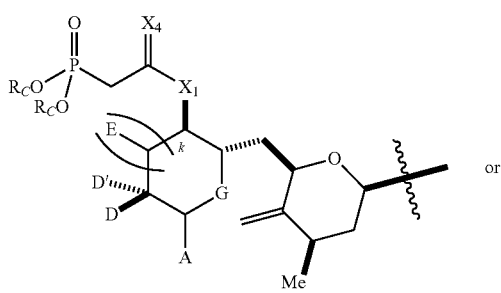
or

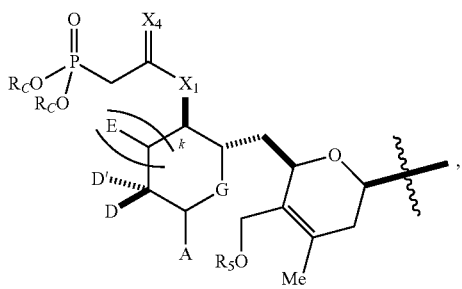

and all remaining variables are as described for the compound of formula (VIG).

The compound of formula (VIGa), in which $R_{10A}$ is —$CH_2$—$CH$—$CH_2$, may be converted to the compound of formula (VIGa), in which $R_{10A}$ is —$(CH_2)_3$—$OP_{10}$, and $P_{10}$ is H, by hydroboration/oxidation reaction. Hydroboration/oxidation reactions are known in the art. For example, 9-BBN or thexyl borane may be used for the hydroboration of $R_{10A}$, and sodium perborate or hydrogen peroxide and base may be used for the oxidation step providing —$(CH_2)_3$—$OP_{10}$, and $P_{10}$ is H. The compound of formula (VIGa), in which $R_{10A}$ is —$(CH_2)_3$—$OP_{10}$, and $P_{10}$ is H, may be converted to the compound of formula (VIG).

In general, the method described herein includes an allylic reduction at C.25. This reaction can be performed at any point prior to the formation of the halichondrin macrolide or analog thereof. For example,

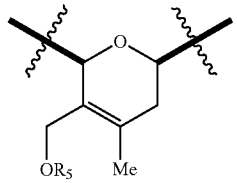

may be converted to

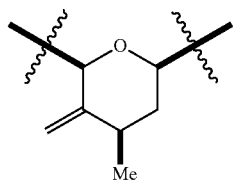 [SMILES: *[C@H]1C[C@@H](C)C(=C)[C@@H](*)O1]

using an allylic reducing agent.

C.12-C.13 Bond-Forming Macrocyclization

In still another approach, a halichondrin macrolide or analog thereof may be prepared from the compound of of formula (VIIIB):

(VIIIB)

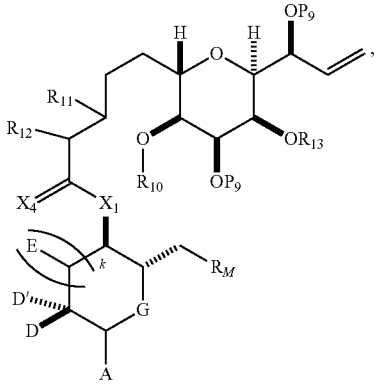

where $X_1$ is —$CH_2$—, —CH(Y)—, —C(Y)$_2$—, or —O—, where each Y is independently —COOR$_C$ or —SO$_2$R$_D$;

$X_4$ is oxo, or $X_4$, together with the atom to which it is attached, is —(CH(OP$_{12}$))—, where P$_{12}$ is H or a hydroxyl protecting group; each R$_C$, when present, is independently optionally substituted alkyl, optionally substituted aryl, or optionally substituted arylalkyl;

each R$_D$, when present, is independently optionally substituted aryl or optionally substituted non-enolizable alkyl;

(i) R$_{10}$ is a hydroxyl protecting group, R$_{11}$ is alkyl ether, and R$_{12}$ is H;

(ii) R$_{10}$ is a hydroxyl protecting group, and R$_4$ and R$_5$ combine to form a double bond;

or (iii) R$_{10}$ and R$_{11}$ combine to form a bond, and R$_{12}$ is H;

each P$_9$ and R$_{13}$ is independently a hydroxyl protecting group;

R$_M$ is

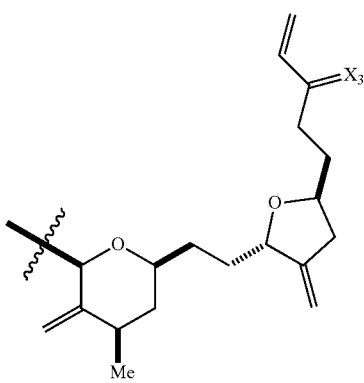

or

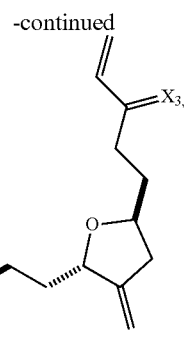

where

R$_5$ is optionally substituted acyl; and $X_3$ is oxo or $X_3$, together with the carbon atom to which it is attached, is —(CH(OP$_{11}$))—, where P$_{11}$ is H or a hydroxyl protecting group;

and the remaining variables are as described for the halichondrin macrolide or analog thereof.

The compound of formula (VIIIB) can be subjected to ring closing metathesis to produce a compound of formula (VIIIC):

(VIIC)

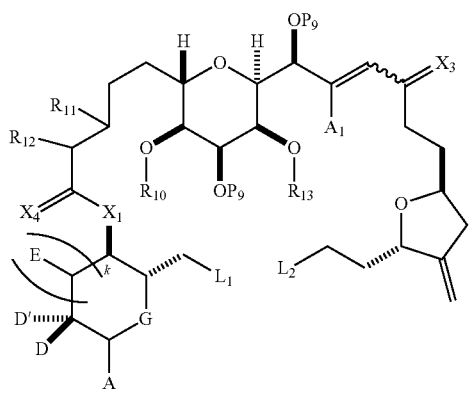

where

A$_1$ is H or —OP'', where P'' is H or a hydroxyl protecting group;

L is

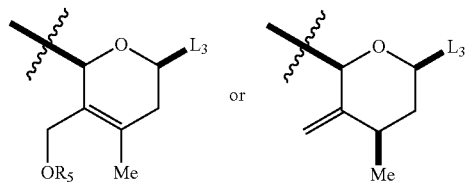

where L$_2$ and L$_3$ combine to form a bond; and and the remaining variables are as described for the compound of formula (VIIB).

The halichondrin macrolide or analog thereof is then produced from the compound of formula (VIIIC), e.g., according to the methods described in WO 2016/179607.

In general, the fragments may be coupled in any order when forming compound (VIIIB). For example, the C.0-C.1 or O-C.1 bond between fragment (IIA) and fragment (VIIIA) can be formed, as described herein, prior to or after the Sakurai and/or Prins reaction. Similarly, installation of the C.13 olefin may occur before or after any of the Sakurai, Prins, and C.0-C.1 or O-C.1 bond forming reactions.

In one embodiment, the compound of formula (VIIIB) is produced from a compound of formula (VIIIA), a compound of formula (IIA), and a compound of formula (IIB), a compound of formula (IIIC), and $R_5OH$. The compound of formula (IIA) is:

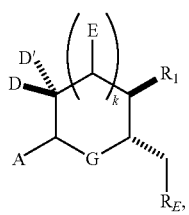
(IIA)

where $R_1$ is —$OP_6$, —$CH(Y)_2$, or —$CH_2(Y)$, where $P_6$ is H or a hydroxyl protecting group, and each Y is independently -$COOR_C$ or —$SO_2R_D$;

each $R_C$, when present, is independently optionally substituted alkyl, optionally substituted aryl, or optionally substituted arylalkyl;

each $R_D$, when present, is independently optionally substituted aryl or optionally substituted non-enolizable alkyl; and $R_E$ is —CHO or —$CH_{(1+m)}(OR_F)_{(2-m)}$, where
m is 1, and $R_F$ is a hydroxyl protecting group,
or
m is 0, and
(i) each $R_F$ is independently an alkyl or hydroxyl protecting group, or
(ii) both $R_F$ combine to form an alkylene.

The compound of formula (VIIIA) is:

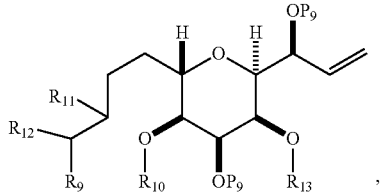
(VIIIA)

where
(i) $R_{10}$ is a hydroxyl protecting group, $R_{11}$ is alkyl ether, and $R_{12}$ is H;
(ii) $R_{10}$ is a hydroxyl protecting group, and $R_4$ and $R_5$ combine to form a double bond; or
(iii) $R_{10}$ and $R_{11}$ combine to form a bond, and $R_{12}$ is H;
$R_9$ is —CHO or —COOH; and
each $P_9$ and $R_{13}$ is independently a hydroxyl protecting group.

The compound of formula (IIIC) is:

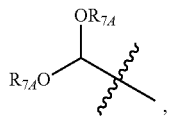
(IIIC)

where
$R_7$ is —CHO or

where each $R_{7A}$ is independently an optionally substituted alkyl; and $R_{4C}$ is

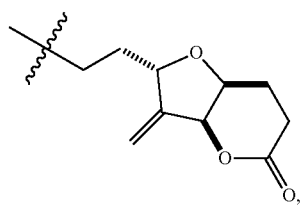

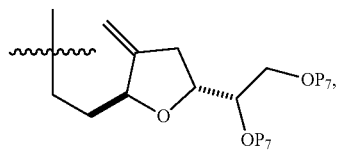

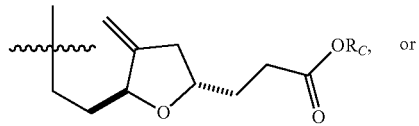 or

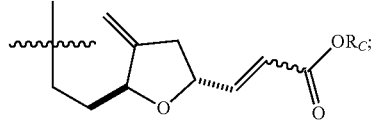

where $R_C$ is optionally substituted alkyl, optionally substituted aryl, or optionally substituted arylalkyl; and $P_7$, when present, is independently H or a hydroxyl protecting group.

The compound of formula (IIB) is:

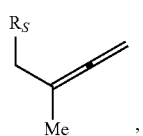
(IIB)

where $R_S$ is silyl.

In certain embodiments, a compound of formula (IIC):

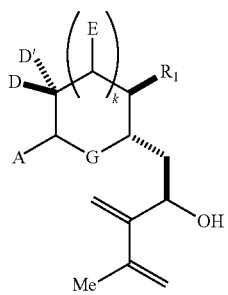

is produced from the compound of formula (IIA) and the compound of formula (IIB), e.g., by reacting with a Lewis acid, such as an oxophilic Lewis acid (e.g., boron trifluoride or a solvate thereof).

A compound of formula (IF):

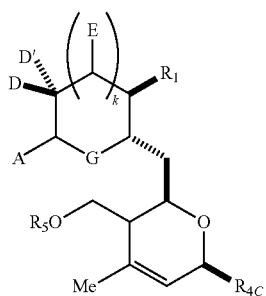

can be produced from the compound of formula (IIC), the compound of formula (IIIC), and R₅OH, e.g., by reacting with a Lewis acid, such as an oxophilic Lewis acid (e.g., boron trifluoride or a solvate thereof) (which may or may not be different from a Lewis acid used to react compounds of formulas (IIA) and (IIB)).

A compound of formula (IJ):

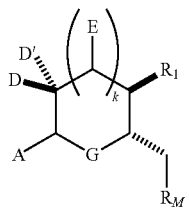

can be produced from the compound of formula (IF). The compound of formula (IF) may be converted to the compound of formula (IJ) using reaction conditions known in the art. For example, the compound of formula (IF) may be reacted with an allylic reducing agent to give the compound of formula (IJ). A non-limiting example of an allylic reducing agent is a palladium complex (e.g., Pd(PPh₃)₄) in combination with a formic acid salt (e.g., trialkylammonium formate).

The compound of formula (VIIIB) can be produced from the compound of formula (VIIIA) and the compound of formula (IJ) as described herein.

Preparation of the compound of formula (VIIIB) may include an esterification reaction between $R_1$ that is —OP₆, where P₆ is H, and $R_9$ that is —COOH. Alternatively, preparation of the compound of formula (VIIIB) may include a reaction between $R_1$ that is —CH(Y)₂ or —CH₂(Y), and $R_9$ that is —CHO (e.g., under Claisen reaction conditions). Oxidation of the Claisen product ($X_4$, together with the atom to which it is attached, is —(CH(OP₁₂))—, where P₁₂ is H) with an oxidizing agent capable of converting an alcohol to a carbonyl group may produce $X_4$ that is oxo. Further desulfonylation or decarboxylation of this compound of formula (VIIIB) may produce the compound of formula (VIIIB), in which $X_1$ is —CH₂—.

Alternatively, the compound of formula (VIIIB) may be produced from the compound of formula (IF) and the compound of formula (VIIIA). For example, a compound of formula (VIIID) may be produced from the compound of formula (IF) and the compound of formula (VIIIA) using methods described herein. The compound of formula (VIIID) is:

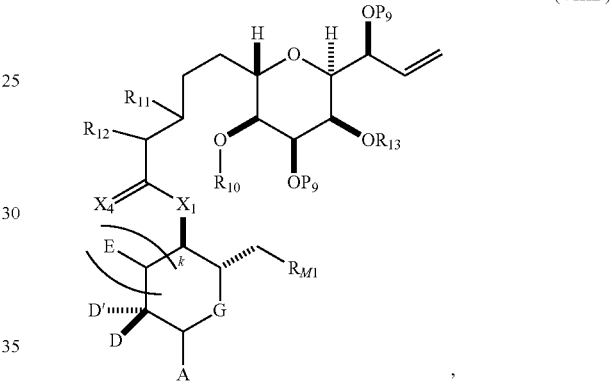

where $R_{M1}$ is

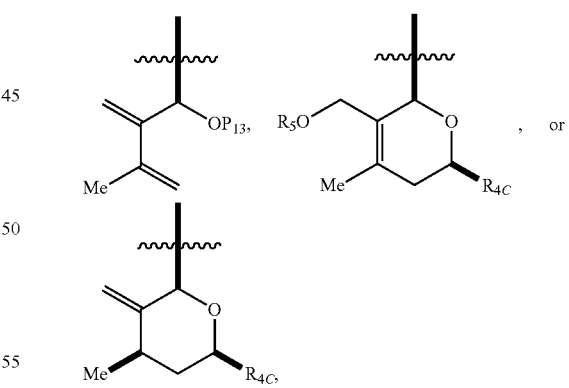

$R_5$ is optionally substituted acyl;
$P_{13}$ is H or a hydroxyl protecting group;
and the remaining variables are as described for the compound of formula (IF) and the compound of formula (VIIIB).

Alternatively, the compound of formula (VIIID) may be prepared from the compound of formula (IIC) and the compound of formula (VIIIA) as follows. The compound of formula (IIC) may be protected with a hydroxyl protecting group to give a compound of formula (IIJ):

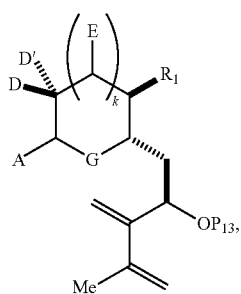

(IIJ)

where $P_{13}$ is a hydroxyl protecting group, and the remaining variables are as described for the compound of formula (IIC).

The compound of formula (IIJ) may be reacted with the compound of formula (VIIIA) using methods described herein to produce the compound of formula (VIIID), in which $R_{M1}$ is:

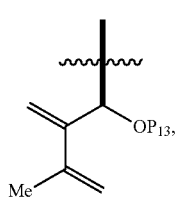

where $P_{13}$ is a hydroxyl protecting group.

The compound of formula (VIIID), in which $R_{M1}$ is

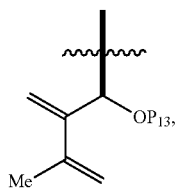

and $P_{13}$ is H, may be reacted with the compound of formula (IIIC) and $R_5OH$ under Prins reaction conditions to produce the compound of formula (VIIID), in which $R_{M1}$ is

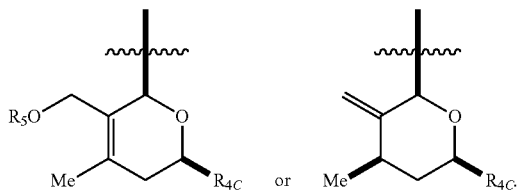

The compound of formula (VIIID) may also be produced according to the following strategy. The compound of formula (IIA) and the compound of formula (VIIIA) may be converted to a compound of formula (VIIIE) using methods described herein. The compound of formula (VIIIE) is:

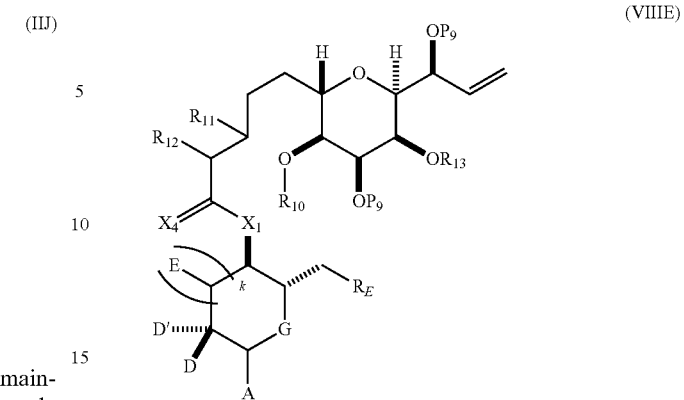

(VIIIE)

where all variables are as described for the compound of formula (VIIID) and the compound of formula (IIA).

The compound of formula (VIIID), in which $R_{M1}$ is

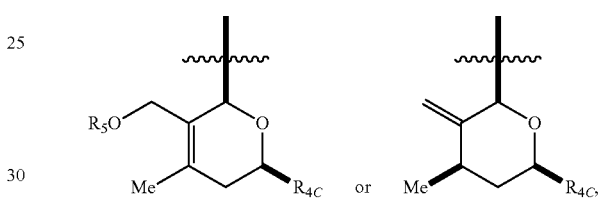

may be converted to the compound of formula (VIIIB) as described herein.

In general, the method described herein includes an allylic reduction at C.25. This reaction can be performed at any point prior to the formation of the halichondrin macrolide or analog thereof.

In certain embodiments, the method includes converting

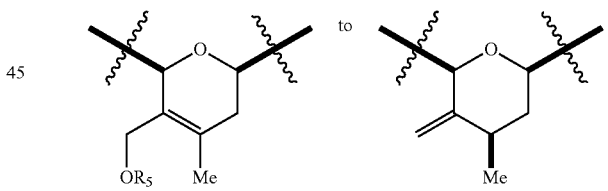

using an allylic reducing agent.

Generally, the C.12 olefin can be introduced at any point prior to the metathesis reaction via several routes. For example if $R_{4C}$ is

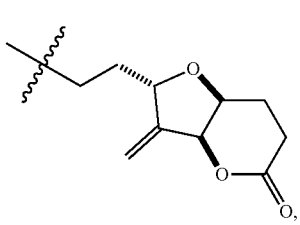

reaction with an allylic reducing agent can produce a compound in which $R_{4C}$ is

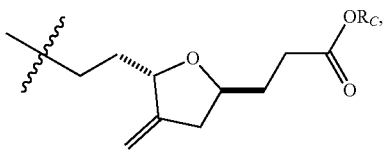

which can be reduced with a 1,2-reducing agent (e.g., DIBAL-H) to produce the corresponding aldehyde, which can be reacted with a vinyl nucleophile.

If $R_{4C}$ is

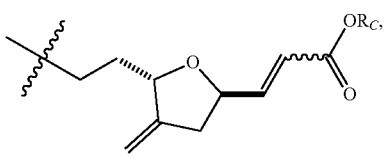

the compound can be reduced with a 1,4-reducing agent (e.g., Stryker's reagent), and the product can be reduced with a 1,2-reducing agent (e.g., DIBAL-H) to produce the corresponding aldehyde, which can be reacted with a vinyl nucleophile.

If $R_{4C}$ is

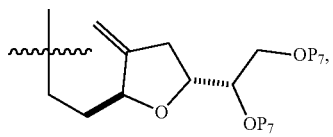

the compound can be reacted with a glycol cleaving agent (e.g., $NaIO_4$), $(R_CO)_2P(O)-CH_2-COOR_C$ (under Horner-Wadsworth-Emmons reaction conditions), a 1,4-reducing agent (e.g., Stryker's reagent), and a 1,2-reducing agent (e.g., DIBAL-H) to produce the corresponding aldehyde, which can be reacted with a vinyl nucleophile. Vinyl nucleophiles are known in the art. Vinyl nucleophiles may be prepared in situ or in a separate reaction vessel. Reaction conditions for adding vinyl nucleophiles to carbonyl groups are known in the art.

The compound of formula (VIIIC) can be formed by reacting the compound of formula (VIIIB) with an olefin metathesis catalyst.

The halichondrin macrolide may be produced from the compound of formula (VIIIC) using reaction conditions known in the art and those described herein. For example, the compound of formula (VIIIC) may be reacted with a hydroxyl protecting group removing agent to produce the halichondrin macrolide.

In general, the method described herein includes an allylic reduction at C.25. This reaction can be performed at any point prior to the formation of the halichondrin macrolide or analog thereof. For example,

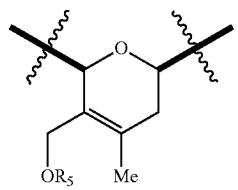

may be converted to

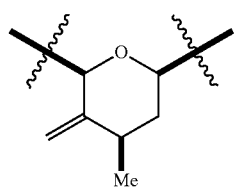 [SMILES: *[C@H]1C[C@@H](C)C(=C)[C@@H](*)O1]

using an allylic reducing agent.

C.13-C.14 Bond-Forming Macrocyclization

In still another approach, a halichondrin macrolide or analog thereof (e.g., eribulin or a salt thereof (e.g., eribulin mesylate)) may be prepared from the compound of formula (VIID):

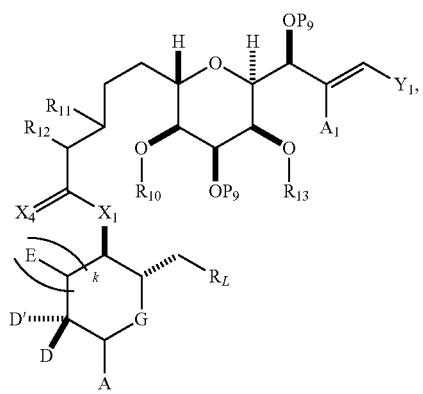

(VIID)

where
(i) $R_{10}$ is a hydroxyl protecting group, $R_{11}$ is alkyl ether, and $R_{12}$ is H;
(ii) $R_{10}$ is a hydroxyl protecting group, and $R_{11}$ and $R_{12}$ combine to form a double bond;
or
(iii) $R_{10}$ and $R_{11}$ combine to form a bond, and $R_{12}$ is H;
$X_1$ is $-CH_2-$, $-CH(Y)-$, $-C(Y)_2-$, or $-O-$,
where each Y is independently $-COOR_C$ or $-SO_2R_D$;
each $R_C$, when present, is independently optionally substituted alkyl, optionally substituted aryl, or optionally substituted arylalkyl;
each $R_D$, when present, is independently optionally substituted aryl or optionally substituted non-enolizable alkyl;
$X_4$ is oxo, or $X_4$, together with the atom to which it is attached, is $-(CH(OP_{12}))-$, where $P_{12}$ is H or a hydroxyl protecting group;
$A_1$ is H or $-OP''$, where P'' is H or a hydroxyl protecting group;
$Y_1$ is chloro, bromo, iodo, trifluoromethanesulfonate, or trialkylsilane;

$R_{13}$ and each $P_9$ is independently a hydroxyl protecting group;

$R_L$ is

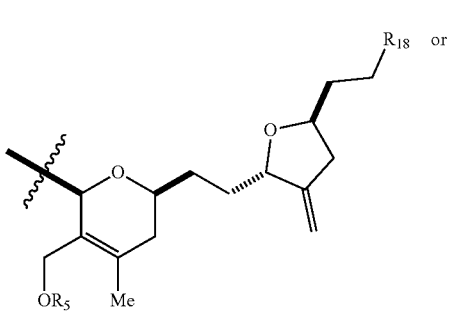

or

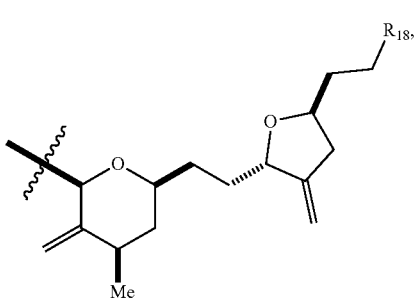

where $R_{18}$ is —CHO or —CH$_2$OP$_7$;

$R_5$ is optionally substituted acyl; and $P_7$, when present, is independently H or a hydroxyl protecting group;

and the remaining variables are as described for the halichondrin macrolide or analog thereof.

The compound of formula (VIID) is then converted to a compound of formula (VIIE):

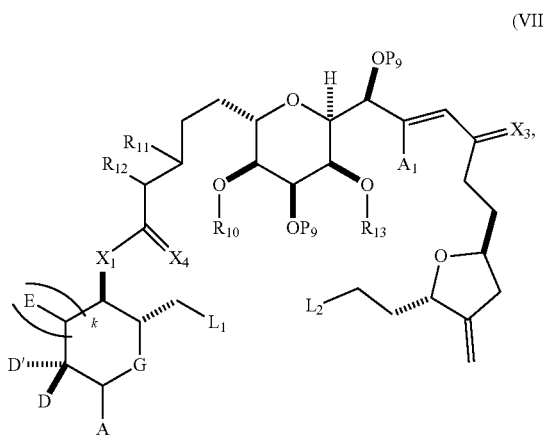 (VIIE)

where $L_1$ is

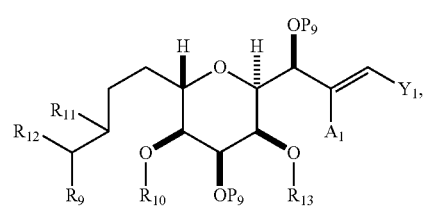

where $L_2$ and $L_3$ combine to form a bond;

each $P_9$ is independently a hydroxyl protecting group, and $X_3$ is oxo or $X_3$, together with the carbon atom to which it is attached, is —(CH(OP$_{11}$))—, where $P_{11}$ is H or a hydroxyl protecting group;

and the remaining variables are as described for the compound of formula (VIID).

In certain embodiments, the compound of formula (VIID), in which $R_{18}$ is —CHO, is subjected to Nozaki-Hiyama-Kishi reaction conditions to produce the compound of formula (VIIE).

The compound of formula (VIIE) may then be converted to a halichondrin macrolide or analog thereof using methods described herein and those known in the art, e.g., those described in US 2009/0203771, US 2016/0264594, and WO 2016/179607.

In general, the fragments may be coupled in any order when forming the compound of formula (VIID). For example, the C.0-C.1 or O-C.1 bond in the compounds of formula (VIID) can be formed, as described herein, prior to or after the Sakurai and/or Prins reaction.

In some embodiments, a compound of formula (VIID) is produced from a compound of formula (IIA), a compound of formula (IIB), a compound of formula (IIIC), and $R_5$OH, where $R_5$ is optionally substituted acyl.

The compound of formula (VIIA) is:

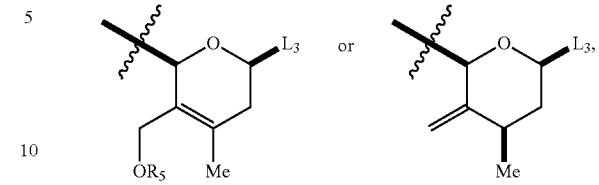 (VIIA)

where $R_9$ is —CHO or —COOH; and the remaining variables are as described for the compound of formula (VIID).

The compound of formula (IIA) is:

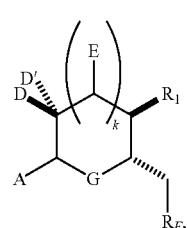 (IIA)

where
R₁ is —OP₆, —CH(Y)₂, or —CH₂(Y),
where P₆ is H or a hydroxyl protecting group, and each Y is independently —COOR_C or —SO₂R_D;
each R_C, when present, is independently optionally substituted alkyl, optionally substituted aryl, or optionally substituted arylalkyl;
each R_D, when present, is independently optionally substituted aryl or optionally substituted non-enolizable alkyl;
and
R_E is —CHO or —CH_{(1+m)}(OR_F)_{(2-m)},
where
m is 1, and R_F is a hydroxyl protecting group, or
m is 0, and (i) each R_F is independently an alkyl or hydroxyl protecting group, or
(ii) both R_F combine to form an alkylene.
The compound of formula (IIB) is:

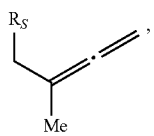
(IIB)

where R_S is silyl
The compound of formula (IIIC) is:

R_{4C}-R_7,   (IIIC)

where
R_{4C} is

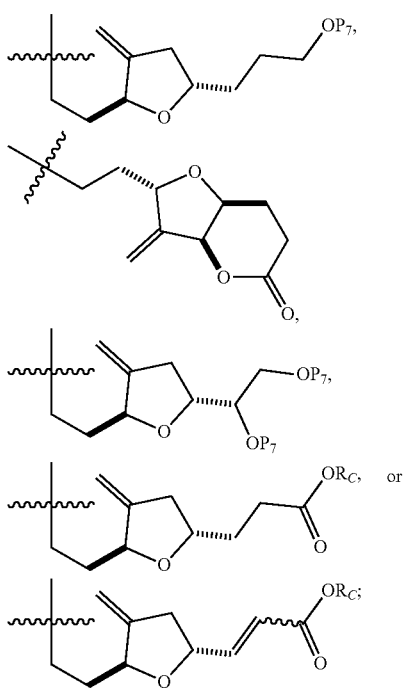

R_7 is —CHO or

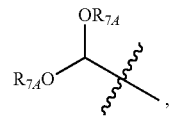

where each R_{7A} is independently an optionally substituted alkyl; and
the remaining variables are as described for the compound of formula (VIID).

Preparation of the compound of formula (VIID) includes a Sakurai reaction between R_E that is —CHO and the compound of formula (IIB) producing a group of the structure:

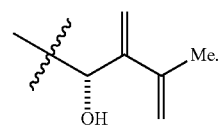 [SMILES: *[C@@H](O)C(=C)C(=C)C]

This product may then be reacted with the compound of formula (IIIC) under the Prins reaction conditions to produce a group of the structure:

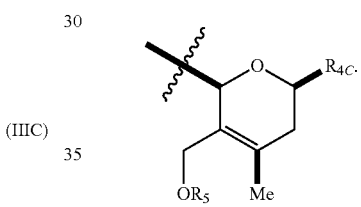

This group may be converted to R_L as described herein.

If the stereochemistry of the secondary alcohol in the Sakurai reaction product differs from the desired stereochemistry, this group may be subjected to epimerization reaction conditions described herein (e.g., oxidation followed by Corey-Bakshi-Shibata reduction; alternatively, Mitsunobu reaction may be used to invert the stereogenic center).

If R_E is —CH_{(1+m)}(OR_F)_{(2-m)}, preparation of the compound of formula (VIID) may further include conversion of R_E to —CHO under acetal deprotecting conditions, e.g., through a reaction with an aqueous Brønsted acid (e.g., when m is 0), or through oxidation using an oxidizing agent capable of converting an alcohol to a carbonyl group (e.g., when m is 1).

Preparation of the compound of formula (VIID) may include an esterification reaction between R₁ that is —OP₆, where P₆ is H, and R₉ that is —COOH. Alternatively, preparation of the compound of formula (VIID) may include a reaction between R₁ that is —CH(Y)₂ or —CH₂(Y), and R₉ that is —CHO (e.g., under Claisen reaction conditions). Further desulfonylation or decarboxylation of this compound of formula (VIID) may produce the compound of formula (VIID), in which X₁ is —CH₂—.

In some embodiments, preparation of the compound of formula (VIID) includes producing a compound of formula (IIC) from the compound of formula (IIA) and the compound of formula (IIB) (e.g., under Sakurai reaction conditions). The compound of formula (IIC) is:

(IIC)

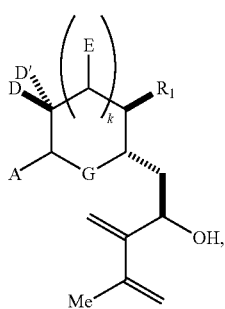

where all variables are as described for the compound of formula (IIA).

The compound of formula (IIC) may be reacted with the compound of formula (IIB), the compound of formula (IIIC), and $R_5OH$ to produce a compound of formula (IF):

(IF)

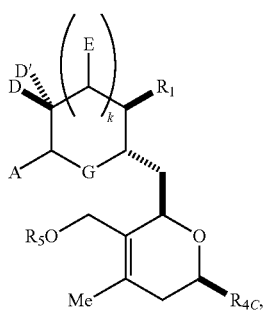

where all variables are as described for the compound of formula (IIA), the compound of formula (IIIC), and $R_5OH$.

Preparation of the compound of formula (IF) may include a Prins reaction between the compound of formula (IIC), the compound of formula (IIC), and $R_5OH$.

The compound of formula (IF) may be converted to a compound of formula (IH):

(IH)

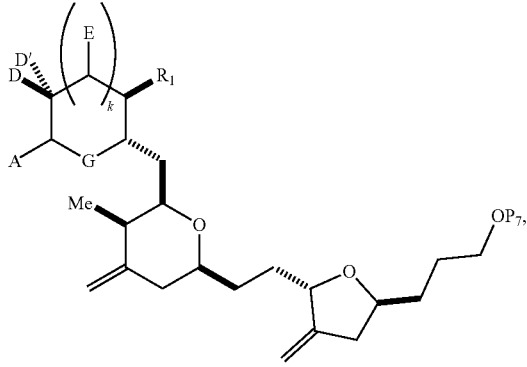

where all variables are described for the compound of formula (IF).

In general, the method described herein includes an allylic reduction at C.25. This reaction can be performed at any point prior to the formation of the halichondrin macrolide or analog thereof. For example,

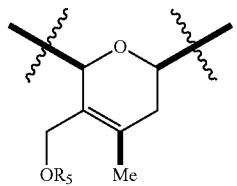

may be converted to

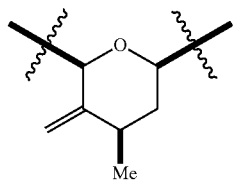 [SMILES: *[C@H]1C[C@@H](C)C(=C)[C@@H](*)O1]

using an allylic reducing agent.

In certain embodiments, the compound of formula (IF) may be reacted with an allylic reducing agent to produce the compound of formula (IH).

In the reactions described herein, the requisite transformations of groups $R_{4C}$ may be performed using reaction conditions known in the art. In some embodiments, the transformations of groups $R_{4C}$ are as described herein.

C.15-C.16 Bond-Forming Macrocyclization

In one approach, the macrocyclization reaction is a carbon-carbon bond-forming reaction (e.g., olefin metathesis) that provides a C.15-C.16 bond in a halichondrin macrolide or analog thereof (e.g., eribulin or a salt thereof (e.g., eribulin mesylate)). A non-macrocyclic intermediate in the synthesis of the halichondrin macrolide or analog thereof (e.g., eribulin or a salt thereof (e.g., eribulin mesylate)) may be a compound of formula (IVB).

The compound of formula (IVB) is:

(IVB)

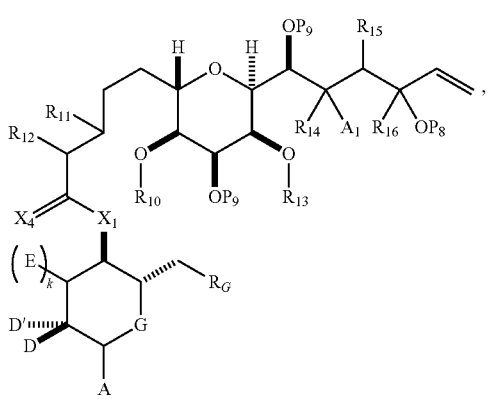

where each $P_9$ is independently a hydroxyl protecting group;

(a1) $R_{10}$ is H or a hydroxyl protecting group, $R_{11}$ is alkyl ether, and $R_{12}$ is H;

(a2) $R_{10}$ is H or a hydroxyl protecting group, and $R_{11}$ and $R_{12}$ combine to form a double bond;

or (a3) $R_{10}$ and $R_{11}$ combine to form a bond, and $R_{12}$ is H;

(b1) $A_1$ and $R_{14}$ combine to form oxo, $R_{13}$ is H or a hydroxyl protecting group, and $R_{15}$ is H;

or (b2) $A_1$ is H or —OP''', and:

(i) $R_{13}$ is H or a hydroxyl protecting group, and $R_{14}$ and $R_{15}$ combine to form a double bond;

or (ii) $R_{13}$ and $R_{14}$ combine to form a bond, and $R_{15}$ is H or —OP'''; and (c1) $R_{16}$ is H, and $P_8$ is H or a hydroxyl protecting group;

or (c2) $R_{16}$ and $P_8$ combine to form a double bond;

each P''', when present, is independently H or a hydroxyl protecting group $X_1$ is —O—, —C(Y)$_2$—, —CH(Y)—, or —CH$_2$—, where each Y is independently -COOR$_C$ or —SO$_2$R$_D$, where each R$_C$, when present, is independently optionally substituted alkyl, optionally substituted aryl, or optionally substituted arylalkyl, and each R$_D$, when present, is independently optionally substituted aryl or optionally substituted non-enolizable alkyl;

$R_G$ is

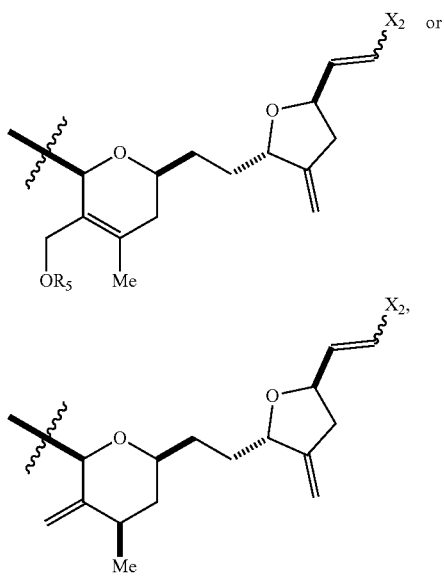

where $R_5$ is an optionally substituted acyl, and $X_2$ is H or —CH$_2$—X$_{2A}$—CH$_2$—CH=CH$_2$, where $X_{2A}$ is —O—, —C(R$_H$)$_2$—, or —NR$_I$—, where each R$_H$ is independently H or —COOR$_J$, R$_I$ is an N-protecting group, and R$_J$ is C$_{1-6}$ alkyl;

and $X_4$ is oxo, or $X_4$, together with the atom to which it is attached, is —(CH(OP$_{12}$))—, where P$_{12}$ is H or a hydroxyl protecting group;

and the remaining variables are as described for the halichondrin macrolide or analog thereof.

In some embodiments, the compound of formula (IVB) is a compound of formula (IVBa):

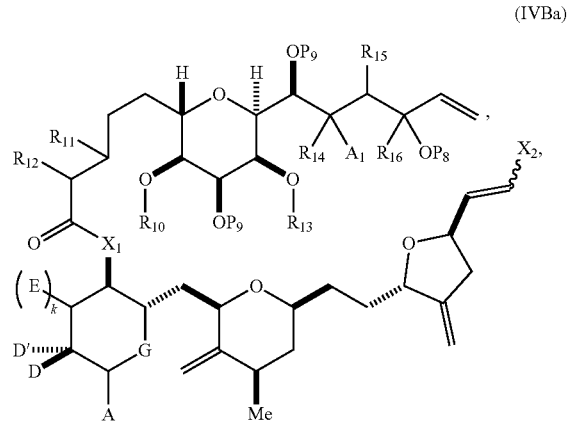

(IVBa)

where all variables are as described in the compounds of formula (IVB).

The compound of formula (IVB) (e.g., the compound of formula (IVBa)) is converted to the compound of formula (IVC) through an olefin metathesis reaction. The compound of formula (IVC) is:

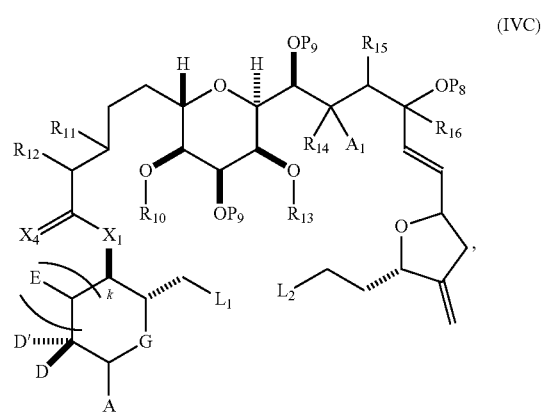

(IVC)

where $L_1$ is

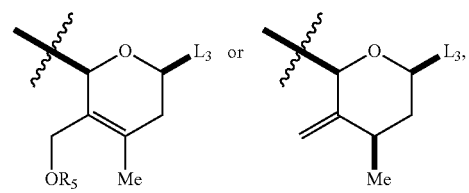

where $L_2$ and $L_3$ combine to form a bond;

and the remaining variables are as described for the compound of formula (IVB).

The compound of formula (IVC) is then converted to the compound of formula (IVD):

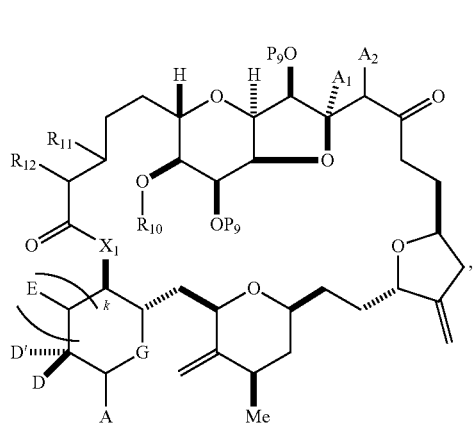

(IVD)

where each of $A_1$ and $A_2$ is independently H or —OP''', and the remaining variables are as described for the compound of formula (IVC).

The compound of formula (IVC) may be converted to the compound of formula (IVD) using reaction conditions known in the art. For example, the compound of formula (IVC) may be reacted with a 1,4-reducing agent to give the compound of formula (IVD).

Preparation of the compound of formula (IVD) may further include reacting the compound of formula (IVA), (IVB), or (IVC), in which $P_8$ and $R_{16}$ are both H, with an oxidizing agent capable of converting an alcohol to a carbonyl group (e.g., Dess-Martin periodinane or a dimethylsulfonium compound) to give the compound of formula (IVA), (IVB), or (IVC), in which $R_{16}$ and $P_8$ combine to form a double bond (e.g., the compound of formula IVCa)). If $P_8$ is a hydroxyl protecting group, prior to oxidation, the compound of formula (IVA), (IVB), or (IVC) may be treated with a hydroxyl protecting group removing agent. In a non-limiting example, preparation of the compound of formula (IVD) includes oxidizing the compound of formula (IVC), in which P is H, $R_{16}$ is H, with an oxidizing agent capable of converting an alcohol to a carbonyl group (e.g., Dess-Martin periodinane or a dimethylsulfonium compound) to give a compound of formula (IVCa):

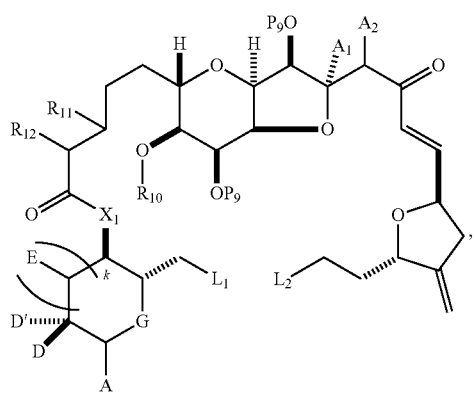

(IVCa)

where all variables are described for the compound of formula (IVC).

The compound of formula (IVD) is then converted to the halichondrin macrolide or analog thereof using methods described herein and those known in the art, e.g., those described in US 2016/0264594 and WO 2016/179607.

If the compound of formula (IVD) includes hydroxyl protecting groups as $R_3$ and/or $P_5$, these hydroxyl protecting groups can be removed with a hydroxyl protecting group removing agent. For example, a hydroxyl protecting group removing agent may be a fluoride source, if the hydroxyl protecting group is a silyl group.

If, in the compound of formula (IVD), each $P_9$ is H, and $X_3$ is oxo, the synthesis may further involve a reaction with a Brønsted acid (e.g., a Brønsted acid having a pKa of 5±3), e.g., after the reaction of the compound of formula (IVD) with a hydroxyl protecting group removing agent (e.g., to convert $P_9$ from a hydroxyl protecting group into H).

If, in the compound of formula (IVD), $X_3$ is oxo, $R_{10}$ is a hydroxyl protecting group, and $R_{11}$ and $R_{12}$ combine to form a double bond, treatment with a hydroxyl protecting group removing agent can provide the compound of formula (IVD), in which $R_{10}$ and $R_{11}$ combine to form a bond, and $R_{12}$ is H.

In general, the fragments may be coupled in any order when forming compound (IVB). For example, the C.0-C.1 or O-C.1 bond between fragment (IIA) and fragment (IVA) can be formed, as described herein, prior to or after the Sakurai and/or Prins reaction. Similarly, installation of the C.15 olefin may occur before or after any of the Sakurai, Prins, and C.0-C.1 or O-C.1 bond forming reactions.

In certain embodiments, the compound of formula (IVB) is produced from a compound of formula (IIA), a compound of formula (IIB), a compound of formula (IIIA), a compound of formula (IVA), and $R_5OH$.

The compound of formula (IVA) is:

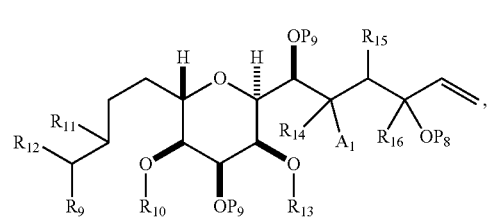

(IVA)

where
$R_9$ is —CHO or —COOH,
and the remaining variables are as described for the compound of formula (IVB).

The compound of formula (IIA) is:

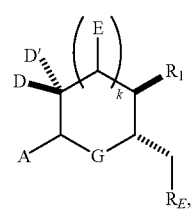

(IIA)

where $R_1$ is —$OP_6$, —$CH(Y)_2$, or —$CH_2(Y)$, where $P_6$ is H or a hydroxyl protecting group, and each Y is independently —$COOR_C$ or —$SO_2R_D$;

$R_E$ is —CHO or —$CH_{(1+m)}(OR_F)_{(2-m)}$, where m is 1, and $R_F$ is a hydroxyl protecting group, or m is 0, and (i) each $R_F$ is independently an alkyl or hydroxyl protecting group, or (ii) both $R_F$ combine to form an alkylene;

and the remaining variables are as described for the compound of formula (IVB).

The compound of formula (IIB) is:

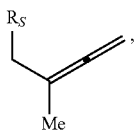

(IIB)

where $R_S$ is silyl.

The compound of formula (IIIA) is:

(IIIA)

where $R_7$ is —CHO or

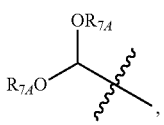

where each $R_{7A}$ is independently an optionally substituted alkyl; and $R_{4A}$ is

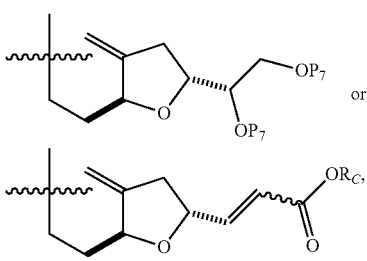

where $R_C$ is optionally substituted alkyl, optionally substituted aryl, or optionally substituted arylalkyl, and each $P_7$ is independently H or a hydroxyl protecting group.

Preparation of the compound of formula (IVB) includes a Sakurai reaction between $R_E$ that is —CHO and the compound of formula (IIB) producing a group of the structure:

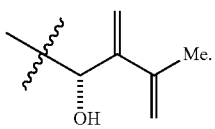 [SMILES: *[C@@H](O)C(=C)C(=C)C]

This product may then be reacted with the compound of formula (IIIA) under Prins reaction conditions to produce a group of the structure:

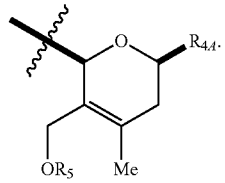

This group may be converted to $R_G$ as described herein.

If the stereochemistry of the secondary alcohol in the Sakurai reaction product differs from the desired stereochemistry, this group may be subjected to epimerization reaction conditions described herein (e.g., oxidation followed by Corey-Bakshi-Shibata reduction; alternatively, Mitsunobu reaction may be used to invert the stereogenic center).

If $R_E$ is —$CH_{(1+m)}(OR_F)_{(2-m)}$, preparation of the compound of formula (IVB) may further include conversion of $R_E$ to —CHO under acetal deprotecting conditions, e.g., through a reaction with an aqueous Brønsted acid (e.g., when m is 0), or through oxidation using an oxidizing agent capable of converting an alcohol to a carbonyl group (e.g., when m is 1).

Preparation of $R_G$ may include reacting $R_{4A}$ that is

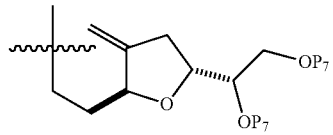

with a glycol cleaving agent, and subjecting the resulting product to Horner-Wadsworth-Emmons reaction with $(R_CO)_2P(O)$—$CH_2$—$COOR_C$ to produce $R_{4A}$ that is

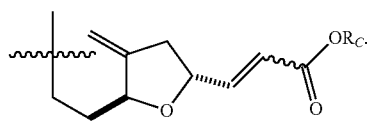

This reaction may be performed after Sakurai and Prins reactions.

Preparation of $R_G$ may further include a reaction of $R_{4A}$ that is

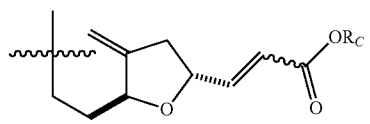

with a 1,2-reducing agent and reacting the resulting product with an allyl halide or allyl pseudohalide. This reaction may be performed after Sakurai and Prins reactions.

Group $R_E$ may be converted to $R_G$ before or after the reaction of the compound of formula (IIA) with the compound of formula (IVA). For example, conversion of $R_E$ to $R_G$ before the reaction of the compound of formula (IIA) with the compound of formula (IVA) may be carried out via compounds of formulae (IB) and (IC), as described herein. Conversion of $R_E$ to $R_G$ after the reaction of the compound of formula (IIA) with the compound of formula (IVA) may be carried out via a compound of formula (IVAa):

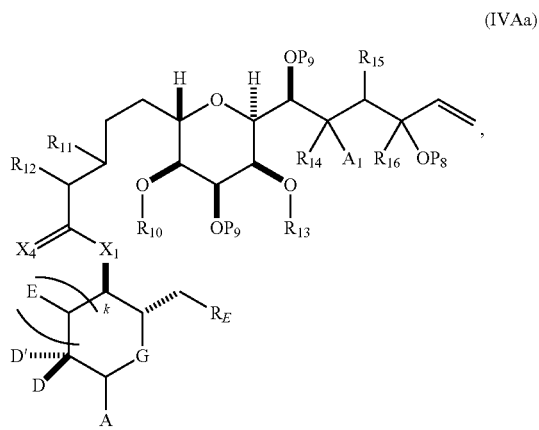

(IVAa)

where
$X_1$ is —CH$_2$—, —CH(Y)—, —C(Y)$_2$—, or —O—, where each Y is independently —COOR$_C$ or —SO$_2$R$_D$;
each $R_C$, when present, is independently optionally substituted alkyl, optionally substituted aryl, or optionally substituted arylalkyl;
each $R_D$, when present, is independently optionally substituted aryl or optionally substituted non-enolizable alkyl;
$X_4$ is oxo, or $X_4$, together with the atom to which it is attached, is —(CH(OP$_{12}$))—, where $P_{12}$ is H or a hydroxyl protecting group; and
the remaining variables are as described for the compound of formulae (IIA) and (IVA).

The compound of formula (IVAa), in which $R_E$ is —CHO, may be reacted with the compound of formula (IIB) under Sakurai reaction conditions to produce a compound of formula (IVAb):

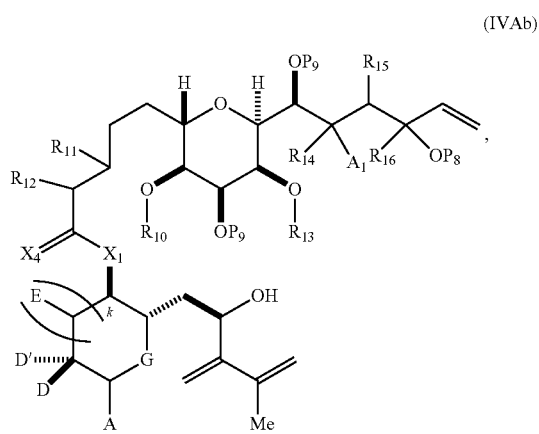

(IVAb)

where all variables are as described for the compound of formula (IVAa).

A compound of formula (IVAc) may be produced from the compound of formula (IVAb), the compound of formula (IIA), and R$_5$OH. The compound of formula (IVAc) is:

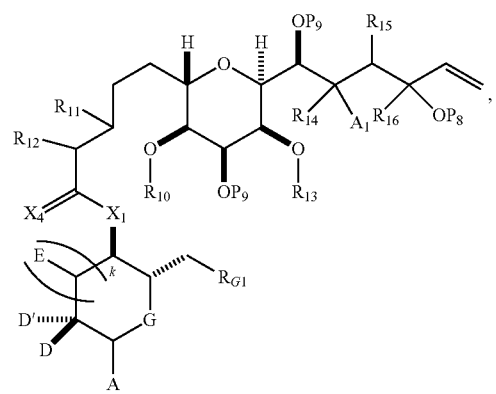

(IVAc)

where
$R_{G1}$ is

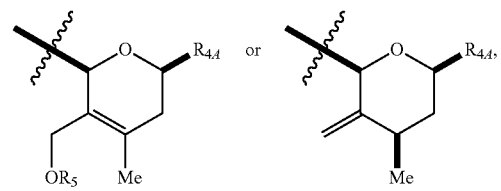

$R_5$ is optionally substituted acyl, and
the remaining variables are as described for the compound of formula (IVAb).

For example, the compound of formula (IVAb) may be reacted with the compound of formula (IIIA) and R$_5$OH under Prins reaction conditions to produce the compound of formula (IVAc), in which $R_{G1}$ is

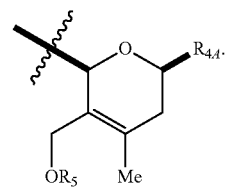

The compound of formula (IVAc) may be converted to the compound of formula (IVB) as described herein.

If the compound described herein (e.g., a Prins reaction product) includes:

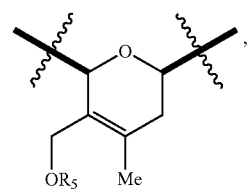

the synthesis may further include reacting such compound with an allylic reducing agent to produce the group

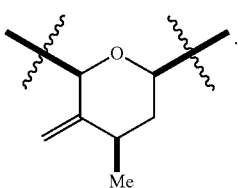 [SMILES: *[C@H]1C[C@@H](C)C(=C)[C@@H](*)O1]

A non-limiting example of an allylic reducing agent is a palladium complex (e.g., Pd(PPh$_3$)$_4$) in combination with a formic acid salt (e.g., trialkylammonium formate).

Alternatively, preparation of the compound of formula (IVB) may include producing a compound of formula (IA) from a compound of formula (IIA), a compound of formula (IIIA), and R$_5$OH. The compound of formula (IA) is:

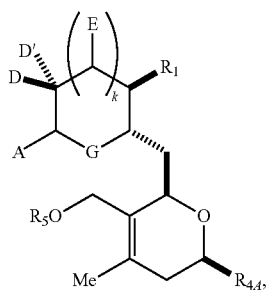

(IA)

where all variables are as described for the compound of formula (IIA), the compound of formula (IIIA), and R$_5$OH.

The compound of formula (IA) may be reacted with the compound of formula (IVA) to form the compound of formula (IVB). For example, the compound of formula (IA) may be converted to the compound of formula (IB), which may then be converted to the compound of formula (IC). The compound of formula (IB) is:

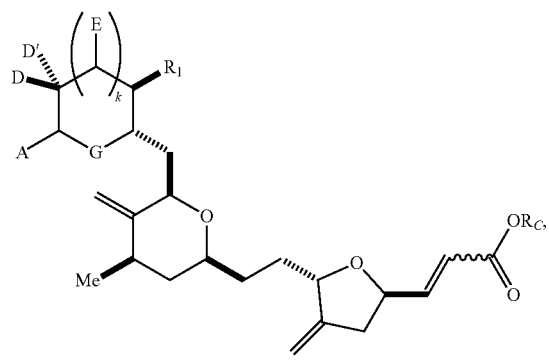

(IB)

where all variables are as described for the compound of formula (IA).

Preparation of the compound of formula (IB) may include reacting the compound of formula (IA) with an allylic reducing agent.

The compound of formula (IC) is:

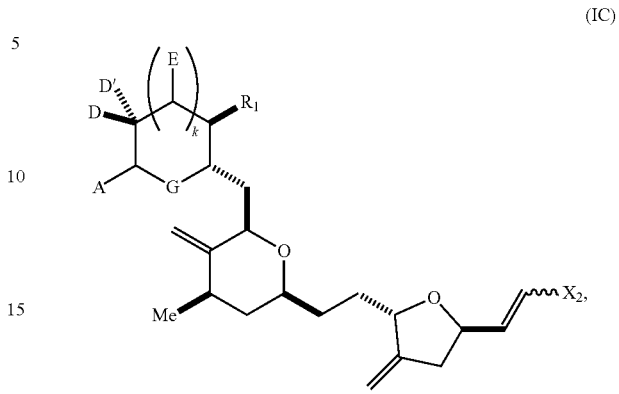

(IC)

where X$_2$ is as described for the compound of formula (IVB), and the remaining variables are as described for the compound of formula (IB).

The compound of formula (IVB) may be prepared from the compound of formula (IC) and the compound of formula (IVA) as described herein.

Preparation of the compound of formula (IVB), in which X$_1$ is —C(Y)$_2$—, —CH(Y)—, or —CH$_2$—, may include a reaction (e.g., Claisen reaction) between an intermediate (e.g., the compound of formula (IVA), in which R$_9$ is —CHO) and another intermediate (e.g., the compound of formula (IIA), (IA), (IB), or (IC), in which R$_1$ is —CH(Y)$_2$ or —CH$_2$(Y)) that was treated with a Brønsted base to produce an intermediate (e.g., the compound of formula (IVB), in which X$_1$ is —C(Y)$_2$—, —CH(Y)—, or —CH$_2$—). If X$_1$ in the compound of formula (IVB) is —CH$_2$—, the preparation of the compound of formula (IVB) may further include a desulfonylation or decarboxylation reaction.

Alternatively, preparation of the compound of formula (IVB), in which X$_1$ is —O—, may include a reaction (e.g., an esterification reaction) between an intermediate (e.g., the compound of formula (IVA), in which R$_9$ is —COOH) and another intermediate (e.g., the compound of formula (IIA), (IA), (IB), or (IC), in which R$_1$ that is —OP$_6$, where P$_6$ is H) to produce an intermediate (e.g., the compound of formula (IVB), in which X$_1$ is —O—).

Preparation of certain compounds of formula (IVB) or (IVC) may further involve conversion of the compound of formula (IVB) or (IVC), in which A$_1$ is H, and R$_{14}$ and R$_{15}$ combine to form a double bond, into the compound of formula (IVB) or (IVC), respectively, in which R$_{14}$ and A$_1$ combine to form oxo. In a non-limiting example, the enone in the compound of formula (IVB) or (IVC), in which R$_{14}$ and R$_{15}$ combine to form a double bond can be converted into a C.12-C.13 epoxide using a nucleophilic peroxide agent, e.g., t-butyl hydroperoxide, which can then be converted into the compound of formula (IVB) or (IVC), in which A$_1$ and R$_{14}$ combine to form oxo, using methods known in the art, e.g., by reacting with a bidentate phosphine ligand and a source of Pd(0) (see, e.g., Muzart, J., *Eur. J. Org. Chem.*, 4717-4741, 2011). Thus, the compound of formula (IVB) or (IVC), in which A$_1$ is OP'', can be prepared. Other transformations may involve α-oxygenation to produce the compound of formula (IVB) or (IVC), in which R$_{15}$ is OP''.

In general, the method described herein includes an allylic reduction at C.25. This reaction can be performed at any point prior to the formation of the halichondrin macrolide or analog thereof. For example,

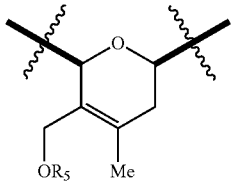

may be converted to

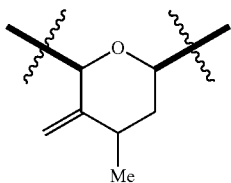 [SMILES: *[C@H]1CC(C)C(=C)[C@@H](*)O1]

using an allylic reducing agent.

C.19-C.20 Bond-Forming Macrocyclization

In another approach, the macrocyclization reaction can be a carbon-carbon bond-forming reaction (e.g., olefin metathesis) that provides a C.19-C.20 bond in a halichondrin macrolide or analog thereof (e.g., eribulin or a salt thereof (e.g., eribulin mesylate)). A non-macrocyclic intermediate in the synthesis of the halichondrin macrolide or analog thereof (e.g., eribulin or a salt thereof (e.g., eribulin mesylate)) may be a compound of formula (VB).

The compound of formula (VB) is:

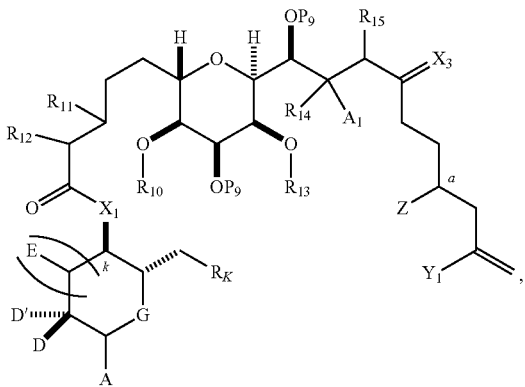

(VB)

where
a designates (R)-stereogenic center, and Z is a sulfonate, chloride, bromide, or iodide; or a designates (S)-stereogenic center, and Z is $OR_{16}$, where $R_{16}$ is a hydroxyl protecting group;

$X_1$ is —$CH_2$—, —CH(Y)—, —C(Y)$_2$—, or —O—, where each Y is independently —$COOR_C$ or —$SO_2R_D$;

each $P_9$ is independently a hydroxyl protecting group, and $X_3$ is oxo; or both $P_9$ groups and $X_3$, together with the atoms to which each is attached, combine to form a ketal;

$Y_1$ is iodide, bromide, or trifluoromethanesulfonate;

each $R_C$, when present, is independently optionally substituted alkyl, optionally substituted aryl, or optionally substituted arylalkyl;

each $R_D$, when present, is independently optionally substituted aryl or optionally substituted non-enolizable alkyl;

$R_K$ is

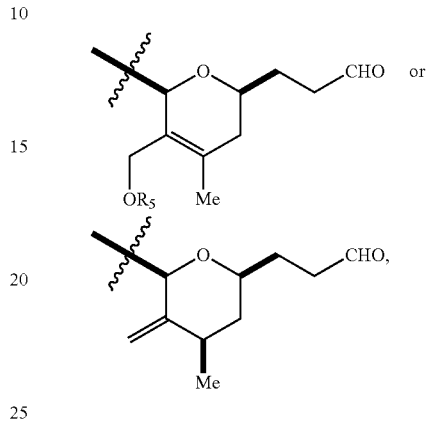

where $R_5$ is optionally substituted acyl;

(a1) $R_{10}$ is a hydroxyl protecting group, $R_{11}$ is alkyl ether, and $R_{12}$ is H;

(a2) $R_{10}$ is a hydroxyl protecting group, and $R_{11}$ and $R_{12}$ combine to form a double bond;

or (a3) $R_{10}$ and $R_{11}$ combine to form a bond, and $R_{12}$ is H;

(b1) $A_1$ and $R_{14}$ combine to form oxo, $R_{13}$ is a hydroxyl protecting group, and $R_{15}$ is H;

or (b2) $A_1$ is H or —OP''', and:

(i) $R_{13}$ is a hydroxyl protecting group, and $R_{14}$ and $R_{15}$ combine to form a double bond;

or (ii) $R_{13}$ and $R_{14}$ combine to form a bond, and $R_{15}$ is H or —OP''';

each P''' is independently a hydroxyl protecting group;

and the remaining variables are as described for the halichondrin macrolide or analog thereof.

The compound of formula (VB) is then converted to the compound of formula (VC) using reaction conditions known in the art. For example, the compound of formula (VB) may be subjected to Nozaki-Hiyama-Kishi reaction conditions known in the art to produce the compound of formula (VC). Nozaki-Hiyama-Kishi reaction on the compound of formula (VB) can include reacting the compound of formula (VB) with a Cr(II) salt and a Ni(II) salt. Ancillary ligands can be used in combination with the metal salts. In a non-limiting example, a substituted 1,10-phenanthroline can be used in combination with a Ni(II) salt. Chiral ancillary ligands can be used to render the reaction stereoselective. In a non-limiting example, chiral N-(dihydrooxazolyl-phenyl)-sulfonamides can be used with a Cr(II) salt to control the stereochemistry of the carbonyl carbon, to which a vinyl nucleophile is added in the course of Nozaki-Hiyama-Kishi reaction.

The compound of formula (VC) is:

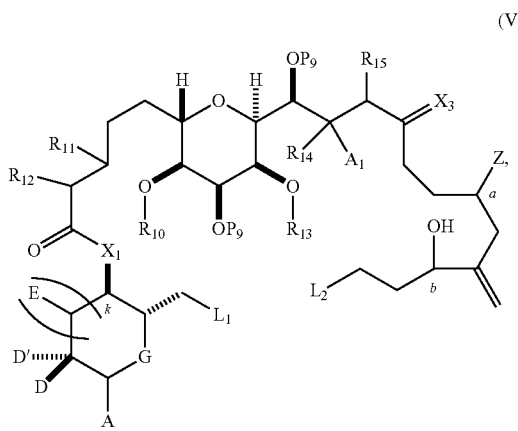

(VC)

where
$L_1$ is

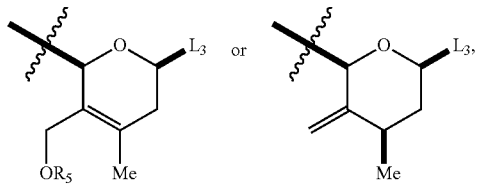

where $L_2$ and $L_3$ combine to form a bond;
b designates (S)-stereogenic center, if a designates (R)-stereogenic center;
and
b designates (R)-stereogenic center, if a designates (S)-stereogenic center;
and the remaining variables are as described for the compound of formula (IVB).

The compound of formula (VC) is then converted to the halichondrin macrolide or analog thereof using methods described herein and those known in the art, e.g., those described in US 2016/0264594, US 2009/0203771, and WO 2016/179607.

The compound of formula (VC), in which Z is $OR_{16}$, $R_{16}$ is a hydroxyl protecting group ester, a designates (S)-stereogenic center, and b designates (R)-stereogenic center, can be converted to a compound of formula (VD):

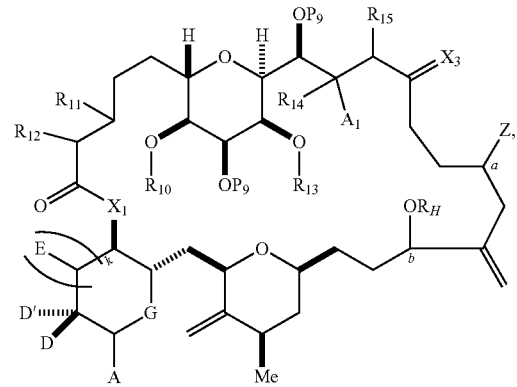

(VD)

where a designates (S)-stereogenic center, b designates (R)-stereogenic center, Z is $OR_{16}$, in which $R_{16}$ is a hydroxyl protecting group (e.g., $R_{16}$, together with the atom to which it is attached, combine to form an ester), $R_H$ is sulfonyl, and the remaining variables are as described for the compound of formula (VC).

The compound of formula (VC), in which Z is $OR_{16}$, $R_{16}$ is a hydroxyl protecting group ester, a designates (S)-stereogenic center, and b designates (R)-stereogenic center, may be converted to the compound of formula (VD), e.g., by reacting with a sulfonyl electrophile, such as a sulfonyl chloride or a sulfonyl anhydride. In the compound of formula (VD), a hydroxyl protecting group in Z may be removed, resulting in the formation of the C.16-C.20 furan ring in the structure of the halichondrin macrolide or analog thereof (e.g., eribulin or a salt thereof (e.g., eribulin mesylate)). In a non-limiting example, the concomitant removal of a hydroxyl protecting group in Z (e.g., if Z is an ester) and the formation of the C.16-C.20 furan ring in the structure of the halichondrin macrolide or analog thereof may be achieved by the treatment of the compound of formula (VD) with a strong base (e.g., a $C_{1-6}$ alkoxide (e.g., KOMe)).

The compound of formula (VB), in which Z is a sulfonate, chloride, bromide, or iodide, a designates (S)-stereogenic center, and b designates (R)-stereogenic center, may be converted to the halichondrin macrolide or analog thereof (e.g., eribulin or a salt thereof (e.g., eribulin mesylate)) directly upon formation of the compound of formula (VC), e.g., upon the reaction work up and/or purification (e.g., on silica gel).

If the compound of formula (VD) includes hydroxyl protecting groups as $R_3$ and/or $P_5$, these hydroxyl protecting groups can be removed with a hydroxyl protecting group removing agent. For example, a hydroxyl protecting group removing agent may be a fluoride source, if the hydroxyl protecting group is a silyl group.

If, in the compound of formula (VC), each $P_9$ is H, and $X_3$ is oxo, the synthesis may further involve a reaction with a Brønsted acid (e.g., a Brønsted acid having a pKa of 5±3), e.g., after the formation of the C.16-C.20 furan ring.

If, in the compound of formula (VC), (VD), or a C.16-C.20 furan cyclization product thereof, $X_3$ is oxo, $R_{13}$ is a hydroxyl protecting group, and $R_{14}$ and $R_{15}$ combine to form a double bond, treatment with a hydroxyl protecting group removing agent can provide the compound of formula (VC), (VD), or a C.16-C.20 furan cyclization product thereof, in which $R_{13}$ and $R_{14}$ combine to form a bond, and $R_{15}$ is H.

Preparation of the halichondrin macrolides or analogs thereof may further involve conversion of the compound of formula (VC), (VD), or a C.16-C.20 furan cyclization product thereof, in which $A_1$ is H, and $R_{14}$ and $R_{15}$ combine to form a double bond, into the compound of formula (VC), (VD), or a C.16-C.20 furan cyclization product thereof, respectively, in which $R_{14}$ and $A_1$ combine to form oxo. In a non-limiting example, the enone in the compound of formula (VC), (VD), or a C.16-C.20 furan cyclization product thereof, in which $X_3$ is oxo, and $R_{14}$ and $R_{15}$ combine to form a double bond, can be converted into a C.12-C.13 epoxide using a nucleophilic peroxide agent, e.g., t-butyl hydroperoxide, which can then be converted into the compound of formula (VC), (VD), or a C.16-C.20 furan cyclization product thereof, in which $A_1$ and $R_{14}$ combine to form oxo, using methods known in the art, e.g., by reacting with a bidentate phosphine ligand and a source of Pd(0) (see, e.g., Muzart, J., *Eur. J. Org. Chem.*, 4717-4741, 2011). Thus, the compound of formula (VC), (VD), or a C.16-C.20 furan cyclization product thereof, in which $A_1$ is OP'', can be prepared. Other transformations may involve α-oxygenation to produce the compound of formula (VC), (VD), or a C.16-C.20 furan cyclization product thereof, in which $R_{15}$ is OP''.

In general, the fragments may be coupled in any order when forming compound (VB). For example, the C.0-C.1 or O-C.1 bond between fragment (IIA) and fragment (VA) can be formed, as described herein, prior to or after the Sakurai and/or Prins reaction.

In some embodiments, the compound of formula (VB) is produced from a compound of formula (IIA), a compound of formula (IIB), a compound of formula (IIIB), and, $R_5OH$, where $R_5$ is optionally substituted acyl.

The compound of formula (VA) is:

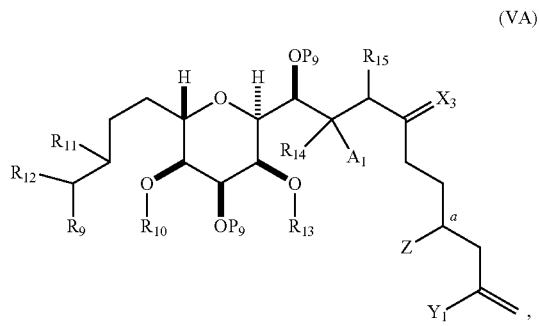

(VA)

where
$R_9$ is —CHO or —COOH;
and the remaining variables are as described for the compound of formula (VB).

The compound of formula (IIA) is:

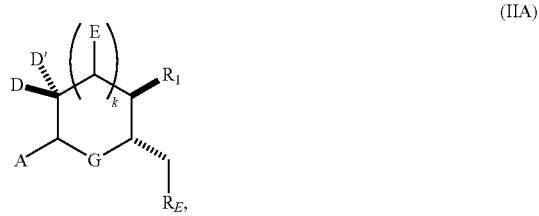

(IIA)

where
$R_1$ is —$OP_6$, —$CH(Y)_2$, or —$CH_2(Y)$, where $P_6$ is H or a hydroxyl protecting group, and each Y is independently-$COOR_C$ or —$SO_2R_D$;

each $R_C$, when present, is independently optionally substituted alkyl, optionally substituted aryl, or optionally substituted arylalkyl;

each $R_D$, when present, is independently optionally substituted aryl or optionally substituted non-enolizable alkyl;

$R_E$ is —CHO or —$CH_{(1+m)}(OR_F)_{(2-m)}$,
where
m is 1, and $R_F$ is a hydroxyl protecting group, or
m is 0, and (i) each $R_F$ is independently an alkyl or hydroxyl protecting group, or
(ii) both $R_F$ combine to form an alkylene;
and the remaining variables are as described for the compound of formula (VB).

The compound of formula (IIB) is:

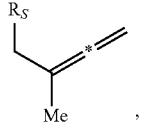

(IIB)

where $R_S$ is silyl.
The compound of formula (IIIB) is:

(IIIB)

where
$R_7$ is —CHO or

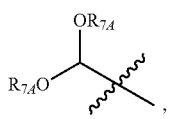

where each $R_{7A}$ is independently an optionally substituted alkyl, and
$R_{4B}$ is but-3-en-1-yl,

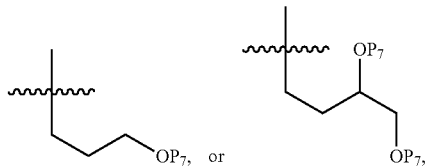

where each $P_7$ is independently H or a hydroxyl protecting group.

Preparation of the compound of formula (VB) includes a Sakurai reaction between $R_E$ that is —CHO and the compound of formula (IIB) producing a group of the structure:

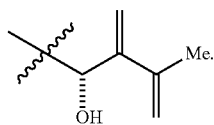 [SMILES: *[C@@H](O)C(=C)C(=C)C]

This product may then be reacted with the compound of formula (IIIB) under Prins reaction conditions to produce a group of the structure:

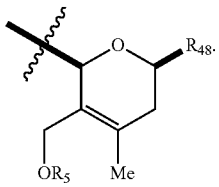

This group may be converted to $R_K$ as described herein.

If the stereochemistry of the secondary alcohol in the Sakurai reaction product differs from the desired stereochemistry, this group may be subjected to epimerization reaction conditions described herein (e.g., oxidation followed by Corey-Bakshi-Shibata reduction; alternatively, Mitsunobu reaction may be used to invert the stereogenic center).

If $R_E$ is $-CH_{(1+m)}(OR_F)_{(2-m)}$, preparation of the compound of formula (VB) may further include conversion of $R_E$ to $-CHO$ under acetal deprotecting conditions, e.g., through a reaction with an aqueous Brønsted acid (e.g., when m is 0), or through oxidation using an oxidizing agent capable of converting an alcohol to a carbonyl group (e.g., when m is 1).

When $R_{4B}$ is but-3-en-1-yl, preparation of the compound of formula (VB) includes conversion of the but-3-en-1-yl group to $-(CH_2)_2-CHO$. For example, the but-3-en-1-yl group may be reacted with a dihydroxylating agent to produce $R_{4B}$ that is

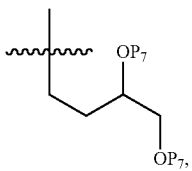

and cleaving with a glycol cleaving agent.

When $R_{4B}$ is

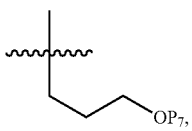

preparation of the compound of formula (VB) includes conversion of

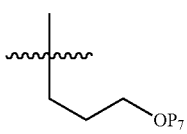

to $-(CH_2)_2-CHO$, e.g., by reacting with an oxidizing agent capable of converting an alcohol into a carbonyl group.

When $R_{4B}$ is

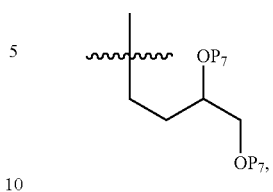

preparation of the compound of formula (VB) includes conversion of

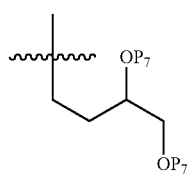

to $-(CH_2)_2-CHO$, e.g., using a glycol cleaving agent.

If at least one $P_7$ is a hydroxyl protecting group in the compound of formula (IIIB), preparation of the compound of formula (VB) may further include treating with a hydroxyl protecting group removing agent.

Group $R_E$ may be converted to $R_K$ before or after the reaction of the compound of formula (IIA) with the compound of formula (VA). For example, conversion of $R_E$ to $R_K$ before the reaction of the compound of formula (IIA) with the compound of formula (VA) may be carried out via compounds of formulae (ID) and (IE), as described herein. Conversion of $R_E$ to $R_K$ after the reaction of the compound of formula (IIA) with the compound of formula (VA) may be carried out via a compound of formula (VAa):

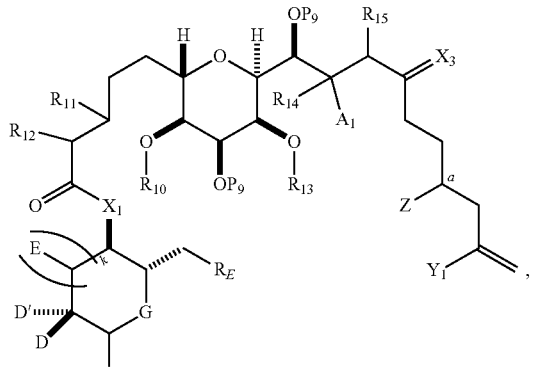

(VAa)

where all variables are as described for the compound of formulae (IIA) and (VA).

The compound of formula (VAa) may be reacted with the compound of formula (IIB) under Sakurai reaction conditions to produce a compound of formula (VAb):

(VAb)

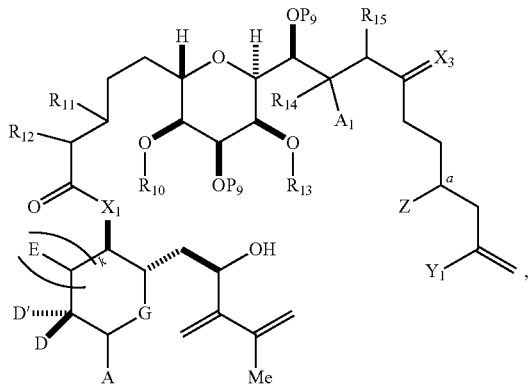

where all variables are as described for the compound of formula (VA).

A compound of formula (VAc) may be prepared from the compound of formula (VAb), the compound of formula (IIIB), and $R_5OH$ through Prins reaction. The compound of formula (VAc) is:

(VAc)

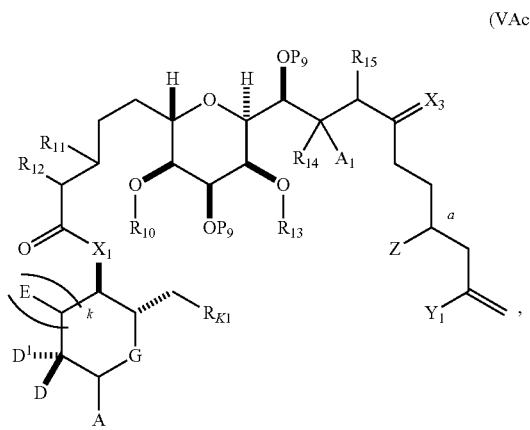

where
$R_{K1}$ is

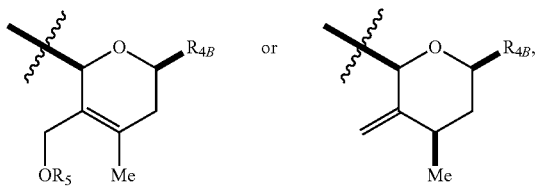

and the remaining variables are as described for the compound of formula (VA) and the compound of formula (IIIB).

The compound of formula (VAc) may be converted to the compound of formula (VB) as described herein.

In particular embodiments, the Sakurai reaction product is a compound of formula (IIC):

(IIC)

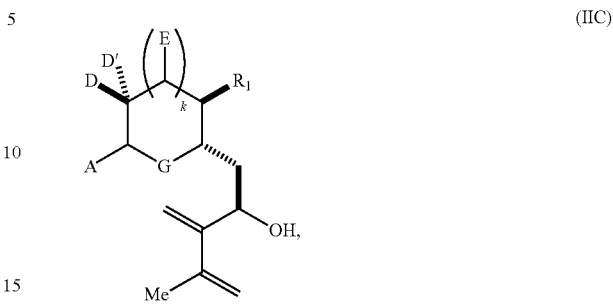

where all variables are as described for the compound of formula (IIA).

In certain embodiments, the Prins reaction product is a compound of formula (ID):

(ID)

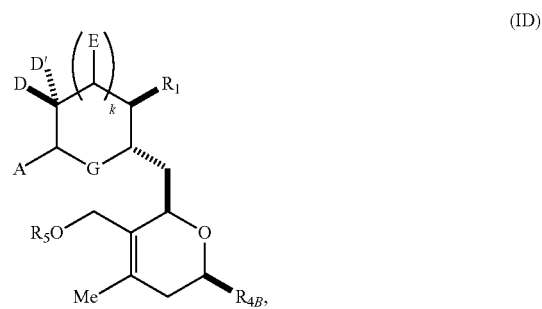

where all variables are as described for the compound of formula (IIA), the compound of formula (IIIB), and $R_5OH$.

In further embodiments, a compound of formula (IE) may be prepared from the compound of formula (ID) (e.g., the compound of formula (ID) is reacted with an allylic reducing agent to produce the compound of formula (IE)). The compound of formula (IE) is:

(IE)

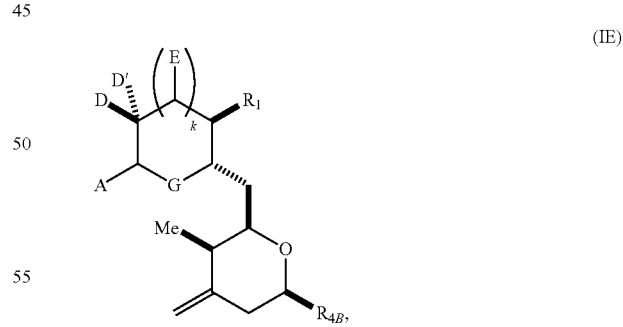

where all variables are as described for the compound of formula (ID).

The compound of formula (IE) may be reacted with the compound of formula (VA), as described herein, to produce the compound of formula (VB).

Preparation of the compound of formula (VB), in which $X_1$ is $—C(Y)_2—$, $—CH(Y)—$, or $—CH_2—$, may include a reaction (e.g., Claisen reaction) between an intermediate (e.g., the compound of formula (VA), in which $R_9$ is —CHO) and another intermediate (e.g., the compound of formula (IIA), (ID), (IIC), or (IE), in which $R_1$ is —CH(Y)$_2$ or —CH$_2$(Y)) that was treated with a Brønsted base to produce an intermediate (e.g., the compound of formula (VB), in which $X_1$ is —C(Y)$_2$—, —CH(Y)—, or —CH$_2$—). If $X_1$ in the compound of formula (VB) is —CH$_2$—, the preparation of the compound of formula (VB) may further include a desulfonylation or decarboxylation reaction.

Alternatively, preparation of the compound of formula (VB), in which $X_1$ is —O—, may include a reaction (e.g., an esterification reaction) between an intermediate (e.g., the compound of formula (VA), in which $R_9$ is —COOH) and another intermediate (e.g., the compound of formula (IIA), (ID), (IIC), or (IE), in which $R_1$ is —OP$_6$, where $P_6$ is H) to produce an intermediate (e.g., the compound of formula (VB), in which $X_1$ is —O—).

In general, the method described herein includes an allylic reduction at C.25. This reaction can be performed at any point prior to the formation of the halichondrin macrolide or analog thereof. For example,

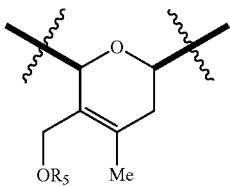

may be converted to

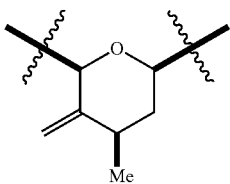 [SMILES: *[C@H]1C[C@@H](C)C(=C)[C@@H](*)O1]

using an allylic reducing agent.

C.23-C.24 Macrocyclization

In another approach, a halichondrin macrolide or analog thereof may be prepared from the compound of formula (IXB):

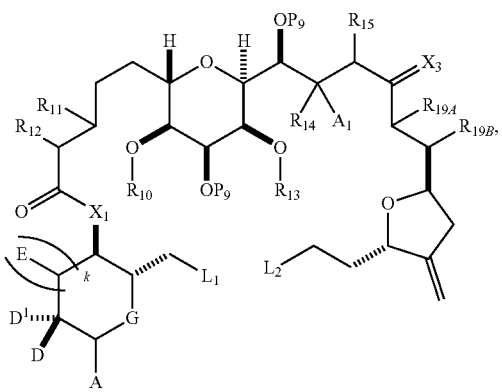

(IXB)

where $X_1$ is —CH$_2$—, —CH(Y)—, —C(Y)$_2$—, or —O—, each Y is independently —COOR$_C$ or —SO$_2$R$_D$;

each $R_C$, when present, is independently optionally substituted alkyl, optionally substituted aryl, or optionally substituted arylalkyl;

each $R_D$, when present, is independently optionally substituted aryl or optionally substituted non-enolizable alkyl;

$L_1$ is

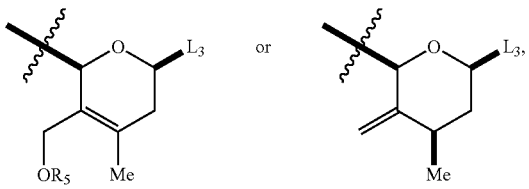

where $L_2$ and $L_3$ combine to form a bond;

$R_5$ is optionally substituted acyl;

$A_1$ and $R_{14}$ combine to form oxo, $R_{13}$ is H or a hydroxyl protecting group, and $R_{15}$ is H;

or $A_1$ is H or —OP''', and (i) $R_{13}$ is H or a hydroxyl protecting group, and $R_{14}$ and $R_{15}$, together with the atoms to which each is attached, combine to form a double bond;

or (ii) $R_{13}$ and $R_{14}$ combine to form a bond, and $R_{15}$ is H or —OP'''; each $P_9$ is independently H or a hydroxyl protecting group, $X_3$ is oxo, or $X_3$, together with the atom to which it is attached, combines to form —(CH(OP$_{11}$))—, where $P_{11}$ is H or a hydroxyl protecting group; or both $P_9$ and $X_3$, together with the atoms to which each is attached, combine to form a ketal; and $R_{19A}$ is H, —OP''', or Y, and $R_{19B}$ is H; or $R_{19A}$ and $R_{19B}$, together with the atoms to which each is attached, combine to form a double bond.

The compound of formula (IXB) can be produced from a compound of formula (IXA), a compound of formula (IIB), a compound of formula (IIA), a compound of formula (IIIE), and $R_5$OH. The compound of formula (IXA) is:

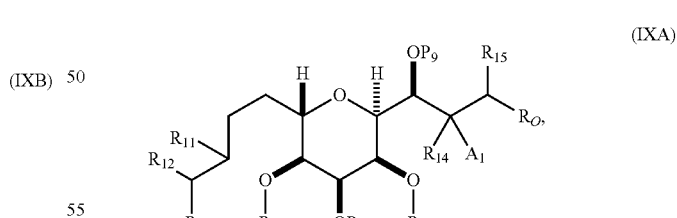

(IXA)

where $R_9$ is —CHO or —COOP''';

(a1) $R_{10}$ is a hydroxyl protecting group, $R_{11}$ is alkyl ether, and $R_{12}$ is H;

(a2) $R_{10}$ is a hydroxyl protecting group, and $R_{11}$ and $R_{12}$ combine to form a double bond; or (a3) $R_{10}$ and $R_{11}$ combine to form a bond, and $R_{12}$ is H;

$A_1$ and $R_{14}$ combine to form oxo, $R_{13}$ is H or a hydroxyl protecting group, and $R_{15}$ is H;

or

A₁ is H or —OP‴, and:
(i) $R_{13}$ is H or a hydroxyl protecting group, and $R_{14}$ and $R_{15}$ combine to form a double bond;
or
(ii) $R_{13}$ and $R_{14}$ combine to form a bond, and $R_{15}$ is H or —OP‴;

$R_O$ is —CHO, —CH₂OP‴, —CH=CH₂, —CH(OP‴)CH₂OP‴, —C(O)—CH₂P(O)(OR_C)₂, or halogen;

each $R_C$, when present, is independently optionally substituted alkyl, optionally substituted aryl, or optionally substituted arylalkyl;

each P‴ is independently H or a hydroxyl protecting group; and each $P_9$ is independently a hydroxyl protecting group.

The compound of formula (IIA) is:

(IIA)

[chemical structure showing cyclohexane with substituents D′, E, D, A, G, $R_1$, $R_E$, k]

where $R_1$ is —OP₆, —CH(Y)₂, or —CH₂(Y), where P₆ is H or a hydroxyl protecting group, and each Y is independently —COOR_C or —SO₂R_D;

each $R_C$, when present, is independently optionally substituted alkyl, optionally substituted aryl, or optionally substituted arylalkyl;

each $R_D$, when present, is independently optionally substituted aryl or optionally substituted non-enolizable alkyl;

$R_E$ is —CHO or —CH$_{(1+m)}$(OR_F)$_{(2-m)}$, where m is 1, and $R_F$ is a hydroxyl protecting group, or m is 0, and
(i) each $R_F$ is independently an alkyl or hydroxyl protecting group, or
(ii) both $R_F$ combine to form an alkylene.

The compound of formula (IIIE) is:

$R_{4E}$-$R_7$,  (IIIE)

where $R_{4E}$ is

[three chemical structures showing tetrahydrofuran rings with $R_8$, OP₇, and OP₇/OP₇ substituents]

or

[chemical structure showing fused bicyclic system with oxygen-containing rings]

where each $P_7$ is independently H or a hydroxyl protecting group; and $R_8$ is —CH₂CH₂—COOR_C, —CH=CH—COOR_C, —CH₂CH₂—SO₂R_D, or —CH=CH—SO₂R_D; and $R_7$ is —CHO or

[structure showing $R_{7A}$O—C—OR_{7A}]

where each $R_{7A}$ is independently an optionally substituted alkyl.

The compound of formula (IIB) is:

(IIB)

[structure showing $R_S$—CH₂—C(Me)=CH₂]

where $R_S$ is silyl.

In some embodiments, the compound of formula (IXB) is produced according the following strategy. For example, a compound of formula (IXC) may be produced from the compound of formula (IXA), the compound of formula (IIA), in which $R_E$ is —CH$_{(1+m)}$(OR_F)$_{(2-m)}$, the compound of formula (IIB), and R₅OH, as follows. The compound of formula (IXA) may be reacted with the compound of formula (IIA) to produce a compound of formula (IXC):

(IXC)

[large chemical structure showing complex polycyclic structure with $R_{10}$, $R_{11}$, $R_{12}$, $R_{13}$, $R_{14}$, $R_{15}$, OP₉, A₁, $R_O$, $R_E$, X₁, X₄, D, D′, E, G, A, k labels]

where

X₁ is —CH₂—, —CH(Y)—, —C(Y)₂—, or —O—;

X₄ is oxo, or X₄, together with the atom to which it is attached, is —(CH(OP₁₂))—, where P₁₂ is H or a hydroxyl protecting group; and the remaining variables are as described for the compound of formula (IXA) and the compound of formula (IIA).

Preparation of the compound of formula (IXC) may include an esterification reaction between $R_1$ that is —$OP_6$, where $P_6$ is H, and $R_9$ that is —COOP″, where P″ is H. Alternatively, preparation of the compound of formula (IXC) may include a reaction between $R_1$ that is —$CH(Y)_2$ or —$CH_2(Y)$, and $R_9$ that is —CHO (e.g., under Claisen reaction conditions). Further, the compound of formula (IXC), in which $X_4$, together with the atom to which it is attached, is —(CH($OP_{12}$))—, where $P_{12}$ is H, may be oxidized to produce the compound of formula (IXC), in which $X_4$ is oxo. Reaction conditions useful for this oxidation are known in the art. Further desulfonylation or decarboxylation of this compound of formula (IXC) may produce the compound of formula (IXC), in which $X_1$ is —$CH_2$—.

The compound of formula (IXC) may be converted to a compound of formula (IXD):

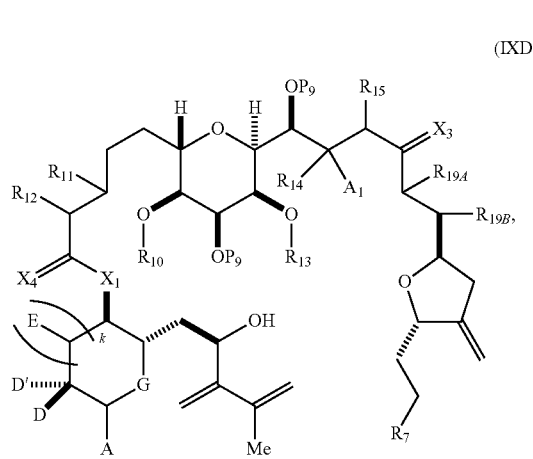

(IXD)

where $R_7$ is —CHO, —$CH_2OP_A$ or

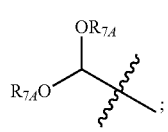

and the remaining variables are as described for the compound of formula (IXB).

The compound of formula (IXD) may be prepared from the compound of formula (IXC) and the compound of formula (IIIE) as follows. The compound of formula (IIIE) may be converted to a compound of formula (IIIF):

$R_{4F}$-$R_7$,  (IIIF)

where $R_{4F}$ is

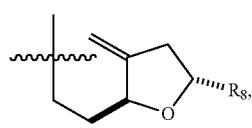

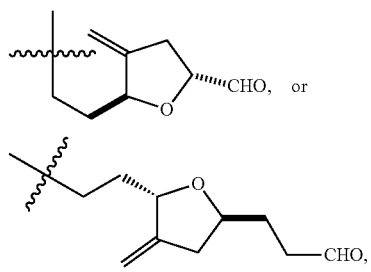

where $R_8$ is —$CH_2CH_2$—$COOR_C$ or —$CH_2CH_2$—$SO_2R_D$; and $R_7$ is —CHO or

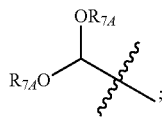

where each $R_{7A}$ is independently an optionally substituted alkyl.

$R_{4E}$ that is

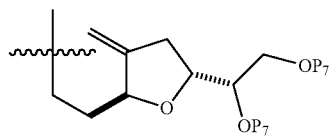

may be converted to $R_{4F}$ that is

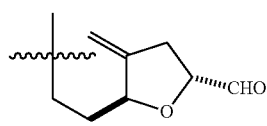 [SMILES: *CC[C@@H]1O[C@@H](C=O)CC1=C]

using a glycol cleaving agent.

$R_8$ that is —CH=CH—$COOR_C$ or —CH=CH—$SO_2R_D$ may be reacted with a 1,4-reducing agent to produce $R_8$ that is —$CH_2CH_2$—$COOR_C$ or —$CH_2CH_2$—$SO_2R_D$, respectively.

$R_{4E}$ that is

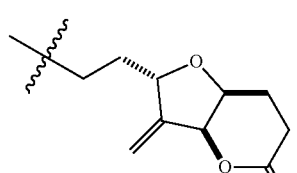

may be reacted with an allylic reducing agent to produce

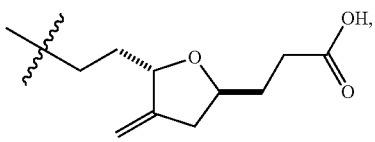 [SMILES: *CC[C@@H]1O[C@@H](CCC(=O)O)CC1=C]

which, upon reduction with a 1,2-reducing agent may produce $R_{4F}$ that is

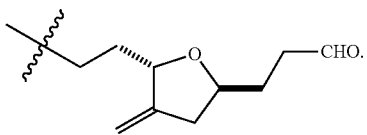 [SMILES: *CC[C@@H]1O[C@@H](CCC=O)CC1=C]

A compound of formula (IXE) may be produced from the compound of formula (IIIF) and the compound of formula (IXC). The compound of formula (IXE) is:

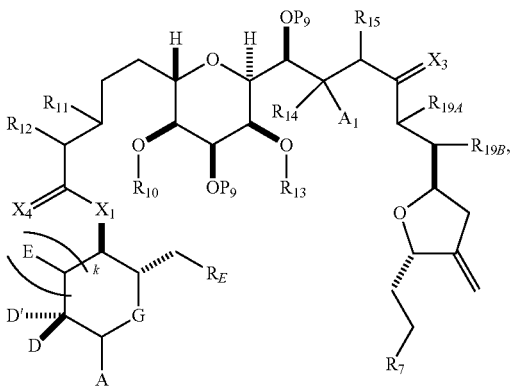
(IXE)

where all variables are as described for the compound of formula (IXC) and the compound of formula (IXD).

$R_{4F}$ that is

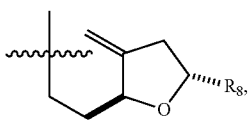

where $R_8$ is —$CH_2CH_2$—$COOR_C$ or —$CH_2CH_2$—$SO_2R_D$, may be reacted with $R_O$ that is —CHO under Claisen reaction conditions. This reaction may produce the compound of formula (IXE), in which $R_{19A}$ is Y.

$R_{4F}$ that is

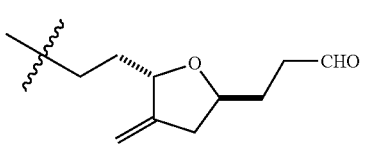 [SMILES: *CC[C@@H]1O[C@@H](CCC=O)CC1=C]

may be reacted with $R_O$ that is halogen under Nozaki-Hiyama-Kishi reaction conditions. This reaction may produce the compound of formula (IXE), in which $X_3$, together with the atom to which it is attached, combines to form —(CH($OP_{11}$))—, where $P_{11}$ is H.

$R_{4F}$ that is

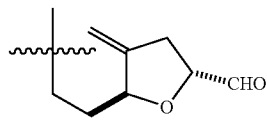 [SMILES: *CC[C@@H]1O[C@@H](C=O)CC1=C]

may be reacted with $R_O$ that is —C(O)—$CH_2P(O)(OR_C)_2$ under Horner-Wadsworth-Emmons reaction conditions. This reaction may produce the compound of formula (IXE), in which $R_{19A}$ and $R_{19B}$, together with the atoms to which each is attached, combine to form a double bond.

The compound of formula (IXE) may be converted to the compound of formula (IXD) by reacting with the compound of formula (IIB) under Sakurai reaction conditions.

The compound of formula (IXD), in which $R_7$ is —CHO, may reacted with $R_5OH$ under Prins reaction conditions to produce the compound of formula (IXB), in which $L_1$ is:

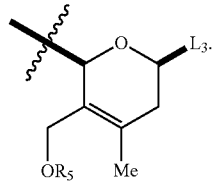

In further embodiments, the compound of formula (IXD) may be prepared by reacting the compound of formula (IXC), in which $R_E$ is —CHO, with a compound of formula (IIB) to produce a compound of formula (IXF):

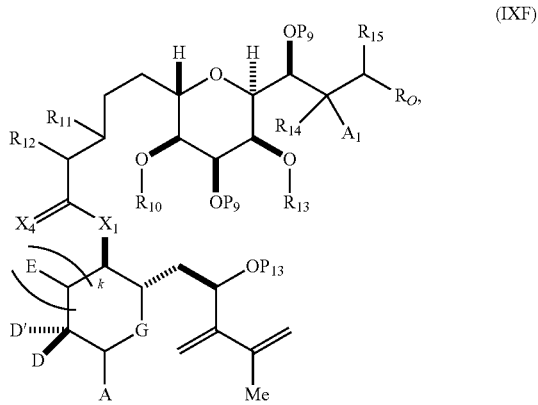
(IXF)

where $P_{13}$ is H or a hydroxyl protecting group; and the remaining variables are as described for the compound of formula (IXC).

The compound of formula (IXD) may be produced from the compound of formula (IXF) and the compound of formula (IIIF) as described herein. Preparation of the compound of formula (IXD) may further include converting $P_{13}$ that is a hydroxyl protecting group to $P_{13}$ that is H.

In yet further embodiments, the compound of formula (IXD) may be prepared as follows. A compound of formula (IXG) may be prepared from the compound of formula (IXA) and the compound of formula (IIIF) using methods described herein. The compound of formula (IXG) is:

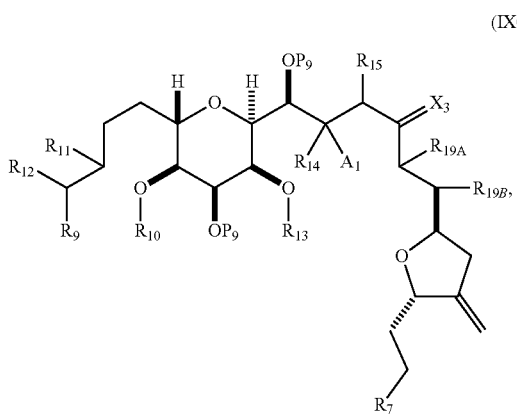

(IXG)

where all variables are as described for the compound of formula (IXD) and the compound of formula (IXA).

The compound of formula (IXE) may be prepared from the compound of formula (IXG) and the compound of formula (IIA) using methods described herein. Preparation of the compound of formula (IXD) from the compound of formula (IXE) is then carried out as described herein.

The compound of formula (IXD) may be prepared from the compound of formula (IXG) and the compound of formula (IIC). For example, the compound of formula (IIC) may be protected with a hydroxyl protecting group to produce a compound of formula (IIJ):

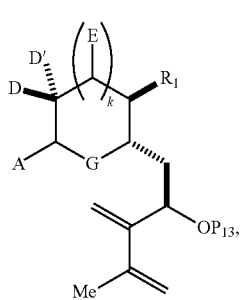

(IIJ)

where $P_{13}$ is a hydroxyl protecting group, and the remaining variables are as described for the compound of formula (IIC).

The compound of formula (IXD) may be produced from the compound of formula (IIJ) and the compound of formula (IXG) using methods described herein.

In general, the methods described herein can include reacting $R_E$ that is —CHO with the compound of formula (IIB) and a first Lewis acid (e.g., an oxophilic Lewis acid) to produce a group of the structure:

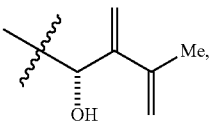 [SMILES: *[C@@H](O)C(=C)C(=C)C]

which may be reacted with $R_7$, $R_5OH$, and a second Lewis acid (e.g., an oxophilic Lewis acid) (same as or different from the first Lewis acid) to produce a group of the structure:

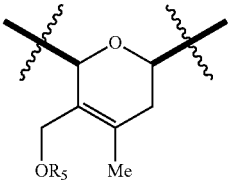

In other embodiments, $R_1$ that is —OP$_6$ is reacted with $R_9$ under esterification reaction conditions to produce a group of the structure —X$_1$—C(O)—, where P$_6$ is H, R$_9$ is —COOH, and X$_1$ is —O—. Alternatively, $R_1$ that is —CH(Y)$_2$ or —CH$_2$(Y) is reacted with Re under Claisen reaction conditions to produce a group of the structure —X$_1$—C(O)—, where R$_9$ is —CHO, and X$_1$ is —C(Y)$_2$— or —CH(Y)—.

The compound of formula (IXB) may also be accessed using methods and compounds described in PCT/US17/40401.

In general, the method described herein includes an allylic reduction at C.25. This reaction can be performed at any point prior to the formation of the halichondrin macrolide or analog thereof. In certain embodiments, the compound of formula (IXB) is reacted with an allylic reducing agent to produce the halichondrin or analog thereof.

In general, the method described herein includes an allylic reduction at C.25. This reaction can be performed at any point prior to the formation of the halichondrin macrolide or analog thereof. For example,

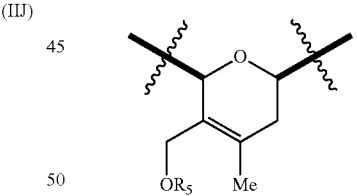

may be converted to

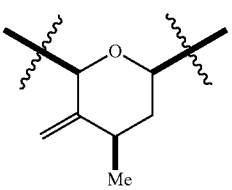 [SMILES: *[C@H]1C[C@@H](C)C(=C)[C@@H](*)O1]

using an allylic reducing agent.

Compounds of Formula (Z) and (Z8)

Compounds of formula (Z) and (Z8) may be used as the compound of formula (III) in the syntheses described herein.

Compound of Formula (Z)

The compound of formula (Z) is:

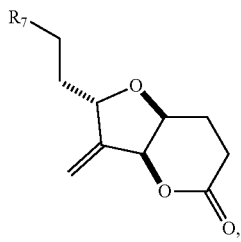
(Z)

where $R_7$ is —CHO or

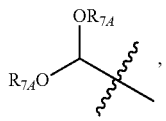, and each $R_{7A}$ is independently alkyl or a hydroxyl protecting group; or both $R_{7A}$ combine to form an optionally substituted alkylene.

The compound of formula (Z) may be prepared as described herein. For example, a compound of formula (Z2) may be produced from a compound of formula (Z1) and

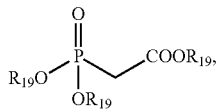

where each $R_{19}$ is independently optionally substituted alkyl.

The compound of formula (Z1) is:

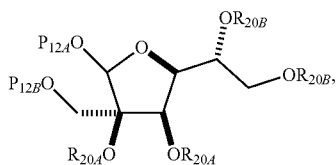
(Z1)

where each $R_{20A}$ is independently a hydroxyl protecting group, or both $R_{20A}$, together with the atoms to which each is attached, combine to form an acetal, ketal, cyclic carbonate, dicarbonyl-dioxo, or silylene-dioxo;

each $R_{20B}$ is independently a hydroxyl protecting group, or both $R_{20B}$, together with the atoms to which each is attached, combine to form an acetal, ketal, cyclic carbonate, dicarbonyl-dioxo, or silylene-dioxo;

$P_{12A}$ is H;

$P_{12B}$ is H or a hydroxyl protecting group.

The compound of formula (Z2) is:

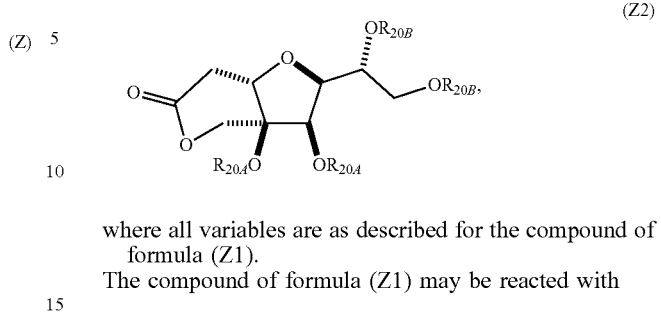
(Z2)

where all variables are as described for the compound of formula (Z1).

The compound of formula (Z1) may be reacted with

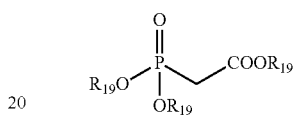

under Horner-Wadsworth-Emmons reaction conditions to produce the compound of formula (Z2).

A compound of formula (Z3) may be produced from the compound of formula (Z2) and

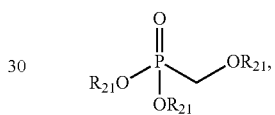, in which each $R_{21}$ is independently optionally substituted alkyl. The compound of formula (Z3) is:

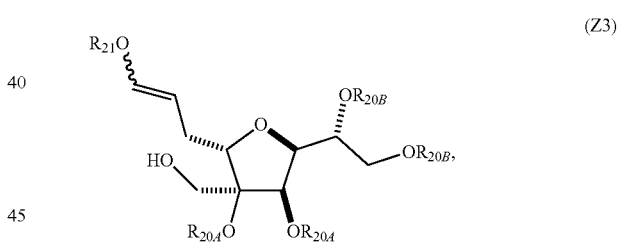
(Z3)

where all variables are as described for the compound of formula (Z2) and for

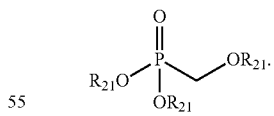.

The compound of formula (Z2) may be reacted with

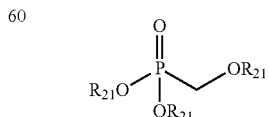

under Horner-Wadsworth-Emmons reaction conditions to produce the compound of formula (Z3).

The compound of formula (Z3) may be converted to the compound of formula (Z4):

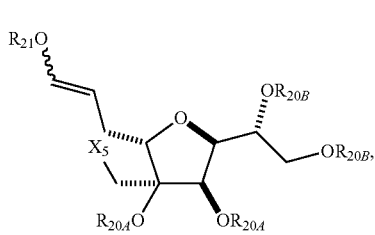

(Z4)

where $X_5$ is a halogen, and the remaining variables are as described for the compound of formula (Z3).

The free hydroxyl in the compound of formula (Z3) may be substituted with a halogen (e.g., iodide) as described herein. Reaction conditions for halogen substitution with a halogen are known in the art. In a non-limiting example, the compound of formula (Z3) may reacted with a sulfonyl anhydride (e.g., trifluoromethanesulfonic anhydride or methanesulfonic anhydride) to produce the corresponding sulfonate (e.g., trifluoromethanesulfonate or methanesulfonate), which, upon reaction with a halide source (e.g., alkali iodide), may produce the compound of formula (Z4).

The compound of formula (Z4) may be converted to the compound of formula (Z5):

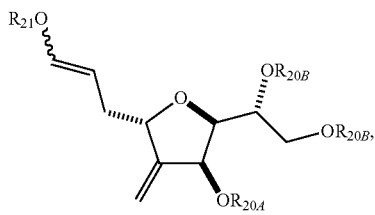

(Z5)

where all variables are as described for the compound of formula (Z4).

The compound of formula (Z4) may be subjected to reductive metal conditions to produce the compound of formula (Z5). Reductive metal conditions are known in the art. In a non-limiting example, the compound of formula (Z4) may be reacted with a metal capable of inserting into carbon-halogen bonds (e.g., Zn(0) or an alkyl lithium (e.g., t-BuLi) in combination with a Brønsted acid (e.g., acetic acid) to produce the compound of formula (Z5). When the metal is Zn(0), the Brønsted acid is an ingredient of the reaction mixture. When the reaction is performed with an alkyl lithium, the Brønsted acid is added to quench the reaction.

The compound of formula (Z5) may be reacted with $R_{7A}OH$ to produce the compound of formula (Z6):

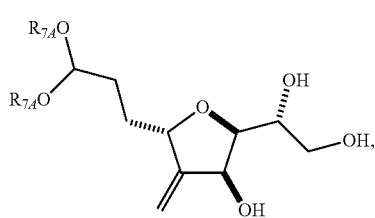

(Z6)

where $R_{7A}$ is as described for the compound of formula (Z).

The compound of formula (Z5) may be reacted with $R_{7A}OH$ in the presence of a Brønsted acid to produce the compound of formula (Z6).

A compound of formula (Z7) may be produced from the compound of formula (Z6) and

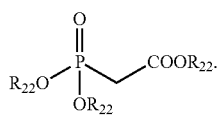

in which each $R_{22}$ is independently optionally substituted alkyl. The compound of formula (Z7) is:

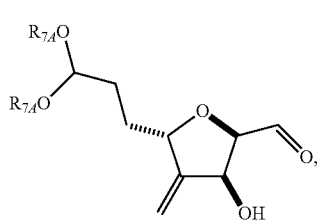

(Z7)

where all variables are as described for the compound of formula (Z) and for

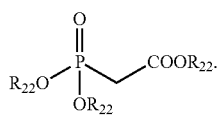

The compound of formula (Z6) may be reacted with a glycol cleaving agent to produce aldehyde (Z6A):

(Z6A)

where all variables are as described for the compound of formula (Z5).

The aldehyde (Z6A) can be reacted with

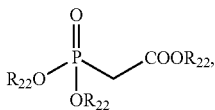

in which each $R_{22}$ is independently optionally substituted alkyl, under Horner-Wadsworth-Emmons reaction conditions to produce the compound of formula (Z7).

The compound of formula (Z) may be produced from the compound of formula (Z7). In a non-limiting example, the compound of formula (Z7) may be reacted with a 1,4-reducing agent to produce the compound of formula (Z).

Compound of Formula (Z8)

The compound of formula (Z8) is:

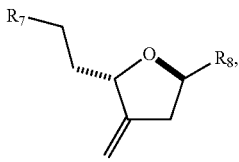

where
$R_7$ is —CHO or

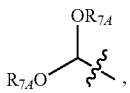

and
each $R_{7A}$ is independently alkyl or a hydroxyl protecting group; or
both $R_{7A}$ combine to form an optionally substituted alkylene;
$R_8$ is —CH$_2$CH$_2$—COOR$_C$, —CH=CH—COOR$_C$, —CH$_2$CH$_2$—SO$_2$R$_D$, or —CH=CH—SO$_2$R$_D$;
$R_C$, when present, is independently optionally substituted alkyl, optionally substituted aryl, or optionally substituted arylalkyl; and
$R_D$, when present, is independently optionally substituted aryl or optionally substituted non-enolizable alkyl.

The compound of formula (Z8) may be prepared from the compound of formula (Z5) as follows.

The compound of formula (Z5) may be reacted with $R_{7A}$OH in the presence of a Brønsted acid to produce the compound of formula (Z5A):

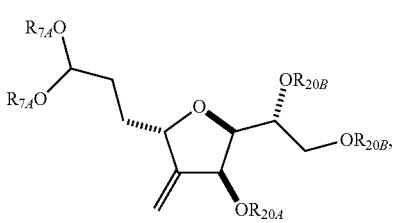

where
$R_{20A}$ is H or a hydroxyl protecting group;
each $R_{20B}$ is independently H or a hydroxyl protecting group, or both $R_{20B}$, together with the atoms to which each is attached, combine to form an acetal, ketal, cyclic carbonate, dicarbonyl-dioxo, or silylene-dioxo; and all remaining variables are as described for the compound of formula (Z8).

The compound of formula (Z5A) may be converted to a compound of formula (Z5B):

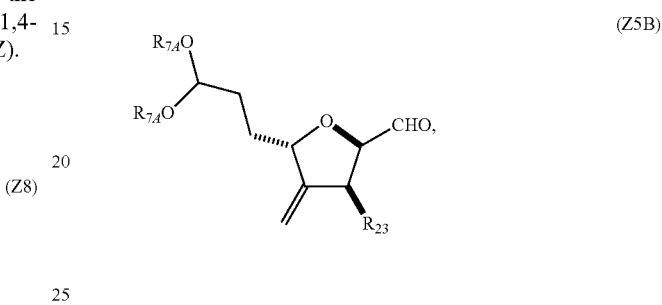

where
$R_{23}$ is H or —OR$_{20A}$; and
all remaining variables are as described for the compound of formula (Z8). The compound of formula (Z5A), in which both $R_{20B}$ are H, can be reacted with a glycol cleaving agent to produce the compound of formula (Z5B). Conversion of —OR$_{20A}$ in formula (Z5A) to H in the compound of formula (Z5B) ($R_{23}$ is H) can be achieved using allylic deoxygenation methods known in the art, e.g., using allylic reducing agents, when $R_{20A}$ is a hydroxyl protecting group that is an ester. Alternatively, when $R_{20A}$ is H, —OR$_{20A}$ may be converted to H using deoxygenation reactions known in the art. Deoxygenation reactions are known in the art, e.g., Barton-McCombie deoxygenation and tin-free versions thereof (see, e.g., Chenneberg and Ollivier, *Chimia,* 70:67-76, 2016). The reaction replacing —OR$_{20A}$ with H can be performed before or after the glycol cleavage.

The compound of formula (Z5B) may be converted to the compound of formula (Z8), in which $R_8$ is —CH=CH—COOR$_C$ or —CH=CH—SO$_2$R$_D$, by a reaction with

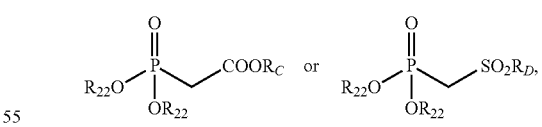

in which each $R_{22}$ is independently optionally substituted alkyl, under Horner-Wadsworth-Emmons reaction conditions. The compound of formula (Z8), in which $R_8$ is —CH=CH—COOR$_C$ or —CH=CH—SO$_2$R$_D$, can be converted to the compound of formula (Z8), in which $R_8$ is —CH$_2$CH$_2$—COOR$_C$ or —CH$_2$CH$_2$—SO$_2$R$_D$, respectively, by a reaction with a 1,4-reducing agent. A reaction replacing —OR$_{20A}$ with H can be performed before or after the Horner-Wadsworth-Emmons reaction and/or the reaction with a 1,4-reducing agent.

Further Compounds

The invention provides a compound of formula (II):

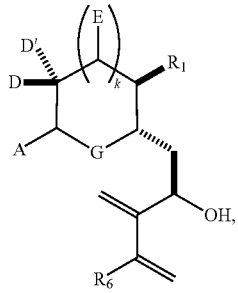
(II)

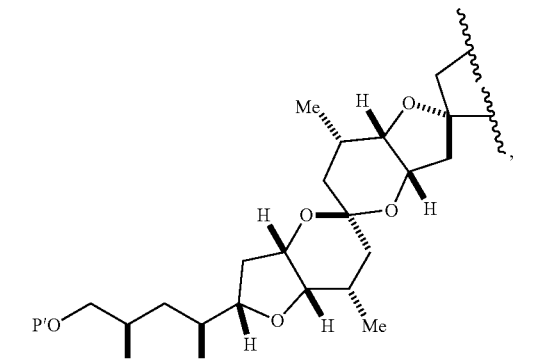

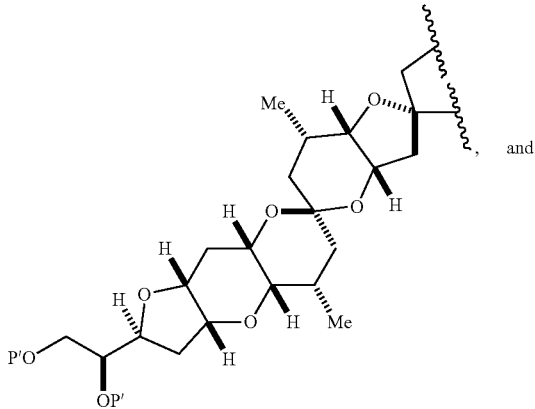
and where
each of D and D' is independently H, optionally substituted alkyl, or $OP_1$, provided that only one of D and D' is $OP_1$, where $P_1$ is H, alkyl, a hydroxyl protecting group, and A is a $C_{1-6}$ saturated or $C_{2-6}$ unsaturated hydrocarbon skeleton, the skeleton being unsubstituted or having from 1 to 10 substituents independently selected from the group consisting of cyano, halo, azido, oxo, and $Q_1$, or A is a group of formula (1):

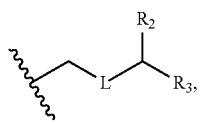
(1)

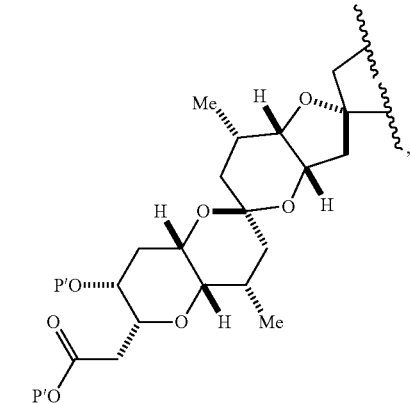

where
L is —(CH(OP$_2$))—, —(C(OH)(OP$_2$))—, or —C(O)—;
$R_2$ is H and $P_1$ is absent, H, alkyl, or a hydroxyl protecting group, or $R_2$ and $P_1$ combine to form a bond;
(i) $R_3$ is H, and $P_2$ is absent, H, optionally substituted alkyl, or a hydroxyl protecting group;
(ii) $R_3$ is —(CH$_2$)$_n$NP$_3$P$_4$, where $P_3$ is H or an N-protecting group, and (a) $P_2$ is absent, H, optionally substituted alkyl, or a hydroxyl protecting group, and $P_4$ is H or an N-protecting group, (b) $P_2$ and $P_4$ combine to form an alkylidene, or (c) each of $P_2$ and $P_4$ is H;
(iii) $R_3$ is —(CH$_2$)$_n$OP$_5$, where $P_2$ is absent, H, optionally substituted alkyl, or a hydroxyl protecting group, and $P_6$ is H, optionally substituted alkyl, or a hydroxyl protecting group; or $P_2$ and $P_5$, together with the atoms to which each is attached, combine to form a ketal, a cyclic carbonate, a dicarbonyl-dioxo, or silylene-dioxo; or
(iv) $R_3$ and $P_2$ combine to form an optionally substituted ethylene or a structure selected from the group consisting of:

where each P' is independently H or a hydroxyl protecting group;
E is H, optionally substituted alkyl, or optionally substituted alkoxy;
G is O, S, CH$_2$, or NR$_N$, where $R_N$ is H, an N-protecting group, or optionally substituted alkyl;
each $Q_1$ is independently $OR_A$, $SR_A$, $SO_2R_A$, $OSO_2R_A$, $NR_BR_A$, $NR_B(CO)R_A$, $NR_B(CO)(CO)R_A$, $NR_B(CO)NR_BR_A$, $NR_B(CO)OR_A$, $(CO)OR_A$, $O(CO)R_A$, $(CO)NR_BR_A$, or $O(CO)NR_BR_A$, where each of $R_A$ and $R_B$ is independently H, alkyl, haloalkyl, hydroxyalkyl, aminoalkyl, aryl, haloaryl, hydroxyaryl, alkoxyaryl, arylalkyl, alkylaryl, haloarylalkyl, alkylhaloaryl, (alkoxyaryl)alkyl, heterocyclic radical, or heterocyclic radical-alkyl;
n, when present, is 0, 1, or 2;
k is 0 or 1;
$R_1$ is —OP$_6$, —CH(Y)$_2$, or —CH$_2$(Y), where $P_6$ is H or a hydroxyl protecting group;

R$_6$ is H, optionally substituted alkyl, or optionally substituted aryl; and

Y is independently —COOR$_C$ or —SO$_2$R$_D$;

R$_C$, when present, is optionally substituted alkyl, optionally substituted aryl, or optionally substituted arylalkyl; and R$_D$, when present, is optionally substituted aryl or optionally substituted non-enolizable alkyl.

The invention also provides the compounds of formula (IID), (IIE), (IIF), (IIG), (IIH), (IIi), (IVAb), (VAb), (VIIAa), (VIAa), (VIIID), (IXD), (IXF), (IXG), (Z), (Z1), (Z2), (Z3), (Z4), (Z5), (Z5A), (Z5B), or (Z6).

Amination

Compounds disclosed herein, in which R$_3$ is —(CH$_2$)$_n$OP$_5$, can be aminated to afford eribulin, as described herein. Amination conditions can be those known in the art. In a non-limiting example, C.35 hydroxyl in the compounds disclosed herein can be sulfonylated (e.g., by a reaction with a sulfonyl anhydride or a sulfonyl chloride) and reacted with a nitrogen source (e.g., ammonia, azide, sulfamic acid, urea (H$_2$NCONH$_2$), or thiourea (H$_2$NCSNH$_2$)) to afford eribulin or a pharmaceutically acceptable salt thereof upon optional unmasking of the amino group (if the nitrogen source was azide, urea, or thiourea). In another non-limiting example, C.35 hydroxyl in the compounds disclosed herein can be halogenated (e.g., by Appel reaction or a reaction with thionyl chloride, sulfuryl chloride, phosphorus(III) chloride, or phosphorus(V) oxychloride) and reacted with a nitrogen source (e.g., ammonia, azide, sulfamic acid, a phthalimide salt, urea (H$_2$NCONH$_2$), or thiourea (H$_2$NCSNH$_2$)) to afford eribulin or a pharmaceutically acceptable salt thereof upon optional unmasking of the amino group (if the nitrogen source was azide, a phthalimide salt, urea, or thiourea). Amino unmasking agents are further described herein. The amination reaction can provide a pharmaceutically acceptable salt of eribulin directly. Alternatively, the amination reaction can provide eribulin in a free base form. A pharmaceutically acceptable salt of eribulin can be prepared from eribulin through a salification reaction as described herein.

Masked Amines and Amine Unmasking Agents

The compounds used in the methods of the invention can contain a masked or unmasked amine (e.g., at C.35 carbon of the structure of the halichondrin macrolide analog, such as eribulin). An unmasked amine is —NH$_2$. An amine can be masked using methods known in the art, e.g., by protecting the amine with an N-protecting group. Alternatively, an amine can be masked as a nitrogen-containing moiety, which can be reacted with an amine unmasking agent to afford an amine. Non-limiting examples of the nitrogen-containing moieties include azide and an imide (e.g., phthalimide). Amine unmasking agents can be those known in the art for removing N-protecting groups from amines. In a non-limiting example, a Boc group can be removed using amine unmasking agents known in the art, e.g., a Brønsted acid (e.g., HCl in 1,4-dioxane or trifluoroacetic acid). When amine is masked as azide, the amine can be unmasked by subjecting the compound containing the masked amine to Staudinger reaction conditions (e.g., by contacting with a phosphine, such as trialkylphosphine, dialkylarylphosphine, alkyldiarylphosphine, or triarylphosphine) or by reacting the compound containing the masked amine with a reducing agent (e.g., LiAlH$_4$). When amine is masked as an imide (e.g., phthalimide), the amine can be unmasked by reacting with an amine unmasking agent known in the art, e.g., hydrazine.

Oxidizing Agents Capable of Converting an Alcohol to a Carbonyl Group

Oxidizing agents capable of converting an alcohol to a carbonyl group are known in the art. Non-limiting examples of these oxidizing agents include Dess-Martin periodinane, TEMPO (in the presence of bleach or BAIB), a dimethylsulfonium compound (e.g., dimethylchlorosulfonium chloride), aluminum trialkoxide with an excess of a ketone (e.g., acetone), and catalytic tetrapropylammonium perruthenate (TPAP) (in the presence of N-methylmorpholine oxide). The dimethylsulfonium compound can be prepared in situ under the conditions known for Parikh-Doering oxidation, Swern oxidation, Corey-Kim oxidation, or Pfitzner-Moffatt oxidation. Alternatively, the dimethylsulfonium compound can be prepared in situ by a reaction between trichloroacetic acid anhydride and dimethyl sulfoxide. An oxidation reaction of an alcohol to a carbonyl group (e.g., a ketone) can be performed using aluminum trialkoxide and an excess of a ketone (e.g., acetone) under the conditions known in the art for Oppenauer oxidation. Allylic and benzylic alcohols can also be oxidized with MnO$_2$.

Reducing Agents

Reducing agents that can be used in the methods of the invention are those known in the art. A reducing agent can be an electron-transfer reducing agent, a metal hydride, or a metalloid hydride. Non-limiting examples of electron-transfer reducing agent include alkali metals in oxidation state (0), alkali earth metals in oxidation state (0), alkali arenides, lanthanide (II) salts (e.g., SmI$_2$), Zn(0), Fe(0), and Mn(0). Non-limiting examples of metal hydrides and metalloid hydrides include boron hydride compounds (e.g., NaBH$_4$, LiBH$_4$, LiHBEt$_3$, selectrides (e.g., L-selectride), and boranes (e.g., 9-BBN and alpine borane)), aluminum hydride compounds (e.g., LiAlH$_4$, Red-Al®, and alanes (e.g., diisobutylaluminum hydride (DIBAL))), hydrosilanes (e.g., PMHS and Ph$_2$SiH$_2$), hydrostannanes (e.g., Bu$_3$SnH), copper hydride complexes (e.g., Stryker's reagent), palladium hydride complexes, platinum hydride complexes, iridium hydride complexes, rhodium hydride complexes, and ruthenium hydride complexes. Reducing agents can be formed in situ, e.g., a copper hydride complex can be formed by a reaction of a copper salt with, e.g., a boron hydride compound or a hydrosilane. Thus, some reducing reagents (e.g., boron hydride compounds, hydrosilanes, and hydrostannanes) can be used in combination with a catalytic quantity of a metal salt (e.g., Cu, Pd, Pt, Ir, Rh, or Ru salt). Alternatively, catalytic reducing agents can be metal salts (e.g., aluminum isopropoxide or a ruthenium complex) in combination with an alcohol, which undergo transfer hydrogenation of carbonyl-containing compounds without intermediacy of a metal hydride. Non-limiting examples of transfer hydrogenation reactions include Meerwein-Ponndorf-Verley reduction (e.g., using aluminum isopropoxide/isopropanol) and Ru-catalyzed transfer hydrogenation (e.g., Hashiguchi et al., *J. Am. Chem. Soc.,* 117:7562-7563, 1995).

When a substrate is an α,β-unsaturated carbonyl or sulfone compound (e.g., an α,β-enone or a vinyl sulfone), a reducing agent can be a 1,2-reducing agent or a 1,4-reducing agent. For example, a reaction between an α,β-unsaturated carbonyl compound and a 1,2-reducing agent can afford, e.g., an allylic alcohol (or an allylic amine, if the starting compound is an enamide), whereas a reaction between an α,β-unsaturated carbonyl compound and a 1,4-reducing agent can afford an α,β-saturated compound and can leave the carbonyl group intact after work up of the reaction mixture. Non-limiting examples of 1,2-reducing agents include metal hydrides and metalloid hydrides, e.g., aluminum hydride compounds, boron hydride compounds (e.g., CeCl$_3$ with NaBH$_4$), and ruthenium hydride complexes. Non-limiting examples of 1,4-reducing agents include boron hydride compounds (e.g., LiHBEt$_3$ and L-selectride), hydrostannanes, copper hydride complexes (e.g., Stryker's reagent), palladium hydride complexes, platinum hydride complexes, iridium hydride complexes, rhodium hydride complexes, and ruthenium hydride complexes. Non-limiting examples of the 1,4-reducing agents include copper (I) hydrides, which can be isolated (e.g., Stryker's reagent) or prepared in situ (e.g., from a copper (I) or copper (II) salt and a hydride source). Catalytic quantities of a copper salt (either copper (I) or copper (II) salt) in combination with stoichiometric or superstoichiometric quantities of a hydride source (e.g., a borohydride salt, borane, PMHS, or a hydrosilane (e.g., Ph$_2$SiH$_2$)). A non-limiting example of the reaction conditions that can be used for 1,4-reduction is described, e.g., in Baker et al., *Org. Lett.*, 10:289-292, 2008, the disclosure of which is incorporated herein by reference. Other metals can be used to catalyze 1,4-reduction, e.g., Ru, Pd, and Ir compounds.

Methods of the invention may include the use of selective reduction techniques to reduce some reactive groups with retention of other reactive groups. For example, a carboxylic acid may be reduced in the presence of esters and/or olefins using sodium borohydride and iodine. Alternatively, a carboxylic acid may be reduced in the presence of esters and/or 1,1-disubstituted olefins by converting the carboxylic acid to a mixed anhydride (e.g., using N-methylmorpholine and i-butylchloroformate) and reducing the resulting mixed anhydride using borane reducing agents (e.g., 9-BBN).

A compound having an allylic leaving group (e.g., a carboxylate, a halide, or a sulfonate) can be treated with an allylic reducing agent to replace the leaving group with a hydrogen atom. A non-limiting example of allylic reducing agent is a palladium salt or complex (e.g., Pd(PPh$_3$)$_4$) in combination with a formic acid salt (e.g., trialkylammonium formate).

Hydroxyl Protecting Groups and Hydroxyl Protecting Group Removing Agents

Hydroxyl protecting groups can be as defined herein. In particular, a hydroxyl protecting group can be an acyl, a sulfonyl, an arylalkyl (e.g., benzyl or p-methoxybenzyl), an aryl (e.g., p-methoxyphenyl), or an optionally substituted silyl (e.g., TMS, TES, TBS, TIPS, TBDPS, or TPS). Hydroxyl protecting groups, hydroxyl protecting agents, and hydroxyl protecting reaction conditions can be selected to protect selectively certain hydroxyl groups in a compound, while leaving other hydroxyl groups unprotected. The choice of hydroxyl protecting groups for a compound can facilitate subsequent deprotection strategies, as some hydroxyl protecting groups can be removed in the presence of others using appropriate hydroxyl protecting group removing agents. Some of these strategies involving the choice of silyl hydroxyl protecting groups are discussed in, e.g., *Silicon-Based Blocking Agents*, Gelest, Inc., 2011.

Hydroxyl protecting group removing agents are those agents that can react with a compound having a protected hydroxyl group to afford the compound with a deprotected hydroxyl group. Hydroxyl protecting group removing agents and deprotection reaction conditions can be those known in the art. In a non-limiting example, hydroxyl masked as silyl ether can be unmasked by a reaction with a fluoride source (e.g., a fluoride salt, such as KF or TBAF). Alternatively, hydroxyl protected as TMS or TES ether can be deprotected by a reaction with a Brønsted acid (e.g., a carboxylic acid). In another non-limiting example, hydroxyl protected as an ester can be deprotected by a reaction with a base (e.g., alkali hydroxide (e.g., lithium hydroxide, sodium hydroxide, or potassium hydroxide) or C$_{1-6}$ alkoxide (e.g., alkali C$_{1-6}$ alkoxide or alkali earth C$_{1-6}$ alkoxide)). Alternatively, hydroxyl protected as an ester (e.g., pivaloyl ester) can be deprotected by a reaction with a 1,2-reducing agent (e.g., DIBAL-H). In yet another non-limiting example, hydroxyl protected as an arylalkyl ether (e.g., 1-arylalk-1-yl ether) can be deprotected using a reduction reaction, e.g., with Pd/C and H$_2$ or with Na/NH$_3$. Alternatively, hydroxyl protected as an alkoxy-arylalkyl ether (e.g., MPM ether) can be deprotected by a reaction with 2,3-dichloro-5,6-dicyano-1,4-benzoquinone (DDQ). In still another non-limiting example, hydroxyl protected as alkoxyalkyl ether (e.g., 1-alkoxyalk-1-yl) or THP ether can be deprotected by a reaction with a Brønsted acid. Cyclic protected diols, such as acetals or ketals (e.g., as 2-alkyl-1,3-dioxolane, 2,2-dialkyl-1,3-dioxolane, 2-alkyl-1,3-dioxane, or 2,2-dialkyl-1,3-dioxane), can be deprotected by a reaction with a Brønsted acid (e.g., a carboxylic acid).

Decarboxylation and Desulfonylation

The conditions for the decarboxylation reaction can be those known in the art, e.g., Krapcho decarboxylation or a sequence including deprotection, if R$_C$ is not H, by converting R$_C$ to H and subsequent protodecarboxylation. The conditions for the desulfonylation reaction can be those known in the art. For example, the desulfonylation reaction can include contacting the compound of formula (IA) or formula (IB) or an intermediate downstream of the compound of formula (IA) or formula (IB) with an electron-transferring reducing agent (e.g., SmI$_2$; Cr(III) salt and Mn(0); or Mg(0)). For exemplary desulfonylation conditions, see WO 2009/064029.

Nozaki-Hiyama-Kishi Reaction

Nozaki-Hiyama-Kishi reaction conditions that may be used in transformation described herein can be those known in the art. Nozaki-Hiyama-Kishi reaction can include reacting substrates (an aldehyde and a vinyl halide or pseudohalide) with a Cr(II) salt and a Ni(II) salt. Ancillary ligands can be used in combination with the metal salts. In a non-limiting example, a substituted 1,10-phenanthroline can be used in combination with a Ni(II) salt. Chiral ancillary ligands can be used to render the reaction stereoselective. In a non-limiting example, chiral N-(dihydrooxazolyl-phenyl)-sulfonamides can be used with a Cr(II) salt to control the stereochemistry of the carbonyl carbon, to which a vinyl nucleophile is added in the course of Nozaki-Hiyama-Kishi reaction.

Olefin Metathesis

Olefin metathesis catalysts are known in the art and include Ru-carbene complexes (e.g., Grubbs and Hoveyda-Grubbs catalysts). Olefin metathesis-competent catalysts that may be used in the olefin metathesis reactions described herein are known in the art (e.g., second generation Hoveyda-Grubbs-type catalysts, e.g., those in which the Ru-benzylidene moiety is modified to include electron-withdrawing and/or electron-donating groups). Non-limiting examples of the useful olefin metathesis reaction conditions are provided in, e.g., U.S. patent application publication No. 2016/0264594 and International patent application publication No. WO 2016/179607.

Salification

Eribulin mesylate can be produced by salification of eribulin, as described herein. Salification reaction conditions are known in the art. Salification of eribulin can afford a pharmaceutically acceptable salt of eribulin (e.g., eribulin mesylate). In particular, salification reaction can involve contacting eribulin with a Brønsted acid (e.g., a pharmaceutically acceptable Brønsted acid (e.g., methanesulfonic acid)) to afford a pharmaceutically acceptable salt of eribulin (e.g., *Handbook of Pharmaceutical Salts: Properties, Selection and Use*, ed.: Stahl and Wermuth, Wiley-VCH/VHCA, Weinheim/Zurich, 2002). Pharmaceutically acceptable salts of eribulin, e.g., eribulin mesylate, can be formed by methods known in the art, e.g., in situ during the final isolation and purification of the compound or separately by reacting the free base group with a suitable organic acid. In one example, eribulin is treated with a solution of MsOH and NH$_4$OH in water and acetonitrile. The mixture is concentrated. The residue is dissolved in DCM-pentane, and the solution is added to anhydrous pentane. The resulting precipitate is filtered and dried under high vacuum to provide eribulin mesylate.

Epimerizations

Epimerization reactions can be used to invert a stereogenic center having an undesired stereochemical identity. For example, through epimerization, R stereogenic center can be converted to S stereogenic center and vice versa. Epimerization of a stereogenic sp$^3$-carbon bonded to one hydrogen atom and to one hydroxyl group can be achieved through a reaction sequence involving oxidation of the hydroxyl group to a carbonyl group followed by a 1,2-reduction reaction. The 1,2-reduction reaction can provide the desired stereochemical identity diastereoselectively, or the reaction can be carried out using a chiral catalyst, chiral auxiliary, or a chiral reducing agent. Non-limiting examples of chiral reducing agents include alpine borane and prapine borane. Non-limiting examples of 1,2-reduction reactions involving chiral catalysts are Corey-Bakshi-Shibata reduction, Noyori hydrogenation, and Noyori transfer hydrogenation, The oxidation/reduction reaction sequence can be carried out in situ using dynamic kinetic resolution. A dynamic kinetic resolution can further involve a reaction with a hydroxyl protecting agent, which removes the desired stereoisomer from the reduction/oxidation equilibrium. In a non-limiting example, a dynamic kinetic resolution of chiral secondary alcohols can involve reduction/oxidation equilibration using η$^5$-Ph$_5$CpRu(CO)$_2$H in combination with enantioselective esterification using isopropenyl acetate catalyzed by a lipase enzyme (e.g., lipase B from *Candida Antarctica*, see, e.g., Martin-Matute et al., *J. Am. Chem. Soc.*, 127:8817-8825, 2005).

The following examples are meant to illustrate the invention. They are not meant to limit the invention in any way.

EXAMPLES

Example 1

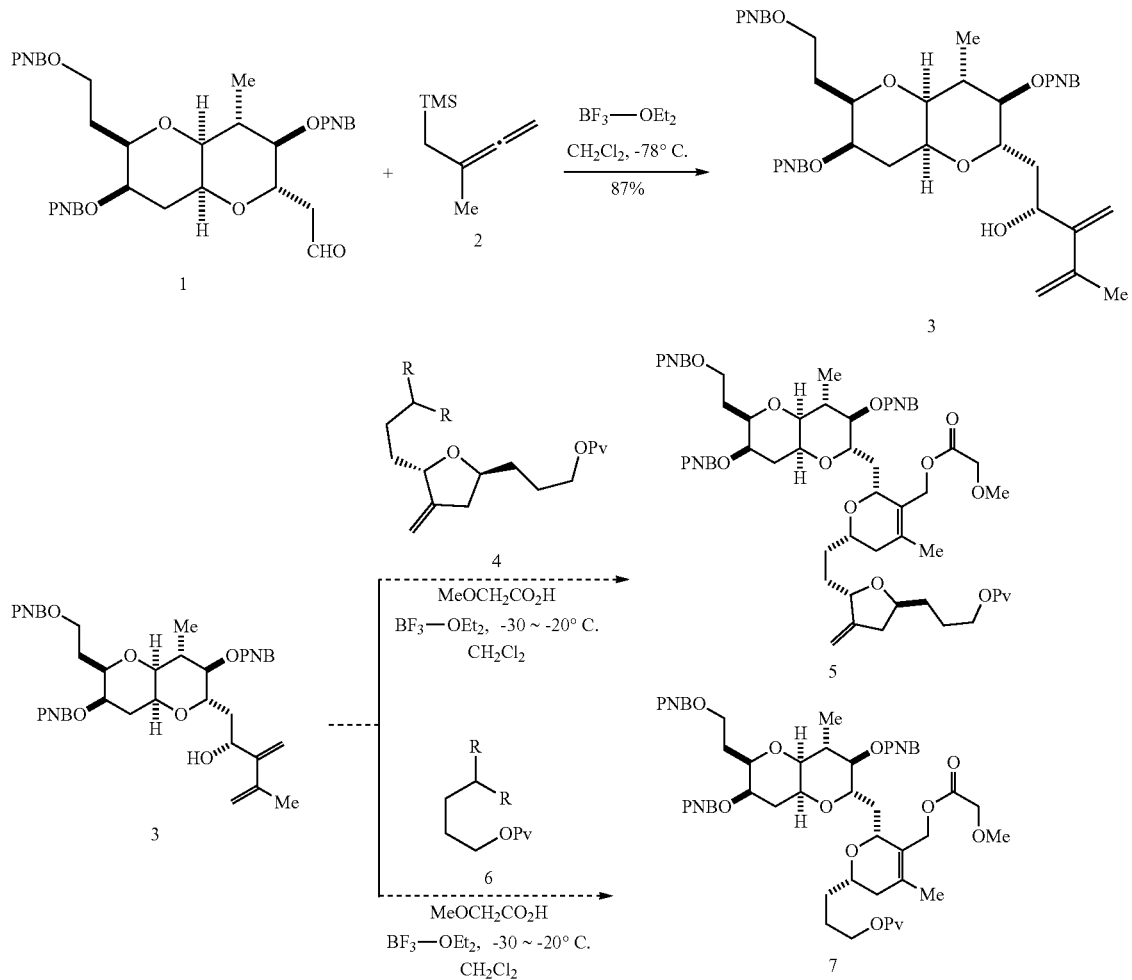

each R is OMe, or
both R groups, together with the atom to which they are attached,
combine to form a carbonyl.

An exemplary compound of formula (IA) can be prepared as shown in the above scheme. This compound may be useful as an intermediate in the synthesis of a halichondrin macrolide. Compound 1 was treated with compound 2 in the presence of $BF_3 \cdot OEt_2$ (exemplary Sakurai reaction conditions) to give compound 3.

Compound 5 can be prepared by treating compound 3 with compound 4 in the presence of $BF_3 \cdot OEt_2$ and methoxyacetic acid (exemplary Prins reaction conditions). Compound 7 can be prepared by treating compound 3 with compound 6 in the presence of $BF_3 \cdot OEt_2$ and methoxyacetic acid (exemplary Prins reaction conditions).

A halichondrin macrolide can be prepared from compound 5 or 7 using methods and intermediates disclosed, e.g., WO 2016/179607, the synthesis of which is hereby incorporated by reference and described herein. For example, compounds 5 and 7 may be converted to a halichondrin macrolide, as described for the compound of formula (VIIIC) in WO 2016/179607.

Example 2

An exemplary compound of formula (IA) for the synthesis of a halichondrin macrolide analog can be prepared as shown in this Example. Compound 8 was treated with compound 2 in the presence of $BF_3 \cdot OEt_2$ (exemplary Sakurai reaction conditions) to give compound 9.

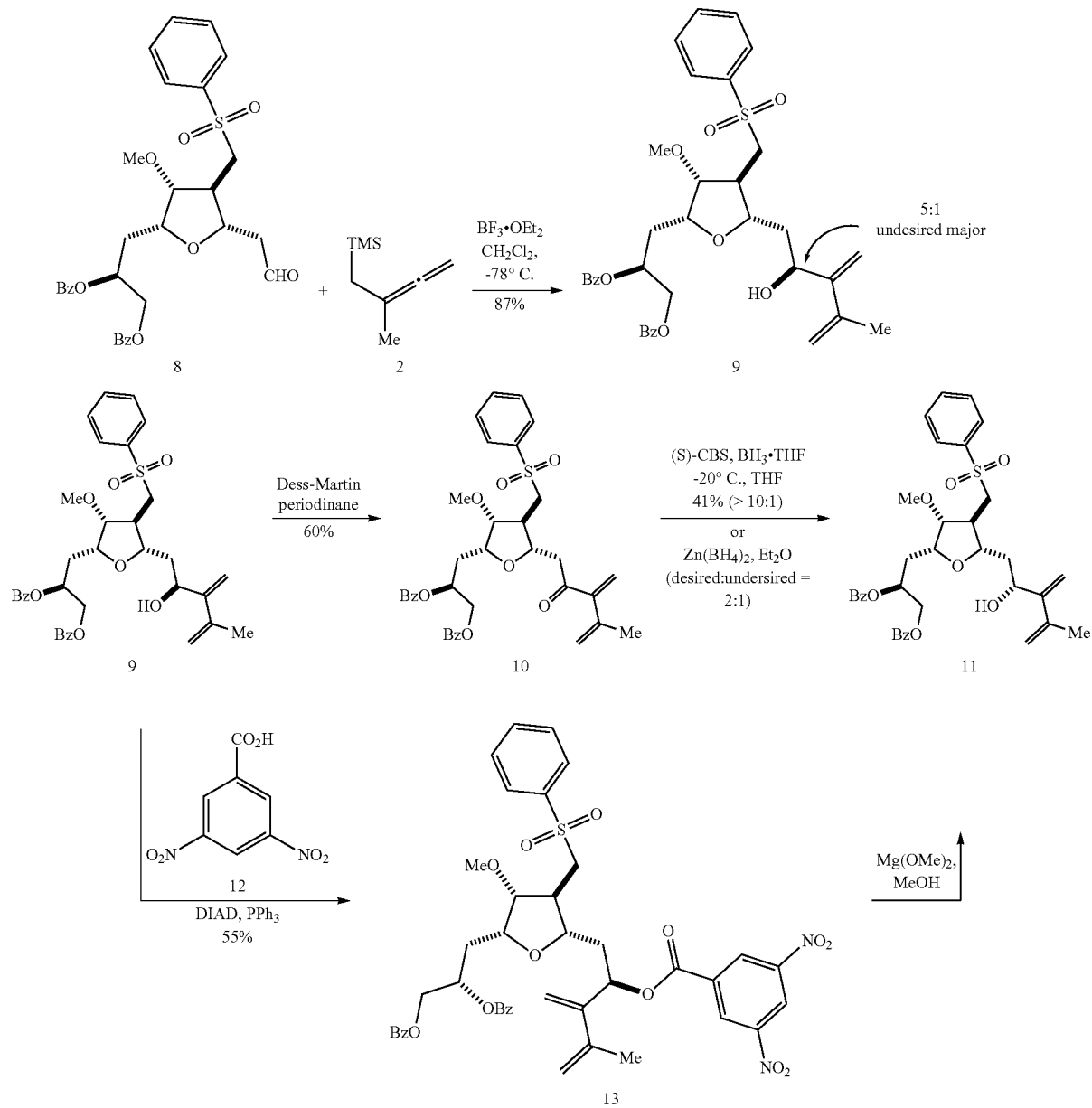

The scheme above illustrates two exemplary synthetic routes that can be used to access compound 11 from compound 9. In one approach, compound 9 was reacted with Dess-Martin periodinane to afford enone 10, which, upon reduction with either (S)-(−)-2-methyl-CBS-oxazaborolidine and BH$_3$.THF or Zn(BH$_4$)$_2$, provided compound 11 as the major diastereomer. (S)-(−)-2-methyl-CBS-oxazaborolidine is:

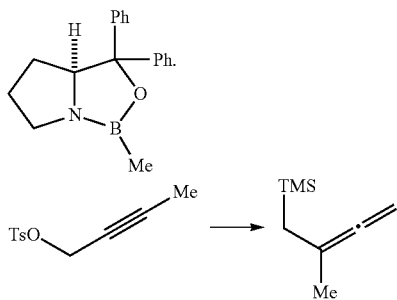

Trimethyl(2-methylbuta-2,3-dien-1-yl)silane. Lithium chloride (4.0 g, 94 mmol) was charged a round bottom flask and dried with heating under vacuum. After cooling to room temperature, the flask was charged with diethyl ether (100 mL) and copper(I) cyanide (4.0 g, 45 mmol). The mixture was cooled to 0° C. and treated with 1 M TMSCH$_2$MgCl (45.0 mL, 45.0 mmol) over 10 min maintaining the internal temperature below 5° C. The mixture was stirred at 0° C. for 1 h. After cooling to −78° C., the mixture was treated with 2-butynyl p-toluenesulfonate (10.0 g, 44.5 mmol) in 3 portions. The mixture was slowly warmed up to room temperature over 18 h. The reaction mixture was filtered through a celite pad and rinsed with diethyl ether. The filtrate was concentrated with slight vacuum (bath: 10° C.) to give the title compound (4.09 g, 65.3%).

$^1$H NMR (400 MHz, CHLOROFORM-d) δ 4.51-4.58 (m, 2H), 1.70 (t, J=3.13 Hz, 3H), 1.33 (t, J=2.54 Hz, 2H), 0.06 (s, 9H).

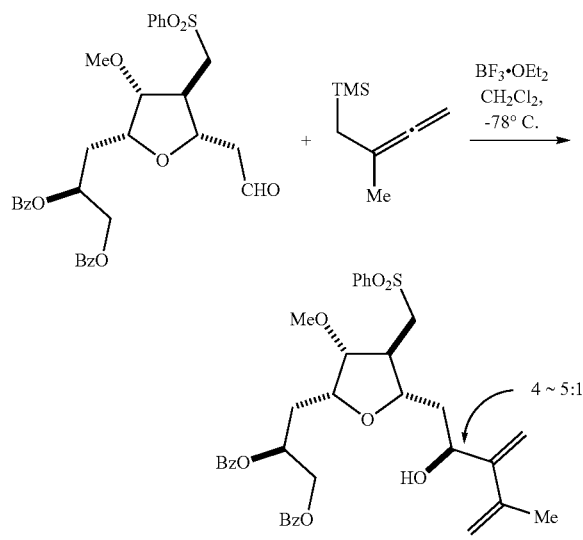

(S)-3-((2R,3R,4S,5S)-5-((S)-2-hydroxy-4-methyl-3-methylenepent-4-en-1-yl)-3-methoxy-4-((phenylsulfonyl)methyl)tetrahydrofuran-2-yl)propane-1,2-diyl dibenzoate. A mixture of (S)-3-((2R,3R,4S,5S)-3-methoxy-5-(2-oxoethyl)-4-((phenylsulfonyl)methyl)tetrahydrofuran-2-yl)propane-1,2-diyl dibenzoate (1.61 g, 2.77 mmol) and trimethyl (2-methylbuta-2,3-dien-1-yl)silane (0.78 g, 5.5 mmol) in CH$_2$Cl$_2$ (32 mL) was cooled to −78° C., treated with BF$_3$.OEt$_2$ (0.70 mL, 5.5 mmol) and stirred at −78° C. for 1 h. The reaction was quenched with sat. aq. NaHCO$_3$ (80 mL) and the mixture was extracted twice with MTBE (30 mL). The organic layers were combined, washed with brine (32.1 mL), and concentrated in vacuo. The residue was purified by silica gel column chromatography (ethyl acetate in n-heptane=10% to 50%) to give the title compound (960 mg, 53.5%) and a 1:1 mixture of the title compound and its epimer (631 mg, 35%). $^1$H NMR (400 MHz, CHLOROFORM-d) δ 8.04-8.10 (m, 2H), 7.97-8.04 (m, 2H), 7.88-7.96 (m, 2H), 7.64-7.72 (m, 1H), 7.50-7.62 (m, 4H), 7.37-7.48 (m, 4H), 5.54-5.70 (m, 1H), 5.27 (s, 1H), 5.17 (s, 1H), 4.99 (s, 1H), 4.95 (s, 1H), 4.63 (br d, J=8.60 Hz, 1H), 4.57 (d, J=5.08 Hz, 2H), 3.87-3.97 (m, 2H), 3.76-3.85 (m, 1H), 3.41 (s, 3H), 3.01-3.19 (m, 2H), 2.52-2.63 (m, 1H), 2.19-2.35 (m, 2H), 1.93-2.03 (m, 1H), 1.88 (s, 3H), 1.68-1.79 (m, 1H).

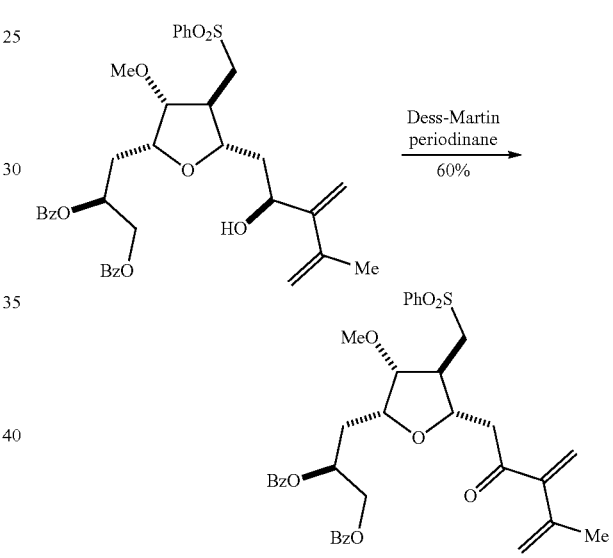

(S)-3-((2R,3R,4S,5S)-3-methoxy-5-(4-methyl-3-methylene-2-oxopent-4-en-1-yl)-4-((phenylsulfonyl)methyl)tetrahydrofuran-2-yl)propane-1,2-diyl dibenzoate. A solution of (S)-3-((2R,3R,4S,5S)-5-((S)-2-hydroxy-4-methyl-3-methylenepent-4-en-1-yl)-3-methoxy-4-((phenylsulfonyl) methyl)tetrahydrofuran-2-yl)propane-1,2-diyl dibenzoate (0.63 g, 0.97 mmol) in CH$_2$Cl$_2$ (12.6 mL) was treated with sodium bicarbonate (0.16 g, 1.9 mmol) and Dess-Martin periodinane (0.495 g, 1.17 mmol). After stirring at room temperature for 1 h, the reaction was quenched with sat. NaHCO$_3$ (6.3 mL) and 20% (w/v) aq. Na$_2$SO$_3$ (6.3 mL), and extracted twice with MTBE (12.6 mL). The organic layers were combined, washed with brine (6.3 mL), and concentrated in vacuo. The residue was purified by silica gel column chromatography (ethyl acetate in n-heptane=10% to 40%) to give the title compound (378 mg, 60%).

$^1$H NMR (400 MHz, CHLOROFORM-d) δ 7.98-8.11 (m, 4H), 7.89-7.97 (m, 2H), 7.62-7.72 (m, 1H), 7.50-7.62 (m, 4H), 7.35-7.49 (m, 4H), 5.54-5.69 (m, 3H), 5.08 (s, 1H), 4.97 (s, 1H), 4.57 (d, J=5.08 Hz, 2H), 3.97-4.05 (m, 2H), 3.90-3.96 (m, 1H), 3.49 (dd, J=3.91, 14.07 Hz, 1H), 3.42 (s,

3H), 3.05-3.24 (m, 2H), 2.98 (dd, J=7.03, 17.58 Hz, 1H), 2.47-2.58 (m, 1H), 2.18-2.35 (m, 2H), 1.82-1.91 (s, 3H).

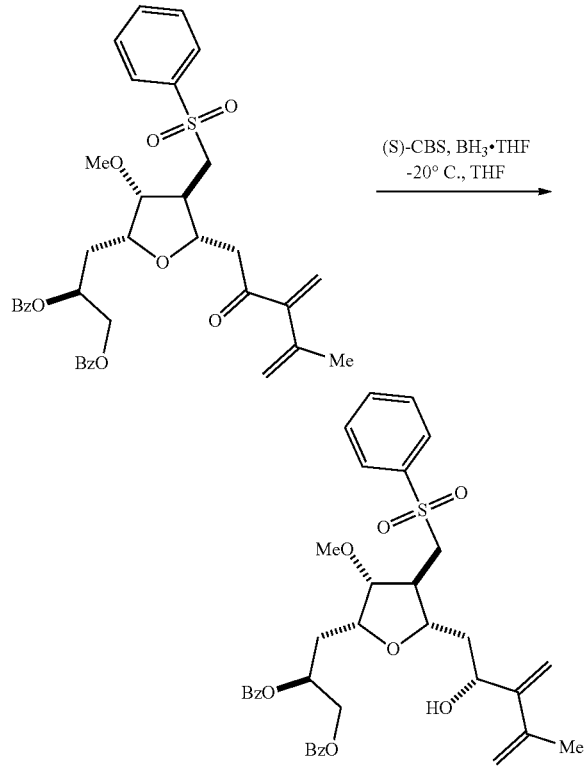

(S)-3-((2R,3R,4S,5S)-5-((R)-2-hydroxy-4-methyl-3-methylenepent-4-en-1-yl)-3-methoxy-4-((phenylsulfonyl)methyl)tetrahydrofuran-2-yl)propane-1,2-diyl dibenzoate. (S)-CBS oxazaborolidine (0.056 g, 0.20 mmol) was dissolved in THF (5.8 mL) and treated with 1 M BH$_3$.THF in THF (0.90 mL, 0.90 mmol). The mixture was stirred at room temperature for 1 h. After cooling to −40° C., the mixture was treated with a solution of (S)-3-((2R,3R,4S,5S)-3-methoxy-5-(4-methyl-3-methylene-2-oxopent-4-en-1-yl)-4-((phenylsulfonyl)methyl)tetrahydrofuran-2-yl)propane-1,2-diyl dibenzoate (0.29 g, 0.45 mmol) in THF (5.8 mL) and stirred at a temperature between −30 and −15° C. for 3 h. The reaction was quenched with methanol (0.18 mL) and sat. aq. NH$_4$Cl (15 mL). The mixture was extracted twice with MTBE (29 mL), washed with brine, and concentrated in vacuo. The residue was purified by silica gel column chromatography (ethyl acetate in n-heptane=10% to 50%) to give the title compound (120 mg, 41%).

$^1$H NMR (400 MHz, CHLOROFORM-d) δ 7.95-8.09 (m, 4H), 7.86-7.93 (m, 2H), 7.62-7.72 (m, 1H), 7.49-7.60 (m, 4H), 7.35-7.45 (m, 4H), 5.49-5.59 (m, 1H), 5.30-5.37 (m, 1H), 5.15-5.21 (m, 1H), 4.99 (s, 1H), 4.96 (s, 1H), 4.58-4.65 (m, 1H), 4.49-4.57 (m, 2H), 3.83-3.97 (m, 2H), 3.77-3.82 (m, 1H), 3.36 (s, 3H), 3.03-3.15 (m, 2H), 2.60-2.70 (m, 1H), 2.26 (t, J=6.44 Hz, 2H), 2.03-2.11 (m, 1H), 1.89 (s, 3H), 1.71-1.83 (m, 1H).

In another approach, compound 9 was subjected to Mitsunobu reaction with 3,5-dinitrobenzoic acid, DIAD, and PPh$_3$ to give compound 13. Alcoholysis of compound 13 with Mg(OMe)$_2$ gave compound 11.

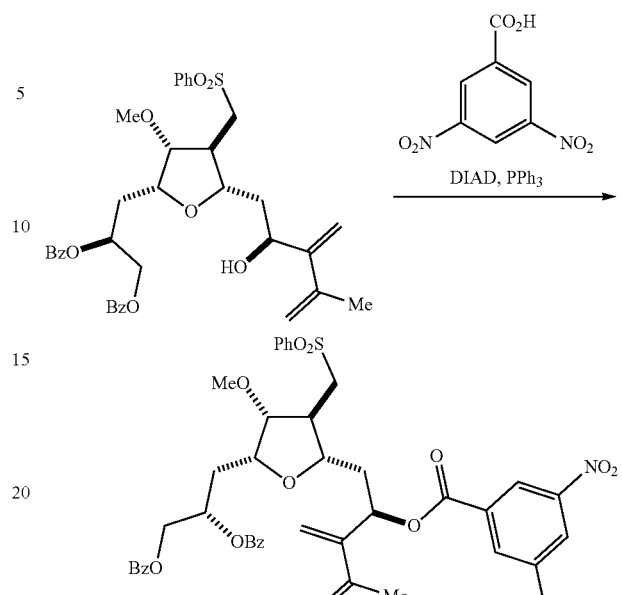

(S)-3-((2R,3R,4S,5S)-5-((R)-2-((3,5-dinitrobenzoyl)oxy)-4-methyl-3-methylenepent-4-en-1-yl)-3-methoxy-4-((phenylsulfonyl)methyl)tetrahydrofuran-2-yl)propane-1,2-diyl dibenzoate. A solution of (S)-3-((2R,3R,4S,5S)-5-((S)-2-hydroxy-4-methyl-3-methylenepent-4-en-1-yl)-3-methoxy-4-((phenylsulfonyl)methyl)tetrahydrofuran-2-yl) propane-1,2-diyl dibenzoate (0.33 g, 0.51 mmol) in THF (13.2 mL) was treated with 3,5-dinitrobenzoic acid (0.65 g, 3.1 mmol) and triphenylphosphine (0.80 g, 3.1 mmol). The mixture was treated with DIAD (0.49 mL, 2.5 mmol) and stirred at room temperature for 20 h. The reaction was quenched with sat. aq. NaHCO$_3$ (6.6 mL) and extracted twice with MTBE (9.9 mL). The organic layers were combined, washed with brine, and concentrated in vacuo. The residue was purified by column chromatography (ethyl acetate in n-heptane=10% to 30%) to give the title compound (235 mg, 55%).

$^1$H NMR (400 MHz, CHLOROFORM-d) δ 9.13-9.17 (m, 2H), 9.10-9.13 (m, 1H), 7.89-7.99 (m, 6H), 7.65-7.72 (m, 1H), 7.50-7.62 (m, 4H), 7.35-7.45 (m, 4H), 5.98-6.08 (m, 1H), 5.36-5.46 (m, 1H), 5.31 (s, 1H), 5.29 (s, 1H), 5.27 (s, 1H), 5.11 (s, 1H), 4.43-4.49 (m, 2H), 3.83-3.92 (m, 2H), 3.69-3.77 (m, 1H), 3.31 (s, 3H), 3.01-3.17 (m, 2H), 2.64-2.75 (m, 1H), 2.28-2.37 (m, 2H), 2.07-2.28 (m, 2H), 1.94 (s, 3H).

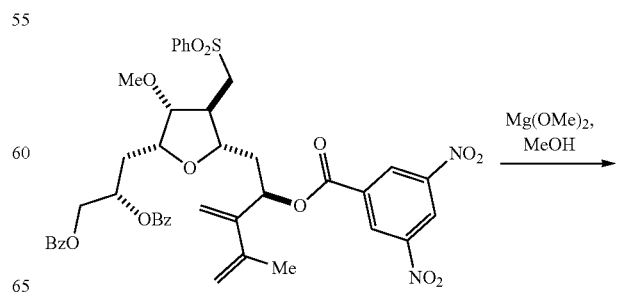

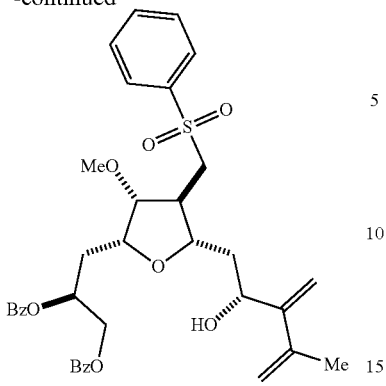

(S)-3-((2R,3R,4S,5S)-5-((R)-2-hydroxy-4-methyl-3-methylenepent-4-en-1-yl)-3-methoxy-4-((phenylsulfonyl)methyl)tetrahydrofuran-2-yl)propane-1,2-diyl dibenzoate. A solution of (S)-3-((2R,3R,4S,5S)-5-((R)-2-((3,5-dinitrobenzoyl)oxy)-4-methyl-3-methylenepent-4-en-1-yl)-3-methoxy-4-((phenylsulfonyl)methyl)tetrahydrofuran-2-yl)propane-1,2-diyl dibenzoate (0.235 g, 0.279 mmol) in methanol (4.7 mL) and THF (0.24 mL) was treated with 6-10% Mg(OMe)$_2$ in methanol (0.22 g, 0.17 mmol) and stirred at room temperature for 1 h. The reaction mixture was diluted with MTBE (23.5 mL) and washed with sat. aq. NaHCO$_3$ (4.7 mL) and brine. The aqueous layer was extracted with MTBE (5 mL). The organic layers were combined, concentrated in vacuo, and purified by silica gel column chromatography (ethyl acetate in n-heptane=10% to 40%) to give the title compound (40 mg, 22%).

$^1$H NMR (400 MHz, CHLOROFORM-d) δ 7.95-8.09 (m, 4H), 7.86-7.93 (m, 2H), 7.62-7.72 (m, 1H), 7.49-7.60 (m, 4H), 7.35-7.45 (m, 4H), 5.49-5.59 (m, 1H), 5.30-5.37 (m, 1H), 5.15-5.21 (m, 1H), 4.99 (s, 1H), 4.96 (s, 1H), 4.58-4.65 (m, 1H), 4.49-4.57 (m, 2H), 3.83-3.97 (m, 2H), 3.77-3.82 (m, 1H), 3.36 (s, 3H), 3.03-3.15 (m, 2H), 2.60-2.70 (m, 1H), 2.26 (t, J=6.44 Hz, 2H), 2.03-2.11 (m, 1H), 1.89 (s, 3H), 1.71-1.83 (m, 1H).

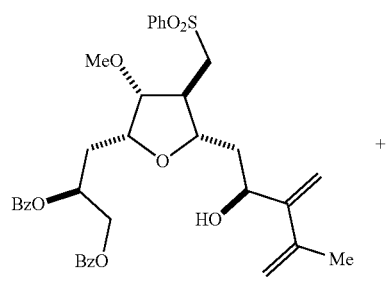

+

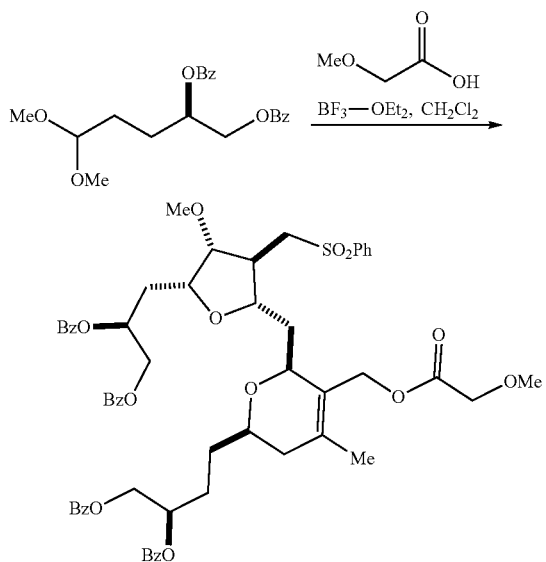

(S)-3-((2R,3R,4S,5S)-5-(((2S,6R)-6-((R)-3,4-bis(benzoyloxy)butyl)-3-((2-methoxyacetoxy)methyl)-4-methyl-5,6-dihydro-2H-pyran-2-yl)methyl)-3-methoxy-4-((phenylsulfonyl)methyl)tetrahydrofuran-2-yl)propane-1,2-diyl dibenzoate. A mixture of (S)-3-((2R,3R,4S,5S)-5-((S)-2-hydroxy-4-methyl-3-methylenepent-4-en-1-yl)-3-methoxy-4-((phenylsulfonyl)methyl)tetrahydrofuran-2-yl)propane-1,2-diyl dibenzoate (0.035 g, 0.054 mmol) and (R)-5,5-dimethoxypentane-1,2-diyl dibenzoate (0.030 g, 0.081 mmol) in CH$_2$Cl$_2$ (2.1 mL) was cooled to −30° C. and treated with methoxyacetic acid (0.062 mL, 0.81 mmol) and BF$_3$-OEt$_2$ (0.021 mL, 0.162 mmol). The mixture was stirred at a temperature between −30 and −20° C. for 1.5 h, quenched with sat. aq. NaHCO$_3$ (3.5 mL) and extracted twice with MTBE (3.5 mL). The organic layers were combined, washed with brine (1.8 mL), and concentrated in vacuo. The residue was purified by silica gel column chromatography (ethyl acetate in n-heptane=20% to 50%) to give the title compound (21 mg, 37%).

$^1$H NMR (400 MHz, CHLOROFORM-d) δ 7.91-8.06 (m, 8H), 7.87 (d, J=7.42 Hz, 2H), 7.60 (m, 1H), 7.45-7.55 (m, 6H), 7.30-7.41 (m, 8H), 5.53-5.65 (m, 1H), 5.42-5.52 (m, 1H), 4.62-4.70 (m, 1H), 4.40-4.57 (m, 5H), 4.05-4.18 (m, 1H), 3.98 (s, 2H), 3.90 (s, 2H), 3.71-3.80 (m, 1H), 3.40 (s, 3H), 3.37 (s, 3H), 3.28-3.36 (m, 1H), 2.97-3.11 (m, 2H), 2.45-2.55 (m, 1H), 2.10-2.28 (m, 2H), 1.82-1.99 (m, 3H), 1.72-1.82 (m, 1H), 1.67 (s, 3H), 1.44-1.63 (m, 4H).

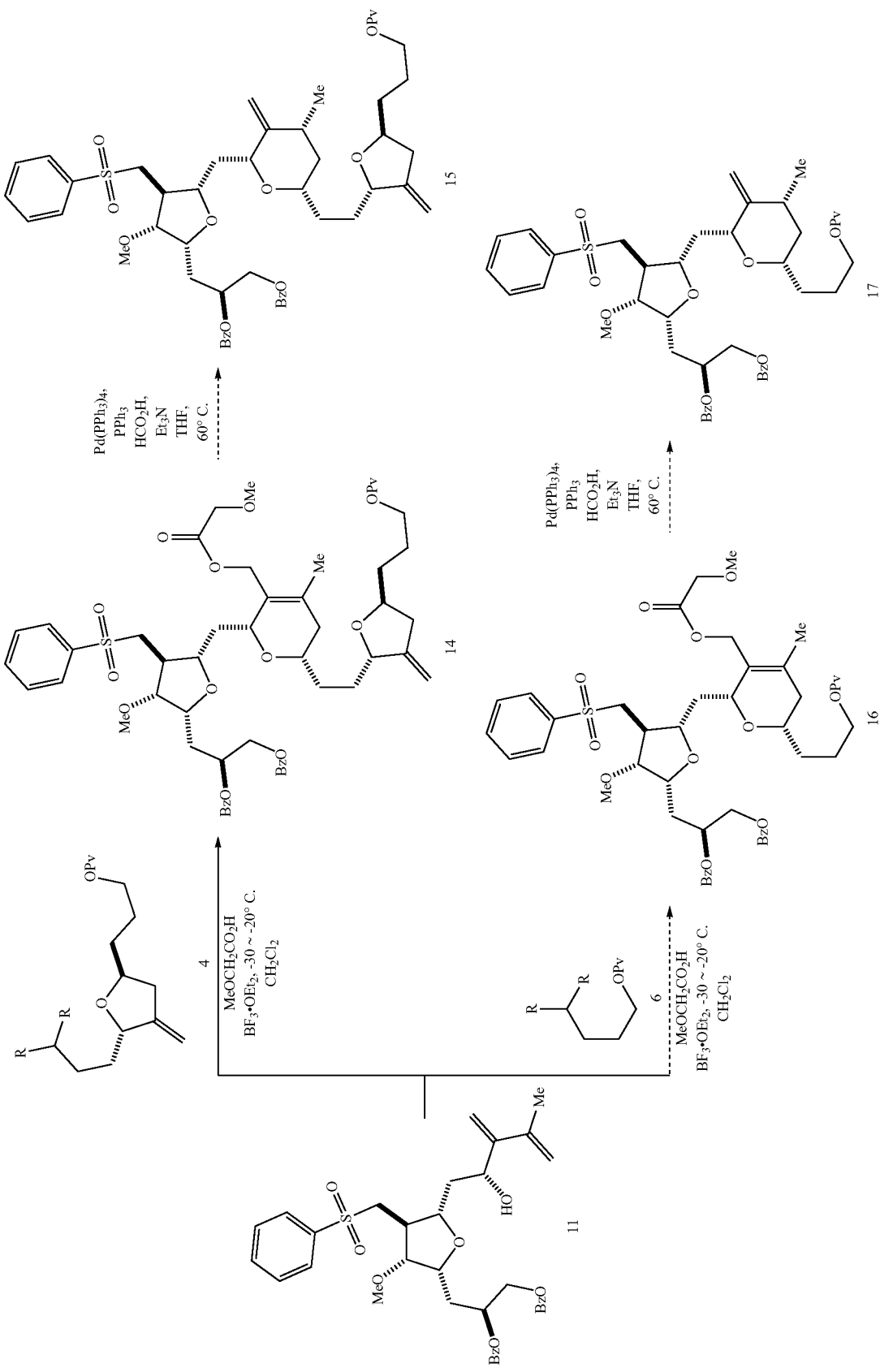
each R is OMe, or both R groups, together with the atom to which they are attached, combine to form a carbonyl.

Compound 14 can be prepared by treating compound 11 with compound 4 in the presence of BF$_3$.OEt$_2$ and methoxyacetic acid (exemplary Prins reaction conditions):

Compound 15 can be prepared by treating compound 14 with an allylic reducing agent (e.g., Pd(PPh$_3$)$_4$/HCO$_2$H/Et$_3$N).

Alternatively, compound 16 can be prepared by treating compound 11 with compound 6 in the presence of BF$_3$-OEt$_2$ and methoxyacetic acid (exemplary Prins reaction conditions). Compound 17 can be prepared by treating compound 16 with an allylic reducing agent (e.g., Pd(PPh$_3$)$_4$/HCO$_2$H/Et$_3$N).

A halichondrin macrolide analog can be prepared from compound 15 or 17 using methods and intermediates disclosed, e.g., WO 2015/066729, the synthesis of which is hereby incorporated by reference and described herein. For example, compounds 15 and 17 may be converted to a halichondrin macrolide analog, as described for the compound of formula (VIIE) in WO 2015/066729.

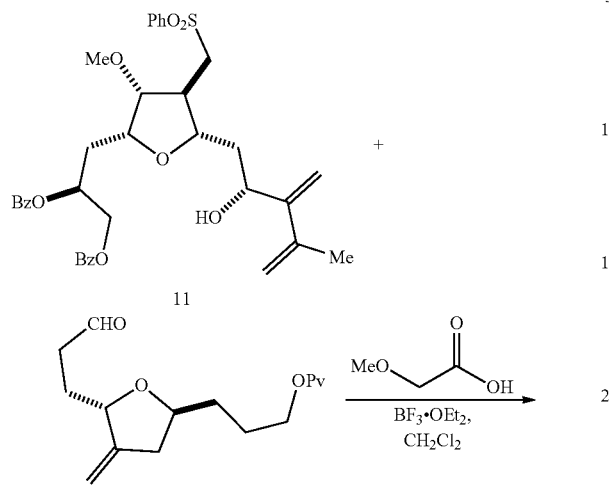

Example 3

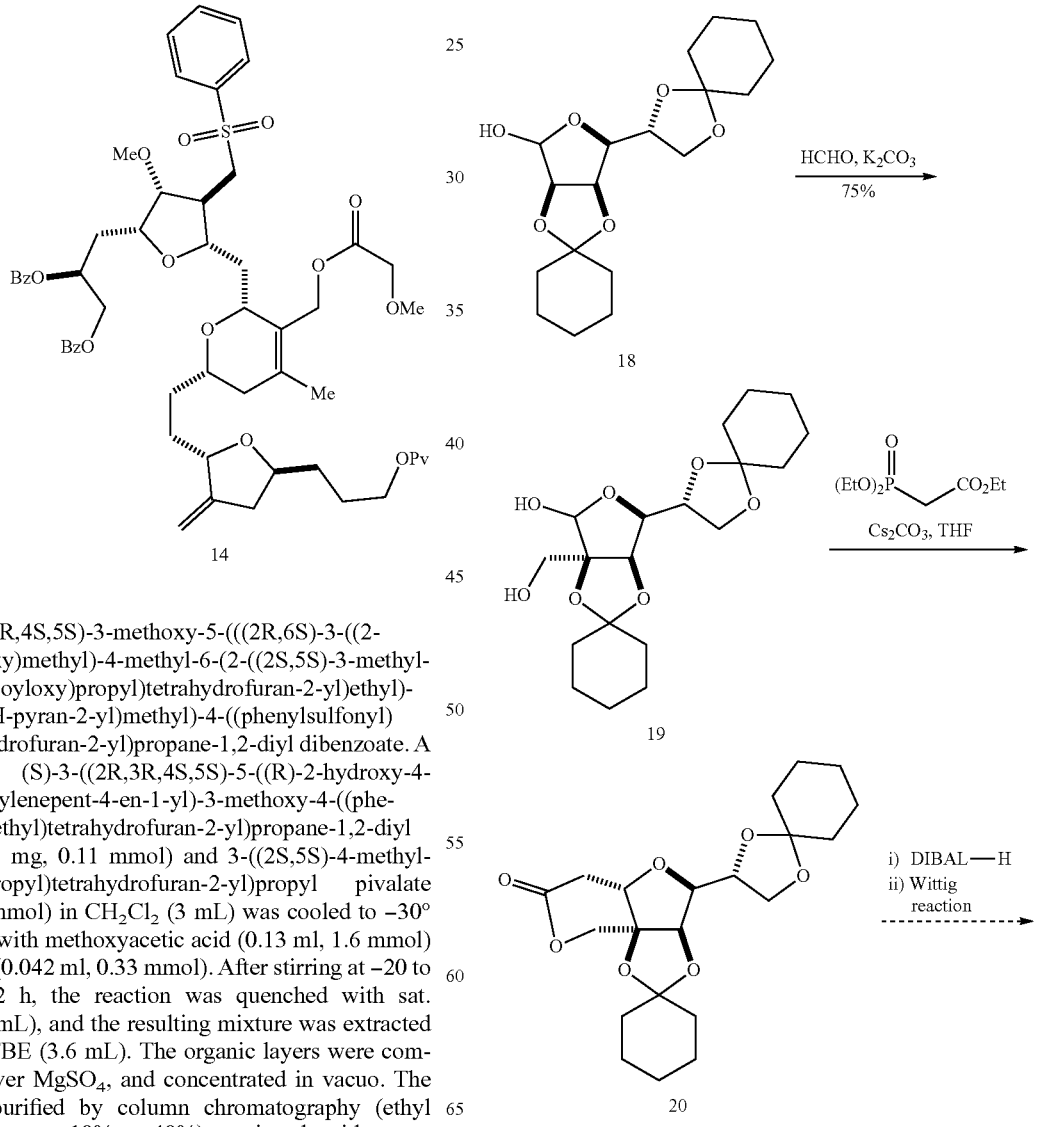

(S)-3-((2R,3R,4S,5S)-3-methoxy-5-(((2R,6S)-3-((2-methoxyacetoxy)methyl)-4-methyl-6-(2-((2S,5S)-3-methylene-5-(3-(pivaloyloxy)propyl)tetrahydrofuran-2-yl)ethyl)-5,6-dihydro-2H-pyran-2-yl)methyl)-4-((phenylsulfonyl)methyl)tetrahydrofuran-2-yl)propane-1,2-diyl dibenzoate. A mixture of (S)-3-((2R,3R,4S,5S)-5-((R)-2-hydroxy-4-methyl-3-methylenepent-4-en-1-yl)-3-methoxy-4-((phenylsulfonyl)methyl)tetrahydrofuran-2-yl)propane-1,2-diyl dibenzoate (71 mg, 0.11 mmol) and 3-((2S,5S)-4-methylene-5-(3-oxopropyl)tetrahydrofuran-2-yl)propyl pivalate (43 mg, 0.15 mmol) in CH$_2$Cl$_2$ (3 mL) was cooled to −30° C. and treated with methoxyacetic acid (0.13 ml, 1.6 mmol) and BF$_3$.OEt$_2$ (0.042 ml, 0.33 mmol). After stirring at −20 to −30° C. for 2 h, the reaction was quenched with sat. NaHCO$_3$ (3.6 mL), and the resulting mixture was extracted twice with MTBE (3.6 mL). The organic layers were combined, dried over MgSO$_4$, and concentrated in vacuo. The residue was purified by column chromatography (ethyl acetate in n-heptane=10% to 40%) to give the title compound (4 mg, 4%). Mass (M+Na$^+$): 757.4

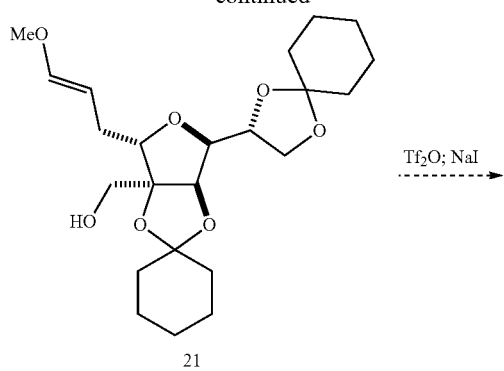

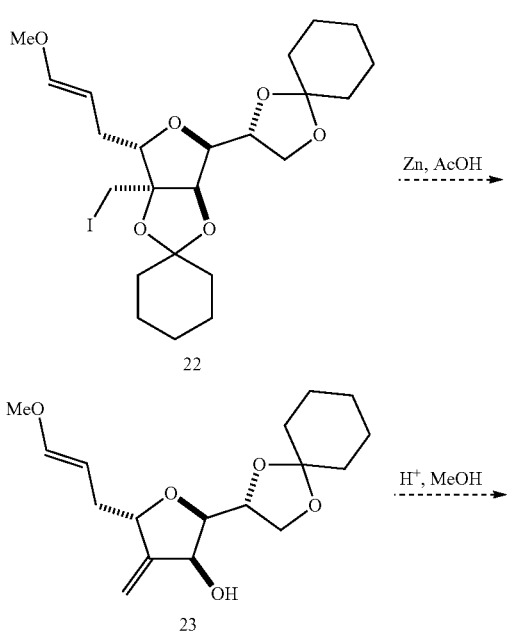

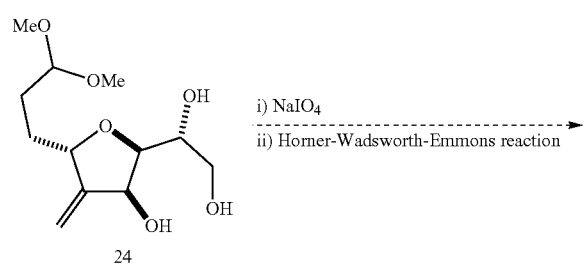

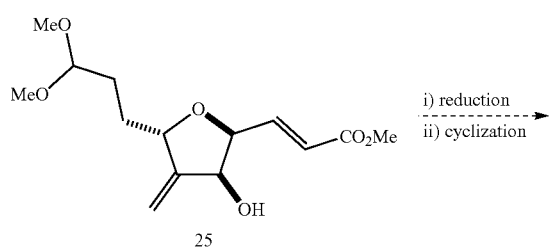

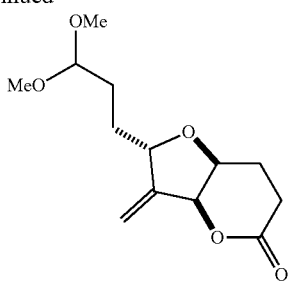

26

An exemplary compound of formula (III) can be prepared as shown in the above scheme. Compound 18 was subjected to an aldol reaction with HCHO in the presence of $K_2CO_3$ to afford compound 19. Compound 19 was treated with triethyl phosphonoacetate, which was deprotonated with $Cs_2CO_3$, to afford compound 20.

Compound 21 can be prepared from compound 20 by treating with a 1,2-reducing agent (e.g., DIBAL-H) followed by an alkoxymethyl phosphonate, e.g., diethyl-(methoxymethyl)-phosphonate, under Wittig reaction conditions. Compound 22 can be prepared from compound 21 by treating with a sulfonyl halide or sulfonyl anhydride, e.g., $Tf_2O$, followed by a halide salt, e.g., NaI or KI. Compound 23 can be prepared from compound 22 by treating with a reducing metal, e.g., elemental zinc, and a Brønsted acid, e.g., acetic acid. Compound 24 can be prepared from compound 23 by a reaction with methanol in the presence of a Brønsted acid, e.g., HC. Compound 25 can be prepared from compound 24 by a reaction with a glycol cleaving agent, e.g., $NaIO_4$, followed by a Horner-Wadsworth-Emmons reaction with alkylated phosphonoacetate, e.g., trimethyl phosphonoacetate, that has been deprotonated with a base (e.g., NaH or $Cs_2CO_3$). Compound 26 can be prepared from compound 25 by treating with a 1,4-reducing agent (e.g., Stryker's reagent), followed by a cyclization reaction. The cyclization reaction may proceed spontaneously after the 1,4-reduction, e.g., on work-up or during purification.

Example 4

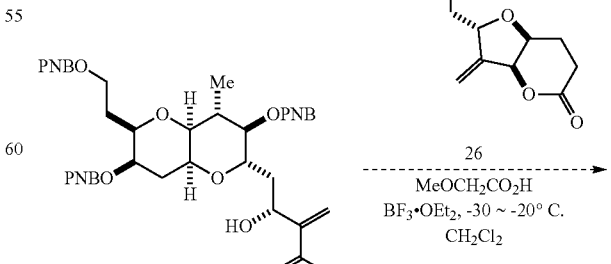

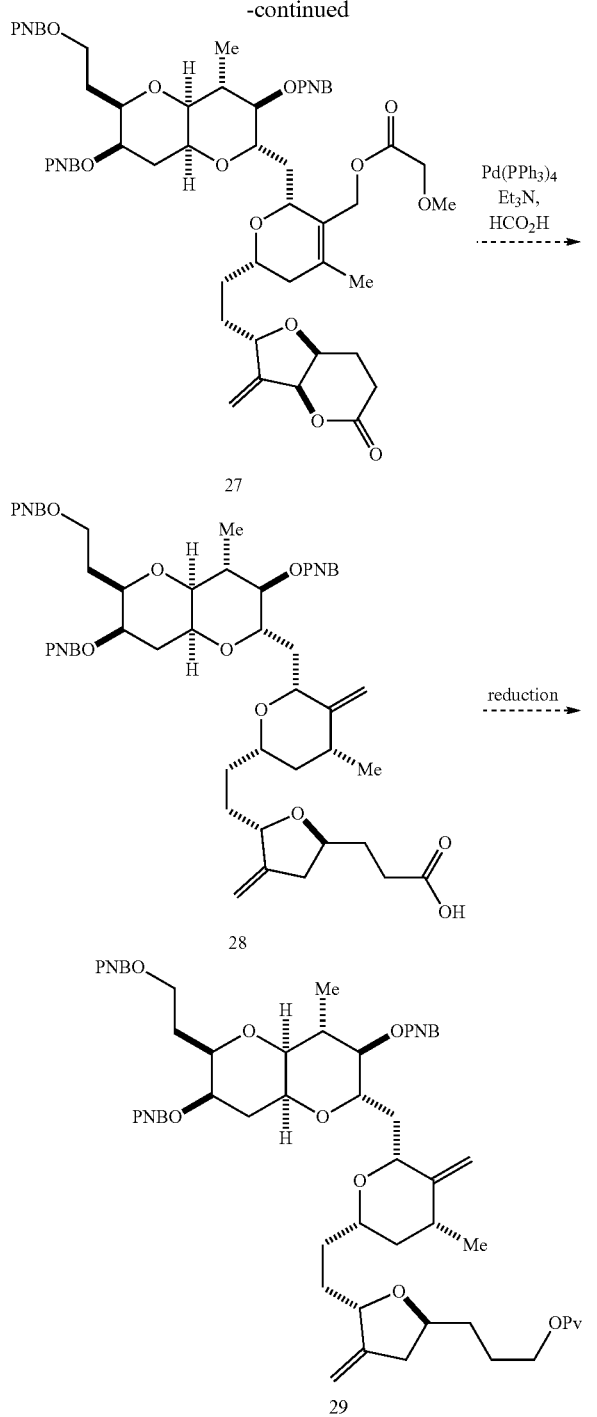

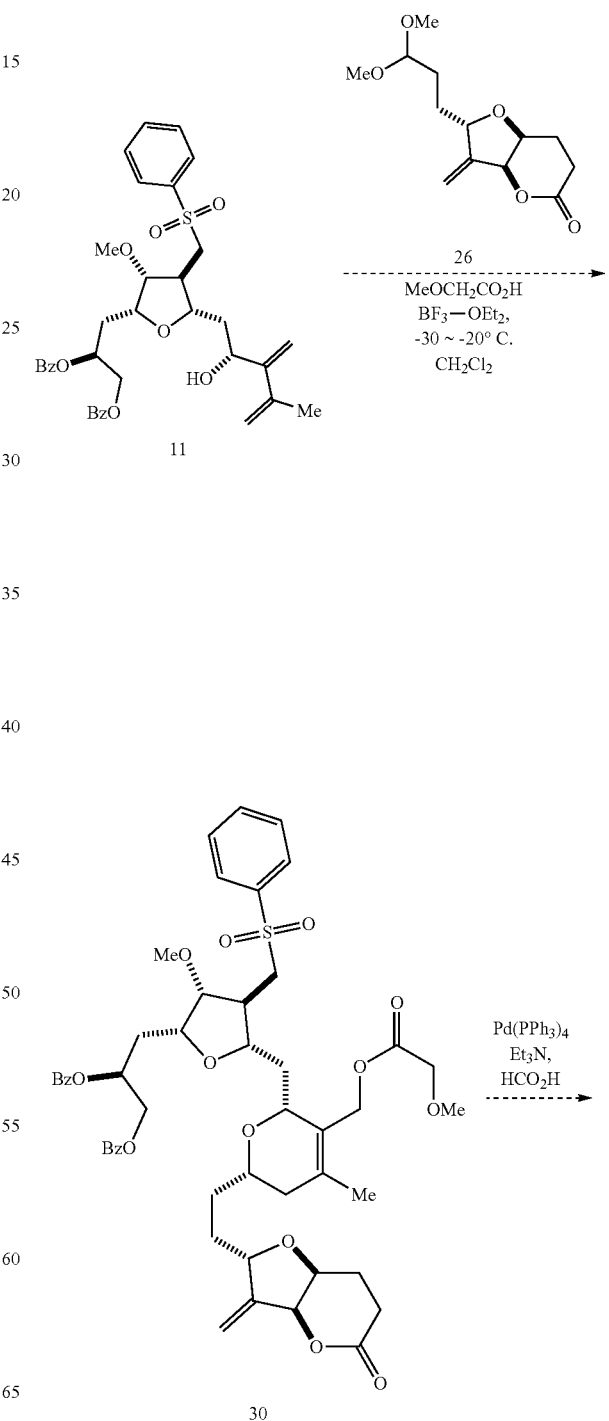

A halichondrin macrolide can be prepared from compound 29 using methods and intermediates disclosed, e.g., WO 2016/179607, the synthesis of which is hereby incorporated by reference and described herein. For example, compound 29 can be converted to a halichondrin macrolide, as described for the compound of formula (VIIID) in WO 2016/179607.

Example 5

An exemplary intermediate of formula (IA) can be prepared from compounds 3 and 26. Compound 3 can be treated with compound 26 in the presence of $BF_3.OEt_2$ and methoxyacetic acid (exemplary Prins reaction conditions) to afford compound 27. Compound 27 can be treated with an allylic reducing agent (e.g., $Pd(PPh_3)_4/HCO_2H/Et_3N$) to afford compound 28. Compound 28 can be converted to compound 29 using methods known in the art, e.g., using $NaBH_4/I_2$ or by converting the carboxylic acid in compound 28 to a mixed anhydride (e.g., using N-methylmorpholine and i-butylchloroformate) reducing the resulting mixed anhydride using borane reducing agents (e.g., 9-BBN).

211

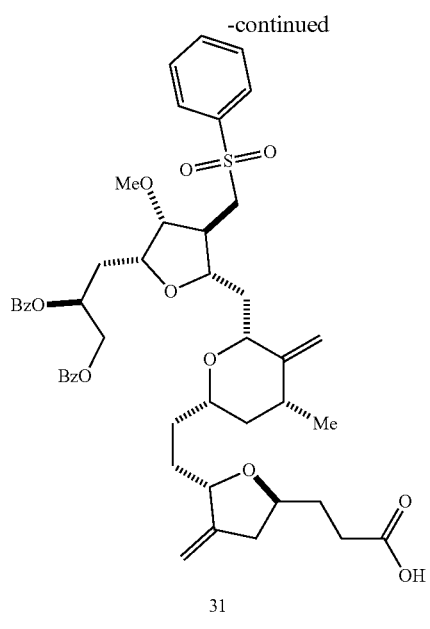

31

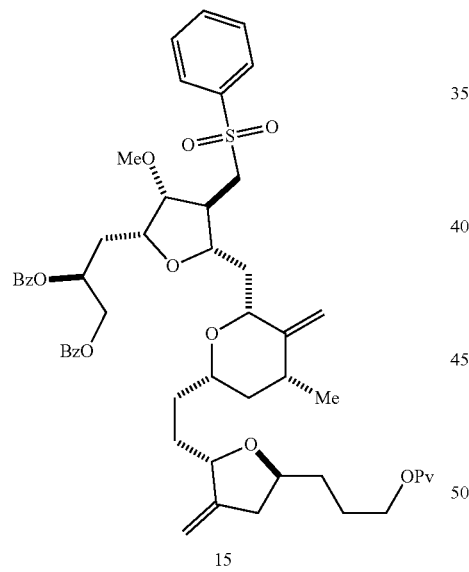

15

An exemplary intermediate of formula (IA) can be preparation from compounds 11 and 26. Compound 11 can be treated with compound 26 in the presence of BF$_3$.OEt$_2$ and methoxyacetic acid (exemplary Prins reaction conditions) to afford compound 30. Compound 30 can be treated with an allylic reducing agent (e.g., Pd(PPh$_3$)$_4$/HCO$_2$H/Et$_3$N) to afford compound 31. Compound 31 can be converted to compound 15 using methods known in the art, e.g., using NaBH$_4$/I$_2$ or by converting the carboxylic acid in compound 28 to a mixed anhydride (e.g., using N-methylmorpholine and i-butylchloroformate) and reducing the resulting mixed anhydride using borane reducing agents (e.g., 9-BBN).

212

A halichondrin macrolide analog can be prepared from compound 15 using methods and intermediates disclosed, e.g., WO 2015/066729, the synthesis of which is hereby incorporated by reference. For example, compound 15 may be converted to a halichondrin macrolide analog, as described for the compound of formula (VIIE) in WO 2015/066729.

Example 6

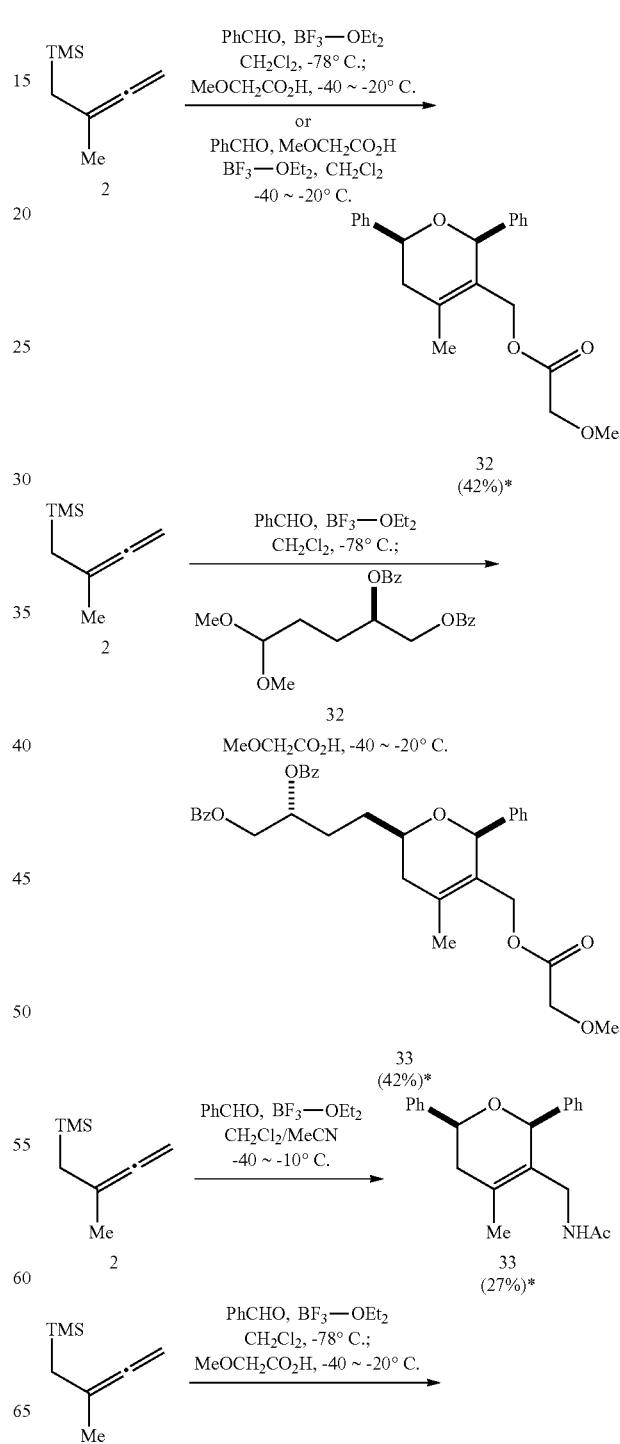

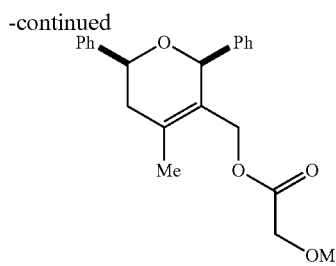

* yields are not optimized (4-methyl-2,6-cis-diphenyl-5,6-dihydro-2-pyran-3-yl)methyl 2-methoxyacetate. A mixture of trimethyl(2-methylbuta-2,3-dien-1-yl)silane (0.050 g, 0.36 mmol) and benzaldehyde (0.11 mL, 1.1 mmol) in CH$_2$Cl$_2$ (4.0 mL) was cooled to −78° C. and treated with BF$_3$.OEt$_2$ (0.14 mL, 1.1 mmol). The mixture was stirred at −78° C. for 1.5 h. After addition of methoxyacetic acid (0.41 mL, 5.4 mmol), the mixture was warmed to −40° C. and then slowly warmed to −20° C. over 2 h with stirring. The reaction was quenched with sat. aq. NaHCO$_3$ (5.0 mL) and extracted twice with MTBE (5.0 mL). The organic layers were combined, washed with brine (2.5 mL), and concentrated in vacuo. The residue was purified by silica gel column chromatography (ethyl acetate in n-heptane=5% to 15%) to give the title compound (53 mg, 42%).

$^1$H NMR (400 MHz, CHLOROFORM-d) δ 7.34-7.44 (m, 4H), 7.20-7.33 (m, 6H), 5.31 (br s, 1H), 4.65-4.76 (m, 2H), 4.13-4.23 (m, 1H), 3.87 (d, J=16.41 Hz, 1H), 3.72 (d, J=16.41 Hz, 1H), 3.36 (s, 3H), 2.48-2.63 (m, 1H), 2.16-2.31 (m, 1H), 1.85 (s, 3H).

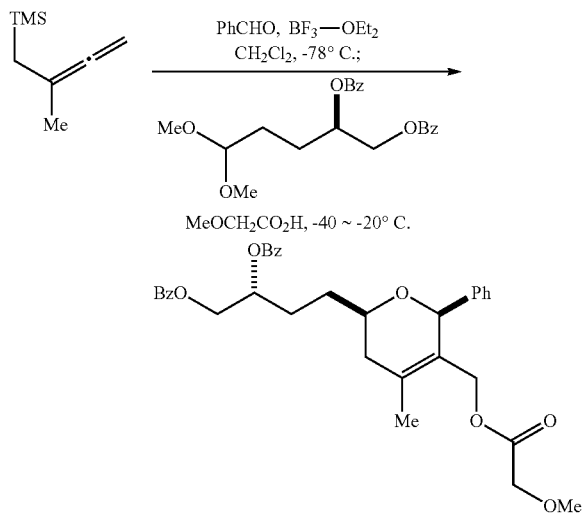

(R)-4-((2R,6S)-5-((2-methoxyacetoxy)methyl)-4-methyl-6-phenyl-3,6-dihydro-2-pyran-2-yl)butane-1,2-diyl dibenzoate. A mixture of trimethyl(2-methylbuta-2,3-dien-1-yl)silane (0.057 g, 0.41 mmol) and benzaldehyde (0.034 mL, 0.34 mmol) in CH$_2$Cl$_2$ (2 mL) was cooled to −78° C. and treated with BF$_3$.OEt$_2$ (0.13 mL, 1.0 mmol). The mixture was stirred at −78° C. for 1.5 h. After addition of methoxyacetic acid (0.39 mL, 5.1 mmol) and a solution of (R)-5,5-dimethoxypentane-1,2-diyl dibenzoate (0.16 g, 0.44 mmol) in CH$_2$Cl$_2$ (1.2 mL), the mixture was stirred at −35° C. for 10 min and warmed up to −10° C. over 2 h. The reaction was quenched with sat. aq. NaHCO$_3$, extracted twice with MTBE (3.6 mL), washed with brine (1.8 mL), and concentrated in vacuo. The residue was purified by silica gel column chromatography (ethyl acetate in n-heptane=10%, 20% and 30%) to give the title compound (82 mg, 42%).

$^1$H NMR (400 MHz, CHLOROFORM-d) δ 7.91-8.06 (m, 4H), 7.46-7.59 (m, 2H), 7.32-7.45 (m, 6H), 7.19-7.31 (m, 3H), 5.84-5.93 (m, 1H), 5.07-5.17 (m, 2H), 3.95-4.08 (m, 1H), 3.78-3.87 (m, 2H), 3.70-3.77 (m, 2H), 3.64-3.78 (m, 1H), 3.34 (s, 3H), 2.15-2.31 (m, 2H), 1.95-2.07 (m, 1H), 1.82-1.94 (m, 2H), 1.78 (s, 3H), 1.58-1.76 (m, 1H).

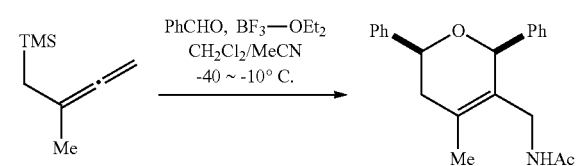

N-((4-methyl-2,6-cis-diphenyl-5,6-dihydro-2H-pyran-3-yl)methyl)acetamide. A mixture of trimethyl(2-methylbuta-2,3-dien-1-yl)silane (0.098 g, 0.70 mmol) and benzaldehyde (0.21 mL, 2.1 mmol) in CH$_2$Cl$_2$ (2 mL) and acetonitrile (2 mL) was cooled to −40° C. and treated with BF$_3$-OEt$_2$ (0.27 mL, 2.1 mmol). The mixture was slowly warmed up to −10° C. over 3 h. The reaction was quenched with sat. aq. NaHCO$_3$ (3.9 mL) and extracted twice with MTBE (3.92 mL). The organic layers were combined, washed with brine (4.90 mL), and concentrated in vacuo. The residue was purified by silica gel column chromatography (ethyl acetate in N-heptane=10% to 90%) to give the title compound (60 mg, 27%).

$^1$H NMR (400 MHz, CHLOROFORM-d) δ 7.28-7.49 (m, 10H), 5.21 (br s, 1H), 4.72 (dd, J=3.12, 10.93 Hz, 1H), 4.50 (br s, 1H), 3.93 (dd, J=6.44, 14.25 Hz, 1H), 3.41 (dd, J=3.51, 14.06 Hz, 1H), 2.44-2.64 (m, 1H), 2.15-2.28 (m, 1H), 1.83 (s, 3H), 1.64 (s, 3H).

The experiments described herein show that Sakurai and Prins reactions can be performed as a single-pot Sakurai-Prins cascade reaction.

OTHER EMBODIMENTS

Various modifications and variations of the described compositions and methods of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the art are intended to be within the scope of the invention.

Other embodiments are in the claims.

What is claimed is:

1. A method of preparing a compound of formula (A), the method comprising producing the compound of formula (A) from a compound of formula (B), a compound of formula (C), and R$_5$OH:

wherein R$_5$ is optionally substituted acyl;
wherein the compound of formula (A) is:

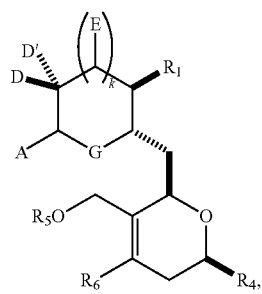
(A)

wherein
each of D and D' is independently H, optionally substituted alkyl, or OP$_1$, provided that only one of D and D' is OP$_1$, wherein P$_1$ is H, alkyl, or a hydroxyl protecting group, and A is a C$_{1-6}$ saturated or C$_{2-6}$ unsaturated hydrocarbon skeleton, the skeleton being unsubstituted or having from 1 to 10 substituents independently selected from the group consisting of cyano, halo, azido, oxo, and Q$_1$, or A is a group of formula (1):

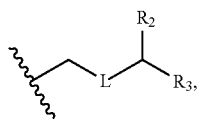
(1)

wherein
L is —(CH(OP$_2$))—, —(C(OH)(OP$_2$))—, or —C(O)—;
R$_2$ is H, or R$_2$ and P$_1$ combine to form a bond;
(i) R$_3$ is H; and P$_2$ is absent when L is —C(O)—, or P$_2$ is H, optionally substituted alkyl, or a hydroxyl protecting group when L is —(CH(OP$_2$))— or —(C(OH)(OP$_2$))—;
(ii) R$_3$ is —(CH$_2$)$_n$NP$_3$P$_4$, wherein P$_3$ is H or an N-protecting group, and (a) P$_2$ is absent when L is —C(O)—, or P$_2$ is H, optionally substituted alkyl, or a hydroxyl protecting group when L is —(CH(OP$_2$))— or —(C(OH)(OP$_2$))—, and P$_4$ is H or an N-protecting group, (b) P$_2$ and P$_4$ combine to form an alkylidene, or (c) each of P$_2$ and P$_4$ is H;
(iii) R$_3$ is —(CH$_2$)$_n$OP$_5$, wherein P$_2$ is absent when L is —C(O)—, or P$_2$ is H, optionally substituted alkyl, or a hydroxyl protecting group when L is —(CH(OP$_2$))— or —(C(OH) (OP$_2$))—, and P$_5$ is H, optionally substituted alkyl, or a hydroxyl protecting group; or P$_2$ and P$_5$, together with the atoms to which each is attached, combine to form a ketal, a cyclic carbonate, a dicarbonyl-dioxo, or silylene-dioxo; or
(iv) R$_3$ and P$_2$ combine to form an optionally substituted ethylene or a structure selected from the group consisting of:

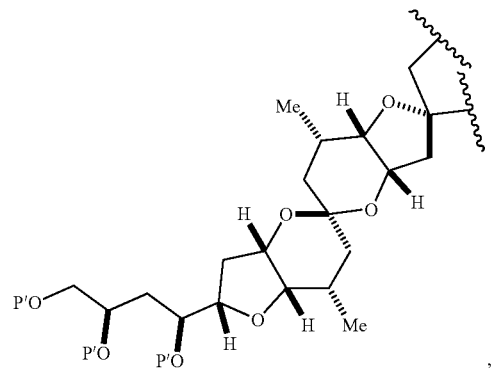

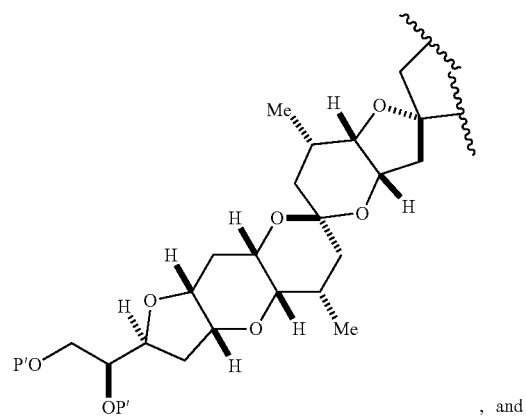
, and

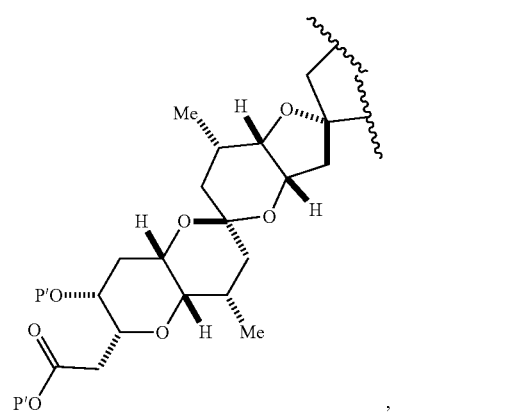
, wherein each P' is independently H or a hydroxyl protecting group;
E is H, optionally substituted alkyl, or optionally substituted alkoxy;
G is O, S, CH$_2$, or NR$_N$, wherein R$_N$ is H, an N-protecting group, or optionally substituted alkyl;
each Q$_1$ is independently OR$_A$, SR$_A$, SO$_2$R$_A$, OSO$_2$R$_A$, NR$_B$R$_A$, NR$_B$(CO)R$_A$, NR$_B$(CO)(CO) R$_A$, NR$_B$(CO)NR$_B$R$_A$, NR$_B$(CO)OR$_A$, (CO)OR$_A$, O(CO)R$_A$, (CO)NR$_B$R$_A$, or O(CO)NR$_B$R$_A$, wherein each of R$_A$ and R$_B$ is independently H, alkyl, haloalkyl, hydroxyalkyl, aminoalkyl, aryl, haloaryl, hydroxyaryl, alkoxyaryl, arylalkyl, alkylaryl, haloarylalkyl, alkylhaloaryl, (alkoxyaryl)alkyl, heterocyclic radical, or heterocyclic radicalalkyl;

n, when present, is 0, 1, or 2;

k is 0 or 1;

R₁ is —OP₆, —CH(Y)₂, or —CH₂(Y), wherein P₆ is H or a hydroxyl protecting group;

R₄ is optionally substituted alkyl, optionally substituted alkenyl, optionally substituted alkynyl,

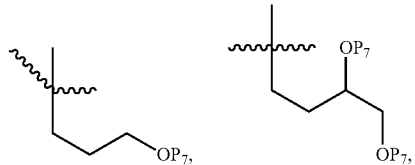

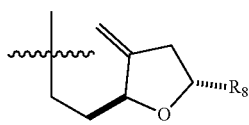

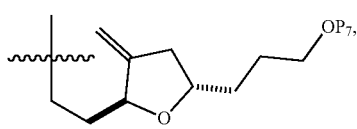

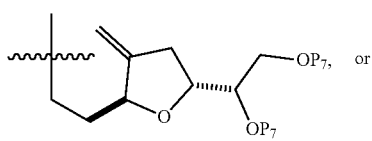

or

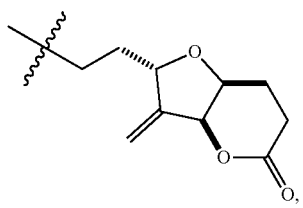

wherein
each P₇ is independently H or a hydroxyl protecting group; and
R₈ is —CH₂CH₂—COOR_C, —CH=CH—COOR_C, —CH₂CH₂—SO₂R_D, or —CH=CH—SO₂R_D;

R₆ is H, optionally substituted alkyl, or optionally substituted arylalkyl;

each Y is independently —COOR_C or —SO₂R_D;

each R_C, when present, is independently optionally substituted alkyl, optionally substituted aryl, or optionally substituted arylalkyl; and each R_D, when present, is independently optionally substituted aryl or optionally substituted non-enolizable alkyl;

wherein the compound of formula (B) is:

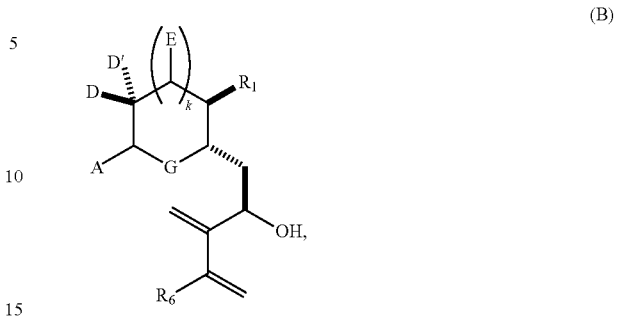

(B)

and
wherein the compound of formula (C) is:

R₄-R₇,   (C)

wherein R₇ is —CHO or

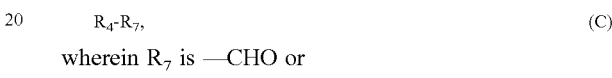

wherein each R_{7A} is independently an optionally substituted alkyl.

2. The method of claim 1, wherein the producing the compound of formula (A) comprises reacting the compound of formula (B), the compound of formula (C), R₅OH, and a Lewis acid; and/or wherein the compound of formula (B) is produced by reacting a compound of formula (D), a compound of formula (E), and a second Lewis acid,
wherein the compound of formula (D) is:

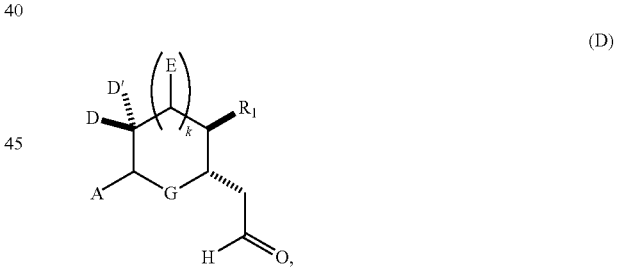

(D)

and
where the compound of formula (E) is:

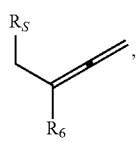

(E)

where R₅ is silyl.

3. The method of claim 2, wherein the Lewis acid or second Lewis acid is an oxophilic Lewis acid.

4. The method of claim 3, wherein the oxophilic Lewis acid is boron trifluoride or a solvate thereof.

5. The method of claim 2, wherein:
the Lewis acid and the second Lewis acid are the same; and/or
the preparing the compound of formula (B) and the preparing the compound of formula (A) are performed as a single-pot transformation; and/or
the product of reacting the compound of formula (D), the compound of formula (E), and the second Lewis acid is epimerized.

6. The method of claim 1, wherein:
(i)
D' is OP$_1$, wherein P$_1$ is alkyl; and/or
D is H; and/or
wherein A is of the following structure:

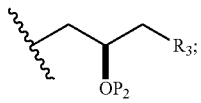

and/or
k is 0; and/or
R$_3$ is —(CH$_2$)$_n$NP$_3$P$_4$ or —(CH$_2$)$_n$OP$_5$, wherein n is 0; and/or
G is O;
or
(ii)
D' is H; and/or
A and D combine to form the following structure:

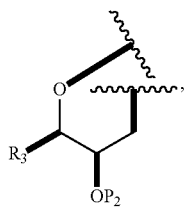

wherein, the bond to oxygen atom originates at the carbon atom, to which D is attached in formula (A), and
wherein R$_3$ is —(CH$_2$)$_n$NP$_3$P$_4$ or —(CH$_2$)$_n$OP$_5$, wherein n is 2; and/or
k is 1, and E is optionally substituted alkyl; and/or
G is O.

7. A compound of formula (B):

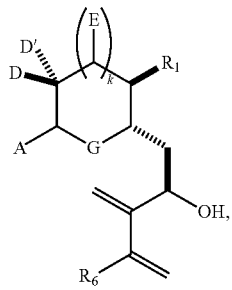

wherein
each of D and D' is independently H, optionally substituted alkyl, or OP$_1$, provided that only one of D and D' is OP$_1$, wherein P$_1$ is H, alkyl, or a hydroxyl protecting group, and A is a C$_{1-6}$ saturated or C$_{2-6}$ unsaturated hydrocarbon skeleton, the skeleton being unsubstituted or having from 1 to 10 substituents independently selected from the group consisting of cyano, halo, azido, oxo, and Q$_1$, or A is a group of formula (1):

wherein
L is —(CH(OP$_2$))—, —(C(OH)(OP$_2$))—, or —C(O)—;
R$_2$ is H, or R$_2$ and P$_1$ combine to form a bond;
(i) R$_3$ is H, and P$_2$ is absent when L is —C(O)—, or P$_2$ is H, optionally substituted alkyl, or a hydroxyl protecting group when L is —(CH(OP$_2$))— or —(C(OH)(OP$_2$))—;
(ii) R$_3$ is —(CH$_2$)$_n$NP$_3$P$_4$, wherein P$_3$ is H or an N-protecting group, and (a) P$_2$ is absent when L is —C(O)—, or P$_2$ is H, optionally substituted alkyl, or a hydroxyl protecting group when L is —(CH(OP$_2$))— or —(C(OH)(OP$_2$))—, and P$_4$ is H or an N-protecting group, (b) P$_2$ and P$_4$ combine to form an alkylidene, or (c) each of P$_2$ and P$_4$ is H;
(iii) R$_3$ is —(CH$_2$)$_n$OP$_5$, wherein P$_2$ is absent when L is —C(O)—, or P$_2$ is H, optionally substituted alkyl, or a hydroxyl protecting group when L is —(CH(OP$_2$))— or —(C(OH)(OP$_2$))—, and P$_5$ is H, optionally substituted alkyl, or a hydroxyl protecting group; or P$_2$ and P$_5$, together with the atoms to which each is attached, combine to form a ketal, a cyclic carbonate, a dicarbonyl-dioxo, or silylene-dioxo; or
(iv) R$_3$ and P$_2$ combine to form an optionally substituted ethylene or a structure selected from the group consisting of:

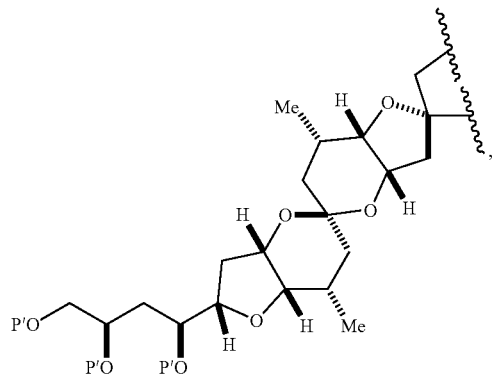

-continued

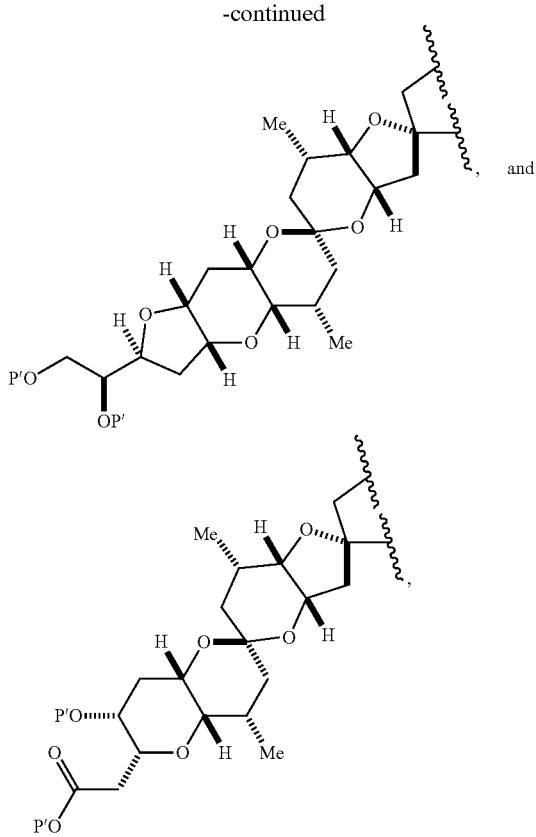

wherein each P' is independently H or a hydroxyl protecting group;

E is H, optionally substituted alkyl, or optionally substituted alkoxy;

G is O, S, $CH_2$, or $NR_N$, wherein $R_N$ is H, an N-protecting group, or optionally substituted alkyl;

each $Q_1$ is independently $OR_A$, $SR_A$, $SO_2R_A$, $OSO_2R_A$, $NR_BR_A$, $NR_B(CO)R_A$, $NR_B(CO)(CO)R_A$, $NR_B(CO)NR_BR_A$, $NR_B(CO)OR_A$, $(CO)OR_A$, $O(CO)R_A$, $(CO)NR_BR_A$, or $O(CO)NR_BR_A$, wherein each of $R_A$ and $R_B$ is independently H, alkyl, haloalkyl, hydroxyalkyl, aminoalkyl, aryl, haloaryl, hydroxyaryl, alkoxyaryl, arylalkyl, alkylaryl, haloarylalkyl, alkylhaloaryl, (alkoxyaryl)alkyl, heterocyclic radical, or heterocyclic radical-alkyl;

n, when present, is 0, 1, or 2;

k is 0 or 1;

$R_1$ is $-OP_6$, $-CH(Y)_2$, or $-CH_2(Y)$, wherein $P_6$ is H or a hydroxyl protecting group;

$R_6$ is H, optionally substituted alkyl, or optionally substituted arylalkyl; and Y is independently $-COOR_C$ or $-SO_2R_D$;

$R_C$, when present, is optionally substituted alkyl, optionally substituted aryl, or optionally substituted arylalkyl; and $R_D$, when present, is optionally substituted aryl or optionally substituted non-enolizable alkyl.

* * * * *